US007176311B2

(12) United States Patent
Bunnage et al.

(10) Patent No.: US 7,176,311 B2
(45) **Date of Patent: *Feb. 13, 2007**

(54) PROCESS FOR PREPARING PHARMACEUTICALLY ACTIVE COMPOUNDS

(75) Inventors: Mark Edward Bunnage, Sandwich (GB); Keith Michael DeVries, Groton, CT (US); Laurence James Harris, Sandwich (GB); Philip Charles Levett, Sandwich (GB); John Paul Mathias, Sandwich (GB); Joanna Teresa Negri, Groton, CT (US); Stephen Derek Albert Street, Sandwich (GB); Albert Shaw Wood, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/753,199

(22) Filed: Jan. 6, 2004

(65) Prior Publication Data

US 2004/0152712 A1 Aug. 5, 2004

Related U.S. Application Data

(62) Division of application No. 09/685,080, filed on Oct. 6, 2000, now Pat. No. 6,677,335.

(60) Provisional application No. 60/231,122, filed on Sep. 8, 2000, provisional application No. 60/168,059, filed on Nov. 30, 1999.

(30) Foreign Application Priority Data

Oct. 11, 1999 (GB) ................................ 9924063.2
Jul. 28, 2000 (GB) ................................ 0018656.9

(51) Int. Cl.
*C07D 487/04* (2006.01)
*C07D 401/12* (2006.01)

(52) U.S. Cl. ..................... 544/262; 544/118; 544/357; 546/275.4

(58) Field of Classification Search ................ 544/118, 544/262, 357; 546/275.4
See application file for complete search history.

(56) References Cited

U.S. PATENT DOCUMENTS

| | | | | |
|---|---|---|---|---|
| 2,089,971 | A | 8/1937 | Lesser | 260/32 |
| 4,663,326 | A | 5/1987 | Hamilton | 514/258 |
| 4,666,908 | A | 5/1987 | Hamilton | 514/229 |
| 4,871,843 | A | 10/1989 | Roger et al. | 540/575 |
| 5,250,534 | A | 10/1993 | Bell et al. | 514/258 |
| 5,272,147 | A | 12/1993 | Bell et al. | 514/234.2 |
| 5,294,612 | A | 3/1994 | Bacon et al. | 514/234.2 |
| 5,346,901 | A | 9/1994 | Bell et al. | 514/258 |
| 5,426,107 | A | 6/1995 | Bell et al. | 514/234.2 |
| 5,719,283 | A | 2/1998 | Bell et al. | 544/262 |
| 5,734,053 | A | 3/1998 | Terrett | 544/277 |
| 5,736,548 | A | 4/1998 | Bacon et al. | 514/258 |
| 5,955,611 | A | 9/1999 | Dunn et al. | 544/262 |
| 6,420,557 | B1 | 7/2002 | Harris et al. | 544/262 |
| 6,699,991 | B2 * | 3/2004 | James et al. | 544/364 |
| 2002/0040140 | A1 | 4/2002 | Harris et al. | 544/262 |

FOREIGN PATENT DOCUMENTS

| | | |
|---|---|---|
| DE | 19540642 | 5/1997 |
| EP | 0201188 | 12/1986 |
| EP | 0352960 | 1/1990 |
| EP | 0463756 | 1/1992 |
| EP | 0526004 | 2/1993 |
| EP | 0349239 | 3/1994 |
| EP | 0636626 | 2/1995 |
| EP | 0425921 | 8/1995 |

(Continued)

OTHER PUBLICATIONS

Czarmiecki et al, Annual Reports in Medicinal Chemistry, 31, 61-70, Dec. (1996).

(Continued)

*Primary Examiner*—Kahsay Habte
(74) *Attorney, Agent, or Firm*—Gregg C. Benson; Martha G. Munchhof

(57) ABSTRACT

A process for the preparation of Compounds of the formula (1):

(I)

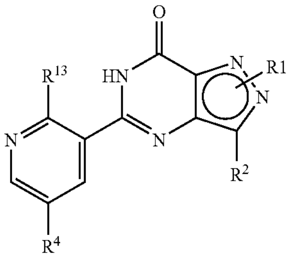

wherein $R^1$, $R^2$, $R^4$ and $R^{13}$ are as defined or a pharmaceutically or veterinarily acceptable salt or polymorph thereof, or a pharmaceutically or veterinarily acceptable solvate or pro-drug thereof: are potent and selective inhibitors of type 5 cyclic guanosine 3',5'-monophosphate phosphodiestbrase (cGMP PDE5) and have utility in the treatment of, inter alia, male erectile dysfunction (MED) and female sexual dysfunction (FSD).

5 Claims, 3 Drawing Sheets

FOREIGN PATENT DOCUMENTS

| | | |
|---|---|---|
| EP | 0812845 | 12/1997 |
| EP | 0992240 | 4/2000 |
| EP | 0995750 | 4/2000 |
| EP | 1020190 | 7/2000 |
| EP | 1074258 | 2/2001 |
| EP | 1090644 | 4/2001 |
| EP | 1092720 | 4/2001 |
| JP | 2000119198 | 4/2000 |
| WO | WO 9306104 | 4/1993 |
| WO | WO 9307149 | 4/1993 |
| WO | WO 9312095 | 6/1993 |
| WO | WO 9315062 | 8/1993 |
| WO | WO 9400453 | 1/1994 |
| WO | WO 9405661 | 3/1994 |
| WO | WO 9428902 | 12/1994 |
| WO | WO 9509636 | 4/1995 |
| WO | WO 9616644 | 6/1996 |
| WO | WO 9616657 | 6/1996 |
| WO | WO 9628429 | 9/1996 |
| WO | WO 9628448 | 9/1996 |
| WO | WO 9843614 | 10/1998 |
| WO | WO 9049166 | 11/1998 |
| WO | WO 9852569 | 11/1998 |
| WO | WO 9930697 | 6/1999 |
| WO | WO 9954333 | 10/1999 |
| WO | WO 9959584 | 11/1999 |
| WO | WO 9964004 | 12/1999 |
| WO | WO 0020033 | 4/2000 |
| WO | WO 0023056 | 4/2000 |
| WO | WO 0024745 | 5/2000 |
| WO | WO 0037061 | 6/2000 |
| WO | WO 0044399 | 8/2000 |
| WO | WO 0053148 | 9/2000 |
| WO | WO 0108659 | 2/2001 |
| WO | WO 0110406 | 2/2001 |
| WO | WO 0127113 | 4/2001 |

OTHER PUBLICATIONS

Henze et al., J. Am. Chem. Soc., Feb. 1939, pp. 433-435.
Terfort et al., J. Chem. Soc. Perkin trans. 1, 1996, pp. 1467-1479.
Dumaltre, J. Med. Chem., 1996, 39, 1635-1644.
Terrett, et al., Bioorg. Med. Chem. Lett, vol. 6, No. 15, 1996, pp. 1819-1824.
Gazz. Chim. Ital., vol. 72, 1942, pp. 325-333.
Hamilton et al., J. Med. Chem. vol. 30, No. 1, 1987, pp. 91-96.
Billotte, SYNLETT, Apr. 1998, pp. 379-380.
Jung, et al., Org. Chem. vol. 56, No. 24, 1991.
Anderson et al., J. org. Chem., vol. 37, No. 24, 1972, pp. 3953-3955.
Byeongmoon, et al., Nature, vol. 388, No. 28, pp. 860-862, Aug. 1997.
Hostyn, et al., J. Fr. Opthalmol., vol. 19, No. 2, pp. 133-139, 1996.
Hye Jung Lee et al., The J. of Pharmacology, vol. 281, No. 3, pp. 1431-1439, 1997.
OluFunmi et al., Nature Medicine, vol. 2, No. 7, pp. 795-799, Jul. 1996.
Takada et al., PDA Jrnl of Pharm. Science and Tech., vol. 49 No. 4, pp. 180-184, Jul.-Aug. 1995.

* cited by examiner

SCHEME 1
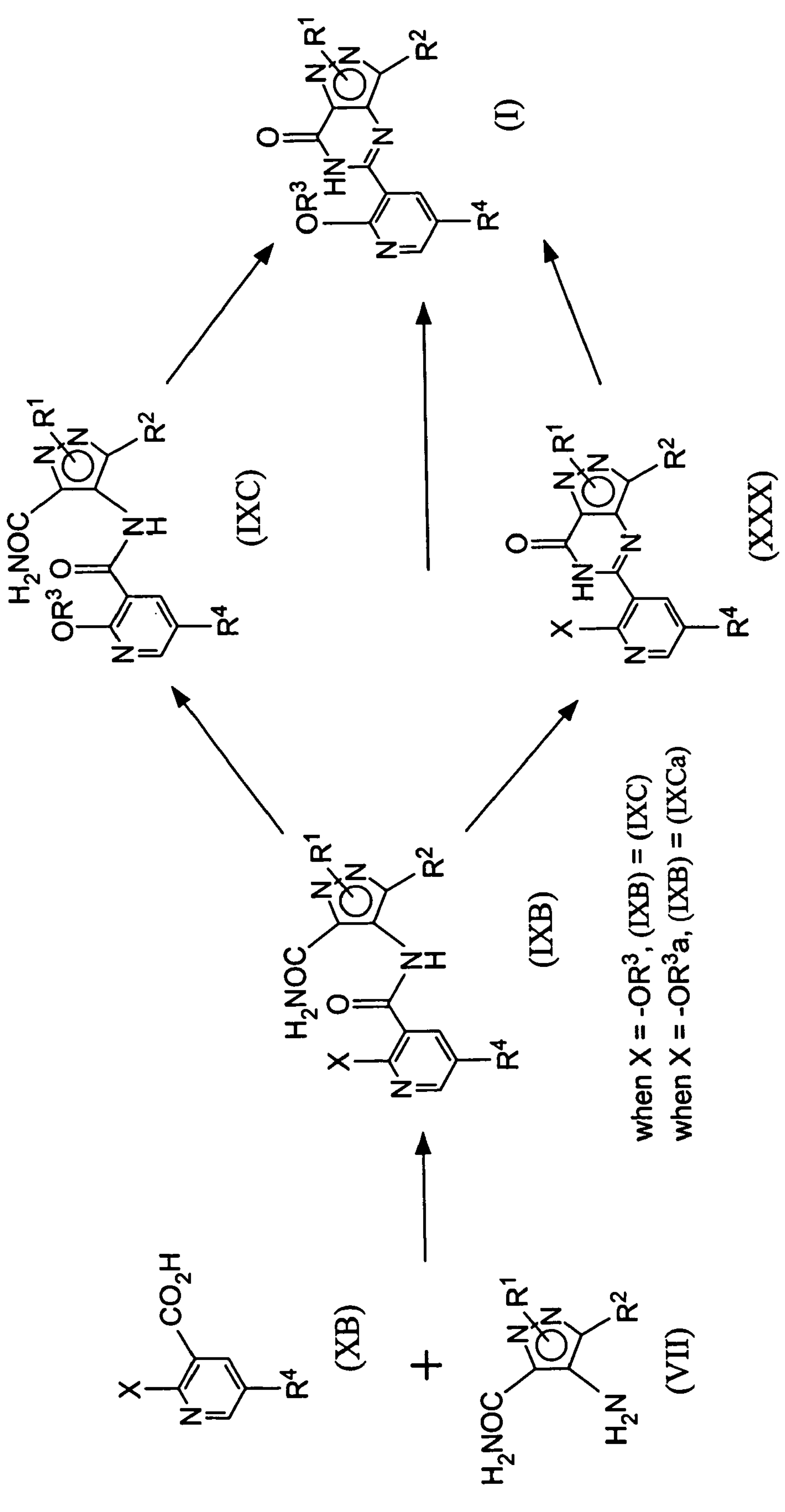
(XB) + (VII) → (IXB) → (IXC), (XXX) → (I)

SCHEME 2
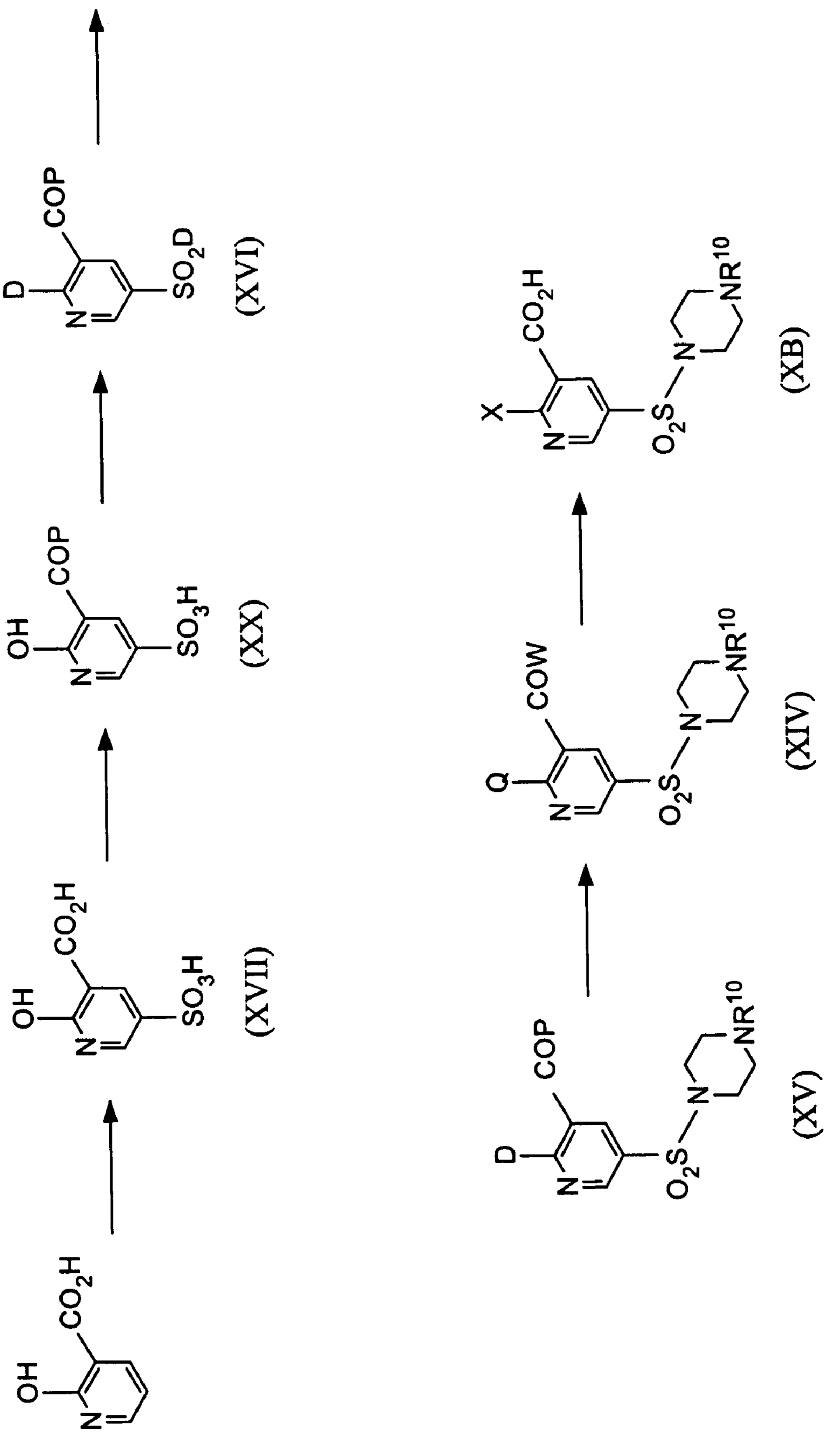
(XVII) (XX) (XVI)
(XV) (XIV) (XB)

SCHEME 3
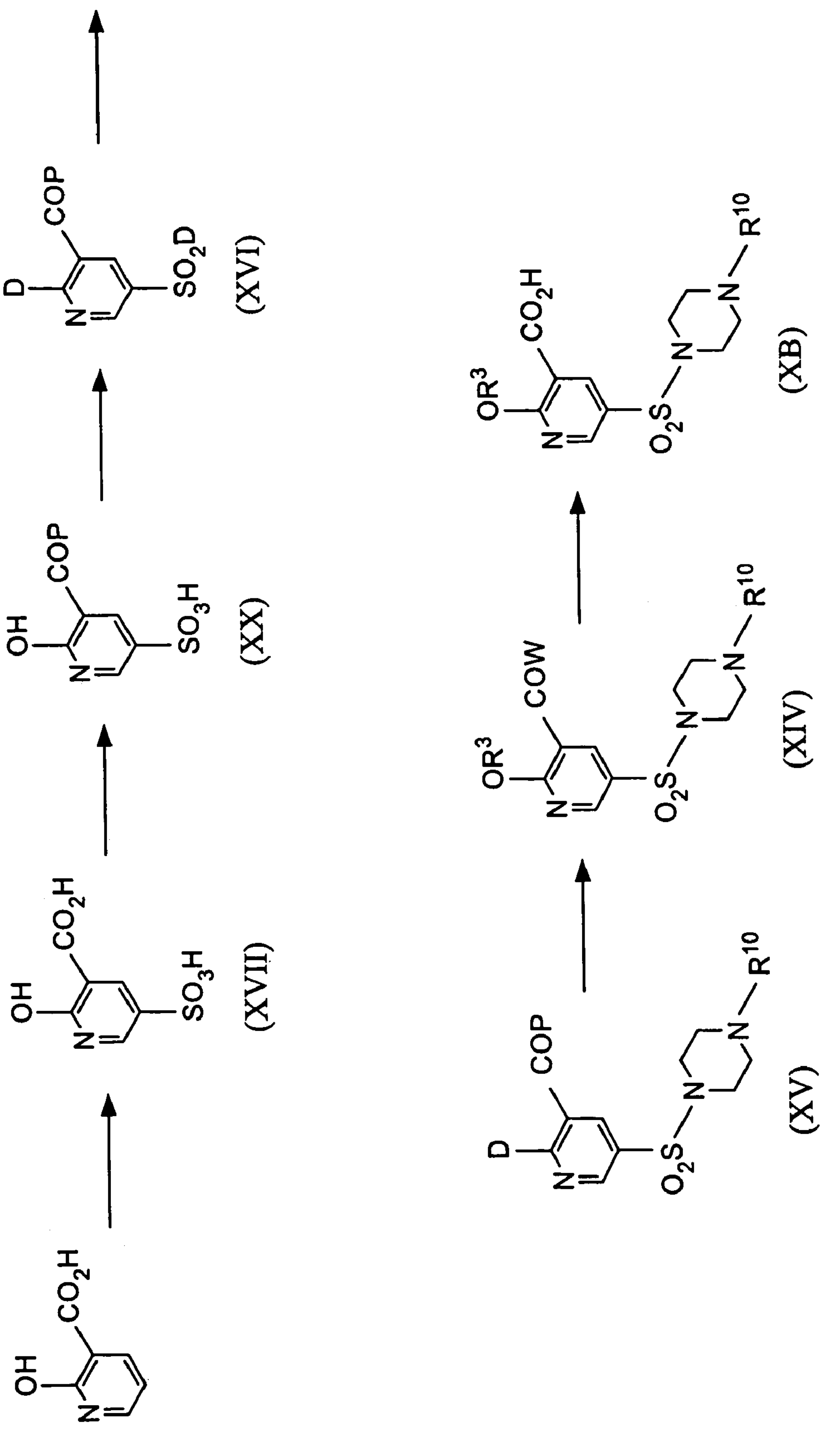
(XVII) (XX) (XVI)
(XV) (XIV) (XB)

PROCESS FOR PREPARING PHARMACEUTICALLY ACTIVE COMPOUNDS

CROSS REFERENCE TO RELATED APPLICATIONS

This application is a divisional of U.S. patent application No. 09/685,080 filed on Oct. 6, 2000, now U.S. Pat. No. 6,677,335, which was filed claiming priority from U.S. provisional application 60/168,059 filed Nov. 30, 1999 and from U.S. provisional application 60/231,122 filed Sep. 8, 2000. The entire text of each of the preceding documents is herein incorporated by reference.

This invention relates to a series of pyrazolo[4,3-d]pyrimidin-7-ones, which inhibit cyclic guanosine 3',5'-monophosphate phosphodiesterases (cGMP PDEs). More notably, the compounds of the invention are potent and selective inhibitors of type 5 cyclic guanosine 3',5'-monophosphate phosphodiesterase (cGMP PDE5) and have utility therefore in a variety of therapeutic areas.

The compounds of the invention are of value for the curative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-occular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof e.g. gastroparesis, peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction as well as the stabilisation of blood pressure during haemodialysis.

Particularly preferred conditions include MED and FSD.

PCT application PCT/IB99/00519 relates to a series of pyrazolo[4,3-d]pyrimidin-7-ones, which inhibit cyclic guanosine 3',5'-monophosphate phosphodiesterases (cGMP PDEs).

Thus the present invention provides compounds of the formula (I):

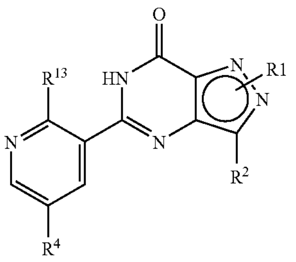

(I)

or a pharmaceutically or veterinarily acceptable salt thereof, or a pharmaceutically or veterinarily acceptable solvate of either entity, wherein $R^1$ is $C_1$ to $C_6$ alkyl or $C_3$ to $C_6$ alkenyl, $C_3$ to $C_6$ cycloalkyl or $C_4$ to $C_6$ cycloalkenyl wherein said alkyl group may be branched or straight chain and wherein when $R^1$ is $C_1$ to $C_3$ alkyl said alkyl group is substituted by;

and wherein when $R^1$ is $C_4$ to $C_6$ alkyl, $C_3$ to $C_6$ alkenyl or $C_3$ to $C_6$ cycloalkyl said alkyl, alkenyl or cycloalkyl group is optionally substituted by;

one or more substituents selected from:

hydroxy;

$C_1$ to $C_4$ alkoxy;

$C_3$ to $C_6$ cycloalkyl;

phenyl substituted with one or more substitutents selected from $C_1$ to $C_3$ alkyl, $C_1$ to $C_4$ alkoxy, $C_1$ to $C_4$ haloalkyl, $C_1$ to $C_4$ haloalkoxy, halo, CN, NO, $NHR^{11}$, $NHCOR^{12}$, $NHSOR^{12}$, $SOR^{12}$, $SO_2NHR^1$, $COR^{11}$ or $CO_2R^{11}$ wherein said haloalkyl and haloalkoxy groups contain one or more halo atoms;

$NR^7R^8$, $CONR^7R^8$ or $NR^7COR^{11}$ wherein $R^7$ and $R^8$ are each independently selected from H, $C_1$ to $C_4$ alkyl, $C_3$ to $C_4$ alkenyl, $CO_2R^9$ or $SO_2R^9$ and wherein said alkyl or alkenyl groups are optionally substituted by $C_1$ to $C_4$ haloalkyl or $C_1$ to $C_4$ haloalkoxy;

$Het^1$;

$Het^2$ or $Het^3$;

or $R^1$ is $Het^4$ or phenyl wherein said phenyl group is optionally substituted by one or more substituents selected from $C_1$ to $C_4$ alkyl, $C_3$ to $C_4$ alkenyl, $C_1$ to $C_4$ alkoxy, halo, CN, $CF_3$, $OCF_3$, $NO_2$, $NHR^{11}$, $NHCOR^{12}$, $NHSO_2R^{12}$, $SO_2R^{12}$, $SO_2NHR^{11}$, $COR^{11}CO_2R^{11}$;

$R^2$ is $C_1$ to $C_6$ alkyl, $C_3$ to $C_6$ alkenyl or $(CH_2)_n(C_3$ to $C_6$ cycloalkyl) wherein n is 0, 1 or 2;

$R^{13}$ is $OR^3$ or $NR^5R^6$;

$R^3$ is $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, $Het^1$, $Het^2$, $Het^3$ or $Het^4$ wherein the $C_1$ to $C_6$ alkyl and $C_1$ to $C_4$ alkoxy groups may optionally be terminated by a haloalkyl group such as $CF_3$ and wherein the $C_3$–$C_5$ cycloalkyl group may optionally be substituted by $C_1$–$C_4$ alkyl, hydroxy or halo; $C_3$ to $C_6$ cycloalkyl; $Het^1$, $Het^2$, $Het^3$ or $Het^4$;

$R^4$ is a piperazin-1-ylsulphonyl group having a substituent $R^{10}$ at the 4-position of the piperazinyl group wherein said piperazinyl group is optionally substituted with one or two $C_1$ to $C_4$ alkyl groups and is optionally in the form of its 4-N-oxide;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^7$ and $R^8$ are each independently selected from H, $C_1$ to $C_4$ alkyl, $C_3$ to $C_4$ alkenyl, $CO_2R^9$ or $SO_2R^9$;

$R^9$ is $C_1$ to $C_4$ alkyl optionally substituted with $C_1$ to $C_4$ haloalkyl, $C_1$ to $C_4$ haloalkoxy or phenyl wherein said phenyl group is optionally substituted by one or more substituents selected from $C_1$ to $C_4$ alkyl optionally substituted by $C_1$ to $C_4$ haloalkyl or $C_1$ to $C_4$ haloalkoxy, $C_1$ to $C_4$ alkoxy, halo, CN, $NO_2$, $NHR^{11}$, $NHCOR^{12}$, $NHSO_2R^{12}$, $SO_2R^{12}$, $SO_2NHR^{11}$, $COR^{11}$ or $CO_2R^{11}$;

$R^{10}$ is H; $C_1$ to $C_4$ alkyl optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_3$ to $C_6$ alkenyl or $Het^4$;

$R^{11}$ is H, $C_1$ to $C_4$ alkyl, $C_3$ to $C_4$ alkenyl, CO($C_1$ to $C_4$ alkyl) or $C_1$ to $C_4$ haloalkyl;

$R^{12}$ is $C_1$ to $C_4$ alkyl, $C_3$ to $C_4$ alkenyl, $C_1$ to $C_4$ haloalkyl or $C_1$ to $C_4$ haloalkoxy;

$Het^1$ is an N-linked 4-, 5- or 6-membered nitrogen-containing heterocyclic group optionally containing one or more further heteroatoms selected from S, N or O;

$Het^2$ is a C-linked 5-membered heterocyclic group containing an O, S or N heteroatom optionally containing one or more heteroatoms selected from N, O or S;

$Het^3$ is a C-linked 6-membered heterocyclic group containing an O or S heteroatom optionally containing one or more heteroatoms selected from O, S or N or $Het^3$ is a C-linked 6-membered heterocyclic group containing three N heteroatoms;

$Het^4$ is a C-linked 4-, 5- or 6-membered heterocyclic group containing one, two or three heteroatoms selected from S, O or N; and wherein any of said heterocyclic groups $Het^1$, $Het^2$, $Het^3$ or $Het^4$ may be saturated, partially unsaturated or aromatic and wherein any of said heterocyclic groups may be optionally substituted with one or more substituents selected from $C_1$ to $C_4$ alkyl, $C_3$ to $C_4$ alkenyl, $C_1$ to $C_4$ alkoxy, halo, $CF_3$, $CO_2R^{11}$, $COR^{11}$, $SO_2R^{12}$, $NHR^{11}$ or $NHCOR^{12}$ and/or wherein any of said heterocyclic groups is benzo-fused;

with the provisos that (a) when $R^1$ is $C_1$ to $C_3$ alkyl then $Het^1$ is not morpholinyl or piperidinyl and (b) when $R^1$ is $C_1$ to $C_3$ alkyl substituted by phenyl then said phenyl group is not substituted by $C_1$ to $C_4$ alkoxy, halo, CN, $CF_3$, $OCF_3$ or $C_1$ to $C_4$ alkyl.

As will be recognised by the skilled chemist, the general formula (I) can be represented by the regio-isomeric general formulae (IA) and (IB). Thus the present invention provides compounds of formulae (IA) and (IB):

(IA)

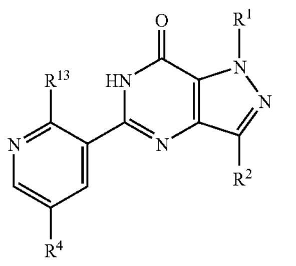

(IB)

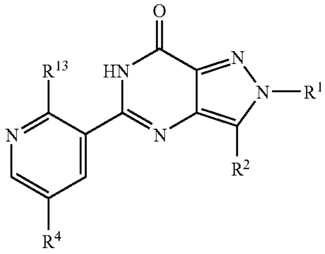

wherein $R^1$, $R^2$, $R^4$ and $R^{13}$ are as defined hereinbefore.

In the above definitions, unless otherwise indicated, alkyl, alkoxy and alkenyl groups having three or more carbon atoms, and alkanoyl groups having four or more carbon atoms, may be straight chain or branched chain. For example, a $C_4$ alkyl substituent can be in the form of normal-butyl (n-butyl), iso-butyl (i-butyl), secondary-butyl (sec-butyl) or tertiary-butyl (t-butyl). The term halo atom includes Cl, Br, F, and 1. Haloalkyl and haloalkoxy are preferably $-CF_3$ and $-OCF_3$ respectively. The term aromatic as defined herein means a fully unsaturated system.

A compound of the formula (I) contains one or more asymmetric carbon atoms and therefore exists in two or more stereoisomeric forms. Where a compound of the formula (I) contains an alkenyl or alkenylene group, cis (E) and trans (Z) isomerism may also occur. The present invention includes the individual stereoisomers of the compounds of the formula (I) and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

The compounds of formulae (IA) and (IB) may also exist in tautomeric forms and the invention includes both mixtures thereof and the individual tautomers.

Also included in the invention are radiolabelled derivatives of compounds of formulae (I), (IA) and (IB) which are suitable for biological studies.

The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, J. Pharm, Sci., 66, 1–19, 1977.

The pharmaceutically acceptable solvates of the compounds of the invention include the hydrates thereof.

Also included within the scope of the compound and various salts of the invention are polymorphs thereof.

A preferred group of compounds of formulae (I), (IA) and (IB) is that wherein, $R^1$ is $C_1$ to $C_6$ alkyl or $C_3$ to $C_6$ alkenyl wherein said alkyl or alkenyl groups may be branched chain or straight chain or $R^1$ is $C_3$ to $C_6$ cycloalkyl or $C_4$ to $C_6$ cycloalkenyl and wherein when $R^1$ is $C_1$ to $C_3$ alkyl said alkyl group is substituted by; and wherein when $R^1$ is $C_4$ to $C_6$ alkyl, $C_3$ to $C_6$ alkenyl, $C_3$ to $C_6$ cycloalkyl or $C_4$ to $C_6$ cycloalkenyl said alkyl, alkenyl, cycloalkyl or cycloalkenyl group is optionally substituted by;

one or more substituents selected from:

hydroxy;

$C_1$ to $C_4$ alkoxy;

$C_3$ to $C_4$ cycloalkyl;

phenyl substituted with one or more substitutents selected from $C_1$ to $C_3$ alkyl, $C_1$ to $C_4$ alkoxy, $C_1$ to $C_4$ haloalkyl or $C_1$ to $C_4$ haloalkoxy, halo, CN, $NO_2$, $NHR^{11}$, $NHCOR^{12}$, $NHSO_2R^{12}$, $SO_2R^{12}$, $SO_2NHR^{11}$, $COR^{11}$, $CO^2R^{11}$ wherein said haloalkyl and haloalkoxy groups contain one or more halo atoms;

$NR^7R^8$, $CONR^7R^8$ or $NR^7COR^{11}$;

a $Het^1$ group which is an N-linked 4-membered N-containing heterocyclic group;

a $Het^2$ group which is a C-linked 5-membered heterocyclic group containing an O, S or N heteroatom optionally containing one or more heteroatoms selected from N, O or S;

a $Het^3$ group which is a C-linked 6-membered heterocyclic group containing an O or S heteroatom optionally containing one or more heteroatoms selected from O, S or N or a $Het^3$ group which is a C-linked 6-membered heterocyclic group containing three N heteroatoms;

wherein $R^7$, $R^8$, $R^{11}$ and $R^{12}$ are as previously defined herein or $R^1$ is a $Het^4$ group which is a C-linked 4- or 5-membered heterocyclic group containing one heteroatom selected from S, O or N; a $Het^4$ group which is a C-linked 6-membered heterocyclic group containing one, two or three heteroatoms selected from S or O; a $Het^4$ group which is a C-linked 6-membered heterocyclic group containing three nitrogen heteroatoms; a $Het^4$ group which is a C-linked 6-membered heterocyclic group containing one or two nitrogen heteroatoms which is substituted by one or more substitutents selected from $C_1$ to $C_4$ alkyl, $C_1$ to C4 alkoxy, $CO_2R^{11}$, $SO_2R^{12}$, $COR^{11}$, $NHR^{11}$ or $NHCOR^{12}$ and optionally including a further heteroatom selected from S, O or N wherein any of said heterocyclic groups $Het^1$, $Het^2$, $Het^3$ or $Het^4$ is saturated, partially unsaturated or aromatic as appropriate and wherein any of said heterocyclic groups is optionally substituted with one or more substituents selected from $C_1$ to $C_4$ alkyl, $C_3$ to $C_4$ alkenyl, $C_1$ to $C_4$ alkoxy, halo, $CO_2R^{11}$, $SO_2R^{12}$, $COR^{11}$ or $NHR^{11}$ wherein $R^{11}$ is as defined hereinbefore and/or wherein any of said heterocyclic groups is benzo-fused;

or $R^1$ is phenyl substituted by one or more substituents selected from $CF_3$, $OCF_3$, $SO_2R^{12}$ or $CO_2R^{12}$ wherein $R^{12}$ is $C_1$ to $C_4$ alkyl which is optionally substituted by phenyl, $C_1$ to $C_4$ haloalkyl or $C_1$ to $C_4$ haloalkoxy wherein said haloalkyl and haloalkoxy groups contain one or more halo atoms;

$R^2$ is $C_1$ to $C_6$ alkyl;

$R^{13}$ is $OR^3$;

$R^3$ is $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, furanyl, tetrahydrofuranyl or pyridinyl wherein said $C_1$ to $C_6$ alkyl and $C_1$ to $C_4$ alkoxy groups may optionally be terminated by a haloalkyl group such as $CF_3$; or $R^3$ is $C_3$ to $C_6$ cycloalkyl, 1-($C_1$ to $C_4$ alkyl)piperidinyl, tetrahydrofuranyl or tetrahydropyranyl;

$R^4$ is a piperazin-1-ylsulphonyl group having a substituent $R^{10}$ at the 4-position of the piperazinyl group wherein said piperazinyl group is optionally substituted with one or two $C_1$ to $C_4$ alkyl groups and is optionally in the form of its 4-N-oxide;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group; and $R^{10}$ is H; $C_1$ to $C_4$ alkyl optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_3$ to $C_6$ alkenyl; $Het^4$;

with the proviso that when $R^1$ is $C_1$ to $C_3$ alkyl substituted by phenyl then said phenyl group is not substituted by $C_1$ to $C_4$ alkoxy; CN; halo; $CF_3$; $OCF_3$; or $C_1$ to $C_4$ alkyl.

A further preferred group of compounds of formulae (I), (IA) and (IB) is that wherein, $R^1$ is $C_1$ to $C_6$ alkyl wherein said alkyl may be branched or straight chain or $R^1$ is $C_3$ to $C_6$ cycloalkyl and wherein when $R^1$ is $C_1$ to $C_3$ alkyl said alkyl group is substituted by; and wherein when $R^1$ is $C_4$ to $C_6$ alkyl or $C_3$ to $C_6$ cycloalkyl said alkyl or cycloalkyl group is optionally substituted by;

one or more substituents selected from:

hydroxy;

$C_1$ to $C_2$ alkoxy;

$C_3$ to $C_5$ cycloalkyl;

$NR^7R^8$, $NR^7COR^{11}$ or $COR^{11}$ wherein $R^7$ and $R^8$ are each independently selected from H, $C_1$ to $C_4$ alkyl or $CO_2R^9$ wherein $R^9$ and $R^{11}$ are as previously defined herein;

a $Het^1$ group which is an N-linked 4-membered N-containing heterocyclic group;

a $Het^3$ group which is a C-linked 6-membered heterocyclic group containing an O or S heteroatom optionally containing one or more heteroatoms selected from O, S or N or a $Het^3$ group which is a C-linked 6-membered heterocyclic group containing three N heteroatoms;

or $R^1$ is a $Het^4$ group which is a C-linked 4-membered heterocyclic group containing one heteroatom selected from S, O or N or $R^1$ is a $Het^4$ group which is a C-linked 6-membered heterocyclic group containing one, two or three heteroatoms selected from S or O wherein any of said heterocyclic groups $Het^1$, $Het^2$, $Het^3$ or $Het^4$ is saturated, partially unsaturated or aromatic and is optionally substituted with one or more substituents selected from $C_1$ to $C_4$ alkyl, $C_1$ to $C_4$ alkoxy, —$CO_2R^{11}$, —$SO_2R^{12}$, —$COR^{11}$ or $NHR^{11}$ wherein $R^{11}$ and $R^{12}$ are as defined hereinbefore and/or wherein any of said heterocyclic groups is benzo-fused;

or $R^1$ is phenyl substituted by one or more substituents selected from: $CF_3$, —$OCF_3$, —$SO_2R^{12}$, —$COR^{11}$, —$CO^2R^{11}$ wherein $R^{11}$ and $R^{12}$ are as defined hereinbefore;

$R^2$ is $C_1$ to $C_6$ alkyl;

$R^{13}$ is $OR^3$;

$R^3$ is methyl, ethyl, n-propyl, i-propyl, n-butyl, sec-butyl, i-butyl or t-butyl alkyl optionally substituted with one or two substituents selected from cyclopropyl, cyclobutyl, hydroxy, methoxy, ethoxy, benzyloxy, phenyl, benzyl, furan-3-yl, tetrahydrofuran-2-ylmethyl, tetrahydrofuran-3-ylmethyl, pyridin-2-yl, pyridin-3-yl or $NR^5R^6$ wherein $R^5$ and $R^6$ are each independently selected from H and $C_1$ to $C_2$ alkyl;

$R^4$ is a piperazin-1-ylsulphonyl group having a substituent, $R^{10}$ at the 4-position of the piperazinyl group wherein said piperazinyl group is optionally substituted with one or two $C_1$ to $C_4$ alkyl groups and is optionally in the form of its 4-N-oxide; and $R^{10}$ is H, $C_1$ to $C_3$ alkyl optionally substituted with one or two substituents selected from hydroxy, $NR^5R^6$, $CONR^5R^6$ wherein $R^5$ and $R^6$ are each independently selected from H, $C_1$ to $C_4$ alkyl and $C_3$ alkenyl.

Preferred compounds of the present invention include:

5-[2-Ethoxy-5-(4-methylpiperazin-1-ylsulphonyl)pyridin-3-yl]-2-[2-methoxyethyl]-3-n-propyl-2,6-dihydro-7H-pyrazolo[4,3-d]pyrimidin-7-one, 5-[2-Ethoxy-5-(4-methylpiperazin-1-ylsulphonyl)pyridin-3-yl]-3-ethyl-2-[2-methoxyethyl]-2,6-dihydro-7H-pyrazolo[4,3-d]pyrimidin-7-one, 5-[2-Ethoxy-5-(4-ethylpiperazin-1-ylsulphonyl)pyridin-3-yl]-2-[2-methoxyethyl]-3-n-propyl-2,6-dihydro-7H-pyrazolo[4,3-d]pyrimidin-7-one, 2-(sec-Butyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-(iso-Butyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-(Cyclopropylmethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-(Cyclobutylmethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-[2-methoxy-1-methylethyl]-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-[2-(methylamino)ethyl]-2,6-dihydro-7H-pyrazolo[4,3-d]pyrimidin-7-one, 2-(2-Dimethylaminoethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(1-methylazetidin-3-yl)-2,6-dihydro-7H-pyrazolo[4,3-d]pyrimidin-7-one, 5-[2-n-Butoxy-5-(4-ethylpiperazin-1-ylsulphonyl)pyridin-3-yl]-2-dimethylaminoethyl-3-ethyl-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(1-ethylazetidin-3-yl)-2,6-dihydro-7H-pyrazolo[4,3-d]pyrimidin-7-one, 2-{2-[Acetyl(methyl)amino]ethyl}-5-[5-(4-ethylpiperazin-1-ylsulphonyl)-2-n-propoxypyridin-3-yl]-3-ethyl-2,6-dihydro-7H-pyrazolo[4,3-d]pyrimidin-7-one, 2-(1-Acetylazetidin-3-yl)-5-[2-n-butoxy-5-(4-ethylpiperazin-1-ylsulphonyl)pyridin-3-yl]-3-ethyl-2,6-dihydro-7H-pyrazolo[4,3-d]pyrimidin-7-one, 5-[2-iso-Butoxy-5-(4-ethylpiperazin-1-ylsulphonyl)pyridin-3-yl]-2-(2-methoxyethyl)-3-n-propyl-2,6-dihydro-7H-pyrazolo[4,3-d]pyrimidin-7-one, 5-[2-n-Butoxy-5-(4-ethylpiperazin-1-ylsulphonyl)pyridin-3-yl]-3-ethyl-2-(2-methoxyethyl)-2,6-dihydro-7H-pyrazolo[4,3-d]pyrimidin-7-one, 3-Ethyl-5-[5-(4-ethylpiperazin-1-ylsulphonyl)-2-(2-methoxyethoxy)pyridin-3-yl]-2-(2-methoxyethyl)-2,6-dihydro-7H-pyrazolo[4,3-d]pyrimidin-7-one, 5-[2-n-Butoxy-5-(4-ethylpiperazin-1-ylsulphonyl)pyridin-3-yl]-3-ethyl-2-(1-methylazetidin-3-yl)-2,6-dihydro-7H-pyrazolo[4,3-d]pyrimidin-7-one, 5-[2-n-Butoxy-5-(4-ethylpiperazin-1-ylsulphonyl)pyridin-3-yl]-3-ethyl-2-(1-ethylazetidin-3-yl)-2,6-dihydro-7H-pyrazolo[4,3-d]pyrimidin-7-one, 5-[2-Benzyloxy-5-(4-ethylpiperazin-1-ylsulphonyl)pyridin-3-yl]-3-ethyl-2-(1-ethylazetidin-3-yl)-2,6-dihydro-7H-pyrazolo[4,3-d]pyrimidin-7-one, 5-[2-iso-Butoxy-5-(4-methylpiperazin-1-ylsulphonyl)pyridin-3-yl]-3-ethyl-2-(2-methoxyethyl)-2,6-dihydro-7H-pyrazolo[4,3-d]pyrimidin-7-one, 3-Ethyl-5-[5-(4-ethylpiperazin-1-ylsulphonyl)-2-n-propoxypyridin-3-yl]-2-(2-methoxyethyl)-2,6-dihydro-7H-pyrazolo[4,3-d]pyrimidin-7-one, 5-[2-n-Butoxy-5-(4-ethylpiperazin-1-ylsulphonyl)pyridin-3-yl]-3-ethyl-2-(2-methoxyethyl)-2,6-dihydro-7H-pyrazolo[4,3-d]pyrimidin-7-one, 3-Ethyl-5-[5-(4-ethylpiperazin-1-ylsulphonyl)-2-iso-propoxypyridin-3-yl]-2-(2-methoxyethyl)-2,6-dihydro-7H-pyrazolo[4,3-d]pyrimidin-7-one, 5-[(S)-2-sec-Butoxy-5-(4-ethylpiperazin-1-ylsulphonyl)pyridin-3-yl]-3-ethyl-2-(2-methoxyethyl)-2,6-dihydro-7H-pyrazolo[4,3-d]pyrimidin-7-one, 5-[(R)-2-sec-Butoxy-5-(4-ethylpiperazin-1-ylsulphonyl)pyridin-3-yl]-3-ethyl-2-(2-methoxyethyl)-2,6-dihydro-7H-pyrazolo[4,3-d]pyrimidin-7-one, 3-Ethyl-5-[5-(4-ethylpiperazin-1-ylsulphonyl)-2-{(pyridin-2-yl)methyl}pyridin-3-yl]-2-(2-methoxyethyl)-2,6-dihydro-7H-pyrazolo[4,3-d]pyrimidin-7-one, 2-sec-Butyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 2-Cyclobutylmethyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 3-Ethyl-5-[5-(4-ethylpiperazin-1-ylsulphonyl)-2-(S)-(2-methoxy-1-methylethoxy)pyridin-3-yl]-2-(2-methoxyethyl)-2,6-dihydro-7H-pyrazolo[4,3-d]pyrimidin-7-one, 3-Ethyl-5-[5-(4-ethylpiperazin-1-ylsulphonyl)-2-(R)-(2-methoxy-1-methylethoxy)pyridin-3-yl]-2-(2-methoxyethyl)-2,6-dihydro-7H-pyrazolo[4,3-d]pyrimidin-7-one, 5-[5-(4-Ethylpiperazin-1-ylsulphonyl)-2-(S)-(2-methoxy-1-methylethoxy)pyridin-3-yl]-2-(2-methoxyethyl)-3-n-propyl-2,6-dihydro-7H-pyrazolo[4,3-d]pyrimidin-7-one, 5-[5-(4-Ethylpiperazin-1-ylsulphonyl)-2-(R)-(2-methoxy-1-methylethoxy)pyridin-3-yl]-2-(2-methoxyethyl)-3-n-propyl-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(2-hydroxyethyl)-2,6-dihydro-7H-pyrazolo[4,3-d]pyrimidin-7-one, 2-(2-Dimethylaminoethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-iso-Butyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one, 2-iso-Butyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 2-Cyclobutylmethyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one, 5-[2-n-Butoxy-5-(4-ethylpiperazin-1-ylsulphonyl)pyridin-3-yl]-2-[2-(dimethylamino)-2-oxoethyl]-3-ethyl-2,6-dihydro-7H-pyrazolo[4,3-d]pyrimidin-7-one, 5-[2-n-Butoxy-5-(4-ethylpiperazin-1-ylsulphonyl)pyridin-3-yl]-3-ethyl-2-{2-[methyl(methylsulphonyl)amino]ethyl}-2,6-dihydro-7H-pyrazolo[4,3-d]pyrimidin-7-one, 2-Cyclobutylpropylmethyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one, 2-n-Butyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one, 5-[2-n-Butoxy-5-(4-methylpiperazin-1-ylsulphonyl)pyridin-3-yl]-3-ethyl-2-(2-methoxyethyl)-2,6-dihydro-7H-pyrazolo[4,3-d]pyrimidin-7-one, 2-(2-Ethoxyethyl)-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(3-methoxypropyl)-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(S)-(2-methoxypropyl)-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(R)-(2-methoxypropyl)-2,6-dihydro-7H-pyrazolo[4,3-d]pyrimidin-7-one, 2-(S)-sec-Butyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-1-(2-methoxyethyl)-1,6-dihydro-7H-pyrazolo[4,3-d]pyrimidin-7-one, 2-(R)-sec-Butyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 2-Cyclobutyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-Cyclopentyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-Cyclopentylmethyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 2-Cyclohexyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one, 5-[2-Ethoxy-5-(4-ethylpiperazin-1-ylsulphonyl)pyridin-3-yl]-2-(2-ethoxyethyl)-3-ethyl-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-[(1S)-1-methyl-2-methoxyethyl)-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-[(1R)-1-methyl-2-methoxyethyl]-2,6-dihydro-7H-pyrazolo[4,3-d]pyrimidin-7-one, 5-[2-Ethoxy-5-(4-ethylpiperazin-1-ylsulphonyl)pyridin-3-yl]-3-ethyl-2-(3-methoxy-n-propyl)-2,6-dihydro-7H-pyrazolo[4,3-d]pyrimidin-7-one, 2-Cyclobutyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one, 5-[2-n-Butoxy-5-(4-methylpiperazin-1-ylsulphonyl)pyridin-3-yl]-3-ethyl-2-(2-methoxyethyl)-2,6-dihydro-7H-pyrazolo[4,3-d]pyrimidinone, 3-Ethyl-5-[2-(2-methoxyethoxy)-5-(4-methylpiperazin-1-ylsulphonyl)pyridin-3-yl]-2-[(1S)-1-methylpropyl]-2,6-dihydro-7H-pyrazolo[4,3-d]pyrimidinone, 3-Ethyl-5-[2-(2-methoxyethoxy)-5-(4-methylpiperazin-1-ylsulphonyl)pyridin-3-yl]-2-[(1R)-1-methylpropyl]-2,6-dihydro-7H-pyrazolo[4,3-d]pyrimidinone, 2-n-Butyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidinone, 2-Cyclopropylmethyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidinone, 2-Cyclobutylmethyl-3-ethyl-5-[5-(4-ethylpiperazin-1-ylsulphonyl)-2-(tetrahydro-2-furanylmethoxy)pyridin-3-yl]-2,6-dihydro-7H-pyrazolo[4,3-d]pyrimidinone, 3-Ethyl-5-[5-(4-ethylpiperazin-1-ylsulphonyl)-2-(2-methoxyethoxy)pyridin-3-yl]-2-(2-methoxyethoxy)-2,6-dihydro-7H-pyrazolo[4,3-d]pyrimidinone, 5-[2-Ethoxy-5-(4-iso-propylpiperazin-1-ylsulphonyl)pyridin-3-yl]-3-ethyl-2-(2-methoxyethyl)-2,6-dihydro-7H-pyrazolo[4,3-d]pyrimidinone and 5-[2-Ethoxy-5-(4-n-propylpiperazin-1-ylsulphonyl)pyridin-3-yl)-3-ethyl-2-(2-methoxyethyl)-2,6-dihydro-7H-pyrazolo[4,3-d]pyrimidinone.

A yet further preferred group of compounds of formulae (I), (IA) or (IB) is that wherein $R^1$ is —$(CH_2)_n(C_3$–$C_6)$cycloalkyl wherein n is 0, 1, 2 or 3; or $R^1$ is methyl, ethyl, iso-propyl or n-propyl substituted by one or more $C_1$ to $C_4$ alkoxy substituents wherein said alkoxy substituent may be directly attached to any C-atom within the ethyl, iso-propyl or n-propyl groups other than the C-atom directly linked to the pyrazole ring; or $R^1$ is a $C_4$ alkyl group selected from i-, n-, sec- or t-butyl optionally substituted by one or more substituents selected from $C_1$ to $C_4$ alkoxy or $C_3$ to $C_4$ cycloalkyl;

$R^2$ is $C_1$ to $C_4$ alkyl;

$R^{13}$ is $OR^3$ wherein $R^3$ is $C_1$ to $C_4$ alkyl optionally substituted with one or two $C_1$ to $C_4$ alkoxy substituents wherein said $C_1$ to $C_4$ alkyl and $C_1$ to $C_4$ alkoxy groups may optionally be terminated by a haloalkyl group such as $CF_3$;

$R^4$ is a piperazin-1-ylsulphonyl group having a single substituent, $R^{10}$ at the 4-position of the piperazinyl group and is optionally in the form of its 4-N-oxide;

and $R^{10}$ is methyl, ethyl, n-propyl or i-propyl.

A particularly preferred group of compounds of formulae (I), (IA) or (IB) is that wherein $R^1$ is $—(CH_2)_n(C_3–C_4)$cycloalkyl wherein n is 1 or 2; or $R^1$ is $—(CH_2)_n(C_3–C_6)$cycloalkyl wherein n is 0; or $R^1$ is -cyclopentyl methyl; or $R^1$ is methyl, ethyl, i-propyl or n-propyl substituted by methoxy, ethoxy, n-propoxy or i-propoxy wherein said alkoxy substituent may be directly attached to any C-atom within the ethyl, iso-propyl or n-propyl groups other than the C-atom directly linked to the pyrazole ring; or $R^1$ is i-, n-, sec- or t-butyl;

$R^2$ is $C_2$ to $C_4$ alkyl;

$R^{13}$ is $OR^3$ wherein the $R^3$ alkyl group is methyl, ethyl, n-propyl, i-propyl, i-butyl, n-butyl, sec-butyl or t-butyl optionally substituted with one or two methoxy, ethoxy, n-propoxy or i-propoxy substituents; and $R^4$ is a 4-methyl, 4-ethyl, 4-n-propyl or 4-i-propylpiperazin-1-ylsulphonyl group.

In highly preferred embodiment of the present invention there is provided a compound of the formula (IB) wherein $R^1$ is $—(CH_2)_n(C_3–C_4)$cycloalkyl wherein n is 1 or 2; or $R^1$ is $—(CH_2)_n(C_3–C_5)$cycloalkyl wherein n is 0; or $R^1$ is -cyclopentylmethyl; or $R^1$ is methyl, ethyl, i-propyl or n-propyl substituted by methoxy, ethoxy, n-propoxy or i-propoxy wherein said alkoxy substituent may be directly attached to any C-atom within the ethyl, iso-propyl or n-propyl groups other than the C-atom directly linked to the pyrazole ring; or $R^1$ is i-, n-, sec- or t-butyl;

$R^2$ is $C_2$ to $C_4$ alkyl; $R^{13}$ is $OR^3$ wherein the $R^3$ alkyl group is methyl, ethyl, n-propyl, i-propyl, i-butyl, n-butyl, sec-butyl or t-butyl; and $R^4$ is a 4-methyl or 4-ethylpiperazin-1-ylsulphonyl group.

Highly preferred compounds according to the present invention include: 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine and salts and polymorphs thereof. Preferred salts of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine are sulphonic acid salts, more preferably the p-toluenesulfonate, benzenesulfonate, camphorsulfonate and ethanesulfonate salts respectively, and especially the benzenesulfonate.

According to a further aspect of the present invention there are provided compounds of the general formula (I):

(I)

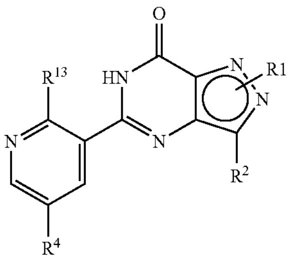

or a pharmaceutically or veterinarily acceptable salt thereof, or a pharmaceutically or veterinarily acceptable solvate of either entity, wherein $R^1$ is $C_1$ to $C_6$ alkyl or $C_3$ to $C_6$ alkenyl, $C_3$ to $C_6$ cycloalkyl or $C_3$ to $C_6$ cycloalkenyl wherein said alkyl group may be branched or straight chain and wherein when $R^1$ is $C_1$ to $C_3$ alkyl said alkyl group is substituted by; and wherein when $R^1$ is $C_4$ to $C_6$ alkyl, $C_3$ to $C_6$ alkenyl or $C_3$ to $C_6$ cycloalkyl said alkyl, alkenyl or cycloalkyl group is optionally substituted by; one or more substituents selected from: hydroxy; $C_1$ to $C_4$ alkoxy; $C_3$ to $C_6$ cycloalkyl; phenyl substituted with one or more substitutents selected from $C_1$ to $C_3$ alkyl, $C_1$ to $C_4$ alkoxy, $C_1$ to $C_4$ haloalkyl or $C_1$ to $C_4$ haloalkoxy wherein said haloalkyl and haloalkoxy groups contain one or more halo atoms, halo, CN, $NO_2$, $NHR^{11}$, $NHSO_2R^{12}$, $SO_2R^2$, $SO_2NHR^{11}$, $COR^{11}$, $CO^2R^{11}$ wherein $R^{11}$ is H, $C_1$ to $C_4$ alkyl, $C_2$ to $C_4$ alkenyl, $C_1$ to $C_4$ alkanoyl, $C_1$ to $C_4$ haloalkyl or $C_1$ to $C_4$ haloalkoxy and wherein $R^{12}$ is $C_1$ to $C_4$ alkyl, $C_2$ to $C_4$ alkenyl, $C_1$ to $C_4$ alkanoyl, $C_1$ to $C_4$ haloalkyl or $C_1$ to $C_4$ haloalkoxy; $NR^7R^8$, $CONR^7R^8$ or $NR^7COR^{11}$ wherein $R^7$ and $R^8$ are each independently selected from H, $C_1$ to $C_4$ alkyl, $C_2$ to $C_4$ alkenyl, $C_1$ to $C_4$ alkoxy, $CO_2R^9$, $SO_2R^9$ wherein said alkyl, alkenyl or alkoxy groups are optionally substituted by $C_1$ to $C_4$ haloalkyl or $C_1$ to $C_4$ haloalkoxy and wherein $R^9$ is $C_1$ to $C_4$ alkyl which is optionally substituted with phenyl wherein said phenyl group is optionally substituted by one or more substituents selected from $C_1$ to $C_4$ alkyl optionally substituted by $C_1$ to $C_4$ haloalkyl or $C_1$ to $C_4$ haloalkoxy, $C_1$ to $C_4$ alkoxy, halo, CN, $NO_2$, $NHR^{11}$, $NHSO_2R^{12}$, $SO_2R^{12}$, $SO_2NHR^{11}$, $COR^{11}$ or $CO_2R^{11}$; $Het^1$; $Het^2$ or $Het^3$; or $R^1$ is $Het^4$ or phenyl wherein said phenyl group is optionally substituted by one or more substituents selected from $C_1$ to $C_4$ alkyl, $C_2$ to $C_4$ alkenyl, $C_1$ to $C_4$ alkoxy, halo, CN, $CF_3$, $OCF_3$, $NO_2$, $NHR^{11}$, $NHSO_2R^{12}$, $SO_2R^{12}$, $SO_2NHR^{11}$, $COR^{11}$, $CO_2R^{11}$;

$R^2$ is $C_1$ to $C_6$ alkyl, $C_3$ to $C_6$ alkenyl or $(CH_2)_n(C_3$ to $C_6$ cycloalkyl) wherein n is 0, 1 or 2;

$R^{13}$ is $OR^3$ or $NR^5R^6$;

$R^3$ is $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, $Het^1$, $Het^2$, $Het^3$ or $Het^4$ wherein the $C_1$ to $C_6$ alkyl and $C_1$ to $C_4$ alkoxy groups may optionally be terminated by a haloalkyl group such as $CF_3$; $C_3$ to $C_6$ cycloalkyl; $Het^1$, $Het^2$, $Het^3$ or $Het^4$;

$R^4$ is a piperazin-1-ylsulphonyl group having a substituent, $R^{10}$ at the 4-position of the piperazinyl group wherein said piperazinyl group is optionally substituted with one or two $C_1$ to $C_4$ alkyl groups and is optionally in the form of its 4-N-oxide;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^{10}$ is H; $C_1$ to $C_4$ alkyl optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_2$ to $C_6$ alkenyl or $Het^4$;

$Het^1$ is an N-linked 4-, 5- or 6-membered nitrogen-containing heterocyclic group optionally containing one or more further heteroatoms selected from S, N or O;

$Het^2$ is a C-linked 5-membered heterocyclic group containing an O, S or N heteroatom optionally containing one or more heteroatoms selected from O or S;

$Het^3$ is a C-linked 6-membered heterocyclic group containing an O or S heteroatom optionally containing one or more heteroatoms selected from O, S or N or $Het^3$ is a C-linked 6-membered heterocyclic group containing three N heteroatoms;

$Het^4$ is a C-linked 4-, 5- or 6-membered heterocyclic group containing one, two or three heteroatoms selected from S, O or N; and wherein any of said heterocyclic groups $Het^1$, $Het^2$, $Het^3$ or $Het^4$ may be saturated, partially unsaturated or aromatic and wherein any of said heterocyclic groups may be optionally substituted with one or more substituents selected from $C_1$ to $C_4$ alkyl, $C_2$ to $C_4$ alkenyl, $C_1$ to $C_4$ alkoxy, halo, $CO_2R^{11}$, $COR^{11}$, $SO_2R^{12}$ or $NHR^{11}$ and/or wherein any of said heterocyclic groups is benzo-fused;

with the provisos that (a) when $R^1$ is $C_1$ to $C_3$ then $Het^1$ is not morpholinyl or piperidinyl and (b) when $R^1$ is $C_1$ to $C_3$ substituted by phenyl then said phenyl group is not substituted by $C_1$ to $C_4$ alkoxy, halo, CN, $CF_3$, $OCF_3$ or $C_1$ to $C_4$ alkyl.

In a further aspect, the present invention provides processes for the preparation of compounds of formulae (I), (IA) and (IB), their pharmaceutically and veterinarily acceptable salts, and pharmaceutically and veterinarily acceptable solvates of either entity, as illustrated below. It will be appreciated by persons skilled in the art that, within certain of the processes described, the order of the synthetic steps employed may be varied and will depend inter alia on factors such as the nature of other functional groups present in a particular substrate, the availability of key intermediates and the protecting group strategy (if any) to be adopted. Clearly, such factors will also influence the choice of reagent for use in the said synthetic steps. Illustrative of a protecting group strategy is the route to the azetidine analogues (Examples 18, 19 and 20), the precursor to which (preparations 63, 66 and 61 respectively) contain t-butoxycarbonyl (Boc) as the nitrogen protecting group.

It will also be appreciated that various standard substituent or functional group interconversions and transformations within certain compounds of formulae (I), (IA) or (IB) will provide other compounds of formulae (I), (IA) or (IB). Examples include alkoxide exchange at the 2-position of the 5-(pyridin-3-yl) substituent (see conversions of Example 3 to Examples 27, Example 8 to Example 28 and 29, Example 21 to Example 32 and 33, Example 4 to Examples 41, Example 9 to Example 43, and Example 66 to Example 75), amine exchange at the 2-position of the 5-(pyridin-3-yl) substituent (see conversions of Example 7 to Examples 78), reactions at a nitrogen containing substituent, such as reductive alkylation (Example 18 to Example 21), acetamide formation (Examples 18, and 20 to Examples 22 and 24 respectively) or sulphonamide formation (Preparations 68, 67 to Examples 25 to 62 respectively), and reduction of a nitro functionality to provide an amino group (Example 63 to Example 64). The deprotection and transformations described herein and as illustrated in the Examples and Preparations sections may be effected in a "one-pot" procedure (see for example the conversion of the compound of preparation 65 into the compound of example 26).

The following processes are illustrative of the general synthetic procedures which may be adopted in order to obtain the compounds of the invention.

1. A compound of formula (I):

(I)

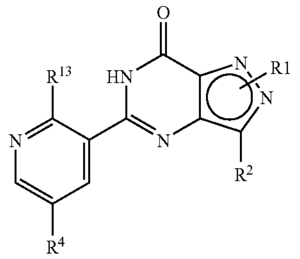

wherein formula (I) may equally be represented by general formulae (IA) and (IB) and wherein $R^1$, $R^2$, $R^4$ and $R^{13}$ are as previously defined herein may be prepared from a compound of general formula (IX):

(IX)

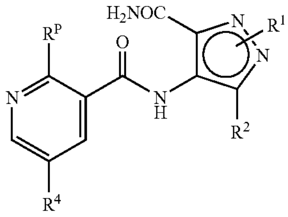

wherein $R^P$ is $R^{13}$ (i.e. $OR^3$ or $NR^5R^6$) or X wherein $R^{13}$, $R^3$, $R^5$ and $R^6$ are as defined hereinbefore and X is a leaving group and wherein general formula (IX) can be represented by formulae (IXA), (IXB) or (IXC) respectively:

(IXA)

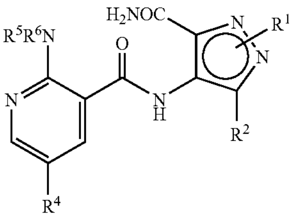

-continued (IXB)

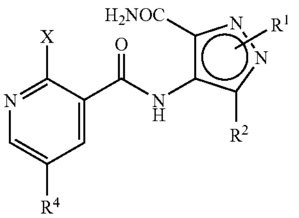

(IXC)

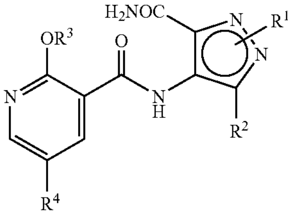

wherein $R^1$, $R^2$, $R^3$, $R^4$, $R^5$ and $R^6$ are as previously defined herein and wherein X is a leaving group and may be any group which is displaceable by an amino group of the formula —$NR^5R^6$ or by an alkoxy group and wherein the intermediate compounds of general formulae (IXA) and (IXB) can be represented by their regioisomeric general formulae as previously illustrated for compounds having the general formulae (1). Suitable leaving groups, X, for use herein include halogen, alkoxy, amino, tosylate groups and further groups are detailed hereinafter.

1.1 A compound of formula (I) wherein $R^{13}$=$NR^5R^6$ may be prepared by cyclisation of a compound of general formula (IXA):

(IXA)

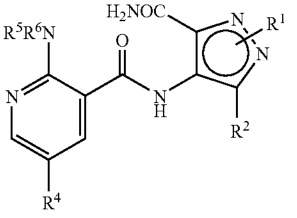

wherein $R^1$, $R^2$, $R^4$, $R^5$ and $R^6$ are as previously defined herein for compounds of the formula (I), (IA) or (IB). Preferably, the cyclisation is base-mediated, using an alkali metal salt of a sterically hindered alcohol or amine. For example, the required cyclisation may be effected using about a 1- to 5-, preferably a 1.2- to 3.5-fold excess of potassium t-butoxide, potassium bis(trimethylsilyl)amide or cesium carbonate, optionally in the presence of molecular sieves, in a suitable solvent, such as for example an inert solvent e.g. DMF or $NHR^5R^6$ or mixtures thereof, at the reflux temperature of the reaction mixture optionally in the presence of about a 1 molar equivalent of ethyl acetate or ethyl pivalate, or, the reaction can optionally be carried out in a sealed vessel at about 100–130° C. optionally in the presence of about a 1 molar equivalent of ethyl acetate or ethyl pivalate.

1.2 A general route for the synthesis of compounds (I) via compounds (IXB) is illustrated in Scheme 1 wherein said intermediate compounds (IXB) have the general formula:

(IXB)

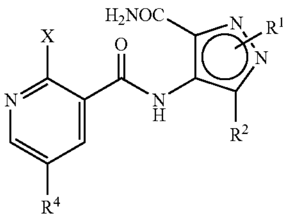

wherein $R^1$, $R^2$ and $R^4$ are as previously defined herein for compounds of the formula (I), (IA) and (IB) and wherein X is a leaving group as defined hereinbefore, by reaction in the presence of $^-OR^3$ and a hydroxide trapping agent. The conversion (IXB) to (I) can be undertaken in either a stepwise process or a one-pot process. A number of stepwise permutations are feasible, some of which are subsets of others. These include i) cyclisation (IXB to XXX) followed by displacement (XXX to I);

ii) cyclisation (IXCa to XXX) followed by displacement (XXX to I);

iii) displacement (IXB to IXC) followed by cyclisation (IXC to I); and iv) displacement (IXCa to IXC) followed by cyclisation (IXC to I) wherein compounds (XXX) and (IXCa) have the general formulae:

(XXX)

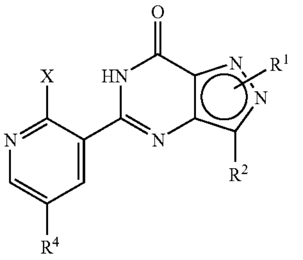

(IXCa)

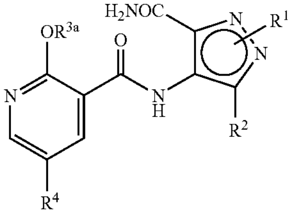

wherein $R^1$, $R^2$, $R^4$ and X are as defined herein before and $OR^{3a}$ is an alkoxy group which is different from and displaceable by the desired $OR^3$ group on the final compounds of general formula (I) and wherein $R^{3a}$ is selected from $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, $Het^1$, $Het^2$, $Het^3$ or $Het^4$ wherein the $C_1$ to $C_6$ alkyl and $C_1$ to $C_4$ alkoxy groups may optionally be terminated by a haloalkyl group such as $CF_3$ and wherein the $C_3$–$C_5$ cycloalkyl group may optionally be substituted by $C_1$–$C_4$ alkyl, hydroxy or halo; $C_3$ to $C_6$ cycloalkyl; $Het^1$, $Het^2$, $Het^3$ or $Het^4$. Preferably $R^{3a}$ is $C_1$ to $C_6$ alkyl.

To effect initial displacement without significant simultaneous cyclisation it is preferred that the displacement with $^-OR^3$ (in (iii) or (iv)) is carried out in the range of from about 80° C. to about 90° C. to provide a compound of the general formula (IXC). Subsequent cyclisation to a compound of general formula (I) is generally carried out at a temperature greater than about 115° C.

To effect initial cyclisation without significant simultaneous displacement it is preferred that, for (IXCa) to (XXX) (in (ii)), the reaction is conducted at a temperature greater than about 110° C. with $^-OR^{3a}$ in $R^{3a}OH$. Subsequent displacement to a compound of general formula (I) is generally carried out with $^-OR^3$ in $R^3OH$ in the range of from about 80° C. to about 90° C.

For conversion of (IXB) to (I) (ie. (i) above), it may be preferred to obtain compounds of general formula (I) directly from compounds of general formula (IXB) since both the cyclisation and displacement components of this reaction can be carried out in a "one-pot" reaction. Such a "one-pot" process can be run at lower pressures (ie. nearer ambient pressure) than say a stepwise cyclisation and displacement process (ie. (ii) above) if the boiling point of $R^3OH$ is higher than that of $R^{3a}OH$ and where the ambient boiling point of $R^{3a}OH$ is less than about 115° C. (ie. too low to effect cyclisation at ambient pressure). It should be noted that is may still be necessary to operate such processes at higher temperatures than the boiling point of $HOR^3$, i.e. at higher pressure.

In the case of compounds of general formula (IXC) as detailed hereinafter wherein X is $OR^3$, compounds of general formula (I) can be obtained by direct cyclisation by reacting in the presence of an auxiliary base, a hydroxide trapping agent and an appropriate solvent $R^3OH$ or an inert solvent or a combination thereof.

The temperature of the reaction of compounds of the general formula (IXB) to compounds of the general formula (I) (such as the corresponding formation of compounds (IA) and (IB)) is preferably at least about 80° C., more preferably about 80 to about 130° C., more preferably still about 100 to about 130 C and most preferably about 115 to about 125° C. These temperatures are also applicable for the conversion of compounds (XXX) to (I), although the temperature in this case could also probably be lower (e.g. about 60° C.) since there is no cyclisation taking place.

Preferably compounds of formula (I), or (IA), or (IB) wherein $R^1$ is $-(CH_2)_n(C_3-C_4)$cycloalkyl wherein n is 1 or 2; or $R^1$ is $-(CH_2)_n(C_3-C_6)$cycloalkyl wherein n is 0; or $R^1$ is -cyclopentylmethyl; or $R^1$ is methyl, ethyl, i-propyl or n-propyl substituted by methoxy, ethoxy, n-propoxy or i-propoxy wherein said alkoxy substituent may be directly attached to any C-atom within the ethyl, iso-propyl or n-propyl groups other than the C-atom directly linked to the pyrazole ring; or $R^1$ is i-, n-, sec- or t-butyl;

$R^2$ is $C_2$ to $C_4$ alkyl; $R^{13}$ is $OR^3$ wherein the $R^3$ alkyl group is methyl, ethyl, n-propyl, i-propyl, i-butyl, n-butyl, sec-butyl or t-butyl optionally substituted with one or two methoxy, ethoxy, n-propoxy or i-propoxy substituents; and $R^4$ is a 4-methyl, 4-ethyl, 4-n-propyl or 4-i-propylpiperazin-1-ylsulphonyl group are prepared from compounds of general formula (IXB) wherein X is $OR^3$ (i.e. compounds of general formula (IXC) as detailed hereinbefore and after).

Thus, according to a further aspect of the present invention there is provided a further process for the preparation of a compound of general formula (I):

(I)

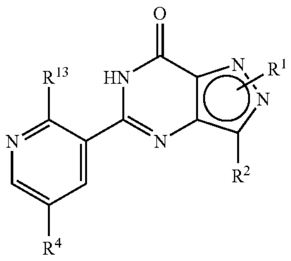

or a compound of general formula (IA), or (IB) wherein $R^1$ is $-(CH_2)_n(C_3-C_4)$cycloalkyl wherein n is 1 or 2; or $R^1$ is $-(CH_2)_n(C_3-C_6)$cycloalkyl wherein n is 0; or $R^1$ is -cyclopentylmethyl; or $R^1$ is methyl, ethyl, i-propyl or n-propyl substituted by methoxy, ethoxy, n-propoxy or i-propoxy wherein said alkoxy substituent may be directly attached to any C-atom within the ethyl, iso-propyl or n-propyl groups other than the C-atom directly linked to the pyrazole ring; or $R^1$ is i-, n-, sec- or t-butyl;

$R^2$ is $C_2$ to $C_4$ alkyl; $R^{13}$ is $OR^3$ wherein the $R^3$ alkyl group is methyl, ethyl, n-propyl, i-propyl, i-butyl, n-butyl, sec-butyl or t-butyl optionally substituted with one or two methoxy, ethoxy, n-propoxy or i-propoxy substituents; and $R^4$ is a 4-methyl, 4-ethyl, 4-n-propyl or 4-i-propylpiperazin-1-ylsulphonyl group comprising reacting a compounds of general formula (IXC):

(IXC)

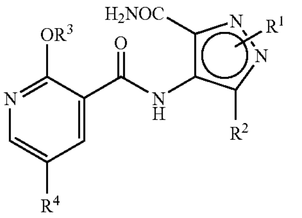

wherein R1, $R^2$, $R^3$ and $R^4$ are as defined previously herein, wherein said reaction is carried out in the presence of $-OR^3$ and a hydroxide trapping agent, or alternatively reacting in the presence of hydroxide trapping agent and an auxiliary base.

Intermediates of the general formula (IXC) and more specifically (IXCA) and (IXCB) form further aspects of the invention.

(IXCA)

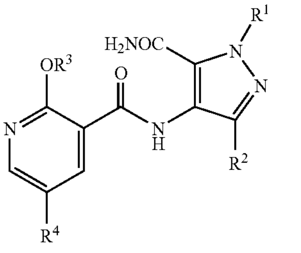

-continued (IXCB)

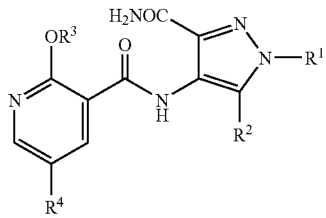

A particular advantage of the use of the hydroxide trapping agent is that a higher yield of final product (compounds of general formula (I), (IA) or (IB)) can be obtained than for the same reaction where the trapping agent is not present.

Preferably the hydroxide trapping agent is an ester. More preferably said hydroxide trapping agent is an ester of the formula:

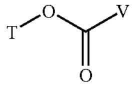

wherein OT is $OR^3$ or the residue of a bulky alcohol or a non-nucleophilic alcohol or TOH is an alcohol which can be azeotropically removed during the reaction; and C(O)V is the residue of a carboxylic acid. For example, where $OR^3$ is OEt in compound (IXC) the hydroxide trapping agent (TOC(O)V) could be e.g. ethyl acetate or ethyl pivalate. Preferably V is a $C_1$ to $C_4$ alkyl group.

Preferably X is selected from the group consisting of —$OR^3$, halo, optionally substituted arylsulphonyloxy, preferably phenylsulphonyloxy, more preferably a para-substituted aryl(phenyl) such as by a $C_1$–$C_4$ alkyl group e.g. p-toluenesulphonyloxy; $C_1$–$C_4$ alkylsulphonyloxy e.g. methanesulphonyloxy; nitro or halo substituted benzenesulphonyloxy preferably para-substituted e.g. p-bromobenzenesulfonyloxy or p-nitrobenzenesulphonyloxy; $C_1$–$C_4$ perfluoroalkylsulphonyloxy e.g. trifluoromethylsulphonyloxy; optionally substituted aroyloxy such as benzoyloxy; $C_1$–$C_4$ perfluoroalkanoyloxy such as trifluoroacetyloxy; $C_1$–$C_4$ alkanoyloxy such as acetyloxy; diazonium; quatenaryammonium $C_1$–$C_4$ alkylsulphonyloxy; halosulphonyloxy e.g. fluorosulphonyloxy and other fluorinated leaving groups; and diarylsulphonylamino e.g. ditosyl ($NTs_2$).

More preferably, X is a $C_1$–$C_6$ primary or secondary alkoxy and is especially a $C_1$–$C_4$ alkoxy group such as ethoxy or methoxy.

$^-OR^3$ can act both as a nucleophile (to displace the leaving group by nucleophilic substitution) and as a base (to bring about the cyclisation).

$^-OR^3$ can be generated in solution from, for example, a salt $ZOR^3$ (wherein Z is a cation) such as a metal salt. More particularly an alkali (such as sodium or potassium) or alkaline earth metal salt of —$OR^3$ in a suitable solvent would give rise to —$OR^3$ in solution. In another embodiment, —$OR^3$ is formed in situ from $R^3OH$ plus an auxiliary base (i.e. a base other than —$OR^3$). However, in another system, $ZOR^3$ could be used in the reaction system with an auxiliary base.

As will be appreciated the solvent in which the reaction takes place can be $R^3OH$ or an inert solvent (or a mixture of both). By inert solvent we mean a solvent which will not form a nucleophile under the reaction conditions or if a nucleophile is formed it is sufficiently hindered or unreactive such that it does not substantially compete in the displacement reaction. When $R^3OH$ is used as a source of —$OR^3$, then a separate solvent is not essentially required but an (auxiliary) inert solvent (i.e. a solvent other than R 30H) may be used as a co-solvent in the reaction.

Suitable solvents are as follows: $R^3OH$, a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

More preferably, the solvent is $R^3OH$, a tertiary $C_4$–$C_{12}$ alkanol, a tertiary $C_4$–$C_{12}$ cycloalkanol, a tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

Most preferably the solvent is $R^3OH$, which means that $^-$OR 3 is formed in situ, such as in the presence of an auxiliary base.

A wide range of auxiliary bases can be used in the process of the invention. Typically the bases would not substantially compete with —$OR^3$ in the nucleophilic substitution of X (i.e. they would be non nucleophilic) such as by suitably being sterically hindered.

Preferably the auxiliary base is selected from the group consisting of a sterically hindered-base, a metal-hydride, metal oxide, metal carbonate and metal bicarbonate.

The sterically hindered base is advantageously a metal salt of a sterically hindered alcohol or amine.

More preferably the auxiliary bases in accordance with the invention are selected from the group consisting of metal salts of a sterically hindered alcohol or amine such as a secondary or tertiary $C_4$–$C_{12}$ alkanol, a $C_3$–$C_{12}$ cycloalkanol and a secondary or tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl) amine, a di($C_3$–$C_8$ cycloalkyl)amine or hexamethyldisilazane; 1,5-diazabicyclo[4,3,0]non-5-ene and 1,8-diazabicyclo[5,4,0]undec-7-ene; a metal hydride, oxide, carbonate, and bicarbonate.

Yet more preferably the auxiliary bases in accordance with the invention are selected from the group consisting of metal salts of a sterically hindered alcohol or amine such as a tertiary $C_4$–$C_{12}$ alkanol, a $C_3$–$C_{12}$ cycloalkanol and a tertiary ($C_3$–$C_8$ cycloalkyl)$C_1$–$C_6$ alkanol, a N-(secondary or tertiary $C_3$–$C_6$ alkyl)-N-(primary, secondary or tertiary $C_3$–$C_6$ alkyl)amine, a N-($C_3$–$C_8$ cycloalkyl)-N-(primary, secondary or tertiary $C_3$–$C_6$ alkyl)amine, a di($C_3$–$C_8$ cycloalkyl)amine or hexamethyldisilazane; 1,5-diazabicyclo[4,3,0]non-5-ene and 1,8-diazabicyclo[5,4,0]undec-7-ene; a metal hydride, oxide, carbonate, and bicarbonate.

More preferably still, the auxiliary base is selected from the sterically hindered bases of the previous paragraph (i.e. all of them except the metal hydride, oxide, carbonate and bicarbonate).

Most preferably still, the auxiliary base is the metal salt of a tertiary $C_4$–$C_6$ alcohol such as the alkali or alkaline earth metal salts (e.g. Na/K) of t-butanol or t-amyl alcohol, or the base is KHMDS.

Most preferably, the auxiliary base is the alkali metal salt of t-butanol (e.g. potassium t-butoxide).

The metal of the salt of $ZOR^3$ and the auxiliary base can be independently selected from alkali metals (lithium, sodium, potassium, rubidium, cesium) or alkaline earth metals (beryllium, magnesium, calcium, strontium, barium). Preferably the metal is sodium, potassium, lithium or magnesium. More preferably the metal is sodium or potassium.

To maximise yields, it is further preferred that when X is any group hereinbefore defined except —$OR^3$, then at least about 1 molecular equivalent of auxiliary base and —$OR^3$ are used. If —$OR^3$ also functions as a base (i.e. there is no auxiliary base present) then preferably at least about 2 equivalents of $^-OR^3$ are present. Suitably, at least about 1 equivalent of trapping agent (preferably at least about 2 equivalents) is present. In the case where X═$OR^3$ (i.e. starting from (IXC) rather than (IXB) then, in theory, at least 1 equivalent of base is required, wherein said base may be —OR3 or auxiliary base.

The temperature of the reaction of compounds of the general formula (IXC) to compounds of the general formula (I) (such as the corresponding formation of compounds (IA) and (IB)) is preferably at least about 80° C., more preferably about 80 to about 130° C., more preferably still about 100 to about 130° C. and most preferably about 115 to about 125° C.

The reaction temperature attainable to effect the conversion of compounds of the general formulae (IXB), (IXC) or (XXX) to compounds of the general formula (I) depends on the solvent, the nature of $^-OR^3$ and X. When X is $OR^{3a}$ (wherein $OR^{3a}$ and $OR^3$ are not the same), i.e. a compound of the formula ($IXC^a$) and $R^3OH$ is the solvent, preferably XH (such as $C_1$–$C_6$ alkohol) is removed azeotropically (of course the reaction vessel must be configured to distill over the azeotrope mixture) with $R^3OH$ by running the reaction at the azeotrope temperature of XH and. $R^3OH$. In this way the yield and quality of the final product can be further improved. For example, (where X is an alkoxy, preferably ethanol) the conversion of compound (XXX), (IXB) or (IXC) to (I) is preferably carried out at the azeotrope temperature of the alcohol (i.e. XH (preferably ethanol)) with $R^3OH$. When X═$OR^3$ and the solvent is $R^3OH$ there is no requirement to azeotrope out $R^3OH$.

Thus in a preferred embodiment of the present invention there is provided a process for the synthesis of compounds of general formula (I), (IA) or (IB) and in particular compounds of general formula (I), (IA) or (IB) wherein $R^1$ is —$(CH_2)_n(C_3$–$C_4)$cycloalkyl wherein n is 1 or 2; or $R^1$ is —$(CH_2)_n(C_3$–$C_6)$cycloalkyl wherein n is 0; or $R^1$ is —$(CH_2)_n$ $(C_5)$cycloalkyl wherein n is 1; or $R^1$ is methyl, ethyl, i-propyl or n-propyl substituted by methoxy, ethoxy, n-propoxy or i-propoxy wherein said alkoxy substituent may be directly attached to any C-atom within the ethyl, isopropyl or n-propyl groups; or $R^1$ is i-, n-, sec- or t-butyl; $R^2$ is $C_2$ to $C_4$ alkyl; $R^{13}$ is $OR^3$ wherein the $R^3$ alkyl group is methyl, ethyl, n-propyl, i-propyl, i-butyl, n-butyl, sec-butyl or t-butyl optionally substituted with one or two methoxy, ethoxy, n-propoxy or i-propoxy substituents; and $R^4$ is a 4-methyl, 4-ethyl, 4-n-propyl or 4-i-propylpiperazin-1-yl-sulphonyl group wherein said process comprises reacting a compound of general formula (XIB), (XIC) or (XID) respectively:

a) with $R^3OH$ and auxiliary base, optionally in an inert solvent and in the presence of said trapping agent; or b) with $ZOR^3$ and an auxiliary base in $R^3OH$ or an inert solvent or both, in the presence of said trapping agent; or c) with $ZOR^3$ and $R^3OH$ or an inert solvent or both, in the presence of said trapping agent; or d) with auxiliary base, inert solvent or $R^3OH$ or a combination thereof and a hydroxide trapping agent for compounds of the general formula (IXC).

1.3 For compounds of the general formula (IXB) wherein X is $OR^3$ and an alcohol is selected as solvent a compound of formula (I) may be prepared by cyclisation of a compound of general formula (IXC):

(IXC)

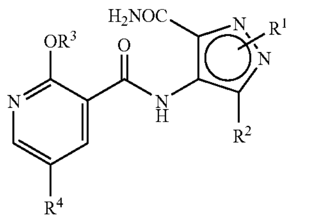

wherein $R^1$, $R^2$, $R^3$ and $R^4$ are as previously defined herein for compounds of the formula (I), (IA) and (IB). In said reaction the appropriate alcohol of formula $R^3OH$ should be employed as the solvent in order to obviate potential problems associated with alkoxide exchange at the 2-position of the pyridine ring or an inert solvent or a mixture of the two. The appropriate alcohol as defined herein means that the solvent alcohol should be of the same alkyl chain length as the alkoxy (—$OR^3$) substituent, for example, where —$OR^3$ is ethoxy, ethanol is the appropriate alcohol. Preferably, said cyclisation is base-mediated, using an alkali metal salt of a sterically hindered alcohol or amine. For example, the required cyclisation may be effected using about a 1- to 8, preferably about a 1- to 5-, more preferably a 1.2- to 3.5-fold excess of potassium t-butoxide or potassium bis(trimethylsilyl)amide, optionally under suitable drying conditions i.e. in the presence of molecular sieves or under azeotroping conditions, in a suitable solvent as described above at the reflux temperature of the reaction mixture optionally in the presence of about 1 to 2 molar equivalents of a hydroxide trapping agent such as ethyl acetate or ethyl pivalate, or, the reaction can optionally be carried out in a sealed vessel at about 100–130° C. optionally in the presence of about 1 to 2 molar equivalents of a hydroxide trapping agent such as ethyl acetate or ethyl pivalate.

Alternative reaction conditions for the cyclisation reactions of compounds of (IXC) wherein X is OR are to conduct the reaction with about 1.2 to 4.5 molecular equivalents of sterically hindered base such as potassium t-butoxide or KHMDS, optionally in a sealed vessel at from about 100° C. to about 150° C. with, rather than an alcohol of formula $R^3OH$ as solvent, a sterically hindered alcohol, e.g. 3-methylpentan-3-ol, as solvent optionally in the presence of about 1 or 2 molar equivalents of ethyl acetate or ethyl pivalate.

A compound of formula (IXA) or a compound of general (IXB) wherein X is $OR^3$ (i.e. a compound of general formula (IXC)) may be prepared by a coupling reaction between a compound of formula (VII):

(VII)

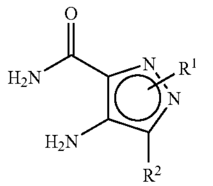

wherein $R^1$ and $R^2$ are as previously defined for formulae (IXA), (IXB) or (IXC) with a compound of formula (XA), (XB) or (XC) respectively:

(XA)

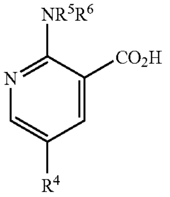

(XB)

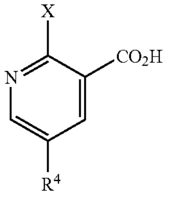

(XC)

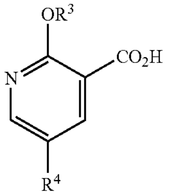

wherein $R^3$, $R^4$, $R^5$, $R^6$ and X are also as previously defined for formulae (IXA), (IXB) or (IXC). Where either $R^5$ and/or $R^6$ in the —$NR^5R^6$ group of formula (XA) are H, then a suitable N-protecting group strategy may be advantageously employed. Any known suitable protecting group strategy may be used.

The coupling reaction may be carried out using conventional amide bond-forming techniques, e.g. via the acyl chloride derivative of (XA) or (XB) in the presence of up to about a five-fold excess of a tertiary amine such as triethylamine or pyridine to act as scavenger for the acid by-product (HY), optionally in the presence of a catalyst such as 4-dimethylaminopyridine, in a suitable solvent such as dichloromethane, at from about 0° C. to about room temperature. For convenience pyridine may also be used as the solvent.

In particular, any one of a host of amino acid coupling variations may be used. For example, the acid of formula (XA), (XB) or (XC) or a suitable salt (e.g. sodium salt) thereof may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole hydrate and/or a catalyst such as 4-dimethylaminopyridine, or by using a halotrisaminophosphonium salt such as bromotris(pyrrolidino)phosphonium hexafluorophosphate or by using a suitable pyridinium salt such as 2-chloro-1-methylpyridinium iodide. Either type of coupling is conducted in a suitable solvent such as dichloromethane, tetrahydrofuran or N,N-dimethylformamide, optionally in the presence of a tertiary amine such as triethylamine or N-ethyldiisopropylamine (for example when either the compound of formula (VII), or the activating reagent, is presented in the form of an acid addition salt), at from about 0° C. to about room temperature. Preferably, from 1 to 2 molecular equivalents of the activating reagent and from 1 to 3 molecular equivalents of any tertiary amine present are employed.

In a further variation, the carboxylic acid function of (XA), (XB) or (XC) may first of all be activated using up to about a 5% excess of a reagent such as N,N-carbonyldiimidazole in a suitable solvent, e.g. ethyl acetate or butan-2-one, at from about room temperature to about 80° C., followed by reaction of the intermediate imidazolide with (VII) at from about 20° C. to about 90° C.

It will be appreciated that the general formula (VII) can also be represented by the regioisomeric formulae (VIIA) and (VIIB):

(VIIA)

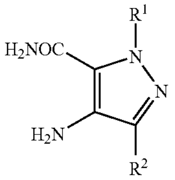

(VIIB)

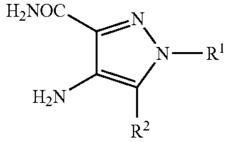

wherein $R^1$ and $R^2$ are as previously defined herein.

The 4-aminopyrazole-5-carboxamide compounds having the general formulae (VII), (VIIA) or (VIIB) may be prepared from pyrazole compounds of the general formula (XIII):

XIII

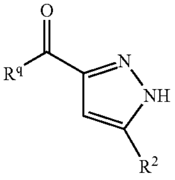

wherein $R^q$ is selected from OH, $C_1$–$C_6$ alkoxy or $NR^5R^6$ wherein $R^5$ and $R^6$ are as hereinbefore defined, according to the procedures detailed in the preparations section herein and as particularly described in Preparations 96(a) to (h).

Compounds having the general formulae (XA) or (XC) may be prepared from the carboxylic acid compounds of the general formulae (VIIIA), (VIIIB) or (VIIIC) respectively:

(VIIIA)

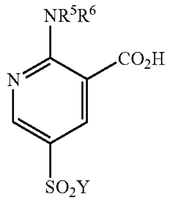

(VIIIB)

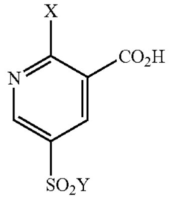

(VIIIC)

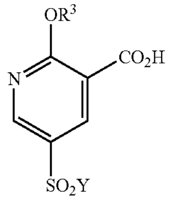

wherein $R^3$, $R^5$ and $R^6$ are as defined for compounds of the general formulae (I), (IA) and (IB) by reaction with a 4-$R^{10}$-piperizinyl compound, such as for example 4-methylpiperizine. Such reaction can be conducted at from about 0° C. to about room temperature, preferably in the presence of an appropriate solvent such as a $C_1$ to $C_3$ alkanol or dichloromethane optionally in the presence of a suitable base such as triethylamine to scavenge the acid by-product (HY). Where either $R^5$ or $R^6$ is H a suitable amino protecting group strategy may be employed as detailed hereinbefore.

Compounds of the general formulae (VIIIA), (VIIIB) or (VIIIC) may be prepared from compounds of the general formulae (XIA), (XIB) or (XIC) respectively:

(XIA)

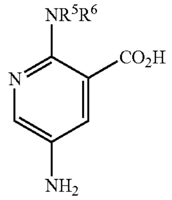

(XIB)

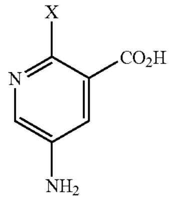

-continued (XIC)

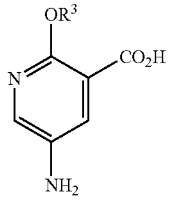

wherein $R^3$, $R^5$, $R^6$ and X are as defined for compounds of the general formulae (I), (IA) and (IB) by the application of known methods for converting amino to an $SO_2Y$ group, wherein Y is halo, preferably chloro. For example, when Y is chloro, by the action of about a two-fold excess of sodium nitrite in a mixture of concentrated hydrochloric acid and glacial acetic acid at from about −25° C. to about 0° C., followed by treatment with excess liquid sulphur dioxide and a solution of about a three-fold excess of cupric chloride in aqueous acetic acid at from about −15° C. to about room temperature. When $R^{13}$ contains a primary or secondary amino group, protection of the said amino group with an acid stable group such as acetyl or benzyl will generally be advantageous.

Compounds of the general formula (XIA), (XIB) and (XIC) may be prepared by reduction of compounds of the general formulae (XIIA), (XIIB) and (XIIC) respectively:

(XIIA)

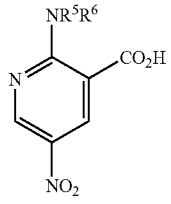

(XIIB)

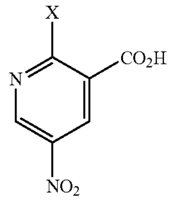

(XIIC)

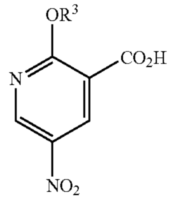

wherein $R^3$, R $R^6$ and X are as previously defined. Such conversion of compounds of the general formulae (XIIA), (XIIB) and (XIIC) to compounds of the general formulae (XIA), (XIB) and (XIC) can be achieved by conventional catalytic or catalytic transfer hydrogenation procedures. Typically, the hydrogenation is achieved using a Raney (RTM) nickel catalyst or a palladium catalyst such as 10% Pd on charcoal, in a suitable solvent such as ethanol at a hydrogen pressure of from about 345 kPa (50 psi) to about 414 kPa (60 psi) at from about room temperature to about 60° C., preferably from about 40° C. to about 50° C.

Intermediates of the general formula (IXC) as described in 1.2 and 1.3 hereinbefore can be prepared via a coupling reaction between a compound of the general formula (XB) and a compound of the general formula (VII) wherein said coupling may be achieved by any of the methods described hereinbefore. Compounds of general formula (XB) may be prepared according to the route outlined in Scheme 2.

With reference to Scheme 2, the intermediate of formula (XB) is formed from a compound of formula (XIV), the exact process being dependent on leaving group X.

For compounds of formula (XB) wherein X=arylsulfonyloxy, $C_1$–$C_4$ alkylsulfonyloxy, $C_1$–$C_4$ perfluoroalkylsulfonyloxy, aryloxy, $C_1$–$C_4$ perfluoroalkanoyloxy, $C_1$–$C_4$ alkanoyloxy, quarternaryammonium $C_1$–$C_4$ alkylsulfonyloxy or halosulfonyloxy, compound (XB) can be formed from compounds (XIV) (wherein Q=OH and W=OH) and an appropriate derivatising agent, more particularly an appropriate sulphonylating agent such as arylsulfonylhalide, $C_1$–$C_4$ alkylsulfonylhalide, $C_1$–$C_4$ perfluoroalkylsulfonylhalide, arylhalide, $C_1$–$C_4$ perfluoroalkanoylhalide, $C_1$–$C_4$ alkanoylhalide, quarternary ammonium $C_1$–$C_4$ alkylsulfonylhalide or halosulfonylhalide, or an appropriate arylating agent such as arylhalide, or an appropriate acylating agent such as $C_1$–$C_4$ perfluoroalkanoylhalide, or $C_1$–$C_4$ alkanoylhalide), respectively (preferably the halide substituent of the above is chloride), in an appropriate solvent. Compounds of formula (XIV) (wherein Q=OH and W=OH) can be formed from compounds (XV) (wherein P is hydrolisable group) via use of a hydrolising agent, preferably a hydroxide base (ideally 2 molar equivalents), more preferably a metal hydroxide such as sodium hydroxide, in an appropriate solvent, such as water. The metal of the hydroxide base can be as defined hereinbefore for Z (in ZOR). This will also apply for other reactions of scheme 2 and 3 hereafter where hydroxide base/hydrolising agent is used. Where P is group which is not hydrolisable by hydroxide then a suitable de-protection strategy should be employed according to standard literature practise.

Compounds of formula (XB) where X=chloro, can be formed from (XIV) wherein Q=Cl and W=P (such as OEt) (i.e. formula XV) and a hydroxide base (ideally 1 molar equivalent), such as sodium hydroxide preferably in an appropriate solvent, such as water and a deprotecting agent.

Preferably the deprotecting agent as used herein in accordance with the invention is a hydrolysing agent, more preferably a hydroxide nucleophile, advantageoulsly a hydroxide base (ideally 1 molar equivalent), such as sodium hydroxide preferably in an appropriate solvent, such as water.

Compounds of formula (XB) wherein X=diazonium, can be formed from (XIV) (wherein Q=$NH_2$, W=OH) and nitrous acid. Compounds of formula (XIV) (wherein Q=$NH_2$, W=OH) can be formed from compounds of formula (XIV) (wherein Q=$NH_2$, W=P, e.g. OEt) and a deprotecting agent such as a hydroxide base e.g. sodium hydroxide, in an appropriate solvent, such as water. Intermediate (XIV) (Q=$NH_2$, W=P, e.g. OEt) is formed from (XV) and an ammoniating agent, such as ammonia, in an appropriate solvent, such as water.

Compounds of formula (XB) wherein X=diarylsulfonylamino, can be formed from (XIV) (wherein Q=$NH_2$, W=OH) and an appropriate derivatising agent, preferably an appropriate sulphonylating agent such as arylsulphonylhalide, preferably arysulfonylchloride (ideally at least 2 molar equivalents) and preferably in the presence of a base (ideally 2 molar equivalents thereof), such as triethylamine in an appropriate solvent.

Compounds of formula (XB) wherein X=$C_1$–$C_6$ (preferably $C_1$–$C_4$) preferably primary or secondary alkoxy, can be formed from (XIV) (wherein Q=$C_1$–$C_6$ (preferably $C_1$–$C_4$) primary or secondary alkoxy and W=P, such as OEt) and a deprotecting agent (for P=OEt), preferably a hydroxide base, such as sodium hydroxide, in an appropriate solvent, such as water. Compounds of formula (XIV) (wherein Q=$C_1$–$C_6$ (preferably $C_1$–$C_4$) primary or secondary alkoxy, W=P e.g. OEt) can be formed from (XV) and an appropriate alkoxide, OR wherein R is $C_1$–$C_6$ alkyl more preferably $C_1$–$C_4$ primary or secondary alkyl, such as sodium ethoxide in an appropriate solvent such as toluene. Most preferably P=X (wherein X is an alkoxy) since this avoids trans-esterification issues.

The compounds of formula (XV) can be formed from compounds of formula (XVI) by reaction with a mono-N-substituted piperazine group wherein the mono-substituent $R^{10}$ as defined herein before, optionally in the presence of a supplementary base (which does not react irreversibly with the sulphonyl chloride moiety) such as triethylamine preferably in an appropriate solvent, such as toluene. “D” in compounds (XV) and (XVI) is Cl or Br. The monosubstituted piperazine group may also be the base where more than one equivalent of monosubstituted piperazine is present. Preferably about 2 equivalents are used.

Where a supplementary base is used it either does not react with the sulphonyl chloride moiety (such as a metal oxide, carbonate or bicarbonate) or it reacts with the sulphonyl chloride moiety in such a way as to keep it activated to nucleophilic attack (e.g. a tertiary amine such as triethylamine). The amine NH(R3)(R4) may also act as a base, in which case preferably more than one equivalent is present, more preferably about 2 equivalents (or more).

The compounds of formula (XVI) can be formed from compounds of formula (XX) in the presence of a chlorinating or brominating agent such as thionyl chloride or thionyl bromide more preferably in the presence of a halogenation catalyst, more preferably still thionyl chloride or thionyl bromide in the presence of dimethylformamide. The thionyl chloro/bromo can also act as the solvent, but more preferably the reaction takes place or in an appropriate other solvent such as toluene. In such case only stoicheometric amounts of thionyl chloride/bromide would be required, preferably at least 2 molar equivalents, more preferably at least 5 molar equivalents.

It is possible to undertake the four step conversion of (XX) to (XB) in a single telescoped step, without intermediate product isolation, using the same solvent throughout (hereinafter the “telescoping solvent”). Thus where X is an alkoxy group (—$OR^3$ group), steps (XX) to (XB) can be telescoped together using a single solvent such as a water immiscible inert organic solvent. More preferably a hydrocarbon solvent (such as toluene, xylene, anisole, chlorobenzene, hexane, heptane, octane, nonane, decane, cyclohexane, methylcyclohexane) or ethers (such as dibutyl ether, diphenyl ether) or ketones (such as methylisobutylketone, methylethylketone) or esters (such as ethyl acetate, butyl acetate) or dimethylformamide. More preferably still a hydrocarbon solvent (such as toluene, xylene, anisole, chlorobenzene, octane, nonane, decane, methylcyclohexane) or ethers (such as dibutyl ether, diphenyl ether) or esters (such as ethyl acetate, butyl acetate). More preferably still the telescoping solvent is toluene.

The intermediate of formula (XX) is formed from a compound of formula (XVII) in the presence of an agent which will form a protecting group (P) for the carboxylic acid (i.e. to form the —COP group). Preferably said agent is an esterification agent, to form a carboxylic acid ester (wherein, e.g. P will be alkoxy and the protecting forming agent will be an alcohol) such as a $C_1$–$C_6$ carboxylic acid ester which will be carried through the reaction scheme and hydrolised under basic conditions to the carboxylic acid function of compound (XB). Most preferably the esterification agent is ethanol. An additional solvent such as toluene may be appropriate.

The intermediate of formula (XVII) is formed from 2-hydroxynicotinic acid or a salt thereof in the presence of a sulphonylating agent, more preferably an agent comprising $SO_3$ (ideally at least 1 molar equivalent of $SO_3$), for example using $SO_3$ in an organic solvent (e.g. THF, dioxan and heptane) or an aprotic solvent (e.g. nitrobenzene, nitromethane, 1,4-dioxane, dichloromethane) or a mineral acid as solvent (e.g. sulphuric acid) or in a liquid carboxylic acid as solvent (e.g. acetic acid) or THF or heptane. More preferably still, the sulphonylating agent is oleum ($SO_3$ in sulphuric acid) such as about 20% to 30% oleum.

Compounds of the general formula (IXB) are formed by the reaction of intermediates of general formula (XB) with compounds of the general formula (VII), as detailed hereinbefore in the presence of a coupling agent, such as N,N'-carbonyldiimidazole and a suitable solvent, such as ethyl acetate.

Methods for the preparation of compounds of the general formula (VII) are described hereinafter.

In a preferred embodiment of Scheme 2, X is an —$OR^3$ alkoxy group and so Q in compound (XIV) represents $OR^3$. Preferably $OR^3$ is a $C_1$ to $C_6$ alkoxy group, more preferably a $C_1$ to $C_4$ primary or secondary alkoxy group and especially ethoxy. However for other leaving groups the general method for Scheme 2 would apply.

This preferred embodiment of Scheme 2 is illustrated in Scheme 3. In Scheme 3 the intermediate of formula (XB) is formed from a compound of formula (XIV) by removal of protecting group P by a deprotecting agent, advantageously by saponification in the presence of a hydroxide base such as sodium hydroxide, preferably in an appropriate solvent such as water and toluene.

The intermediate of formula (XIV) is formed from a compound of formula (XV) in the presence of an appropriate $C_1$–$C_6$ alkoxide nucleophile (—$OR^3$), (such as a primary or secondary alkoxide), preferably a metal alkoxide of the formula $ZOR^3$, wherein the metal (Z) is as defined hereinbefore for ZOR, such as sodium ethoxide, preferably in an appropriate solvent such as toluene or $R^3OH$, wherein $R^3OH$ is as defined hereinbefore and is preferably ethoxy. D in compounds of formulae (XV) and (XVI) is Cl or Br, more preferably D is Cl.

The intermediate of formula (XV) is formed from a compound of formula (XVI) by reaction with N—$R^{10}$piperazine, preferably in the presence of a base, such as triethylamine or excess N—$R^{10}$piperazine, preferably in an appropriate solvent such as toluene.

The intermediate of formula (XVI) is formed from a compound of formula (XX) in the presence of a chlorinating or brominating agent as defined for the same step in Scheme 2 such as thionyl chloride or bromide, preferably thionyl chloride or bromide/dimethylformamide. The former can also act as the solvent, but more preferably the reaction takes place in an appropriate other solvent, such as toluene. In such a case only stoicheiometric amounts of thionyl chloride/bromide would be required, preferably as at least 2 molar equivalents more preferably at least 5 molar equivalents.

The intermediate of formula (XX) is formed from a compound of formula (XVII) in the presence of an agent which will form a protecting group (P) for the carboxylic acid (i.e. to form the —COP group) as defined herein before. Preferably said agent is an esterification agent, to form a carboxylic acid ester such as a $C_1$–$C_6$ carboxylic acid ester which will be carried through the reaction scheme and hydrolysed under basic conditions to the carboxylic acid function of compound (XB). Most preferably the esterification agent is ethanol. An additional solvent such as toluene may be utilised as appropriate.

The intermediate of formula (XVII) is formed from 2-hydroxynicotinic acid with a sulphonylating agent such as 30% oleum.

Again it is possible to undertake the four step conversion of (XX) to (XB) in a single telescoped step (as set out hereinbefore) in the same pot, without intermediate product isolation, using the same solvent (herein the "telescoping" solvent) throughout. The list of solvents described with respect to Scheme 2 are directly applicable here. Most preferably the solvent is toluene.

For example after formation of compound (XVI), the excess chlorinating/brominating agent could be azeotroped off at the azeotrope temperature of the said agent and the telescope solvent. After formation of compound (XV), the HBr/HCl (i.e. HD) salts which are formed could be washed out (in aqueous) or filtered from the reaction vessel and the remainder of the aqueous solvent (where applicable) azeotroped off with some of the telescoping solvent. In the formation of compound (XIV), if the alkoxide used to introduce $OR^3$ is dissolved in solvent (such as ethanol), then this solvent could again be azeotroped off with some of the telescoping solvent. If solid alkoxide is used then this latter azeotroping step is not required. Most preferably the telescoping solvent for any telescoped steps of scheme 3 is toluene.

It will be appreciated that salts of the compounds of Schemes 1 to 3 can be formed in accordance with the invention by converting the relevant compound to a salt thereof (either in situ or as a separate step). Also an acid addition salt of the compound of formula (I) can be formed in accordance with the invention.

1.4. Clearly, for certain compounds of formulae (I), (IA) or (IB) wherein $R^{13}$ is $OR^3$, by exploiting the cyclisation and alkoxide exchange methodology described in sections 1.2 and 2.1 herein, it may be particularly advantageous to generate a compound of formula (I), (IA) or (IB) from a compound of the general formula (IXCa), wherein the 2-alkoxy group of the 5-(pyridin-3-yl) substituent in the former is different from that in the latter, directly in a "one-pot reaction". To achieve this an alternative alcohol ($R^3OH$) should be used wherein the alkyl chain of the —$R^3$ group of the alcohol is different from that of the —$R^{3a}$ group on the starting compound of general formula (IXCa). When the alcohol which is to provide the alternative 2-alkoxy group (—$OR^3$) is too scarce or expensive to be employed as the reaction solvent, then it will be expedient to use a suitable alternative such as 1,4-dioxan as reaction solvent with the required alcohol ($R^{3a}OH$) present in an amount sufficient to effect the desired conversion, typically from about 1 to about 2 molecular equivalents. (IXCa) and $R^{3a}$ are as defined hereinbefore.

2. In a further generally applicable process, compounds of the general formula (I), (IA) or (IB) may be prepared from "alternative" compounds of the general formula (I), (IA) or (IB) wherein said process may comprise either interconversion of differing —$OR^3$ groups, interconversion of X and —$OR^3$ groups or interconversion of —$OR^3$ and —$NR^5R^6$ groups wherein X, $R^3$ and $NR^5R^6$ are as defined hereinbefore.

2.1 As mentioned earlier, certain compounds of formulae (I), (IA) and (IB) can be interconverted by inducing alkoxide exchange or displacement at the 2-position of the 5-(pyridin-3-yl) substituent. This may be achieved, by treating the appropriate alcohol (of formula $R^{3a}OH$ wherein the $R^{3a}$ alkyl group is as defined hereinbefore and is different from the $R^3$ group on the starting material (I), (IA) or (IB) with an alkali metal salt of a sterically hindered alcohol or amine in order to generate the required alkoxide anion which then reacts with the substrate. Typically, in a two-step procedure, a mixture of from about 1 to about 8, more preferably from about 5 to about 8, and especially from about 4 to about 8 molecular equivalents of potassium bis(trimethylsilyl)amide and the required alcohol (of formula $R^{3a}OH$) as solvent is heated at from about 80° C. to about 100° C. for about 25 minutes to about 1 hour, followed by addition of the compound of formula (IA) or (IB) and heating of the reaction mixture at from about 100° C. to about 130° C. for from about 6 to about 24 hours. Alternatively, in a one-step procedure, the substrate may be treated directly, in the required alcohol as solvent, with from about 1.2 to about 6, preferably from about 4 to about 6 molecular equivalents of, for example, potassium bis(trimethylsilyl)amide, potassium t-butoxide or cesium carbonate at from about 80° C. to about 130° C. A hydroxide trapping agent may be optionally included in such alkoxide exchange reactions.

2.2 Alternatively, certain compounds of the general formula (I), (IA) or (IB) wherein $R^{13}$ is —$OR^3$ may be obtained from compounds of the general formula (XXX):

(XXX)

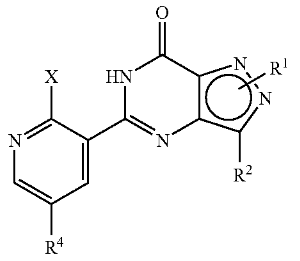

wherein $R^1$, $R^2$, $R^4$ are as defined previously herein and wherein X is anything other than —$OR^3$ by reaction in the presence of —$OR^{3-}$ optionally in the presence of a hydroxide trapping agent as defined hereinbefore.

2.3 In a yet further alternative synthesis compounds of the general formula (I), (IA) or (IB) wherein $R^{13}$ is $NR^5R^6$ may be generated directly from a compound of general formula (I) wherein $R^{13}$=$OR^3$. When $R^{13}$ is $OR^3$, the substrate may be treated with an excess of $R^5R^6NH$, or a suitable acid addition salt thereof, in the presence of an excess of a non-nucleophilic base such as a sterically hindered amine or a suitable inorganic base in a suitable solvent. Typically, $R^5R^6NH$ is used as the free base with about a 3-fold excess (over the substrate) of potassium bis(trimethylsilyl)amide (KHMDS) in dimethylformamide (DMF) as solvent at about 100° C. Alternatively, an excess of $R^5R^6NH$ may be used as the solvent and the reaction conducted in the presence of about a 50% excess of copper(II) sulphate at up to the reflux temperature of the reaction medium. Where the desired amino substituent on the compound of the formula (I), (IA) or (IB) is —$NR^5R^6$ and one of either $R^5$ or $R^6$ is H, then the exchange reaction may be carried out by refluxing with the appropriate amine, and copper(II) sulphate penta- or hepta-hydrate or anhydrous copper (II) sulphate or KHDMS in DMF. Typically, to exchange the $OR^3$ group for alternative amines of the formula $NHR^5R^6$, such as compounds wherein $R^5$ or $R^6$ are selected from aliphatic or cyclic amines, optionally including oxygen (e.g. morpholine), then the reaction is preferably carried out by treating with the appropriate amine and about 3 equivalents of potassium bis(trimethylsilyl)amide in DMF for about 18 hours at 100° C.

3. In a yet further alternative process, a compound of the general formula (I) may be prepared from a compound of general formulae (IIA) or (IIC) respectively:

(IIA)

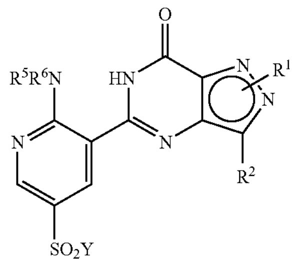

(IIC)

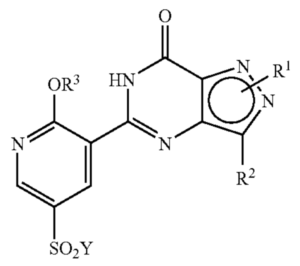

wherein Y is halo, preferably chloro, and $R^1$, $R^2$, $R^3$, $R^5$ and $R^6$ are as previously defined for formulae (IXA) and (IXC), by a reaction with a 4-$R^{10}$-piperazinyl compound as described for the preparation of compounds of formula (XA) and (XB) from compounds of formula (VIIA) and (VIIIB) respectively.

Alternatively, a compound of the general formula (I), (IA) or (IB) may be prepared from a compound of the general formula (IIB):

(IIB)

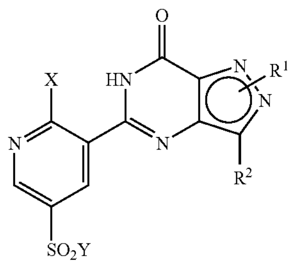

wherein $R^1$, $R^2$, $R^4$ and X are as previously defined herein via reaction with a 4-$R^{10}$ piperazinyl compound followed by an optional displacement reaction in the presence of a hydroxide trapping agent and —$OR^3$— as detailed hereinbefore for the preparation of compound (I) from compound (IXB) or (XXX).

3.1 A compound of general formulae (IIA) or (IIB) or (IIC) may be prepared from a compound of general formula (IVA) or (IVB) or (IVC) respectively:

(IVA)

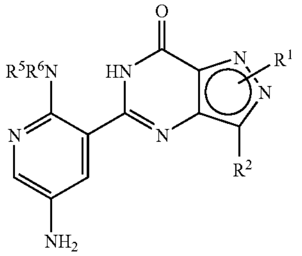

(IVB)

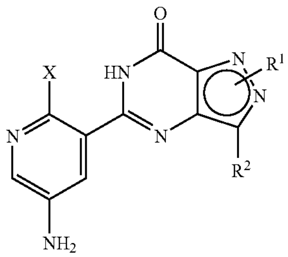

(IVC)

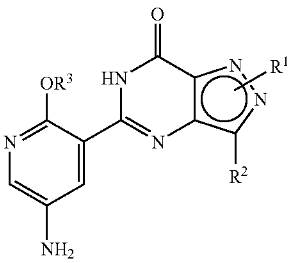

wherein $R^1$, $R^2$, $R^3$, $R^5$, $R^6$ and X are as previously herein, by the application of known methods for converting amino to a $SO_2Y$ group wherein Y is also as previously defined for formulae (IIA), (IIB) and (IIC). Such reactions are previously described for the preparation of compounds of the general formulae (VIIIA) and (VIIIB) from compounds of the general formulae (XIA) and (XIB) respectively.

A compound of the general formula (IVA) or (IVB) or (IVC) may be prepared by cyclisation of a compound of the general formula (VA) or (VB) or (VC) respectively:

(VA)

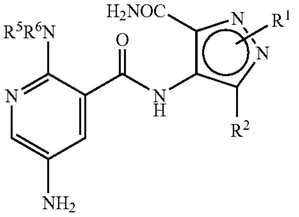

(VB)

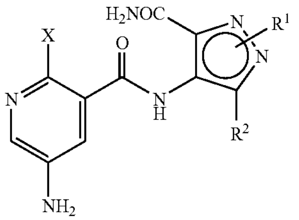

(VC)

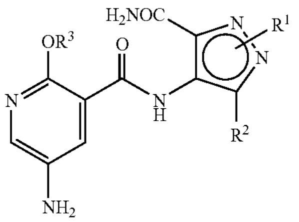

wherein $R^1$, $R^2$, $R^3$, $R^5$, $R^6$ and X are as previously defined herein and wherein the conditions for cyclisation are analogous to those previously described for cyclisation of the compounds of general formulae (IXA), (IXB) or (IXC).

A compound of formula (VA) or (VB) or (VC) may be prepared by reduction of a compound of formula (VIA) or (VIB) or (IVC) respectively:

(VIA)

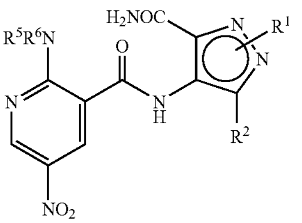

-continued (VIB)

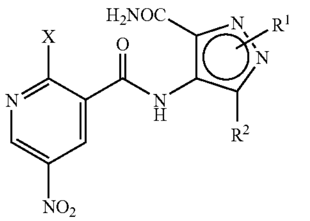

(VIC)

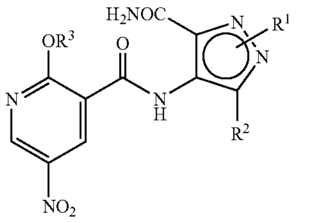

wherein $R^1$, $R^2$, $R^3$, $R^5$, $R^6$ and X are as previously defined for compounds of the general formulae (VA), (VB) and (VC), by conventional catalytic or catalytic transfer hydrogenation procedures as previously detailed for preparation of compounds of the general formulae (XIA) or (XIB) from compounds of the general formulae (XIIA) or (XIIB) respectively.

A compound of formula (VIA), (VIB) or (VIC) may be prepared by reaction of a compound of formula (VII) as defined previously herein with a compound of formula (XIIA) or (XIIB) or (XIIC) respectively:

(XIIA)

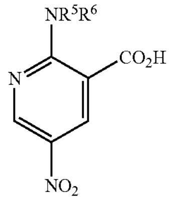

(XIIB)

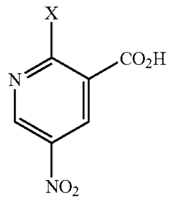

(XIIC)

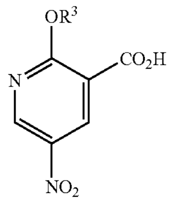

wherein $R^3$, $R^5$, $R^6$ and X are as previously defined for compounds of the general formulae (VIA) or (VIB) or (VIC). Again, as previously detailed a conventional amine protecting group strategy is preferred for (XIIA) when $NR^5R^6$ is a primary or secondary amino group. The coupling reaction is analogous to the reactions of (VII) with the compounds of general formulae (XA) or (XB) or (XC) already described herein.

3.2 A compound of general formulae (IIA) or (IIB) or (IIC) may be prepared from a compound of formula (IVA) or (IVB) or (IVC) respectively as described hereinbefore wherein said compound of the general formulae (IVA) or (IVB) or (IVC) may be prepared by direct cyclisation of a compound of the general formula (VIA) or (VIB) or (VIC) respectively:

(VIA)

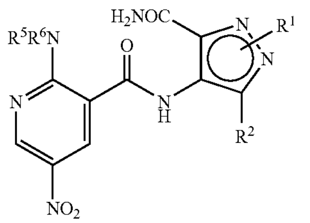

(VIB)

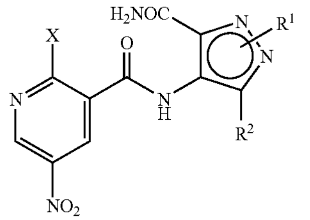

(VIC)

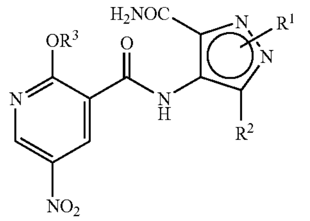

wherein $R^1$, $R^2$, $R^3$, $R^5$, $R^6$ and X are as previously herein and wherein the conditions for said direct cyclisation are analogous to the previously described cyclisation for compounds of the general formulae (IXA) or (IXB) or (IXC) and wherein said cyclisation is followed by reduction of the resultant intermediate compounds according to the methods previously detailed herein to provide compounds of the general formulae (IVA) or (IVB) or (IVC) from compounds of the general formulae (VA) or (VB) or (VC).

Compounds of the general formula (XIIC) wherein X is Cl may be prepared from 2-hydroxy nicotinic acid via nitration followed by esterification then chlorination of the suitably protected nicotinic acid and subsequent ester hydrolysis.

Compounds of the general formula (XIIIC) (i.e. compounds of general formula (XIIIB wherein X is —$OR^3$) can be prepared by analogy with the methods detailed previously herein.

4. A further, generally applicable, synthetic route to compounds of the general formula (I), (IA) or (IB) involves incorporation of the $R^1$ substituent in the final step of the synthesis. Thus a compound of the general formula (I), (IA) or (IB) may be prepared by alkylation of a compound of formula (Ia), (1Aa) or (IBa) wherein $R^1$ is hydrogen and $R^2$, $R^{13}$ and $R^4$ are as previously defined for formulae (I), (IA) and (IB), using one or more of a plethora of well-known methods, such as:

(i) reaction with a compound of formula $R^1J$, wherein $R^1$ is as previously defined for compounds of general formulae (I), (IA) and (IB), and J is a suitable leaving group, e.g. halo (preferably chloro, bromo or iodo), $C_1$–$C_4$ alkanesulphonyloxy, trifluoromethanesulphonyloxy or arylsulphonyloxy (such as benzenesulphonyloxy or p-toluenesulphonyloxy), in the presence of an appropriate base, optionally in the presence of sodium iodide or potassium iodide, at from about −70° C. to about 100° C. Preferably the alkylation is conducted at from about room temperature to about 120° C. Suitable base-solvent combinations may be selected from:

(a) sodium, potassium or cesium carbonate, sodium or potassium bicarbonate, or a tertiary amine such as triethylamine or pyridine, together with a $C_1$ to $C_4$ alkanol, 1,2-dimethoxyethane, tetrahydrofuran, 1,4-dioxan, acetonitrile, pyridine, N,N-dimethylformamide or N,N-dimethylacetamide;

(b) sodium or potassium hydroxide, or a sodium or potassium $C_1$ to $C_4$ alkoxide, together with a $C_1$ to $C_4$ alkanol, water or mixtures thereof;

(c) lithium, sodium or potassium hydride, lithium, sodium or potassium bis(trimethylsilyl)amide, lithium diisopropylamide or butyllithium, together with toluene, ether, 1,2-dimethoxyethane, tetrahydrofuran or 1,4-dioxan; or (d) under phase transfer catalysis conditions, a tetraalkylammonium halide or hydroxide, together with a mixture of an aqueous solution of sodium or potassium hydroxide and dichloromethane, 1,2-dichloroethane or chloroform;

Typically, either about a 10% excess of sodium hydride is added to a solution of the substrate in a suitable solvent, e.g. anhydrous tetrahydrofuran or cesium carbonate in dimethylformamide (DMF) is employed, and the resulting anion treated with about a 10% excess of the required $R^1J$.

(ii) reaction with a compound of formula $R^1OH$, wherein $R^1$ is as previously defined for compounds of the general formulae (I), (IA) and (IB), using classical Mitsunobu methodology. Typical reaction conditions involve treating the substrate with the alkanol in the presence of a triarylphosphine and a di($C_1$ to $C_4$)alkyl azodicarboxylate, in a suitable solvent such as tetrahydrofuran or 1,4-dioxan, at from about −5° C. to about room temperature.

(iii) reaction with a compound of formula $R^1M$, wherein $R^1$ represents optionally substituted phenyl, $Het^2$, $Het^3$ or $Het^4$ and wherein said Het groups are either aromatic or partially unsaturated at the C atom that is attached to M, and wherein M represents an optionally substituted metal or boron group wherein said metal or boron group is suitable for cross-coupling reactions (of metal or boron compounds), for example a dihydroxyborane, in the presence of an appropriate catalyst system (e.g. copper (II) acetate) or under so-called "Goldberg" conditions. Such cross-coupling is preferably carried out in the presence of a suitable base (e.g. pyridine), and a drying agent, typically 4 Å molecular sieves, in a suitable solvent such as dichloromethane or N-methylpyrrolidine, and optionally under microwave irradiation.

(iv) reaction with a compound of formula $R^1E$, where E is halo, preferably bromo, under conditions suitable for cross-coupling of halogenated compounds, where $R^1$ is as defined in (iii). Such reaction is typically carried out in the presence of an appropriate catalyst system (e.g. Palladium catalyst), in the presence of a suitable base, such as for example sodium t-butoxide, in a suitable solvent, such as toluene, with heating, typically at about 70° C.

4.1 Thus, a compound of general formula ($I^a$), ($IA^a$) or ($IB^a$), wherein $R^1$ is hydrogen and $R^2$, $R^{13}$ and $R^4$ are as previously defined for compounds of general formulae (I), (IA) or (IB), may be obtained from a compound of formula ($IXA^a$) or ($IXB^a$) or ($IXC^a$) respectively wherein $R^1$ is hydrogen, and $R^2$, $R^3$, $R^5$, $R^6$ and $R^4$ and X are as previously defined for formulae (IXA), (IXB) or (IXC), under the same conditions as those used for the conversion of a compound of the general formula (IXA), (IXB) or (IXC) to a compound of the general formula (I), (IA) or (IB) respectively when $R^1$ is other than hydrogen, followed by acidification of the reaction mixture to a pH of about 6.

4.2 In a further alternative, generally applicable synthetic route the compounds of the present invention may be prepared by cyclisation of compounds of the general formulae (IXA), (IXB) or (IXC) wherein said compounds of the general formulae (IXA), (IXB) or (IXC) are obtained from compounds of the general formulae ($IXA^a$), ($IXB^a$) or ($IXC^a$) wherein $R^1$ is hydrogen and $R^2$, $R^3$, $R^5$, $R^6$ and $R^4$ are as previously defined herein, using one or more of a plethora of well-known methods such as are detailed hereinbefore for conversion of compounds of the general formulae ($I^a$), ($IA^a$) and ($IB^a$) to compounds of the general formulae (I), (IA) and (IB). Any of the previously detailed methods for such general conversion may be used. Preferred conditions for such conversion use either from about 1.0 to 1.3 equivalents of sodium hydride in tetrahydrofuran solvent at from about −78° to about room temperature and from about 1.1 to about 2.3 equivalents of alkylating agent at from about 60° C. to about 70° C., or from about 2.2 equivalents of cesium carbonate as base in dimethylformamide as solvent and about 1.1. equivalent of alkylating agent at about 60° C.

5. In a yet further alternative synthesis, compounds of the general formula (I), (IA) or (IB) can be obtained from compounds of the general formula (I) wherein $R^{10}$ is H, via a suitable alkylation reaction such as for example with an alkyl halide and a suitable base e.g. cesium carbonate and methyl chloride.

In a preferred process for the preparation of the compounds according to the present invention compounds of general formula (VIIB) are prepared from compounds of the general formula (XIIIB) according to the process detailed in Preparations 96(a) to (h). These compounds of general formula (VIIB) are coupled with compounds of general formula (XC) according to the process detailed in Preparations 29 and 96(i) to provide a compound of general formula (IXC), wherein said compound of general formula (IXC) is prepared according to the process detailed in Preparation 95. The compound of general formula (IXC) is then preferably cyclised under basic conditions according to the process detailed in Examples 8 and 102 to form compounds of general formula (IB) wherein $R^{13}$ is $OR^3$.

The 4-aminopyrazole-5-carboxamides of general formulae (VII), (VIIA) and (VIIB), the pyrazoles of general formula (XIII), the carboxylic acids of formulae (XA), (XB), (XIIA), (XIIB), (XIIC), (VIIA), (VIIB), (VIIC) and (X), or the compounds of the general formula $R^1J$ and $R^1E$ when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formulae (I), (IA) or (IB) to be obtained.

The pharmaceutically acceptable acid addition salts of the compounds of formulae (I), (IA) or (IB) which contain a basic centre may also be prepared in a conventional manner. By way of illustration, acid addition salts of compounds of formula (I) (more particularly IA and IB) can be formed by reacting a compound of formula (I) with an equimolar or excess amount of the appropriate acid, either neat or in a suitable solvent. The salt may then be precipitated out of solution and isolated by filtration or the reaction solvent can be stripped off by conventional means such as by evaporation under vacuum. Typical salts which can be used in the schemes of 1 to 3 are given in PCT/IB99/00519. Example of salts of compounds IA and IB are the p-toluenesulfonate, benzenesulfonate, camphorsulfonate and ethanesulfonate respectively.

Pharmaceutically acceptable base addition salts can be obtained in an analogous manner by treating a solution of a compound of formula (I), (IA) or (IB) with the appropriate base. Both types of salt may be formed or interconverted using ion-exchange resin techniques.

The present invention also includes all suitable isotopic variations of a compound of the formula (I) or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of the formulae (I), (IA) or (IB), which may be made prior to a final de-protection stage, may not possess pharmacological activity as such, but may, in certain instances, be administered orally or parenterally and thereafter metabolised in the body to form compounds of the invention which are pharmacologically active. Such derivatives may therefore be described as "pro-drugs". Further, certain compounds of the formulae (I), (IA) or (IB) may act as pro-drugs of other compounds of the formulae (I), (IA) or (IB).

All protected derivatives, and pro-drugs, of compounds of general formulae (I), (IA) or (IB) are included within the scope of the invention. Suitable protecting groups for use in accordance with the invention can be found in "Protecting Groups" edited by P. J. Kocienski, Thieme, New York, 1994—see particularly chapter 4, page 118–154 for carboxy protecting groups; and "Protective Groups in Organic Synthesis" $2^{nd}$ edition, T. W. Greeene & P. G. M. Wutz, Wiley-Interscience (1991)—see particularly chapter 5 for carboxy protecting groups. Examples of suitable pro-drugs for the compounds of the present invention are described in Drugs of Today, Volume 19, Number 9, 1983, pp. 499–538 and in Topics in Chemistry, Chapter 31, pp 306–316.

The biological activities of the compounds of the present invention were determined by the following test methods.

Phosphodiesterase (PDE) Inhibitory Activity

The compounds of the present invention are potent and selective cGMP PDE5 inhibitors. In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human and rabbit platelets, human cardiac ventricle, human skeletal muscle and bovine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue, human platelets or rabbit platelets; the cGMP-stimulated PDE (PDE2) was obtained from human corpus cavernosum; the calcium/calmodulin (CalCAM)-dependent PDE (PDE1) from human cardiac ventricle; the cAMP-specific PDE (PDE4) from human skeletal muscle; and the photoreceptor PDE (PDE6) from bovine retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to $[^{3}H]$-labeled at a conc ~1/3 $K_m$) such that $IC_{50} \cong K_i$. The final assay volume was made up to 100 μl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 μl yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor $IC_{50}$ values obtained using the 'Fit Curve' Microsoft Excel extension. Results from these tests show that the compounds of the present invention are potent and selective inhibitors of cGMP-specific PDE5.

Preferred compounds of the present invention, such as those of Examples 3–12, 14–17, 19, 21–30, 32, 33, 35–46, 48–59, 61, 62, 65–75, 77, 79–102 have $IC_{50}$ values of less than about 10 nM for the PDE5 enzyme. More preferred compounds, such as those of Examples 3–12, 14, 15, 17, 23–30, 32, 33, 35–46, 48, 50–59, 61, 62, 65, 69–74, 79–102 have $IC_{50}$ values of less than about 5 nM for the PDE5 enzyme. Especially preferred compounds, such as those of Examples 4–10, 15, 17, 23–28, 30, 32, 33, 35–42, 44, 45, 46, 50, 52–56, 58, 59, 61, 62, 65, 69–74, 79–93, 96, 98–102 have $IC_{50}$ values of less than about 2 nM for the PDE5 enzyme.

Especially preferred herein are compounds which have an $IC_{50}$ value of less than about 10, more preferably less than about 5, and most preferably less than about 2 nM for the PDE5 enzyme in combination with selectivity of greater than 10-fold, more preferably greater than 50-fold, more preferably greater than 100-fold and especially greater than 200-fold selectivity for the. PDE5 enzyme versus the PDE6 enzyme.

Functional Activity

This was assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In Vivo Activity

Compounds were screened in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994,13, 71).

The compounds of formulae (I), (IA) or (1B), their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice. For example, the compounds of formulae (I), (IA) or (1B) or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compounds of the invention may also be administered via intracavernosal injection. The compounds of the invention may also be administered via fast dispersing or fast dissolving dosages forms or in the form of a high energy dispersion or as coated particles. Suitable pharmaceutical formulations of the compounds of the invention may be in coated or un-coated form as desired.

Such tablets may contain excipients such as microcrystalline cellulose, lactose, sodium citrate, calcium carbonate, dibasic calcium phosphate, glycine and starch (preferably corn, potato or tapioca starch), disintegrents such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the formula (I), (IA) or (IB) may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion or needless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of formula (I), (IA) or (1B) or salts or solvates thereof will usually be from 10 to 500 mg (in single or divided doses).

Thus, for example, tablets or capsules of the compounds of formulae (I), (IA) or (IB) or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

Example 10 mg Tablet Formulation

| Ingredient | % w/w |
|---|---|
| Besylate salt of Example 103 | 13.038* |
| Lactose | 62.222 |
| Starch | 20.740 |
| Croscarmellose Sodium | 3.000 |
| Magnesium Stearate | 1.000 |

*Quantity adjusted in accordance with drug activity.

Such tablets can be manufactured by standard processes, for example, direct compression or a wet or dry granulation process. The tablet cores may be coated with appropriate overcoats.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I), (IA) or (IB) and a suitable powder base such as lactose or starch.

Aerosol or dry powder formulations are preferably arranged so that each metered dose or "puff" contains from 1 to 50 mg of a compound of the formula (I), (IA) or (IB) for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the formulae (I), (IA) or (IB) or salts or solvates thereof can be administered in the form of a suppository or pessary, or they may be applied topically in the form of a gel, hydrogel, lotion, solution, cream, ointment or dusting powder. The compounds of the formulae (IA) and (IB) or salts or solvates thereof may also be dermally administered. The compounds of the formulae (I), (IA) or (IB) or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formulae (I), (IA) or (IB) or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formulae (I), (IA) or (IB) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 5 to 250 mg of compound when required. In circumstances where the recipient suffers from a swallowing disorder or from impairment of drug absorption after oral administration, the drug may be administered parenterally, sublingually or buccally.

For veterinary use, a compound of formula (I), (IA) or (IB), or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

It is to be appreciated that all references herein to treatment include curative, palliative and prophylactic treatment.

Thus the invention provides a pharmaceutical composition comprising a compound of formula (I), (IA) or (IB), or a pharmaceutically acceptable salt thereof, or a pharmaceutically acceptable solvate or pro-drug thereof, together with a pharmaceutically acceptable diluent or carrier.

It further provides a veterinary formulation comprising a compound of formula (I), (IA) or (IB), or a veterinarily acceptable salt thereof, or a veterinarily acceptable solvate or pro-drug thereof, together with a veterinarily acceptable diluent or carrier.

The invention also provides a compound of formula (I), (IA) or (IB), or a pharmaceutically acceptable salt thereof, or a pharmaceutically acceptable solvate or pro-drug thereof, or a pharmaceutical composition containing any of the foregoing, for use as a human medicament.

In addition, it provides a compound of formula (I), (IA) or (IB), or a veterinarily acceptable salt thereof, or a veterinarily acceptable solvate or pro-drug thereof, or a veterinary formulation containing any of the foregoing, for use as an animal medicament.

In yet another aspect, the invention provides the use of a compound of formula (I), (IA) or (IB), or a pharmaceutically acceptable salt thereof, or a pharmaceutically acceptable solvate or pro-drug thereof, for the manufacture of a human medicament for the curative, palliative or prophylactic treatment of a medical condition for which a cGMP PDE5 inhibitor is indicated. There is further provided the use of a compound of formula (I), (IA) or (IB) or a suitable salt, solvate or pro-drug thereof, in the manufacture of a medicament for the treatment of a medical condition in which inhibition of a cGMP PDE5 is desirable.

It also provides the use of a compound of formula (I), (IA) or (IB), or a veterinarily acceptable salt thereof, or a veterinarily acceptable solvate or pro-drug thereof, for the manufacture of an animal medicament for the curative, palliative or prophylactic treatment of a medical condition for which a cGMP PDE5 inhibitor is indicated.

Moreover, the invention provides the use of a compound of formula (I), (IA) or (IB), or a pharmaceutically acceptable salt thereof, or a pharmaceutically acceptable solvate or pro-drug thereof, for the manufacture of a human medicament for the curative, palliative or prophylactic treatment of male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, selective serotonin re-uptake inhibitor (SSRI) induced sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, peripheral vascular disease, stroke, nitrate induced tolerance, bronchitis, allergic asthma, chronic asthma, allergic rhinitis, diseases and conditions of the eye, diseases characterised by disorders of gut motility, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof e.g. gastroparesis, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation during haemodialysis. Particularly preferred conditions include MED and FSD.

It also provides the use of a compound of formula (I), (IA) or (IB), or a veterinarily acceptable salt thereof, or a veterinarily acceptable solvate or pro-drug thereof, for the manufacture of an animal medicament for the curative, palliatve or prophylactic treatment of male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, selective serotonin re-uptake inhibitor (SSRI) induced sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, peripheral vascular disease, stroke, nitrate induced tolerance, bronchitis, allergic asthma, chronic asthma, allergic rhinitis, diseases and conditions of the eye, diseases characterised by disorders of gut motility, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation during haemodialysis. Particularly preferred conditions include MED and FSD.

Additionally, the invention provides a method of treating or preventing a medical condition for which a cGMP PDE5 inhibitor is indicated, in a mammal (including a human being), which comprises administering to said mammal a therapeutically effective amount of a compound of formula (I), (IA) or (IB), or a tolerance, multiple sclerosis, diabetic nephropathy, neuropathy including autonomic and peripheral neuropathy and in particular diabetic neuropathy and symptoms thereof e.g. gastroparesis, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation during haemodialysis. Particularly preferred conditions include MED and FSD.

It also provides the use of a compound of formula (I), (IA) or (IB), or a veterinarily acceptable salt thereof, or a veterinarily acceptable solvate or pro-drug thereof, for the manufacture of an animal medicament for the curative, palliatve or prophylactic treatment of male erectile dysfunction (MED), impotence, female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, selective serotonin re-uptake inhibitor (SSRI) induced sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, peripheral vascular disease, stroke, nitrate induced tolerance, bronchitis, allergic asthma, chronic asthma, allergic rhinitis, diseases and conditions of the eye, diseases characterised by disorders of gut motility, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation during haemodialysis. Particularly preferred conditions include MED and FSD.

Additionally, the invention provides a method of treating or preventing a medical condition for which a cGMP PDE5 inhibitor is indicated, in a mammal (including a human being), which comprises administering to said mammal a therapeutically effective amount of a compound of formula (I), (IA) or (IB), or a female sexual dysfunction (FSD), clitoral dysfunction, female hypoactive sexual desire disorder, female sexual arousal disorder, female sexual pain disorder, female sexual orgasmic dysfunction (FSOD), sexual dysfunction due to spinal cord injury, selective serotonin re-uptake inhibitor (SSRI) induced sexual dysfunction, premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, peripheral vascular disease, stroke, nitrate induced tolerance, bronchitis, allergic asthma, chronic asthma, allergic rhinitis, diseases and conditions of the eye, diseases characterised by disorders of gut motility, pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof e.g. gastroparesis, peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction or blood pressure stabilisation of during haemodialysis in a mammal (including a human being).

The invention also includes any novel intermediates described herein, for example those of formulae (IXA), (IXB), (VIIA), (VIIB), (VIII), (VIIIA) and (X). The present invention additionally comprises the combined administration of a cGMP $PDE_5$ inhibitor of the general formula (1), wherein said combined administration can be in the form of simultaneous, sequential or joint administration with:

(a) one or more naturally occurring or synthetic prostaglandins or esters thereof. Suitable prostaglandins for use herein include compounds such as alprostadil, prostaglandin $E_1$,prostaglandin $E_0$, 13, 14-dihydroprostaglandin $E_1$, prostaglandin $E_2$, eprostinol, natural synthetic and semi-synthetic prostaglandins and derivatives thereof including those described in U.S. Pat. No. 6,037,346 issued on 14th Mar. 2000 and incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3$α, carboprost tromethamine dinoprost, tromethamine, dinoprostone, lipo prost, gemeprost, metenoprost, sulprostune, tiaprost and moxisylate; and/or (b) one or more α-adrenergic receptor antagonist compounds also known as α-adrenoceptors or α-receptors or α-blockers. Suitable compounds for use herein include: the α-adrenergic receptors as described in PCT application WO99/30697 published on 14th Jun. 1998, the disclosures of which relating to α-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $a_2$-blockers from U.S. Pat. No. 6,037,346 [14th Mar. 2000]-dibenamine, tolazoline, trimazosin and dibenamine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (c) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (d) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (e) one or more dopaminergic agents. Suitable dopaminergic compounds for use herein include $D_2$-agonists such as, pramipexol; apomorphine; and/or (f) one or more vasodilator agents. Suitable vasodilator agents for use herein include nimodepine, pinacidil, cyclandelate, isoxsuprine, chloroprumazine, halo peridol, Rec 15/2739, trazodone, pentoxifylline; and/or (g) one or more thromboxane A2 agonists; and/or (h) one or more CNS active agents; and/or (i) one or more ergot alkoloids; Suitable ergot alkaloids are described in U.S. Pat. No. 6,037,346 issued on 14th Mar. 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (k) one or more compounds which modulate the action of atrial natruretic factor (also known as atrial naturetic peptide), such as inhibitors or neutral endopeptidase; and/or (l) one or more compounds which inhibit angiotensin-converting enzyme such as enapril, and combined inhibitors of angiotensin-converting enzyme and neutral endopeptidase such as omapatrilat; and/or (m) one or more angiotensin receptor antagonists such as losartan; and/or (n) one or more substrates for NO-synthase, such as L-arginine; and/or (o) one or more calcium channel blockers such as amlodipine; and/or (p) one or more antagonists of endothelin receptors and inhibitors or endothelin-converting enzyme; and/or (q) one or more cholesterol lowering agents such as statins and fibrates; and/or (r) one or more antiplatelet and antithrombotic agents, e.g. tPA, uPA, warfarin, hirudin and other thrombin inhibitors, heparin, thromboplastin activating factor inhibitors; and/or (s) one or more insulin sensitising agents such as rezulin and hypoglycaemic agents such as glipizide; and/or (t) L-DOPA or carbidopa; and/or (u) one or more acetylcholinesterase inhibitors such as donezipil; and/or (v) one or more steroidal or non-steroidal anti-inflammatory agents.

The syntheses of the compounds of the invention and of the intermediates for use therein are illustrated by the following Examples and Preparations. A number of the compounds included in the Preparations section are compounds of the formula (I), (IA) or (IB) and are thereby examples of compounds according to the present invention.

$^1H$ Nuclear magnetic resonance (NMR) spectra were recorded using either a Varian Unity 300 or a Varian Inova 400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode.

Room temperature means 20 to 25° C.

EXAMPLE 1

5-[2-Ethoxy-5-(4-methylpiperazin-1-ylsulphonyl)pyridin-3-yl]-2-[2-methoxyethyl]-3-n-propyl-2,6-dihydro-7H-pyrazolo[4,3-d]pyrimidin-7-one

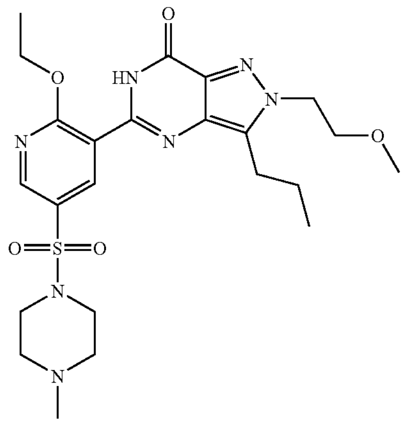

A mixture of the title compound from preparation 28 (560 mg, 1.04 mmol) and potassium tert-butoxide (292 mg, 2.4 mmol) in ethanol (20 ml) was heated at 100° C. in a sealed vessel for 18 hours. The cooled mixture was concentrated under reduced pressure and the residue partitioned between ethyl acetate and water. The organic phase was separated, dried ($MgSO_4$) and evaporated under reduced pressure. The crude product was purified by column chromatography on silica gel using an elution gradient of dichloromethane:methanol (100:0 to 95:5) to afford the title compound, 220 mg.

Found: C, 52.65; H, 6.43; N, 18.39. $C_{23}H_{33}N_7O_5S$; $0.3H_2O$ requires C, 53.16; H, 6.40; N, 18.87%.

δ ($CDCl_3$): 1.02 (3H, t), 1.58 (3H, t), 1.84 (2H, m), 2.28 (3H, s), 2.52 (4H, m), 3.01 (2H, t), 3.15 (4H, m), 3.30 (3H, s), 3.90 (2H, t), 4.45 (2H, t), 4.77 (2H, q), 8.62 (1H, s), 9.02 (1H, s), 10.61 (1H, s).

LRMS: m/z 520 $(M+1)^+$

EXAMPLE 2

5-[2-Ethoxy-5-(4-methylpiperazin-1-ylsulphonyl)pyridin-3-yl]-3-ethyl-2-[2-methoxyethyl]-2,6-dihydro-7H-pyrazolo[4,3-d]pyrimidin-7-one

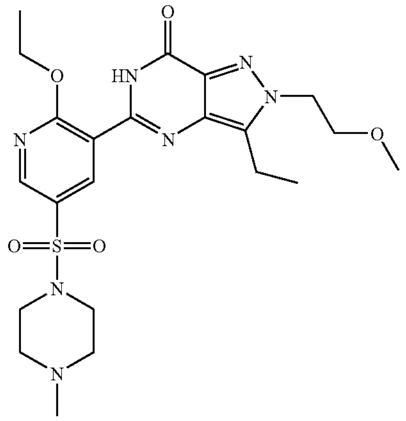

A mixture of the title compound from preparation 27 (420 mg, 0.80 mmol) and potassium bis(trimethylsilyl)amide (240 mg, 1.20 mmol) in ethanol (40 ml) was heated at 100° C. for 18 hours in a sealed vessel. The cooled mixture was concentrated under reduced pressure and the residue purified by column chromatography on silica gel using an elution gradient of dichloromethane:methanol (100:0 to 90:10) to give the title compound, 130 mg.

δ ($CDCl_3$): 1.40 (3H, t), 1.58 (3H, t), 2.27 (3H, s), 2.50 (4H, m), 3.10 (6H, m), 3.30 (3H, s), 3.92 (2H, t), 4.45 (2H, t), 4.75 (2H, q), 8.62 (1H, d), 9.02 (1H, d), 10.65 (1H, s).

LRMS: m/z 506 $(M+1)^+$

EXAMPLE 3

5-[2-Ethoxy-5-(4-ethylpiperazin-1-ylsulphonyl)pyridin-3-yl]-2-[2-methoxyethyl]-3-n-propyl-2,6-dihydro-7H-pyrazolo[4,3-d]pyrimidin-7-one

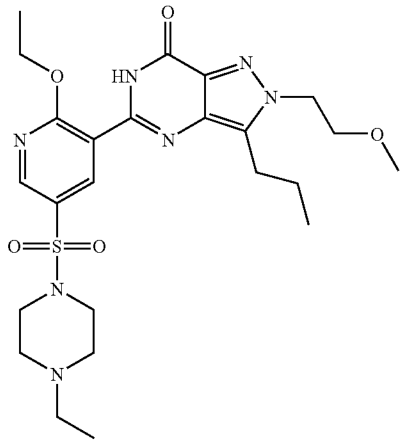

A mixture of the title compound from preparation 30 (740 mg, 1.34 mmol) and potassium bis(trimethylsilyl)amide (321.5 mg, 1.61 mmol) in ethanol (40 ml) was heated at 100° C. for 18 hours in a sealed vessel. Tlc analysis showed starting material remaining, so additional potassium bis (trimethylsilyl)amide (321.5 mg, 1.61 mmol) was added, and the reaction continued for a further 18 hours. The cooled mixture was concentrated under reduced pressure and the residue partitioned between water and ethyl acetate, and the layers separated. The organic phase was evaporated under reduced pressure and the crude product was purified by column chromatography on silica gel using an elution gradient of dichloromethane:methanol (100:0 to 90:10) to give the title compound, 150 mg.

δ ($CDCl_3$): 1.02 (6H, m), 1.58 (3H, t), 1.83 (2H, m), 2.41 (2H, q), 2.56 (4H, m), 3.01 (2H, t), 3.14 (4H, m), 3.29 (3H, s), 3.90 (2H, t), 4.44 (2H, t), 4.75 (2H, q), 8.61 (1H, s), 9.02 (1H, s), 10.61 (1H, s).

LRMS: m/z 534 $(M+1)^+$

EXAMPLE 4

2-(sec-Butyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

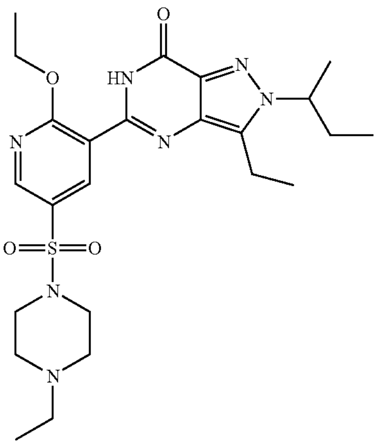

A mixture of the title compound from preparation 39 (400 mg, 0.75 mmol), potassium bis(trimethylsilyl)amide (298 mg, 1.50 mmol) and ethyl acetate (73 μl, 0.75 mmol) in ethanol (10 ml) was heated at 120° C. in a sealed vessel for 12 hours. The cooled mixture was partitioned between ethyl acetate and aqueous sodium bicarbonate solution, and the layers separated. The organic phase was dried ($MgSO_4$), and evaporated under reduced pressure. The crude product was purified by column chromatography on silica gel using dichloromethane:methanol (98:2) as eluant to afford the title compound, 164 mg.

δ ($CDCl_3$): 0.79 (3H, t), 1.02 (3H, t), 1.38 (3H, t), 1.56 (6H, m), 1.90 (1H, m), 2.21 (1H, m), 2.41 (2H, q), 2.57 (4H, m), 2.98–3.18 (6H, m), 4.41 (1H, m), 4.75 (2H, q), 8.61 (1H, s), 9.02 (1H, s), 10.58 (1H, s).

EXAMPLES 5 TO 9

The compounds of the following tabulated examples, of general structure:

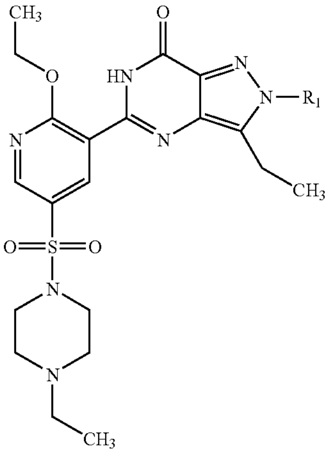

were prepared from the corresponding carboxamides, following a similar procedure to that described in example 4.

| Example | R1 | Yield (%) | Data |
|---|---|---|---|
| 5 | 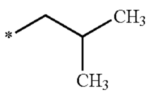 | 23 | δ($CDCl_3$): 0.97(6H, d), 1.02(3H, t), 1.40(3H, t), 1.58(3H, t), 2.41(3H, m), 2.56(4H, m), 3.01(2H, q), 3.14(4H, m), 4.10(2H, d), 4.75(2H, q), 8.61(1H, s), 9.02(1H, s), 10.61(1H, s). |
| 6[1] | 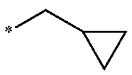 | 28 | δ($CDCl_3$): 0.47(2H, m), 0.63(2H, m), 1.01(3H, t), 1.40(3H, t), 1.48–1.72(4H, m), 2.45(2H, q), 2.56(4H, m), 3.04 (2H, q), 3.15(4H, m), 3.47(2H, q), 4.20 (2H, d), 4.76(2H, q), 8.61(1H, s), 9.02 (1H, s), 10.60(1H, s). LRMS: m/z 516$(M + 1)^+$ |

-continued

| Example | R1 | Yield (%) | Data |
|---|---|---|---|
| 7[1] | 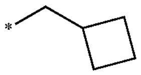 | 48 | δ($CDCl_3$): 1.01(3H, t), 1.20(3H, t), 1.40(3H, t), 1.56(4H, m), 1.88(4H, m), 2.07(2H, m), 2.40(2H, q), 2.56(4H, m), 3.00(2H, m), 3.15(4H, m), 4.34 (2H, d), 4.76(2H, q), 8.61(1H, s), 9.02 (1H, s), 10.60(1H, s). LRMS: m/z 530 $(M + 1)^+$ |
| 8[2] | 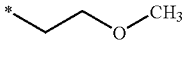 | 27 | Found: C, 53.18; H, 6.48; N, 18.14. $C_{23}H_{33}N_7O_5S$; $0.20C_2H_5CO_2CH_3$ requires C, 53.21; H, 6.49; N, 18.25%. δ($CDCl_3$): 1.04(3H, t), 1.40(3H, t), 1.58(3H, t), 2.41(2H, q), 2.57(4H, m), 3.08(2H, q), 3.14(4H, m), 3.30(3H, s), 3.92(2H, t), 4.46(2H, t), 4.75(2H, q), 8.62(1H, d), 9.04(1H, d), 10.61(1H, s). LRMS: m/z 520$(M + 1)^+$ mp 161–162° C. |
| 9 | 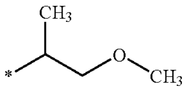 | 47 | δ($CDCl_3$): 1.02(3H, t), 1.38(3H, t), 1.58(6H, m), 2.41(2H, q), 2.57(4H, m), 3.05(2H, m), 3.14(4H, m), 3.22 (3H, s), 3.72(1H, m), 3.96(1H, dd), 4.73(3H, m), 8.61(1H, s), 9.02(1H, s), 10.56(1H, s). LRMS: m/z 534$(M + 1)^+$ |

[1]Purified by ether trituration
[2]additionally, recrystallised from ethyl acetate

EXAMPLE 10

5-[2-Ethoxy-5-(4-ethylpiperazin-1-ylsulphonyl)pyridin-3-yl]-3-ethyl-2-(tetrahydrofuran-2-yl)methyl-2,6-dihydro-7H-pyrazolo[4,3-d]pyrimidin-7-one

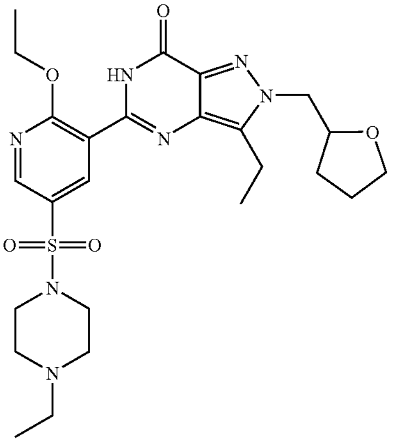

A mixture of the title compound from preparation 42 (250 mg, 0.44 mmol), potassium bis(trimethylsilyl)amide (132 mg, 0.66 mmol) and ethyl acetate (40 μl, 0.41 mmol) in 3-methyl-3-pentanol (4 ml) was heated at 120° C. in a sealed vessel for 18 hours. Tlc analysis showed starting material remaining, so additional potassium bis(trimethylsilyl)amide (132 mg, 0.66 mmol) was added and the reaction heated under reflux for a further 24 hours. The cooled mixture was evaporated under reduced pressure, and the residue purified by column chromatography on silica gel using an elution gradient of dichloromethane:methanol (100:0 to 95:5) to give the title compound, 60 mg.

δ ($CDCl_3$): 1.03 (3H, t), 1.40 (3H, t), 1.58 (3H, t), 1.84 (3H, m), 2.08 (1H, m), 2.41 (2H, q), 2.56 (4H, m), 3.14 (6H, m), 3.70–3.90 (2H, m), 4.30–4.50 (3H, m), 4.75 (2H, q), 8.62 (1H, s), 9.02 (1H, s), 10.62 (1H, s).

LRMS: m/z 546 $(M+1)^+$

EXAMPLE 11

5-[2-Ethoxy-5-(4-ethylpiperazin-1-ylsulphonyl)pyridin-3-yl]-3-ethyl-2-[2-(pyrazol-1-yl)ethyl]-2,6-dihydro-7H-pyrazolo[4,3-d]pyrimidin-7-one

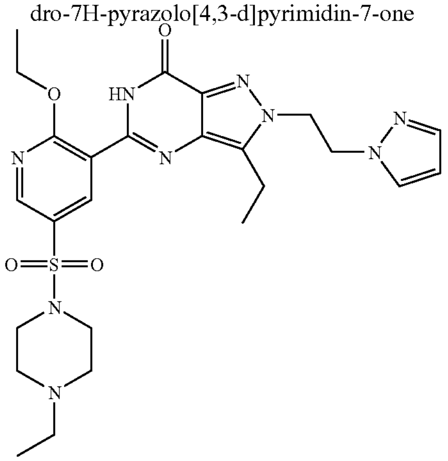

A mixture of the title compound from preparation 48 (300 mg, 0.52 mmol), potassium bis(trimethylsilyl)amide (320 mg, 1.57 mmol) and ethyl acetate (50 μl, 0.52 mmol) in ethanol (40 ml) was heated at 130° C. in a sealed vessel for 18 hours. The cooled mixture was concentrated under reduced pressure and the residue partitioned between water and dichloromethane and the layers separated. The aqueous phase was extracted with dichloromethane, and the combined organic solutions were dried ($Na_2SO_4$), and evaporated under reduced pressure. The crude product was purified by column chromatography on silica gel using an elution gradient of dichloromethane:methanol (100:0 to 90:10), and triturated with ethyl acetate to afford the title compound as a white solid, 80 mg.

δ ($CDCl_3$): 1.01 (3H, t), 1.18 (3H, t), 1.57 (3H, t), 2.41 (2H, q), 2.58 (6H, m), 3.14 (4H, m), 4.77 (6H, m), 6.08 (1H, m), 6.96 (1H, d), 7.57 (1H, d), 8.62 (1H, d), 9.00 (1H, d), 10.67 (1H, s).

LRMS: m/z 556 $(M+1)^+$

EXAMPLE 12

5-[2-Ethoxy-5-(4-ethylpiperazin-1-ylsulphonyl)pyridin-3-yl]-3-ethyl-2-[2-(methylamino)ethyl]-2,6-dihydro-7H-pyrazolo[4,3-d]pyrimidin-7-one

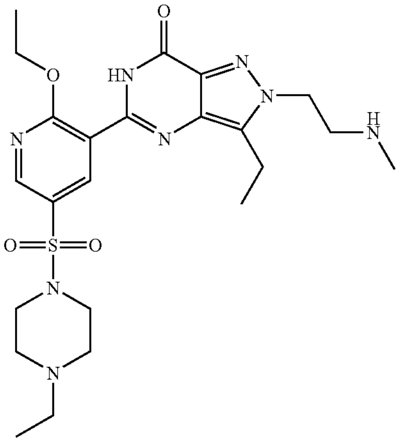

A mixture of the title compound of preparation 54 (130 mg, 0.24 mmol) and potassium bis(trimethylsilyl)amide (58 mg, 0.29 mmol) in ethanol (6 ml) was heated at 130° C. for 16 hours in a sealed vessel. The cooled mixture was concentrated under reduced pressure, the residue suspended in sodium bicarbonate solution (15 ml) and extracted with ethyl acetate (3×15 ml). The combined organic extracts were dried ($MgSO_4$) and evaporated under reduced pressure. The residual gum was purified by column chromatography on silica gel twice, using dichloromethane:methanol:0.88 ammonia (89:10:1) as eluant and repeated using ethyl acetate:methanol:diethylamine. (78:20:2) as eluant to afford the title compound, 32 mg, as a beige foam.

δ ($CDCl_3$): 1.02 (3H, t), 1.41 (3H, t), 1.58 (3H, t), 2.41 (2H, q), 2.56 (7H, m), 3.10 (6H, m), 3.27 (2H, t), 4.47 (2H, t), 4.77 (2H, q), 8.61 (1H, s), 9.00 (1H, s), 10.50–10.80 (1H, br s).

LRMS: m/z 519 $(M+1)^+$

EXAMPLES 13 TO 15

The following tabulated examples of the general structure:

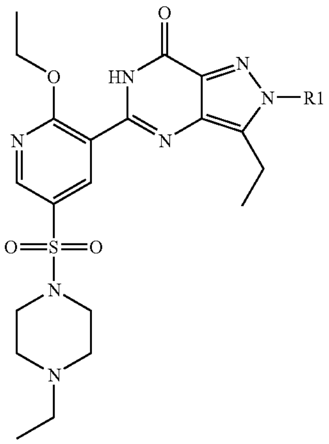

were prepared from the corresponding carboxamides, following a similar procedure to that described in example 12.

| Example | R1 | Yield (%) | $^1$Hnmr |
|---|---|---|---|
| 13[1] | 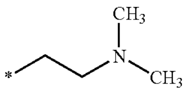 | 81 | δ($CDCl_3$): 1.02(3H, t), 1.42(3H, t), 1.58 3H, t), 2.30(6H, s), 2.41(2H, q), 2.56(4H, m), 2.90(2H, t), 3.05(2H, q), 3.14(4H, m), 4.40(2H, t), 4.75(2H, q), 8.61(1H, s), 9.02(1H, s), 10.62(1H, s). |
| 14[1] | 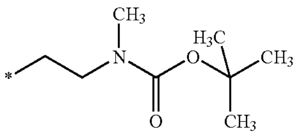 | 21 | δ($CDCl_3$): 1.03(3H, t), 1.40(3H, t), 1.44(9H, s), 1.58(3H, t), 2.41(2H, q), 2.54–2.68(7H, m), 3.01(2H, q), 3.16 (4H, m), 3.78(2H, t), 4.47(2H, m), 4.78 (2H, q), 8.63(1H, s), 9.04(1H, s), 10.66(1H, br s). |
| 15[1] | 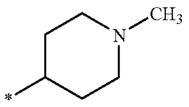 | 58 | δ($CDCl_3$): 1.02(3H, t), 1.40(3H, t), 1.58(3H, t), 1.93(2H, m), 2.16(2H, m), 2.36(3H, s), 2.41(2H, q), 2.56(6H, m), 3.04(4H, m), 3.14(4H, m), 4.22(1H, m), 4.77(2H, q), 8.62(1H, d), 9.01(1H, d), 10.54(1H, s). |

[1]column eluant of dichloromethane:methanol

EXAMPLE 16

5-[2-Ethoxy-5-(4-ethylpiperazin-1-ylsulphonyl)pyridin-3-yl]-3-ethyl-2-(1-methylazetidin-3-yl)-2,6-dihydro-7H-pyrazolo[4,3-d]pyrimidin-7-one

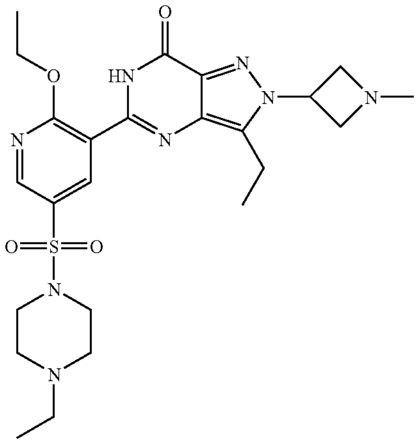

A mixture of the title compound from preparation 53 (470 mg, 0.86 mmol) and potassium bis(trimethylsilyl)amide (600 mg, 3.0 mmol) in ethanol (45 ml) was heated at 130° C. for 16 hours. The cooled mixture was concentrated under reduced pressure, the solution diluted with aqueous sodium bicarbonate solution to give pH 8, and extracted with ethyl acetate (3×). The combined organic extracts were dried ($MgSO_4$) and evaporated under reduced pressure. The crude product was purified by column chromatography on silica gel using dichloromethane:methanol:0.88 ammonia (91.75:7.5:0.75) as eluant to give the title compound, 170 mg.

δ ($CDCl_3$): 1.02 (3H, t), 1.38 (3H, t), 1.58 (3H, m), 2.40 (2H, q), 2.50 (3H, s), 2.57 (4H, m), 3.01 (2H, q), 3.16 (4H, m), 3.79 (2H, t), 3.90 (2H, t), 4.78 (2H, q), 5.12 (1H, m), 8.62 (1H, d), 9.01 (1H, d), 10.62 (1H, s).

EXAMPLE 17

5-[2-n-Butoxy-5-(4-ethylpiperazin-1-ylsulphonyl)pyridin-3-yl]-2-dimethylaminoethyl-3-ethyl-2,6-dihydro-7H-pyrazolo[4,3-d]pyrimidin-7-one

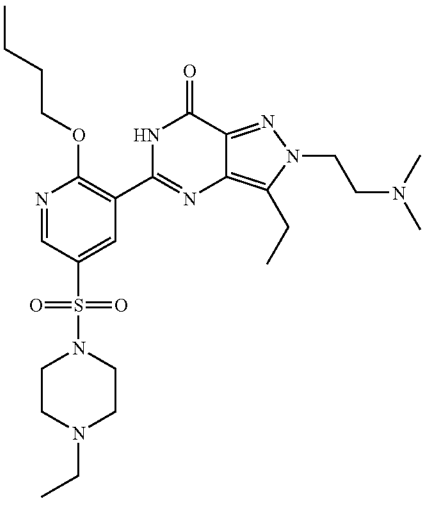

A mixture of the title compound from preparation 55 (150 mg, 0.27 mmol) and potassium bis(trimethylsilyl)amide (109 mg, 0.55 mmol) in n-butanol (5 ml) was heated at 120° C. for 16 hours in a sealed vessel. The cooled reaction mixture was poured into saturated aqueous sodium bicarbonate solution, and extracted with ethyl acetate. The combined organic extracts were dried ($MgSO_4$), and evaporated under reduced pressure. The crude product was purified by column chromatography on silica gel using dichloromethane:methanol (90:10) as eluant to afford the title compound as a white foam, 27 mg.

δ ($CDCl_3$): 1.02 (6H, m), 1.42 (3H, t), 1.57 (2H, m), 1.95 (2H, m), 2.30 (6H, s), 2.41 (2H, q), 2.57 (4H, m), 2.90 (2H, t), 3.05 (2H, q), 3.16 (4H, m), 4.40 (2H, t), 4.66 (2H, t), 8.61 (1H, d), 9.01 (1H, t), 10.60 (1H, s).

EXAMPLE 18

2-(Azetidin-3-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one ditrifluoroacetate

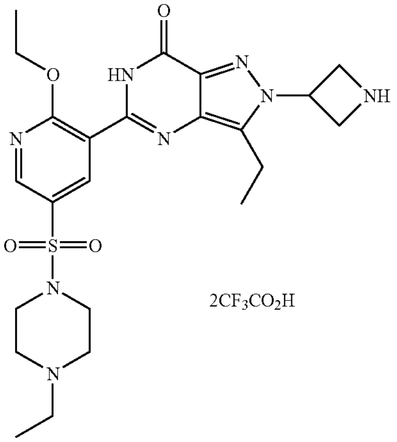

$2CF_3CO_2H$

Trifluoroacetic acid (3 ml) was added to a solution of the title compound from preparation 63 (350 mg, 0.57 mmol) in dichloromethane (3 ml), and the reaction stirred at room temperature for 2½ hours. The reaction was concentrated under reduced pressure and the residual gum was triturated several times with ether. The resulting suspension was sonicated for a minute, then the solid filtered, washed with ether, and dried to give the title compound as a white powder, 280 mg.

Found: C, 42.82; H, 4.80; N, 14.92. $C_{23}H_{32}N_8O_4S$; $2CF_3CO_2H;H_2O$ requires C, 42.52; H, 4.76; N, 14.69%.

δ ($DMSOd_6$): 1.14 (3H, m), 1.21 (3H, t), 1.34 (3H, t), 2.70–3.44 (12H, m), 4.47 (6H, m), 5.68 (1H, m), 8.24 (1H, s), 8.74 (1H, s), 9.14–9.30 (2H, m), 12.02 (1H, s).

EXAMPLE 19

2-(Azetidin-3-yl)-5-[5-(4-ethylpiperazin-1-ylsulphonyl)-2-(1-methylbutoxy)pyridin-3-yl]-3-ethyl-2,6-dihydro-7H-pyrazolo[4,3-d]pyrimidin-7-one ditrifluoroacetate

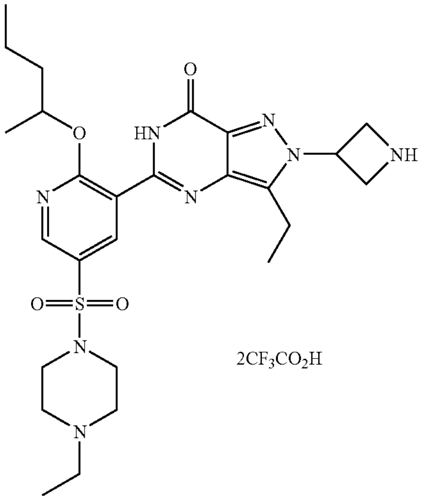

$2CF_3CO_2H$

The title compound was obtained as a beige-coloured powder, (51%), from the title compound of preparation 66, following a similar procedure to that described in example 18.

δ ($DMSOd_6$): 0.86 (3H, t), 1.07–1.46 (12H, m), 2.41–3.50 (12H, m), 4.49 (4H, m), 5.38 (1H, m), 5.68 (1H, m), 8.26 (1H, s), 8.74 (1H, s), 9.00 (1H, m), 9.26 (1H, m), 11.96 (1H, s).

EXAMPLE 20

5-[5-(4-Ethylpiperazin-1-ylsulphonyl)-2-n-propoxypyridin-3-yl]-3-ethyl-2-[2-(methylamino)ethyl]-2,6-dihydro-7H-pyrazolo[4,3-d]pyrimidin-7-one ditrifluoroacetate

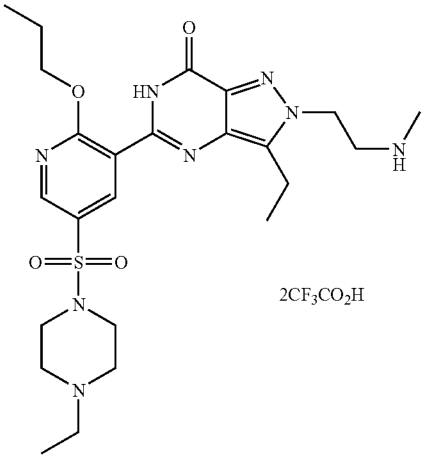

$2CF_3CO_2H$

The title compound was obtained as a white solid, (79%) from the title compound from preparation 61 and trifluoroacetic acid, following the procedure described in example 18.

δ ($DMSOd_6$): 0.94 (3H, t), 1.12 (3H, m), 1.26 (3H, t), 1.73 (2H, m), 2.41 (6H, m), 2.60 (3H, s), 2.68–3.60 (7H, m), 4.39 (2H, t), 4.60 (2H, t), 8.23 (1H, s), 8.57 (2H, m), 8.74 (1H, s), 11.94 (1H, s).

EXAMPLE 21

5-[2-Ethoxy-5-(4-ethylpiperazin-1-ylsulphonyl)pyridin-3-yl]-3-ethyl-2-(1-ethylazetidin-3-yl)-2,6-dihydro-7H-pyrazolo[4,3-d]pyrimidin-7-one

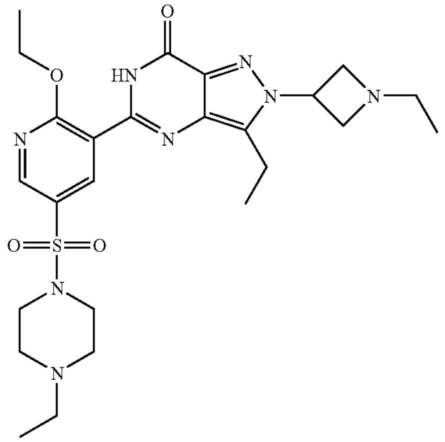

Sodium triacetoxyborohydride (81 mg, 0.38 mmol) was added to a solution of the title compound from example 18 (215 mg, 0.28 mmol), acetaldehyde (17.3 μl, 0.31 mmol), acetic acid (16 μl, 0.28 mmol) and triethylamine (7.9 μl, 0.28 mmol) in tetrahydrofuran (6 ml), and the reaction stirred at room temperature for 16 hours. The reaction mixture was diluted with saturated aqueous sodium bicarbonate solution (30 ml), and this mixture extracted with ethyl acetate (2×30 ml). The combined organic extracts were-dried ($MgSO_4$), and evaporated under reduced pressure. The residual gum was purified by column chromatography on silica gel using dichloromethane:methanol (90:10) as eluant, to give the title compound, 120 mg.

δ ($CDCl_3$): 1.04 (6H, m), 1.38 (3H, t), 1.58 (3H, t), 2.41 (2H, q), 2.57 (4H, m), 2.68 (2H, q), 3.01 (2H, q), 3.15 (4H, m), 3.76 (2H, m), 3.95 (2H, m), 4.76 (2H, q), 5.16 (1H, m), 8.63 (1H, d), 9.02 (1H, d), 10.68 (1H, s).

EXAMPLE 22

2-(1-Acetylazetidin-3-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

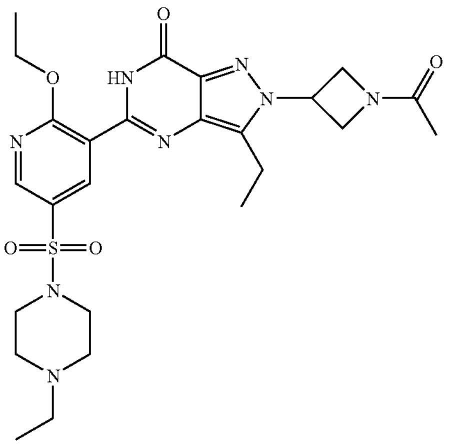

Acetyl chloride (6 mg, 0.076 mmol) was added to a mixture of the title compound from example 18 (43 mg, 0.056 mmol) and triethylamine (8.5 mg, 0.086 mmol) in dichloromethane (2 ml), and the reaction stirred for 36 hours at room temperature. The mixture was treated with aqueous saturated sodium bicarbonate solution and extracted with ethyl acetate (2×). The combined organic extracts were dried ($MgSO_4$), and evaporated under reduced pressure. The residual gum was purified by column chromatography on silica gel using an elution gradient of dichloromethane:methanol (97:3 to 95:5) to give the title compound, 19 mg.

δ ($CDCl_3$): 1.02 (3H, t), 1.38 (3H, t), 1.60 (3H, t), 1.98 (3H, s), 2.42 (2H, q), 2.58 (4H, m), 3.02 (2H, q), 3.16 (4H, m), 4.50 (2H, m), 4.59 (1H, m), 4.78 (2H, q), 5.05 (1H, m), 5.31 (1H, m), 8.62 (1H, d), 9.01 (1H, d), 10.70 (1H, s).

EXAMPLE 23

2-(1-Acetylpiperidin-4-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

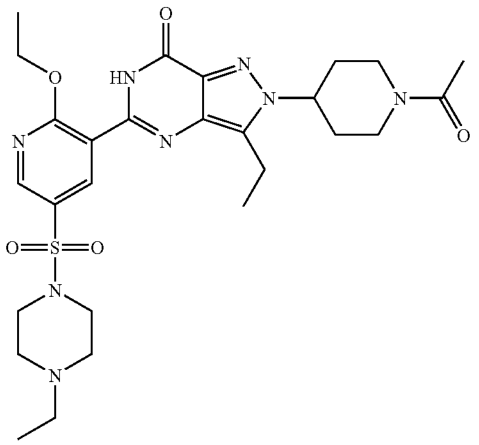

The title compound was obtained (30%) from the compound of preparation 68, and acetyl chloride, following the procedure described in example 22.

δ ($CDCl_3$): 1.02 (3H, t), 1.40 (3H, t), 1.56 (3H, t), 2.00 (2H, m), 2.17 (3H, s), 2.23–2.44 (4H, m), 2.55 (4H, m), 2.78 (1H, m), 3.09 (6H, m), 3.27 (1H, m), 4.06 (1H, m), 4.50 (1H, m), 4.70–4.90 (3H, m), 8.62 (1H, d), 9.02 (1H, d), 10.60 (1H, s).

EXAMPLE 24

2-[2-[Acetyl(methyl)amino]ethyl-5-[5-(4-ethylpiperazin-1-ylsulphonyl)-2-n-propoxypyridin-3-yl]-3-ethyl-2,6-dihydro-7H-pyrazolo[4,3-d]pyrimidin-7-one

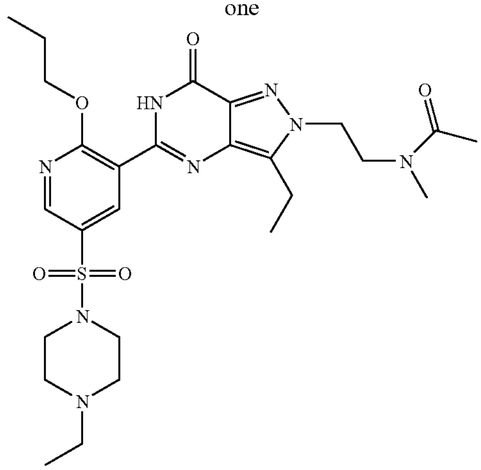

The title compound was obtained (74%) from the compound of example 20, and acetyl chloride, following the procedure described in example 22.

δ ($CDCl_3$): 1.02 (3H, t), 1.14 (3H, t), 1.40 (3H, t), 1.99 (2H, m), 2.06 (3H, s), 2.42 (2H, q), 2.57 (4H, m), 2.80 (3H, s), 3.01 (2H, q), 3.16 (4H, m), 3.93 (2H, t), 4.50 (2H, t), 4.62 (2H, t), 8.62 (1H, d), 9.04 (1H, d), 10.66 (1H, s).

EXAMPLE 25

5-[2-Ethoxy-5-(4-ethylpiperazin-1-ylsulphonyl)pyridin-3-yl]-3-ethyl-2-[1-(methylsulphonyl)piperidin-4-yl]-2,6-dihydro-7H-pyrazolo[4,3-d]pyrimidin-7-one

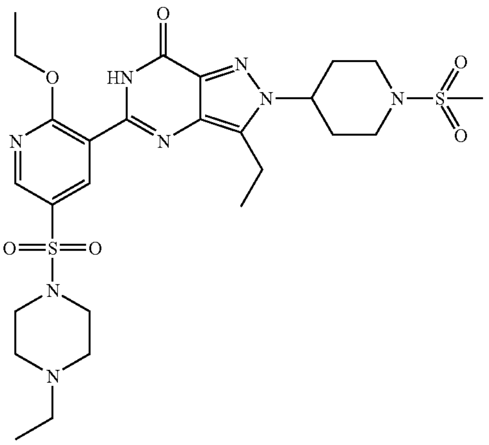

The title compound was obtained (33%) from the title compound from preparation 68 and methanesulphonic anhydride, following a similar procedure to that described in example 22.

δ ($CDCl_3$): 1.02 (3H, t), 1.40 (3H, t), 1.58 (3H, t), 2.10 (2H, m), 2.40 (2H, q), 2.56 (6H, m), 2.90 (3H, s), 3.00–3.20 (8H, m), 4.01 (2H, m), 4.21 (1H, m), 4.78 (2H, q), 8.62 (1H, d), 9.01 (1H, s), 10.61 (1H, s).

EXAMPLE 26

2-(1-Acetylazetidin-3-yl)-5-[2-n-butoxy-5-(4-ethylpiperazin-1-ylsulphonyl)pyridin-3-yl]-3-ethyl-2,6-dihydro-7H-pyrazolo[4,3-d]pyrimidin-7-one

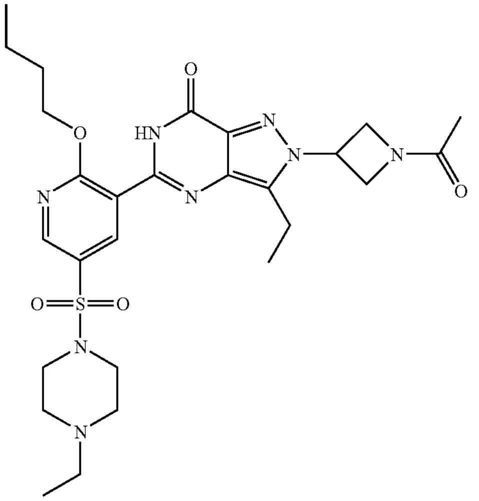

Trifluoroacetic acid (0.5 ml) was added to a solution of the title compound from preparation 65 (28 mg, 0.043 mmol) in dichloromethane (0.5 ml), and the solution stirred for 2½ hours at room temperature. The mixture was evaporated under reduced pressure and the residue triturated with ether several times. The resulting precipitate was filtered off, washed with ether and dried, to give a beige-coloured solid.

Acetyl chloride (16 μl, 0.22 mmol) was added to a solution of this intermediate in dichloromethane (3 ml) and triethylamine (61 μl, 0.44 mmol), and the reaction stirred at room temperature for 16 hours. Aqueous saturated sodium bicarbonate solution (10 ml) was added, and the mixture extracted with ethyl acetate. The combined organic extracts were dried ($MgSO_4$) and evaporated under reduced pressure to give a gum. The crude product was purified by column chromatography on silica gel using an elution gradient of dichloromethane:methanol (98:2 to 95:5) to give the title compound, 7 mg.

δ ($CDCl_3$): 1.02 (6H, m), 1.38 (3H, t), 1.57 (2H, m), 1.94 (5H, m), 2.40 (2H, q), 2.47 (4H, m), 3.02 (2H, q), 3.14 (4H, m), 4.50 (2H, m), 4.59 (1H, m), 4.67 (2H, m), 5.06 (1H, m), 5.31 (1H, m), 8.62 (1H, d), 9.01 (1H, d), 10.68 (1H, s).

EXAMPLE 27

5-[2-iso-Butoxy-5-(4-ethylpiperazin-1-ylsulphonyl)pyridin-3-yl]-2-(2-methoxyethyl)-3-n-propyl-2,6-dihydro-7H-pyrazolo[4,3-d]pyrimidin-7-one

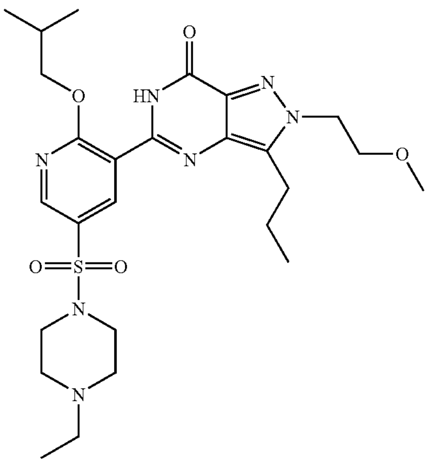

Potassium bis(trimethylsilyl)amide (149.7 mg, 0.75 mmol) was added to a solution of the title compound of example 3 (80 mg, 0.15 mmol) in 2-methyl-n-propanol (5 ml) and the reaction stirred at 120° C. for 18 hours. The cooled mixture was concentrated under reduced pressure and the residue suspended in water (10 ml), and extracted with ethyl acetate (3×10 ml). The combined organic extracts were dried ($MgSO_4$) and evaporated under reduced pressure. The crude product was purified by column chromatography on silica gel, using an elution gradient of dichloromethane:methanol (100:0 to 95:5) to afford the title compound, 67 mg, as a solid.

Found: C, 54.92; H, 7.08; N, 16.92. $C_{26}H_{39}N_7O_5S$; $0.7H_2O$ requires C, 54.38; H, 7.09; N, 17.07%

δ ($CDCl_3$): 1.03 (6H, m), 1.14 (6H, d), 1.83 (2H, m), 2.30 (1H, m), 2.41 (2H, q), 2.55 (4H, m), 3.01 (2H, t), 3.13 (4H, m), 3.30 (3H, s), 3.90 (2H, t), 4.46 (4H, m), 8.61 (1H, s), 9.01 (1H, s), 10.60 (1H, s).

LRMS: m/z 562 $(M+1)^+$

EXAMPLES 28 TO 33

The compounds of the following tabulated examples of general formula:

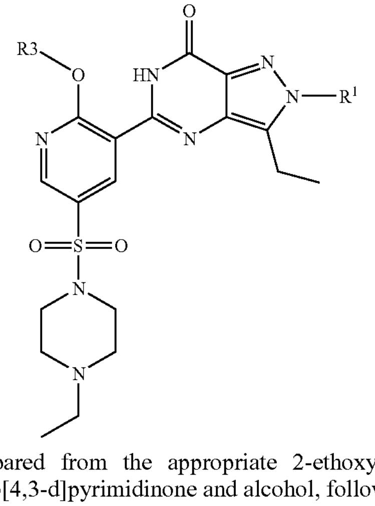

were prepared from the appropriate 2-ethoxypyridin-3-ylpyrazolo[4,3-d]pyrimidinone and alcohol, following similar procedures to that described in example 27.

| Ex | $R_1$ | $R_3$ | Data |
|---|---|---|---|
| 28 | 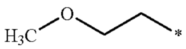 | 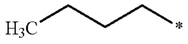 | Found: C, 54.88; H, 7.08; N, 17.13, $C_{26}H_{39}N_7O_5S$; $0.6H_2O$ requires C, 54.55; H, 7.08; N, 17.13% δ($CDCl_3$): 1.02(6H, 2xt), 1.40(3H, t), 1.56(2H, m), 1.83(2H, m), 1.94(2H, m), 2.41(2H, q), 2.55(4H, m), 3.00(2H, t), 3.16(4H, m), 3.30(3H, s), 3.92(2H, t), 4.45(2H, t), 4.67(2H, t), 8.61(1H, s), 9.01(1H, s), 10.60(1H, s). LRMS:m/z 562$(M + 1)^+$ |
| 29 | 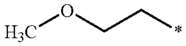 | 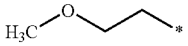 | Found: C, 52.90; H, 6.79; N, 16.86, $C_{25}H_{37}N_7O_6S$ requires C, 53.27; H, 6.62; N, 17.36% δ($CDCl_3$): 1.02(6H, m), 1.84(2H, m), 2.42(2H, q), 2.56(4H, m), 3.01(2H, t), 3.15(4H, m), 3.29(3H, s), 3.57(3H, s), 3.88(4H, m), 4.44(2H, t), 4.78(2H, t), 8.61(1H, s), 8.98(1H, s), 10.76(1H, s). LRMS: m/z 564 $(M + 1)^+$ |
| 30 | 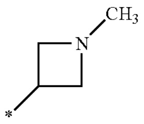 | n-Bu | δ($CDCl_3$): 1.02(6H, t), 1.38(3H, t), 1.57(2H, m), 1.96 (2H, m), 2.41(2H, q), 2.50(3H, s), 2.56(4H, m), 3.00 (2H, q), 3.15(4H, m), 3.79(2H, t), 3.94(2H, t), 4.68 (2H, t), 5.12(1H, m), 8.62(1H, d), 9.01(1H, d), 10.61 (1H, s). |
| 31 | 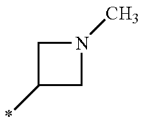 | 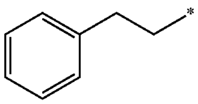 | δ($CDCl_3$): 1.01(3H, t), 1.37(3H, t), 2.40(2H, q), 2.55 (7H, m), 3.00(2H, q), 3.13(4H, m), 3.25(2H, t), 3.80 (2H, t), 3.95(2H, t), 4.88(2H, t), 5.12(1H, m), 7.22 (2H, m), 7.38(3H, m), 8.62(1H, d), 9.00(1H, d), 10.49 (1H, s). |
| 32 | 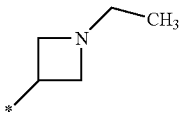 | n-Bu | δ($CDCl_3$): 1.02(9H, t), 1.38(3H, t), 1.57(2H, m), 1.96 (2H, m), 2.41(2H, q), 2.56(4H, m), 2.67(2H, q), 3.01 (2H, q), 3.15(4H, m), 3.74(2H, t), 3.90(2H, t), 4.68 (2H, t), 5.17(1H, m), 8.62(1H, d), 9.01(1H, d), 10.60 (1H, s). |
| 33 | 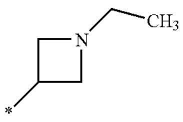 | 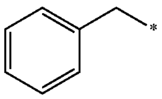 | δ($CDCl_3$): 1.02(6H, m), 1.37(3H, t), 2.41(2H, q), 2.57 (4H, m), 2.69(2H, q), 3.01(2H, q), 3.15(4H, m), 3.76 (2H, t), 3.95(2H, t), 5.18(1H, m), 5.77(2H, s), 7.38 (3H, m), 7.50(2H, m), 8.63(1H, d), 9.00(1H, d), 10.59 (1H, br s). |

wherein for examples 28 and 29 R2 is n-propyl and for examples 30 to 33 R2 is ethyl.

EXAMPLE 34

5-[2-iso-Butoxy-5-(4-methylpiperazin-1-ylsulphonyl)pyridin-3-yl]-3-ethyl-2-(2-methoxyethyl)-2,6-dihydro-7H-pyrazolo[4,3-d]pyrimidin-7-one

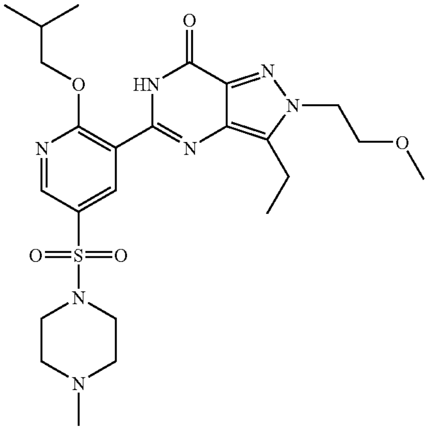

Potassium bis(trimethylsilyl)amide (306 mg, 1.54 mmol) was added to a solution of the title compound of example 2 (155 mg, 0.31 mmol) in 2-methyl-n-propanol (10 ml) and the reaction stirred under reflux for 24 hours. The cooled mixture was evaporated under reduced pressure and the residue purified by column chromatography on silica gel, using an elution gradient of dichloromethane:methanol (100:0 to 95:5) to afford the title compound, 88 mg, as a solid.

Found: C, 52.45; H, 6.43; N, 17.33. $C_{24}H_{35}N_7O_5S$; $1.1H_2O$ requires C, 52.08; H, 6.77; N, 17.71%

δ ($CDCl_3$): 1.14 (6H, d), 1.41 (3H, t), 2.30 (4H, m), 2.52 (4H, m), 3.07 (2H, q), 3.15 (4H, m), 3.30 (3H, s), 3.92 (2H, t), 4.46 (4H, m), 8.62 (1H, s), 9.03 (1H, s).

LRMS: m/z 534 $(M+1)^+$

EXAMPLES 35 TO 40

The compounds of the following tabulated examples of the general formula:

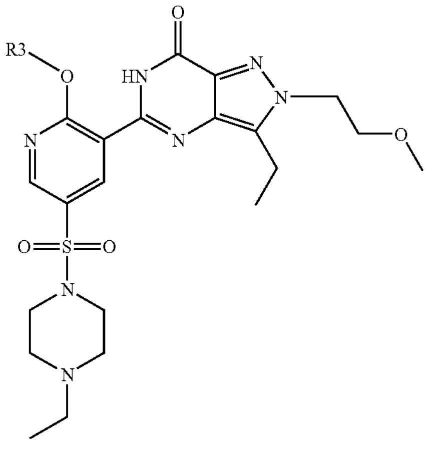

were prepared from the title compound of example 8 and the appropriate alcohol, following similar procedures to that described in example 34.

| Ex | R3 | Data |
|---|---|---|
| 35 | 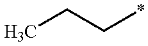 | δ($CDCl_3$): 1.02(3H, t), 1.40(3H, t), 1.52(3H, t), 1.98 (2H, m), 2.40(2H, q), 2.57(4H, m), 3.14(6H, m), 3.32 (3H, s), 3.94(2H, t), 4.46(2H, t), 4.62(2H, t), 8.61(1H, s), 9.02(1H, s), 10.62(1H, s). LRMS: m/z 534$(M + 1)^+$ |
| 36 | 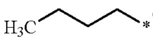 | δ($CDCl_3$): 1.04(6H, 2xt), 1.40(3H, t), 1.55(2H, m), 1.95(2H, m), 2.42(2H, q), 2.55(4H, m), 3.07(2H, q), 3.15(4H, m), 3.30(3H, s), 3.92(2H, t), 4.46(2H, t), 4.66 (2H, t), 8.62(1H, s), 9.02(1H, s), 10.60(1H, s). LRMS: m/z 548$(M + 1)^+$ |
| 37 | 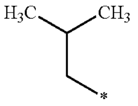 | Found: C, 54.77; H, 6.82; N, 17.75. $C_{25}H_{37}N_7O_5S$ requires C, 54.83; H, 6.81; N, 17.90% δ($CDCl_3$): 1.02(3H, t), 1.12(6H, d), 1.40(3H, t), 2.30 (1H, m), 2.42(2H, q), 2.57(4H, m), 3.08(2H, q), 3.13 (4H, m), 3.30(3H, s), 3.90(2H, t), 4.46(4H, m). 8.62 (1H, s), 9.02(1H, s), 10.60(1H, s). LRMS:m/z 548$(M + 1)^+$ |
| 38[1] | 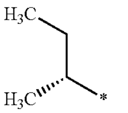 | Found: C, 54.76; H, 6.79; N, 17.72. $C_{25}H_{37}N_7O_5S$ requires C, 54.83; H, 6.81; N, 17.90% δ($CDCl_3$): 1.03(6H, m), 1.40(3H, t), 1.50(3H, d), 1.85 (1H, m), 1.98(1H, m), 2.41(2H, q), 2.58(4H, m), 3.07 2H, q), 3.15(4H, m), 3.30(3H, s),3.92(2H, t), 4.47 (2H, t), 5.57(1H, m), 8.61(1H, s), 9.03(1H, s), 10.65 (1H, s). LRMS: m/z 548$(M + 1)^+$ |
| 39[1] | 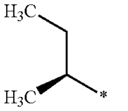 | Found: C, 55.03; H, 6.97; N, 16.84. $C_{25}H_{37}N_7O_5S$ requires C, 54.83; H, 6.81; N, 17.90% δ($CDCl_3$): 1.04(6H, t), 1.40(3H, t), 1.50(3H, d), 1.83 (1H, m), 1.98(1H, m), 2.42(2H, q), 2.58(4H, m), 3.07 (2H, q), 3.15(4H, m), 3.30(3H, s), 3.92(2H, t), 4.46 (2H, t), 5.55(1H, m), 8.61(1H, s), 9.04(1H, s),10.64 (1H, s). LRMS: m/z 548$(M + 1)^+$ |

-continued

| Ex | R3 | Data |
|---|---|---|
| 40 | 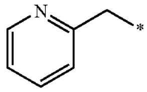 | Found: C, 54.91; H, 5.91; N, 18.85.<br>$C_{27}H_{34}N_8O_5S$;<br>$0.5H_2O$ requires C, 54.81; H, 5.96; N, 18.94%<br>δ($CDCl_3$):<br>1.02(3H, t), 1.42(3H, t), 2.42(2H, q), 2.57 (4H, m), 3.12(6H, m),<br>3.30(3H, s), 3.94(2H, t), 4.46 (2H, t), 5.90(2H, s),<br>7.35(2H, m), 7.78(1H, m), 8.59 (1H, s), 8.84(2H, m), 12.70(1H, s).<br>LRMS:m/z 583(M + 1)$^+$ |

[1]purified using an elution gradient of ethyl acetate:methanol (95:5 to 90:10), followed by ether trituration

EXAMPLE 41

2-(sec-Butyl)-3-Ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one

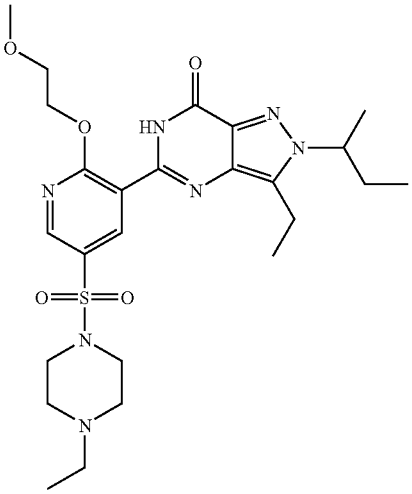

A solution of the title compound from example 4 (129 mg, 0.25 mmol) in 2-methoxyethanol (10 ml) was heated at 110° C. for 15 minutes, then cooled. Potassium bis(trimethylsilyl) amide (249 mg, 1.50 mmol) was added and the reaction stirred at 130° C. for 22 hours. The cooled mixture was partitioned between ethyl acetate and aqueous sodium bicarbonate solution, and the layers separated. The organic phase was dried ($MgSO_4$) and evaporated under reduced pressure. The residue was purified by column chromatography on silica gel using dichloromethane:methanol (98:2) as eluant to afford the title compound as a yellow foam, 59 mg.

δ ($CDCl_3$): 0.79 (3H, t), 1.03 (3H, t), 1.39 (3H, t), 1.60 (3H, d), 1.90 (1H, m), 2.22 (1H, m), 2.41 (2H, q), 2.57 (4H, m), 2.97–3.18 (6H, m), 3.57 (3H, s), 3.85 (2H, m), 4.40 (1H, m), 4.78 (2H, m), 8.62 (1H, s), 8.98 (1H, s), 10.76 (1H, s).

LRMS: m/z 548 (M+1)$^+$

EXAMPLE 42

2-Cyclobutylmethyl-3-Ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one

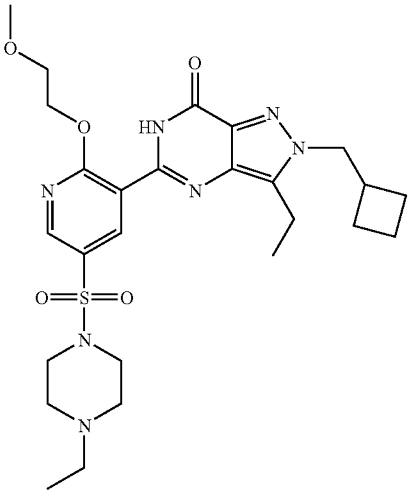

The title compound was obtained as a white solid (64%) from the title compound from example 7 and 2-methoxyethanol, following the procedure described in example 41.

δ ($CDCl_3$): 1.01 (3H, t), 1.40 (3H, t), 1.80–1.98 (5H, m), 2.05 (2H, m), 2.40 (2H, q), 2.54 (4H, m), 3.00 (2H, m), 3.15 (4H, m), 3.55 (3H, s), 3.83 (2H, t), 4.30 (2H, d), 4.76 (2H, t), 8.60 (1H, s), 8.96 (1H, d), 10.74 (1H, br s).

EXAMPLE 43

3-Ethyl-5-[5-(4-ethylpiperazin-1-ylsulphonyl)-2-(2-methoxyethoxy)pyridin-3-yl]-2-(2-methoxy-1-methylethyl)-2,6-dihydro-7H-pyrazolo[4,3-d]pyrimidin-7-one

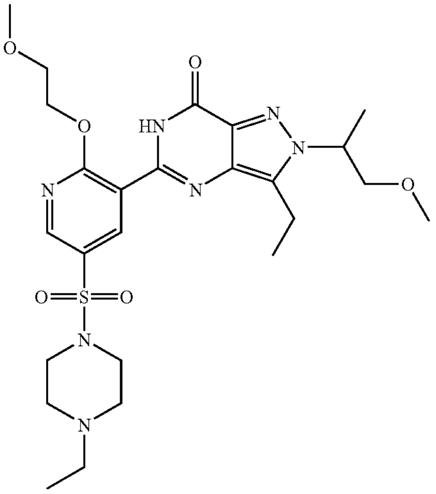

The title compound was obtained as a yellow foam (57%) from the title compound from example 9 and 2-methoxyethanol, following the procedure described in example 41.

δ ($CDCl_3$): 1.02 (3H, t), 1.38 (3H, t), 1.59 (3H, d), 2.41 (2H, q), 2.56 (4H, m), 3.05 (6H, m), 3.22 (3H, s), 3.56 (3H, s), 3.72 (1H, m), 3.84 (2H, m), 3.96 (1H, dd), 4.71 (1H, m), 4.78 (2H, m), 8.61 (1H, s), 8.97 (1H, s), 10.78 (1H, br s).

EXAMPLE 44

3-Ethyl-5-[5-(4-ethylpiperazin-1-ylsulphonyl)-2-(2-methoxy-1-methylethoxy)sulphonyl)pyridin-3-yl]-2-(2-methoxyethyl)-2,6-dihydro-7H-pyrazolo[4,3-d]pyrimidin-7-one and

EXAMPLE 45

3-Ethyl-5-[5-(4-ethylpiperazin-1-ylsulphonyl)-2-(2-methoxy-1-methylethoxy)sulphonyl)pyridin-3-yl]-2-(2-methoxyethyl)-2,6-dihydro-7H-pyrazolo[4,3-d]pyrimidin-7-one

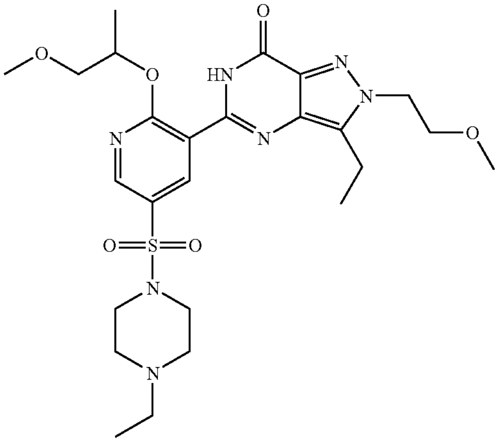

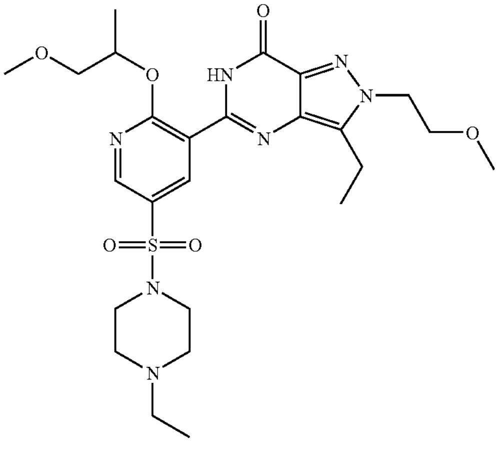

A mixture of the title compound from example 8 (250 mg, 0.48 mmol) and potassium bis(trimethylsilyl)amide (480 mg, 2.41 mmol) in 1-methoxy-2-propanol (20 ml) was heated at 120° C. for 18 hours. The cooled mixture was evaporated under reduced pressure and the residue purified by column chromatography on silica gel using an elution gradient of dichloromethane:methanol (100:0 to 95:5) to give a white solid. This material was purified by HPLC, using a Chiralpak AD 250 column, with hexane: 1% diethylamine in isopropanol (85:15) as eluant, to give the title compound of example 44, 49 mg, δ ($CDCl_3$): 1.02 (3H, t), 1.40 (3H, t), 1.50 (3H, m), 2.42 (2H, q), 2.57 (4H, m), 3.06 (2H, m), 3.15 (4H, m), 3.30 (3H, s), 3.55 (3H, s), 3.64 (1H, m), 3.76 (1H, m), 3.92 (2H, t), 4.45 (2H, t), 5.60 (1H, m), 8.60 (1H, s), 8.90 (1H, s), 10.80 (1H, s).

LRMS: m/z 564 $(M+1)^+$ and the title compound of example 45, 39 mg.

δ ($CDCl_3$): 1.04 (3H, t), 1.40 (3H, t), 1.50 (3H, d), 2.42 (2H, q), 2.57 (4H, m), 3.07 (2H, q), 3.16 (4H, m), 3.29 (3H, s), 3.56 (3H, s), 3.64 (1H, m), 3.75 (1H, m), 3.90 (2H, t), 4.45 (2H, t), 5.60 (1H, m), 8.60 (1H, s), 8.90 (1H, s), 10.80 (1H, s).

LRMS: m/z 564 $(M+1)^+$

EXAMPLE 46

5-[5-(4-Ethylpiperazin-1-ylsulphonyl)-2-(2-methoxy-1-methylethoxy)sulphonyl)pyridin-3-yl]-2-(2-methoxyethyl)-3-n-propyl-2,6-dihydro-7H-pyrazolo[4,3-d]pyrimidin-7-one and

EXAMPLE 47

5-[5-(4-Ethylpiperazin-1-ylsulphonyl)-2-(2-methoxy-1-methylethoxy)sulphonyl)pyridin-3-yl]-2-(2-methoxyethyl)-3-n-propyl-2,6-dihydro-7H-pyrazolo[4,3-d]pyrimidin-7-one

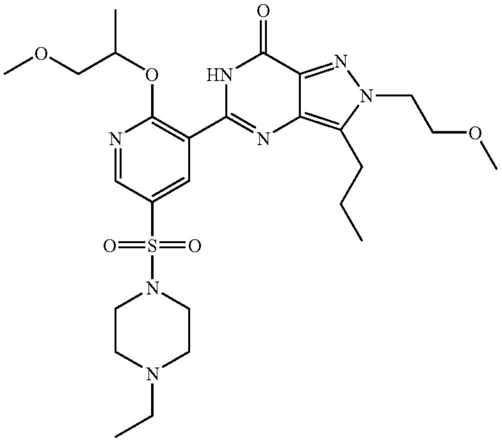

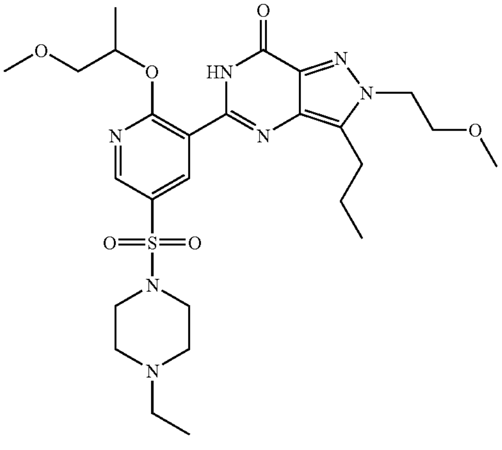

A mixture of the title compound from example 3 (345 mg, 0.65 mmol) and potassium bis(trimethylsilyl)amide (645 mg, 3.24 mmol) in 1-methoxy-2-propanol (2.5 ml) was heated at 110° C. for 16 hours. The cooled mixture was diluted with ethyl acetate, then washed with aqueous ammonium chloride solution, then water, dried ($MgSO_4$), and evaporated under reduced pressure. The residue was purified by column chromatography on silica gel using dichloromethane:methanol (97:3) as eluant to give a yellow gum.

This material was purified by HPLC, using a Chiralpak AD 250 column, with hexane:1% diethylamine in isopropanol (85:15) as eluant, to give the title compound of example 46, 17 mg, δ ($CDCl_3$): 1.02 (6H, m), 1.50 (3H, d), 1.81 (2H, m), 2.41 (2H, q), 2.56 (4H, m), 3.00 (2H, m), 3.14 (4H, m), 3.28 (3H, s), 3.55 (3H, s), 3.62–3.78 (2H, m), 3.90 (2H, t), 4.44 (2H, t), 5.60 (1H, m), 8.60 (1H, s), 8.89 (1H, s), 10.80 (1H, s).

LRMS: m/z 578 $(M+1)^+$ and the title compound of example 47, 64 mg.

δ ($CDCl_3$): 1.01 (6H, m), 1.48 (3H, d), 1.81 (2H, m), 2.40 (2H, q), 2.54 (4H, m), 2.99 (2H, t), 3.10 (4H, m), 3.27 (3H, s), 3.51 (3H, s), 3.60–3.76 (2H, m), 4.87 (2H, t), 4.44 (2H, t), 5.59 (1H, m), 8.60 (1H, s), 8.86 (1H, s).

LRMS: m/z 578 $(M+1)^+$

EXAMPLE 48

3-Ethyl-5-[5-(4-ethylpiperazin-1-ylsulphonyl)-2-(2-methoxy-1-methylethoxy)pyridin-3-yl]-2-(2-hydroxyethyl)-2,6-dihydro-7H-pyrazolo[4,3-d]pyrimidin-7-one and

EXAMPLE 49

5-[2-Ethoxy-5-(4-ethylpiperazin-1-ylsulphonyl)pyridin-3-yl]-3-ethyl-2-(2-hydroxyethyl)-2,6-dihydro-7H-pyrazolo[4,3-d]pyrimidin-7-one

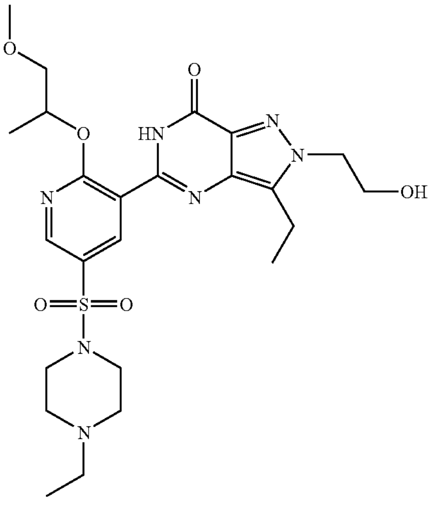

-continued

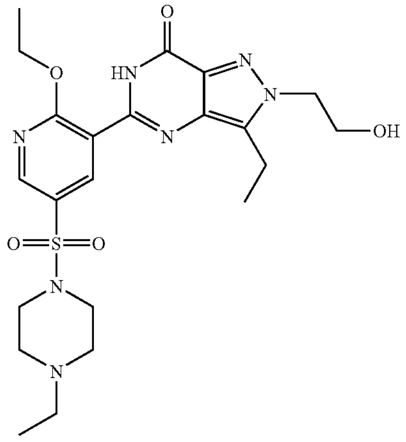

Potassium bis(trimethylsilyl)amide (200 mg, 1.0 mmol) was added to a solution of the title compound from preparation 60 (120 mg, 0.2 mmol) in 1-methoxy-2-propanol (10 ml), and the reaction heated under reflux for 18 hours. The cooled mixture was evaporated under reduced pressure and the residue purified by column chromatography on silica gel using an elution gradient of dichloromethane:methanol (100:0 to 90:10) to give the title compound of example 48, 8 mg.

δ ($CDCl_3$) 1.02 (3H, t), 1.40 (3H, t), 1.50 (3H, d), 2.41 (2H, q), 2.58 (4H, m), 3.10 (7H, m), 3.58 (3H, s), 3.70 (2H, m), 4.20 (2H, m), 4.40 (2H, m), 5.59 (1H, m), 8.61 (1H, d), 8.88 (1H, d), 10.90 (1H, s).

LRMS: m/z 550 $(M+1)^+$ and the title compound of example 49 as a white solid.

δ ($CDCl_3$): 1.02 (3H, t), 1.40 (3H, t), 1.58 (3H, t), 2.41 (2H, q), 2.56 (4H, m), 2.87 (1H, br s), 3.02–3.19 (6H, m), 4.22 (2H, m), 4.42 (2H, t), 4.77 (2H, q), 8.62 (1H, s), 9.02 (1H, s), 10.66 (1H, s).

LRMS: m/z 506 $(M+1)^+$

EXAMPLE 50

2-(2-Ethoxyethyl)-5-[5-(4-ethylpiperazin-1-ylsulphonyl)-2-(2-methoxyethoxy)pyridin-3-yl]-3-ethyl-2,6-dihydro-7H-pyrazolo[4,3-d]pyrimidin-7-one

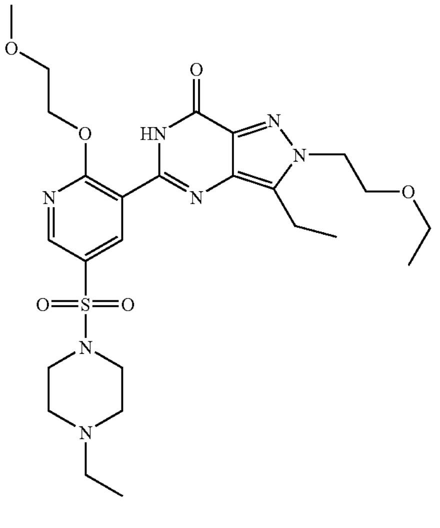

Potassium bis(trimethylsilyl)amide (359 mg, 1.8 mmol) was added to a solution of the title compound from preparation 70 (250 mg, 0.45 mmol) in 2-methoxyethanol (5 ml), and the reaction heated under reflux for 6 hours. Tlc analysis showed starting material remaining, so additional potassium bis(trimethylsilyl)amide (90 mg, 0.45 mmol) was added to the cooled mixture, and the reaction stirred for a further 4 hours under reflux. The cooled mixture was concentrated under reduced pressure and the residue purified by column chromatography on silica gel using dichloromethane:methanol (95:5) as eluant. The product was triturated with ether and pentane to afford the title compound as a crystalline solid, 75 mg.

Found: C, 52.88; H, 6.59; N, 17.39. $C_{25}H_{37}N_7O_6S$ requires C, 53.27; H, 6.62; N, 17.39% d ($CDCl_3$): 1.02 (3H, t), 1.12 (3H, t), 1.40 (3H, t), 2.41 (2H, q), 2.57 (5H, m), 3.06 (2H, q), 3.15 (4H, m), 3.42 (2H, q), 3.57 (3H, s), 3.85 (2H, t), 3.94 (2H, t), 4.44 (2H, t), 4.78 (2H, t), 8.61 (1H, s), 8.98 (1H, s), 10.78 (1H, s).

EXAMPLE 51

2-(iso-Butyl)-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one

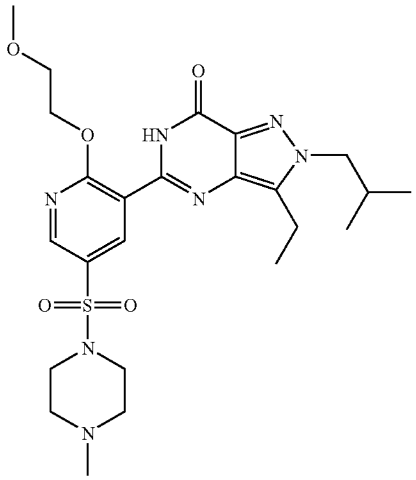

Potassium bis(trimethylsilyl)amide (732 mg, 3.68 mmol) was added to a solution of the title compound from preparation 40 (958 mg, 1.84 mmol) in 2-methoxyethanol (20 ml) and the reaction stirred for 16 hours at 120° C. The cooled mixture was concentrated under reduced pressure, the residue dissolved in water (25 ml) and the pH adjusted to 2 using hydrochloric acid (2N). The solution was washed with ethyl acetate, neutralised and the resulting precipitate filtered off. The solid was dissolved in ethyl acetate, evaporated under reduced pressure and the crude product was purified by column chromatography on silica gel using dichloromethane:methanol:0.88 ammonia (95:5:0.5) as eluant to give the title compound, 53 mg.

δ ($CDCl_3$): 0.97 (6H, d), 1.40 (3H, t), 2.28 (4H, m), 2.52 (4H, m), 3.02 (2H, q), 3.16 (4H, m), 3.57 (3H, s), 3.86 (2H, t), 4.10 (2H, d), 4.78 (2H, t), 8.61 (1H, d) 8.98 (1H, d), 10.79 (1H, s).

LRMS: m/z 534 $(M+1)^+$

EXAMPLE 52

2-(iso-Butyl)-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one

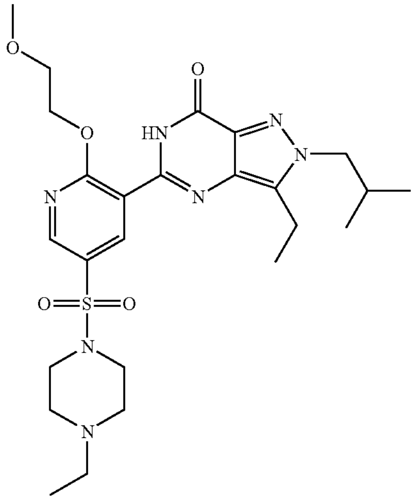

Potassium bis(trimethylsilyl)amide (1.85 g, 9.35 mmol) was added to a solution of the title compound from preparation 36 (1.0 g, 1.89 mmol) in 2-methoxyethanol (8 ml) and the reaction stirred for 18 hours at 120° C. The cooled mixture was concentrated under reduced pressure, and the residue partitioned between water (200 ml) and dichloromethane (200 ml). The resulting precipitate was filtered off, and the layers separated. The aqueous phase was extracted with dichloromethane (2×200 ml), and the combined organic solutions evaporated under reduced pressure, to give a cream solid. The isolated solids were combined and purified by column chromatography on silica gel using dichloromethane:methanol (90:10) as eluant to give the title compound as a pale yellow solid, 220 mg.

δ ($CDCl_3$): 0.95 (6H, d), 1.05 (3H, t), 1.40 (3H, d), 2.40 (3H, m), 2.55 (4H, m), 3.00 (2H, q), 3.10 (4H, m), 3.55 (3H, s), 3.85 (2H, t), 5.05 (2H, d), 4.80 (2H, t), 8.60 (1H, s), 8.95 (1H, s), 10.80 (1H, s).

LRMS: m/z 549 $(M+1)^+$

EXAMPLE 53

2-Cyclobutylmethyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidin-7-one

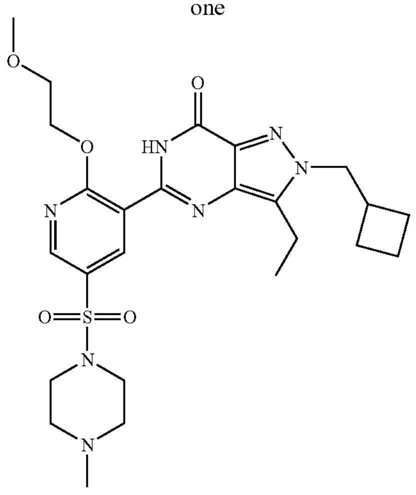

The title compound was obtained as a beige solid (31%) from the title compound from preparation 41 and 2-methoxyethanol, using a similar procedure to that described 52.

δ ($CDCl_3$): 1.41 (3H, t), 1.88 (4H, m), 2.07 (2H, m), 2.26 (3H, s), 2.52 (4H, m), 3.00 (3H, m), 3.15 (4H, m), 3.57 (3H, s), 3.86 (2H, m), 4.33 (2H, d), 4.79 (2H, t), 8.62 (1H, s), 8.98 (1H, s), 10.75 (1H, s).

EXAMPLE 54

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one

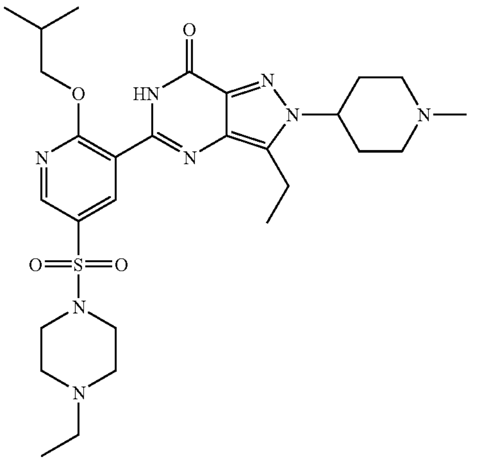

A mixture of the title compound from preparation 52 (90 mg, 0.156 mmol), potassium bis(trimethylsilyl)amide (156 mg, 0.78 mmol) and ethyl acetate (14 mg, 0.156 mmol) in iso-propanol (12 ml) was stirred at 130° C. for 6 hours in a sealed vessel. The cooled reaction mixture was poured into saturated aqueous sodium bicarbonate solution (60 ml), and extracted with ethyl acetate (60 ml). The combined organic extracts were dried ($MgSO_4$), and evaporated under reduced pressure to give a gum. The crude product was purified by column chromatography on silica gel using dichloromethane:methanol:0.88 ammonia (92.6:6.6:0.6) to afford the title compound as a beige foam, 36 mg.

δ ($CDCl_3$): 1.01 (3H, t), 1.12 (6H, d), 1.39 (3H, t), 1.94 (2H, m), 2.15 (2H, m), 2.22–2.44 (6H, m), 2.55 (6H, m), 3.02 (4H, m), 3.14 (4H, m), 4.22 (1H, m), 4.43 (2H, d), 8.60 (1H, d), 9.00 (1H, d), 10.54 (1H, s).

EXAMPLES 55 TO 58

The compounds of the following tabulated examples of general formula:

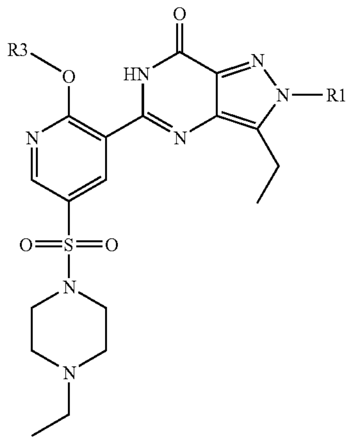

were prepared from the appropriate carboxamide and alcohol, following similar procedures to that described in example 54.

| Ex | R1 | R3 | Data |
|---|---|---|---|
| 55 | 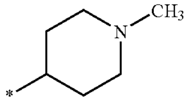 | n-Bu | δ($CDCl_3$): 1.02(6H, m), 1.40(3H, t), 1.57(2H, m), 1.94(4H, m), 2.16(2H, m), 2.37(3H, s), 2.41(2H, q), 2.56(6H, m), 3.03(4H, m), 3.15 (4H, m), 4.22(1H, m), 4.66(2H, t), 8.62(1H, d), 9.01(1H, d), 10.55(1H, s). |
| 56 | 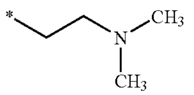 | 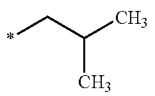 | δ($CDCl_3$): 1.02(3H, t), 1.12(6H, d), 1.42(3H, t), 2.31(7H, m), 2.42(2H, q), 2.57(4H, m), 2.90(2H, t), 3.06(2H, q), 3.16(4H, m), 4.38–4.47 (4H, m), 8.61(1H, d), 9.01(1H, d), 10.60 (1H, s). |
| 57 | 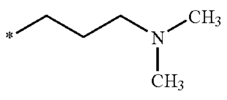 | n-Bu | δ($CDCl_3$): 1.01(6H, t), 1.40(3H, t), 1.56(2H, m), 1.95(2H, m), 2.17(2H, m), 2.21(6H, s), 2.24(2H, t), 2.40(2H, q), 2.57(4H, m), 3.06 (2H, q), 3.17(4H, m), 4.37(2H, t), 4.65(2H, t), 8.61(1H, d), 9.02(1H, d), 10.59(1H, s). |
| 58 | 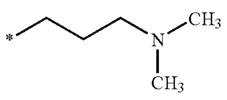 | 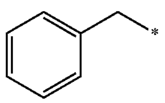 | δ($CDCl_3$): 1.02(3H, t), 1.40(3H, t), 2.17(2H, m), 2.21(6H, s), 2.27(2H, t), 2.40(2H, q), 2.57 (4H, m), 3.05(2H, q), 3.17(4H, m), 4.37(2H, t), 5.77(2H, s), 7.39(3H, m), 7.52(2H, m), 8.63 (1H, d), 9.01(1H, d), 10.54(1H, s). |

EXAMPLE 59

5-[2-n-Butoxy-5-(4-ethylpiperazin-1-ylsulphonyl) pyridin-3-yl]-1-[2-(dimethylamino)-2-oxoethyl]-3-ethyl-1,6-dihydro-7H-pyrazolo[4,3-d]pyrimidin-7-one and

EXAMPLE 60

5-[2-n-Butoxy-5-(4-ethylpiperazin-1-ylsulphonyl) pyridin-3-yl]-2-[2-(dimethylamino)-2-oxoethyl]-3-ethyl-2,6-dihydro-7H-pyrazolo[4,3-d]pyrimidin-7-one

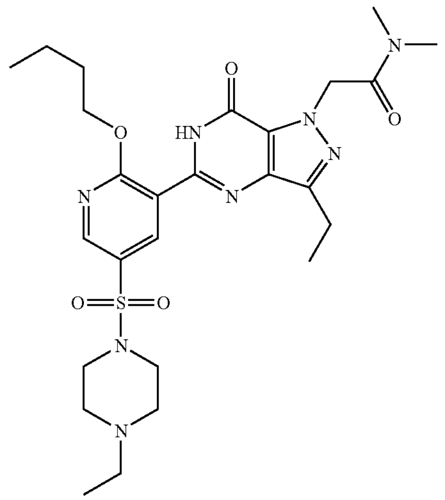

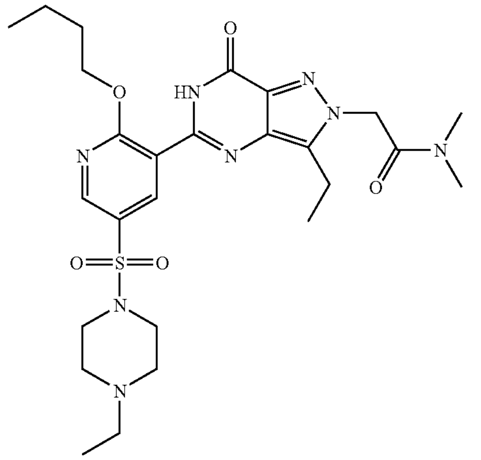

Sodium hydride (13 mg, 60% dispersion in mineral oil, 0.33 mmol) was added to a solution of the title compound from preparation 59 (145 mg, 0.30 mmol) in tetrahydrofuran (2 ml) and the solution stirred for 30 minutes. 2-Chloro-N, N-dimethylacetamide (40 mg, 0.034 mmol) was added and the reaction stirred at room temperature for 16 hours, followed by a further 16 hours at 60° C. The cooled mixture was treated with aqueous sodium bicarbonate solution (15 ml) and extracted with ethyl acetate (2×15 ml). The combined organic extracts were dried ($MgSO_4$) and evaporated under reduced pressure. The crude product was purified by column chromatography on silica gel using dichloromethane:methanol (96.5:3.5) as eluant, and repeated using ethyl acetate:diethylamine (90:10) as eluant, to afford the title compound of example 59, 20 mg, δ ($CDCl_3$): 1.03 (6H, t), 1.41 (3H, t), 1.59 (2H, m), 1.95 (2H, m), 2.4.1 (2H, q), 2.57 (4H, m), 3.00 (5H, m), 3.15 (7H, m), 4.66 (2H, t), 5.44 (2H, s), 8.63 (1H, d), 9.10 (1H, d), 10.85 (1H, s).

and the title compound of example 60, 45 mg.

δ ($CDCl_3$): 1.01 (6H, t), 1.42 (3H, t), 1.55 (2H, m), 1.94 (2H, m), 2.40 (2H, q), 2.55 (4H, m), 3.00 (5H, m), 3.14 (7H, m), 4.64 (2H, t), 5.19 (2H, s), 8.61 (1H, d), 9.01 (1H, d), 10.58 (1H, s).

EXAMPLE 61

5-[2-n-Butoxy-5-(4-ethylpiperazin-1-ylsulphonyl) pyridin-3-yl]-3-ethyl-2-{2-methyl(methylsulphonyl) amino]ethyl}-2,6-dihydro-7H-pyrazolo[4,3-d]pyrimidin-7-one

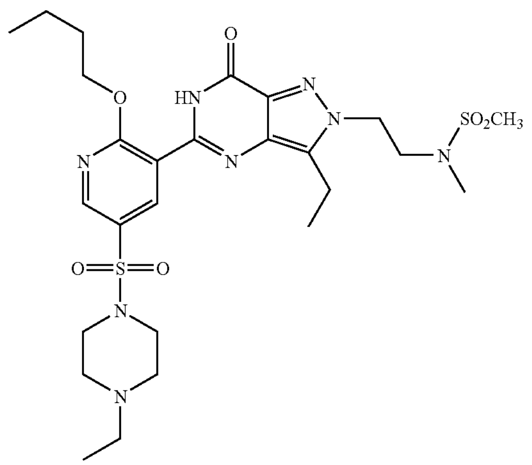

Trifluoroacetic acid (1 ml) was added to a solution of the title compound from preparation 62 (76 mg, 0.117 mmol) in dichloromethane (1 ml), and the solution stirred for 2½ hours at room temperature. The mixture was evaporated under reduced pressure, the residue triturated well with ether, and the resulting precipitate, filtered and dried to give a white powder.

Methanesulphonyl chloride (20 μl, 0.26 mmol) was added to a solution of this intermediate in dichloromethane (2 ml) and triethylamine (65 μl, 0.47 mmol), and the reaction stirred at room temperature for 1½ hours. The mixture was treated with saturated aqueous sodium bicarbonate solution (10 ml), and extracted with ethyl acetate (2×10 ml). The combined organic extracts were dried ($MgSO_4$) and evaporated under reduced pressure to give a gum. The crude product was purified by column chromatography on silica gel using dichloromethane:methanol (96:4) as eluant to afford the title compound as a beige foam, 30 mg.

δ ($CDCl_3$): 1.02 (6H, t), 1.42 (3H, t), 1.54 (2H, m), 1.94 (2H, m), 2.41 (2H, q), 2.57 (4H, m), 2.65 (3H, s), 2.80 (3H, s), 3.13 (6H, m), 3.76 (2H, t), 4.52 (2H, t), 4.67 (2H, t), 8.62 (1H, d), 9.04 (1H, d), 10.68 (1H, s).

EXAMPLE 62

5-[2-n-Butoxy-5-(4-ethylpiperazin-1-ylsulphonyl)pyridin-3-yl]-3-ethyl-2-[1-(methylsulphonyl)piperidin-4-yl]-2,6-dihydro-7H-pyrazolo[4,3-d]pyrimidin-7-one

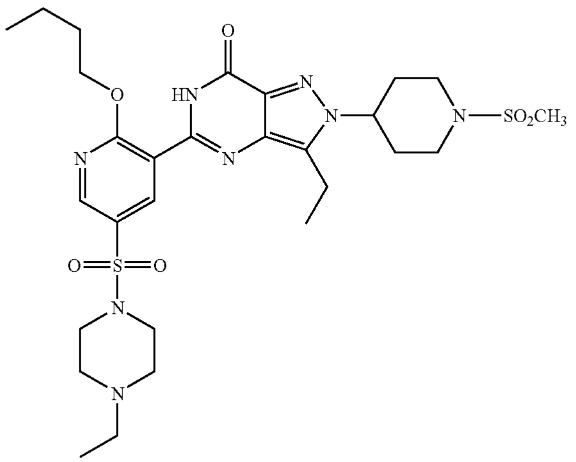

The title compound was obtained as a white solid, (34%), from the title compound from preparation 67 and methanesulphonyl chloride, following the procedure described in example 61.

δ ($CDCl_3$): 1.01 (6H, t), 1.40 (3H, t), 1.55 (2H, m), 1.95 (2H, m), 2.08 (2H, m), 2.42 (2H, q), 2.57 (6H, m), 2.90 (3H, s), 3.01–3.18 (8H, m), 4.01 (2H, m), 4.42 (1H, m), 4.66 (2H, t), 8.62 (1H, d), 9.01 (1H, d), 10.60 (1H, s).

EXAMPLE 63

5-[2-Ethoxy-5-(4-ethylpiperazin-1-ylsulphonyl)pyridin-3-yl]-3-ethyl-2-(4-nitrophenyl)-2,6-dihydro-7H-pyrazolo[4,3-d]pyrimidin-7-one

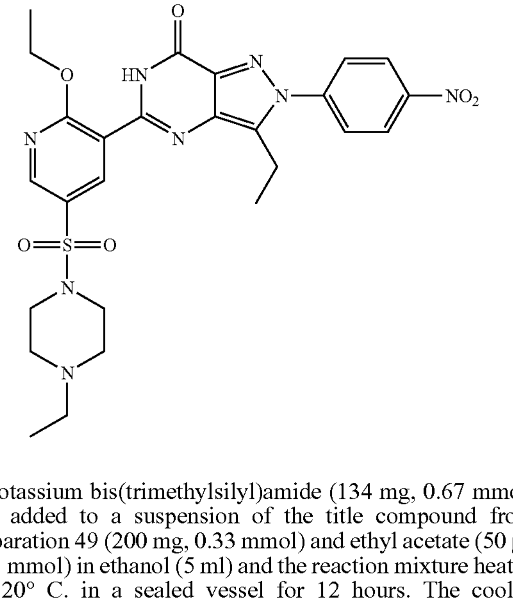

Potassium bis(trimethylsilyl)amide (134 mg, 0.67 mmol) was added to a suspension of the title compound from preparation 49 (200 mg, 0.33 mmol) and ethyl acetate (50 μl, 0.51 mmol) in ethanol (5 ml) and the reaction mixture heated at 120° C. in a sealed vessel for 12 hours. The cooled reaction was concentrated under reduced pressure and the residue partitioned between ethyl acetate and water, and the layers separated. The aqueous phase was extracted with ethyl acetate, the combined organic solutions dried ($MgSO_4$), and evaporated under reduced pressure. The crude product was purified by column chromatography on silica gel using dichloromethane:methanol (98:2) as eluant to give the title compound as a yellow oil, 10 mg.

δ ($CDCl_3$): 1.02 (3H, t), 1.36 (3H, t), 1.60 (3H, t), 2.41 (2H, q), 2.57 (4H, m), 3.17 (6H, m), 4.78 (2H, q), 7.82 (2H, d), 8.42 (2H, d), 8.66 (1H, d), 9.07 (1H, d), 10.78 (1H, br s).

LRMS: m/z 583 $(M+1)^+$

EXAMPLE 64

2-(4-Aminophenyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

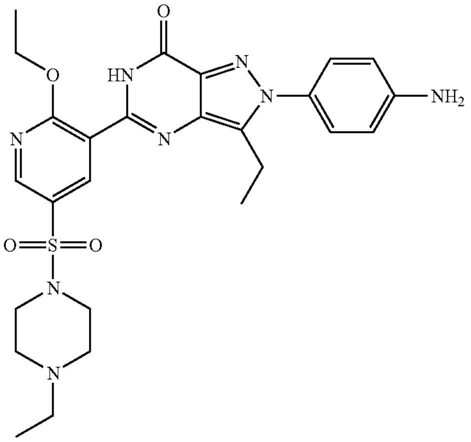

A solution of the title compound from example 63 (100 mg, 0.17 mmol) in methanol (2 ml) was added to a suspension of iron powder (29 mg, 0.52 mmol) in ammonium chloride (45 mg, 0.85 mmol) in water (2 ml), and the reaction heated at 60° C. for 1 hour. The cooled mixture was filtered, and the filtrate evaporated under reduced pressure to give the title compound as a pale brown solid, 93 mg.

δ ($CDCl_3$): 1.02 (3H, t), 1.26 (3H, t), 1.59 (3H, t), 2.41 (2H, q), 2.57 (4H, m), 3.03 (2H, q), 3.16 (4H, m), 3.94 (2H, s), 4.77 (2H, q), 6.78 (2H, d), 7.27 (2H, d), 8.63 (1H, d), 9.07 (1H, d), 10.66 (1H, s).

LRMS: m/z 553 $(M+1)^+$

EXAMPLE 65

5-[2-Ethoxy-5-(4-ethylpiperazin-1-ylsulphonyl)pyridin-3-yl]-3-ethyl-2-{4-[(methylsulphonyl)amino]phenyl}-2,6-dihydro-7H-pyrazolo[4,3-d]pyrimidin-7-one

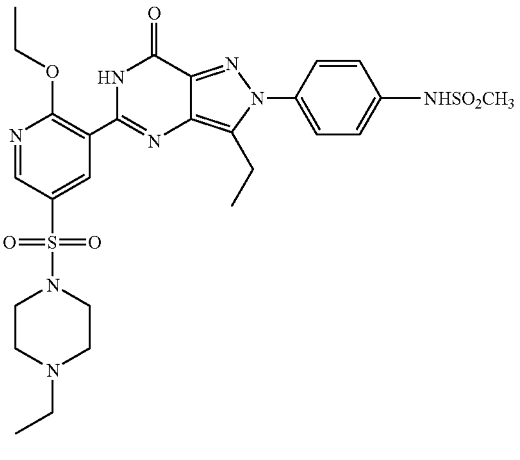

Methanesulphonyl chloride (15 μl, 0.19 mmol) was added to an ice-cooled solution of the title compound from example 64 (93 mg, 0.17 mmol) in pyridine (2 ml), and the reaction allowed to warm to room temperature, and stirred for 90 minutes. Tlc analysis showed starting material remaining, so additional methanesulphonyl chloride (15 μl, 0.19 mmol) was added, and the reaction stirred for a further hour. The reaction was quenched by the addition of aqueous ammonium chloride solution, and extracted with ethyl acetate. The combined organic extracts were dried ($MgSO_4$) and concentrated under reduced pressure. The residual solid was purified by column chromatography on silica gel using dichloromethane:methanol:0.88 ammonia (90:10:1) as eluant, then repeated using dichloromethane:methanol:0.88 ammonia (95:5:1) to afford the title compound, 36 mg.

δ ($CDCl_3$): 1.03 (3H, t), 1.34 (3H, t), 1.59 (3H, t), 2.42 (2H, q), 2.58 (4H, m), 3.14 (9H, m), 4.78 (2H, q), 6.92 (1H, s), 7.44 (2H, d), 7.58 (2H, d), 8.65 (1H, d), 9.07 (1H, d), 10.75 (1H, s).

LRMS: m/z 631 $(M+1)^+$

EXAMPLE 66

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one

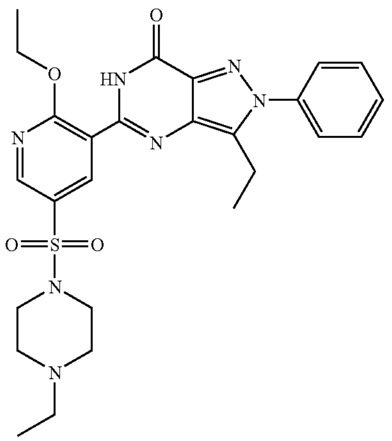

Pyridine (0.1 ml, 1.08 mmol) was added to a mixture of the title compound from preparation 58 (250 mg, 0.64 mmol), copper (II) acetate monohydrate (145 mg, 0.72 mmol), benzeneboronic acid (132 mg, 1.08 mmol) and 4 Å molecular sieves (392 mg) in dichloromethane (5 ml), and the reaction stirred at room temperature for 4 days. The reaction mixture was filtered and the filtrate evaporated under reduced pressure. The crude product was purified by column chromatography on silica gel using dichloromethane:methanol:0.88 ammonia (97:3:0.5) as eluant, and triturated with ether:hexane. The resulting solid was filtered and recrystallised from isopropanol:dichloromethane to give the title compound as a solid, 200 mg.

δ ($CDCl_3$): 1.02 (3H, t), 1.47 (3H, t), 1.60 (3H, t), 2.42 (2H, q), 2.58 (4H, m), 3.10 (2H, q), 3.17 (4H, m), 4.76 (2H, q), 7.40 (1H, m), 7.51 (2H, m), 7.80 (2H, d), 8.67 (1H, d), 9.16 (1H, s), 10.90 (1H, s).

LRMS: m/z 538 $(M+1)^+$

EXAMPLE 67

2-(4-Cyanophenyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

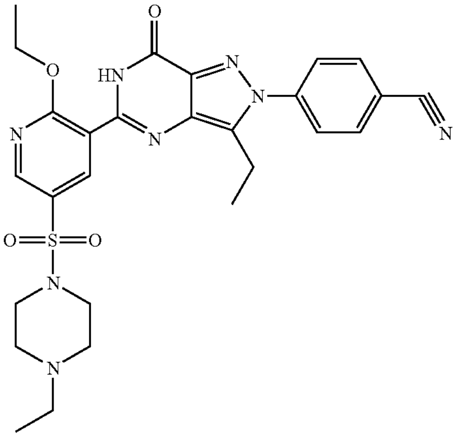

A mixture of the title compound from preparation 58 (100 mg, 0.22 mmol), copper (II) acetate monohydrate (58 mg, 0.29 mmol), 4-cyanobenzeneboronic acid (63 mg, 0.44 mmol) and 4 Å molecular sieves (156 mg) in pyridine (1 ml) and N-methylpyrrolidine (1 ml) was irradiated by microwave at full power for 3×10 seconds, followed by 2×20 seconds. The mixture was evaporated under reduced pressure and the residue purified by column chromatography on silica gel using dichloromethane:methanol:0.88 ammonia (95:5:0.5) as eluant. The product was recrystallised from dichloromethane:isopropanol to give the title compound, 45 mg.

δ ($CDCl_3$): 1.03 (3H, t), 1.49 (3H, t), 1.62 (3H, t), 2.42 (2H, q), 2.58 (4H, m), 3.08 (2H, q), 3.17 (4H, m), 4.58 (2H, q), 7.79 (2H, d), 8.14 (2H, d), 8.70 (1H, d), 9.16 (1H, d), 11.09 (1H, s).

LRMS: m/z 563 $(M+1)^+$

EXAMPLE 68

5-[2-Ethoxy-5-(4-ethylpiperazin-1-ylsulphonyl)pyridin-3-yl]-3-ethyl-2-(pyridin-2-yl)-2,6-dihydro-7H-pyrazolo[4,3-d]pyrimidin-7-one ditrifluoroacetate

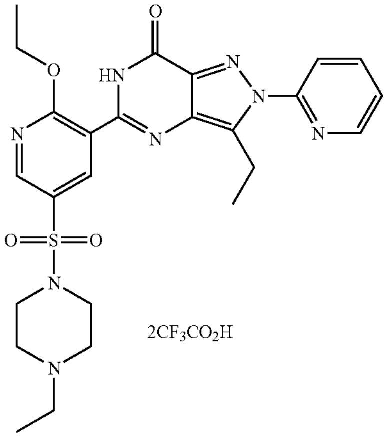

$2CF_3CO_2H$

Tris(dibenzylideneacetone)dipalladium (0) (8 mg, 0.009 mmol), R-BINAP (8 mg, 0.013 mmol), sodium tert-butoxide (41 mg, 0.43 mmol) and 2-bromopyridine (50 μl, 0.52 mmol) were added to a solution of the title compound from preparation 58 (200 mg, 0.43 mmol) in toluene (3 ml), and the reaction heated at 70° C. for 16 hours. The cooled mixture was evaporated under reduced pressure and the residue filtered through silica gel, using dichloromethane: methanol (80:20) as eluant. The product was purified by reverse phase HPLC on silica gel, using an elution gradient of acetonitrile:0.1% aqueous trifluoroacetic acid (5:95 to 85:15) to afford the title compound, as a solid, 13 mg.

δ ($CDCl_3$): 1.36 (3H, t), 1.48 (3H, t), 1.57 (3H, t), 3.00 (2H, m), 3.14 (6H, m), 3.70 (2H, m), 3.96 (2H, m), 4.77 (2H, q), 7.52 (1H, m), 8.15–8.26 (2H, m), 8.69 (2H, m), 8.92 (1H, d), 10.80–11.00 (1H, s).

LRMS: m/z 539 $(M+1)^+$

EXAMPLE 69

5-[2-Ethoxy-5-(4-ethylpiperazin-1-ylsulphonyl)pyridin-3-yl]-3-ethyl-2-(pyrazin-2-yl)-2,6-dihydro-7H-pyrazolo[4,3-d]pyrimidin-7-one di-trifluoroacetate

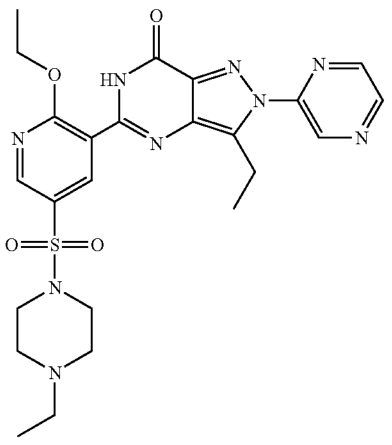

Cesium carbonate (353 mg, 1.09 mmol) followed by 2-chloropyrazine (100 μl, 1.12 mmol) were added to a solution of the title compound from preparation 58 (500 mg, 1.08 mmol) in N,N-dimethylformamide (10 ml), and the reaction heated at 120° C. for 18 hours. The cooled mixture was evaporated under reduced pressure and the residue was purified by column chromatography on silica gel using dichloromethane:methanol:0.88 ammonia (98:2:1) as eluant. The product was further purified by reverse phase HPLC on silica gel, using an elution gradient of acetonitrile:0.1% aqueous trifluoroacetic acid (5:95 to 50:50) to afford the title compound, 86 mg.

δ ($CDCl_3$): 1.38 (6H, 2×t), 1.58 (3H, t), 2.98–3.22 (6H, m), 3.54 (2H, q), 3.76 (2H, m), 4.00 (2H, m), 4.78 (2H, q), 8.57–8.74 (3H, m), 8.98 (1H, d), 9.57 (1H, s).

LRMS: m/z 540 $(M+1)^+$

EXAMPLE 70

5-[2-Ethoxy-5-(4-ethylpiperazin-1-ylsulphonyl)pyridin-3-yl]-3-ethyl-2-(thiazol-2-yl)-2,6-dihydro-7H-pyrazolo[4,3-d]pyrimidin-7-one trifluoroacetate

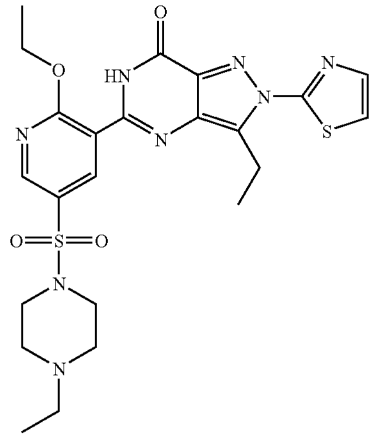

The title compound was obtained, (7%) from the title compound from preparation 58 and 2-bromothiazole, following a similar procedure to that described in example 69.

δ ($CD_3OD$): 1.28–1.41 (6H, m), 1.48 (3H, t), 3.20–3.34 (6H, m), 3.34–3.60 (6H, m), 4.65 (2H, q), 7.59 (1H, d), 7.78 (1H, d), 8.58 (1H, d), 8.78 (1H, d).

LRMS: m/z 545 $(M+1)^+$

EXAMPLE 71

2-(6-Chloropyrimidin-4-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

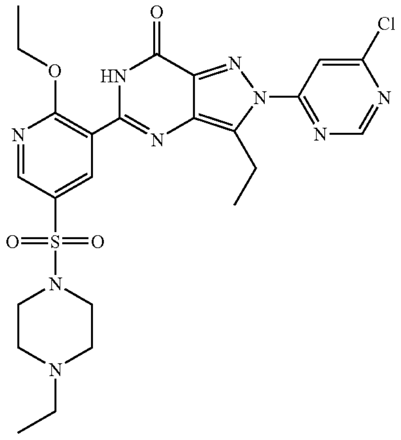

Sodium hydride (22 mg, 60% dispersion in mineral oil, 0.55 mmol) was added to an ice-cooled solution of the title compound from preparation 58 (250 mg, 0.54 mmol) in tetrahydrofuran (5 ml), and the solution then allowed to warm to room temperature. 4,6-Dichloropyrimidine (80 mg, 0.54 mmol) was added, and the reaction stirred at 65° C. for 18 hours. The cooled mixture was evaporated under reduced pressure and the residue purified by column chromatography on silica gel using dichloromethane:methanol:0.88 ammonia (95:5:0.5) as eluant. The product was triturated with dichloromethane to afford the title compound as a pale yellow solid, 5 mg.

δ ($CDCl_3$): 1.02 (3H, t), 1.40 (3H, t), 1.60 (3H, t), 2.42 (2H, q), 2.58 (4H, m), 3.16 (4H, m), 3.62 (2H, q), 4.78 (2H, q), 8.40 (1H, s), 8.67 (1H, d), 8.97 (1H, s), 9.10 (1H, d), 10.79 (1H, s).

LRMS: m/z 574, 576 $(M+1)^+$

EXAMPLE 72

5-[2-Ethoxy-5-(4-ethylpiperazin-1-ylsulphonyl)pyridin-3-yl]-3-ethyl-2-(pyrimidin-2-yl)-2,6-dihydro-7H-pyrazolo[4,3-dl]pyrimidin-7-one

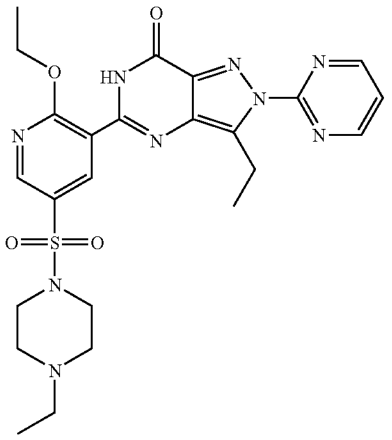

The title compound was obtained (8%), from the compound from preparation 58 and 2-chloropyrimidine, following a similar procedure to that described in example 71.

Found: C, 53.33; H, 5.36; N, 23.12. $C_{24}H_{29}N_9O_4S$ requires C, 53.42; H, 5.42; N, 23.36%.

δ ($CDCl_3$): 1.03 (3H, t), 1.37 (3H, t), 1.59 (3H, t), 2.41 (2H, q), 2.58 (4H, m), 3.17 (4H, m), 3.55 (2H, q), 4.78 (2H, q), 7.42 (1H, m), 8.64 (1H, d), 8.95 (2H, d), 9.11 (1H, d), 10.73 (1H, s).

LRMS: m/z 540 $(M+1)^+$

EXAMPLE 73

5-[5-(4-Ethylpiperazin-1-ylsulphonyl)-2-(2-methoxyethoxy)pyridin-3-yl]-3-ethyl-2-(pyrimidin-2-yl)-2,6-dihydro-7H-pyrazolo[4,3-d]pyrimidin-7-one

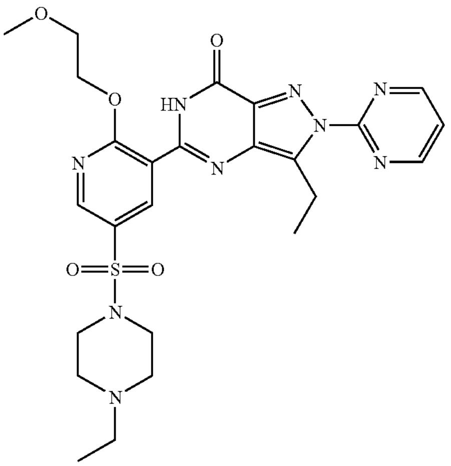

Sodium hydride (19 mg, 60% dispersion in mineral oil, 0.48 mmol) was added to an ice-cold solution of the title compound from preparation 69 (200 mg, 0.41 mmol) in tetrahydrofuran (4 ml), and the solution stirred for 30 minutes. 2-Chloropyrimidine (56 mg, 0.48 mmol) was added, and the reaction heated under reflux for 18 hours. The mixture was evaporated under reduced pressure, the residue diluted with water, and extracted with dichloromethane. The combined organic extracts were dried ($MgSO_4$), and evaporated under reduced pressure. The crude product was purified by column chromatography on silica gel using an elution gradient of dichloromethane:methanol (100:0 to 95:5) to give the title compound, 31 mg.

δ ($CDCl_3$): 1.02 (3H, t), 1.36 (3H, t), 2.42 (2H, q), 2.58 (4H, m), 3.18 (4H, m), 3.50 (2H, q), 3.58 (3H, s), 3.88 (2H, t), 4.80 (2H, t), 7.42 (1H, m), 8.64 (1H, d), 8.95 (2H, d), 9.02 (1H, d), 10.82 (1H, s).

LRMS: m/z 570 $(M+1)^+$

EXAMPLE 74

2-(1,3-Benzoxazol-2-yl)-5-[5-(4-ethylpiperazin-1-ylsulphonyl)-2-(2-methoxyethoxy)pyridin-3-yl]-3-ethyl-2,6-dihydro-7H-pyrazolo[4,3-d]pyrimidin-7-one

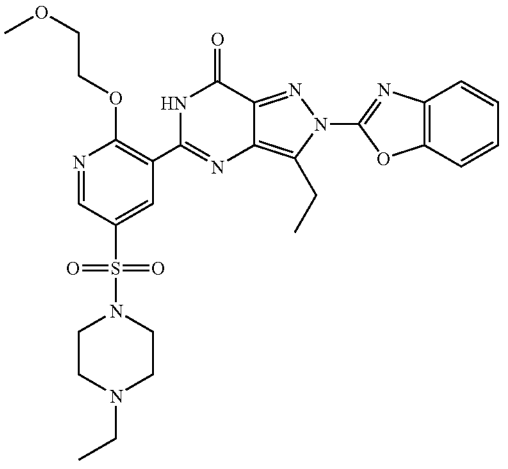

The title compound was obtained (35%), from the title compound from preparation 69 and 2-chlorobenzoxazole, following the procedure described in example 73.

δ ($CDCl_3$): 1.02 (3H, t), 1.50 (3H, t), 2.42 (2H, q), 2.58 (4H, m), 3.18 (4H, m), 3.59 (3H, s), 3.62 (2H, q), 3.87 (2H, t), 4.80 (2H, t), 7.43 (2H, m), 7.64 (1H, m), 7.80 (1H, m), 8.65 (1H, d), 9.02 (1H, d), 10.98 (1H, s).

LRMS: m/z 609 $(M+1)^+$

EXAMPLE 75

3-Ethyl-5-[5-(4-ethylpierazin-1-ylsulphonyl)-2-(2-methoxyethoxy)pyridin-3-yl]-2-phenyl-2,6-dihydro-7H-pyrazolo[4,3-d]pyrimidin-7-one

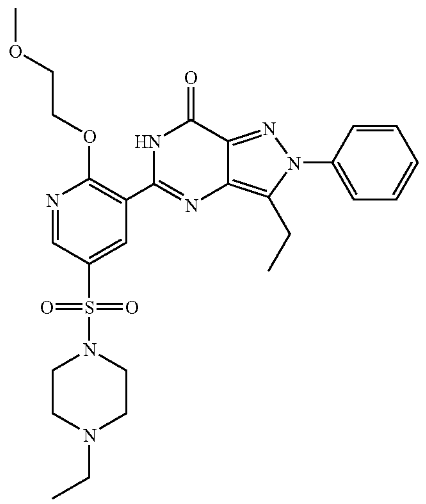

Potassium bis(trimethylsilyl)amide (294 mg, 1.47 mmol) was added to a solution of the compound from example 66 (200 mg, 0.37 mmol) in 2-methoxyethanol (10 ml), and the reaction heated under reflux for 18 hours. The mixture was evaporated under reduced pressure and the residue purified by column chromatography on silica gel using dichloromethane:methanol:0.88 ammonia (97:3:0.5) as eluant. The product was recrystallised from dichloromethane:iso-propanol to give the desired compound as a white solid, 82 mg.

Found: C, 57.06; H, 5.83; N, 17.27. $C_{27}H_{35}N_7O_5S$ requires C, 57.13; H, 5.86; N, 17.27%.

δ ($CDCl_3$): 1.02 (3H, t), 1.46 (3H, t), 2.42 (2H, q), 2.57 (4H, m), 3.16 (2H, q), 3.17 (4H, m), 3.56 (3H, s), 3.84 (2H, t), 4.58 (2H, t), 7.38 (1H, m), 7.48 (2H, m), 7.80 (2H, m), 8.64 (1H, m), 9.04 (1H, m), 11.10 (1H, brs).

LRMS: m/z 568 $(M+1)^+$

EXAMPLE 76

5-[2-Ethoxy-5-(4-methylpiperazin-1-ylsulphonyl)pyridin-3-yl]-1-(2-methoxyethyl)-3-n-propyl-1,6-dihydro-7H-pyrazolo[4,3-d]pyrimidin-7-one

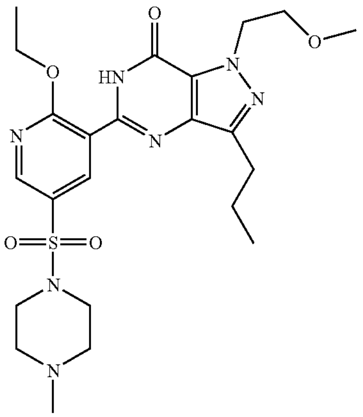

A mixture of the title compound of preparation 57 (440 mg, 0.82 mmol), and potassium bis(trimethylsilyl)amide (196 mg, 0.98 mmol) in ethanol (15 ml) was heated at 100° C. for 18 hours, in a sealed vessel. The cooled mixture was concentrated under reduced pressure, the residue partitioned between ethyl acetate (20 ml) and brine (10 ml), and the layers separated. The organic phase was separated, dried ($MgSO_4$), and evaporated under reduced pressure. The crude product was purified by column chromatography on silica gel, using an elution gradient of dichloromethane:methanol (100:0 to 95:5) to afford the title compound, 275 mg, as a pale yellow solid.

δ ($CDCl_3$) 1.02 (3H, t), 1.60 (3H, t), 1.86 (2H, m), 2.29 (3H, s), 2.52 (4H, m), 2.95 (2H, t), 3.16 (4H, m), 3.35 (3H, s), 3.87 (2H, t), 4.78 (4H, m), 8.64 (1H, s), 9.09 (1H, s), 10.81 (1H, s).

LRMS: m/z 520 $(M+1)^+$

EXAMPLE 77

5-[2-Ethoxy-5-(4-ethylpiperazin-1-ylsulphonyl)pyridin-3-yl]-3-ethyl-1-(2-methoxyethyl)-1,6-dihydro-7H-pyrazolo[4,3-d]pyrimidin-7-one

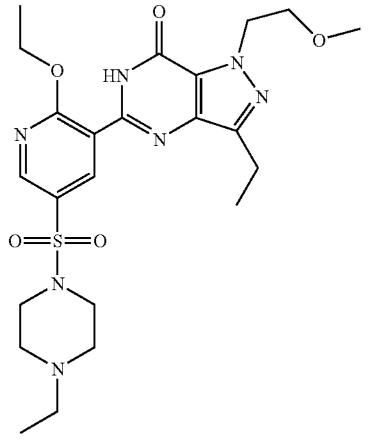

A mixture of the title compound of preparation 56 (1.02 g, 1.9 mmol) and potassium tert-butoxide (533 mg, 4.75 mmol) in ethanol (40 ml) was heated at 100° C. in a sealed vessel for 18 hours. The cooled mixture was concentrated under reduced pressure and the residue partitioned between ethyl acetate (50 ml) and brine (25 ml), and the layers separated. The organic phase was washed with brine (25 ml), dried ($MgSO_4$), and evaporated under reduced pressure. The crude product was purified by column chromatography on silica gel, using an elution gradient of ethyl acetate:methanol (100:0 to 90:10) to afford the title compound, 698 mg, as a pale yellow solid.

Found: C, 53.00; H, 6.39; N, 18.87 $C_{23}H_{33}N_7O_5S$ requires C, 53.16; H, 6.40; N, 18.87%

δ ($CDCl_3$): 1.03 (3H, t), 1.40 (3H, t), 1.59 (3H, t), 2.41 (2H, q), 2.57 (4H, m), 3.00 (2H, q), 3.15 (4H, m), 3.35 (3H, s), 3.88 (2H, t), 4.78 (4H, m), 8.63 (1H, s), 9.09 (1H, s), 10.83 (1H, s).

LRMS: m/z 520 $(M+1)^+$

EXAMPLE 78

2-Cyclobutylmethyl-3-ethyl-5-[5-(4-ethylpiperazin-1-ylsulphonyl)-2-(pyrrolidin-1-yl)pyridin-3-yl]-2,6-dihydro-7H-pyrazolo[4,3-d]pyrimidin-7-one

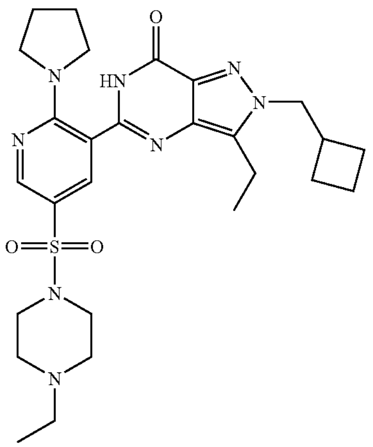

A mixture of the title compound from example 7 (200 mg, 0.38 mmol) and copper sulphate pentahydrate (74 mg, 0.30 mmol) in pyrrolidine (4 ml) was heated under reflux for 18 hours. The cooled mixture was concentrated under reduced pressure and the residue purified by column chromatography on silica gel twice using an elution gradient of dichloromethane:methanol (100:0 to 95:5) to give the title compound as a pale brown solid, 109 mg.

δ ($CDCl_3$): 1.04 (3H, m), 1.38 (3H, t), 1.90 (8H, m), 2.10 (2H, m), 2.37–2.68 (5H, m), 3.00 (2H, q), 3.14 (4H, m), 3.42 (4H, m), 4.32 (2H, d), 8.00 (1H, s), 8.58 (1H, s).

LRMS: m/z 555 $(M+1)^+$

EXAMPLE 79

2-Cyclobutyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

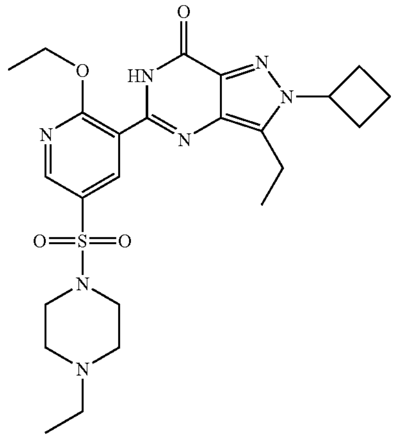

A mixture of the compound from preparation 83 (440 mg, 0.83 mmol), potassium bis(trimethylsilyl)amide (500 mg, 2.51 mmol) and ethyl acetate (100 μl, 1.0 mmol) in ethanol (10 ml) was heated at 120° C. in a sealed vessel for 18 hours. The cooled mixture was evaporated under reduced pressure and the residue was purified by column chromatography on silica gel using an elution gradient of dichloromethane:methanol (100:0 to 95:5) to afford the title compound, 263 mg.

$^1$Hnmr ($CDCl_3$, 300 MHz) δ: 1.01 (3H, t), 1.35 (3H, t), 1.58 (3H, t), 1.96 (2H, m), 2.38–2.60 (8H, m), 2.98 (4H, m), 3.14 (4H, m), 4.76 (2H, q), 4.96 (1H, m), 8.61 (1H, d), 9.02 (1H, d), 10.59 (1H, s).

LRMS: m/z 516 $(MH^+)$

EXAMPLE 80

2-Cyclopentyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

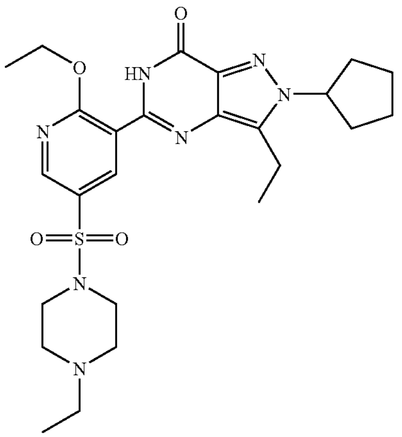

Potasssium bis(trimethylsilyl)amide (450 mg, 2.25 mmol) was added to a suspension of the compound from preparation 84 (243 mg, 0.45 mmol) in ethanol (5 ml), and the mixture heated at 100° C. in a Reactivial® for 24 hours. Tlc analysis showed starting material remaining, so additional potassium bis(trimethylsilyl)amide (250 mg, 1.25 mmol) and ethyl acetate (3 drops) were added, and the reaction heated at 111° C. for 18 hours. The cooled mixture was partitioned between ethyl acetate and sodium bicarbonate solution, and the phases separated. The aqueous layer was extracted with ethyl acetate (2×), the combined organic solutions washed with brine, dried ($MgSO_4$), and evaporated under reduced pressure. The crude product was purified by column chromatography on silica gel using methanol:dichloromethane (2:98) as eluant, and triturated with ether to afford the title compound as a white powder, 55 mg.

$^1$Hnmr ($CDCl_3$, 400 MHz) δ: 1.02 (3H, t), 1.39 (3H, t), 1.55 (3H, t), 1.72 (2H, m), 2.05 (2H, m), 2.17 (2H, m), 2.30 (2H, m), 2.40 (2H, q), 2.56 (4H, m), 3.04 (2H, q), 3.16 (4H, m), 4.76 (2H, q), 4.82 (1H, m), 8.61 (1H, s), 9.02 (1H, s), 10.55 (1H, s).

LRMS: m/z 530.8 $(MH^+)$

Anal. Found: C, 57.17; H, 6.65; N, 18.14. $C_{25}H_{35}N_7O_4S$ requires C, 56.69; H, 6.66; N, 18.51%.

EXAMPLE 81

2-Cyclopentylmethyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

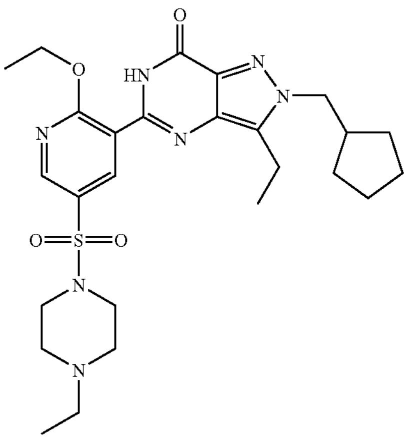

The title compound was obtained as a white powder in 41% yield from the compound from preparation 85, following the procedure described in example 80.

$^1$Hnmr ($CDCl_3$, 0.400 MHz) δ: 1.01 (3H, t), 1.30 (4H, m), 1.40 (3H, t), 1.54 (5H, m), 1.70 (2H, m), 2.40 (2H, q), 2.56 (4H, m), 2.63 (1H, m), 3.02 (2H, q), 3.12 (4H, m), 4.20 (2H, d), 4.74 (2H, q), 8.61 (1H, d), 9.03 (1H, d), 10.60 (1H, s).

LRMS: m/z 547.7 ($MH^+$)

EXAMPLE 82

2-Cyclohexyl-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

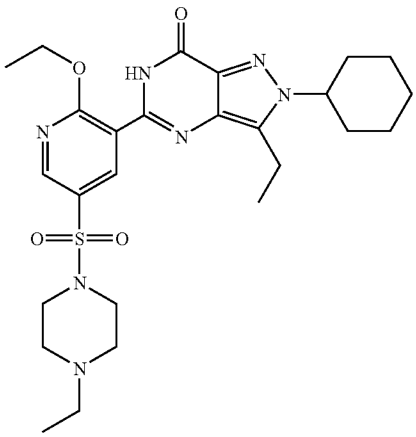

The title compound was obtained as a white solid in 35% yield, from the compound of preparation 86, following a similar procedure to that described in example 80.

$^1$Hnmr ($CDCl_3$, 400 MHz) δ: 1.02 (3H, t), 1.30–1.50 (6H, m), 1.58 (3H, t), 1.78 (1H, m), 1.98 (4H, m), 2.22 (2H, m), 2.41 (2H, q), 2.55 (4H, m), 3.05 (2H, q), 3.16 (4H, m), 4.23 (1H, m), 4.75 (2H, q), 8.61 (1H, s), 9.01 (1H, s), 10.54 (1H, s).

LRMS: m/z 548.8 ($MH^+$)

Anal. Found: C, 57.23; H, 6.96; N, 17.54. $C_{26}H_{37}N_7O_4S$ requires C, 57.44; H, 6.86; N, 18.03%.

EXAMPLE 83

5-[2-Ethoxy-5-(4-ethylpiperazin-1-ylsulphonyl)pyridin-3-yl]-2-(2-ethoxyethyl)-3-ethyl-2,6-dihydro-7H-pyrazolo[4,3-d]pyrimidin-7-one

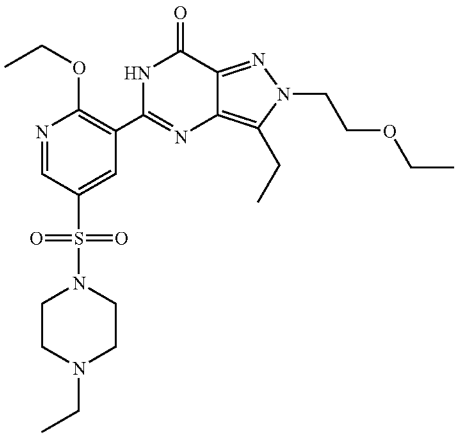

Potassium bis(trimethylsilyl)amide (256 mg, 1.28 mmol) was added to a solution of the compound from preparation 70 (170 mg, 0.30 mmol) and ethyl acetate (30 mg, 0.33 mmol) in ethanol (5 ml), and the reaction heated at 130° C. for 6 hours. The cooled mixture was evaporated under reduced pressure and the residual yellow solid was purified by column chromatography on silica gel using dichloromethane:methanol (97:3) as eluant. The product was triturated with isopropyl ether then re-purified by column chromatography using an elution gradient of dichloromethane: methanol (100:0 to 90:10) to afford the title compound, 20 mg.

$^1$Hnmr ($CDCl_3$, 400 MHz) δ: 1.00 (3H, t), 1.10 (3H, t), 1.40 (3H, t), 1.54 (3H, t), 2.40 (2H, q), 2.50 (4H, m), 3.05 (2H, q), 3.10 (4H, m), 3.40 (2H, q), 3.90 (2H, t), 4.42 (2H, t), 4.70 (2H, q), 8.60 (1H, s), 9.00 (1H, s), 10.60 (1H, s).

LRMS: m/z 535 ($MH^+$)

Anal. Found: C, 53.97; H, 6.64; N, 18.14. $C_{24}H_{35}N_7O_5S$ requires C, 54.02; H, 6.61; N, 18.37%.

EXAMPLE 84

5-[2-Ethoxy-5-(4-ethylpiperazin-1-ylsulphonyl)pyridin-3-yl]-3-ethyl-2-[(1S)-1-methyl-2-methoxyethyl)-2,6-dihydro-7H-pyrazolo[4,3-d]pyrimidin-7-one

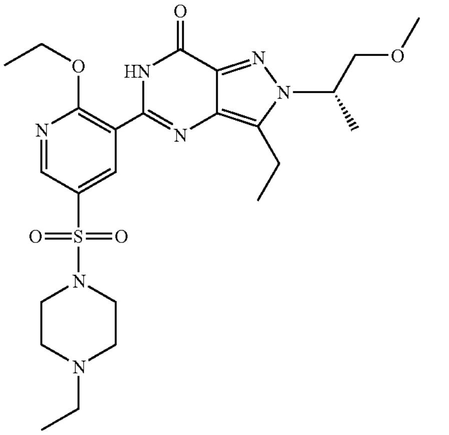

Potassium bis(trimethylsilyl)amide (2.10 g, 10.5 mmol) was added to a solution of the compound from preparation 90 (1.20 g, 2.17 mmol) and ethyl acetate (200%, 2.02 mmol) in ethanol (40 ml), and the reaction heated in a sealed vessel at 130° C. for 6 hours. The cooled mixture was concentrated under reduced pressure and the residue partitioned between ethyl acetate and water, and neutralised by the addition of solid carbon dioxide. The layers were separated, the aqueous phase extracted with ethyl acetate, and the combined organic solutions dried ($Na_2SO_4$) and evaporated under reduced pressure. The crude product was purified by column chromatography on silica gel using an elution gradient of dichloromethane:methanol (99:1 to 96:4), and the product crystallised from ether/pentane to afford the title compound, 250 mg.

$^1$Hnmr ($CDCl_3$, 300 MHz) δ: 1.02 (3H, t), 1.39 (3H, t), 1.58 (6H, m), 2.41 (2H, q), 2.56 (4H, m), 3.08 (6H, m), 3.22 (3H, s), 3.74 (1H, m), 3.98 (1H, m), 4.74 (3H, m), 8.62 (1H, d), 9.02 (1H, d), 10.58 (1H, s).

Anal. Found: C, 53.79; H, 6.61; N, 18.26. $C_{24}H_{35}N_7O_5S$ requires C, 54.02; H, 6.61; N, 18.38%.

EXAMPLE 85

5-[2-Ethoxy-5-(4-ethylpiperazin-1-ylsulphonyl)pyridin-3-yl]-3-ethyl-2-[(1R)-1-methyl-2-methoxyethyl]-2,6-dihydro-7H-pyrazolo[4,3-d]pyrimidin-7-one

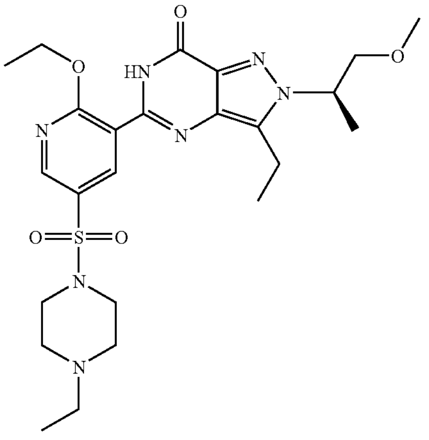

The title compound was obtained as a crystalline solid in 17% yield from the compound from preparation 89, following a similar procedure to that described in example 84.

$^1$Hnmr ($CDCl_3$, 300 MHz) δ: 1.02 (3H, t), 1.39 (3H, t), 1.58 (6H, m), 2.40 (2H, q), 2.55 (4H, m), 3.08 (6H, m), 3.22 (3H, s), 3.70 (1H, m), 3.98 (1H, m), 4.72 (3H, m), 8.61 (1H, d), 9.02 (1H, d), 10.58 (1H, s).

LRMS: m/z 534.4 ($MH^+$)

Anal. Found: C, 53.67; H, 6.62; N, 18.27. $C_{24}H_{35}N_7O_5S$ requires C, 54.02; H, 6.61; N, 18.38%.

EXAMPLE 86

5-[2-Ethoxy-5-(4-ethylpiperazin-1-ylsulphonyl)pyridin-3-yl]-3-ethyl-2-(3-methoxy-n-propyl)-2,6-dihydro-7H-pyrazolo[4,3-d]pyrimidin-7-one

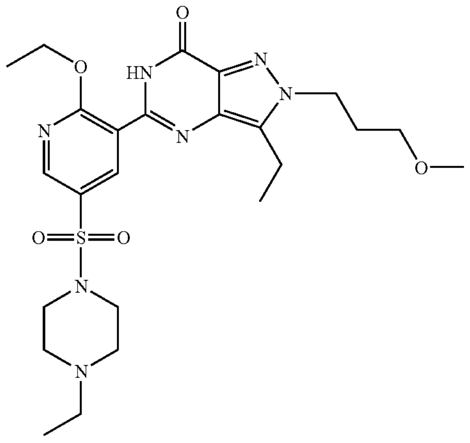

Potassium bis(trimethylsilyl)amide (145 mg, 0.72 mmol) was added to a solution of the compound from preparation 88 (200 mg, 0.36 mmol) in 3-methyl-3-pentanol (4 ml), and the reaction heated at 130° C. for 10 hours, then cooled. The mixture was evaporated under reduced pressure and the residue purified twice by column chromatography on silica gel using dichloromethane:methanol (97:3) as eluant, to afford the title compound, 40 mg.

$^1$Hnmr ($CDCl_3$, 400 MHz) δ: 1.00 (3H, t), 1.40 (3H, t), 1.57 (3H, t), 2.20 (2H, m), 2.42 (2H, m), 2.60 (4H, m), 3.03 (2H, q), 3.15 (4H, m), 3.30 (3H, s), 3.35 (2H, t), 4.40 (2H, t), 4.72 (2H, q), 8.60 (1H, s), 9.00 (1H, s), 10.60 (H, br s).

LRMS: m/z 535 ($MH^+$)

EXAMPLE 87

2-Cyclobutyl-3-ethyl-5-[5-(4-ethylpiperazin-1-ylsulphonyl)-2-(2-methoxyethoxy)pyridin-3-yl]-2,6-dihydro-7H-pyrazolo[4,3-d]pyrimidin-7-one

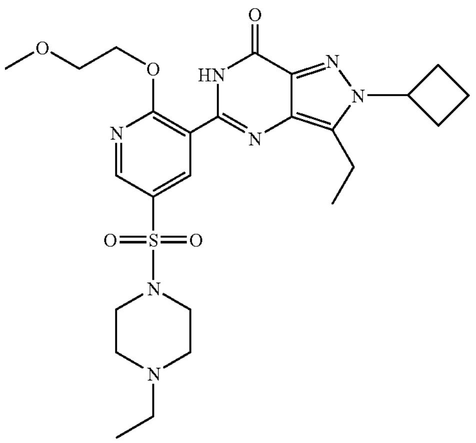

A mixture of the compound from preparation 83 (238 mg, 0.45 mmol) and potassium bis(trimethylsilyl)amide (450 mg, 2.25 mmol) in 2-methoxyethanol (5 ml) was stirred under reflux for 6 hours. The cooled mixture was partitioned between ethyl acetate and sodium bicarbonate solution, and the layers separated. The organic phase was washed with brine, dried ($MgSO_4$) and evaporated under reduced pressure. The residual orange oil was purified by column chromatography on silica gel using dichloromethane:methanol (98:2) as eluant to afford the title compound as an off-white foam, 150 mg.

$^1$Hnmr ($CDCl_3$, 300 MHz) δ: 1.00 (3H, t), 1.38 (3H, t), 1.85–2.05 (2H, m), 2.40 (2H, q), 2.45 (2H, m), 2.54 (4H, m), 2.90–3.05 (4H, m), 3.15 (4H, m), 3.55 (3H, s), 3.80 (2H, m), 4.74 (2H, m), 4.95 (1H, m), 8.60 (1H, s), 8.98 (1H, s), 10.75 (1H, s).

LRMS: m/z 546.4 ($MH^+$)

Anal. Found: C, 54.53; H, 6.59; N, 17.77. $C_{25}H_{35}N_7O_5S$ requires C, 55.03; H, 6.47; N, 17.97%.

EXAMPLES 88 TO 92

The compounds of the following general structure:

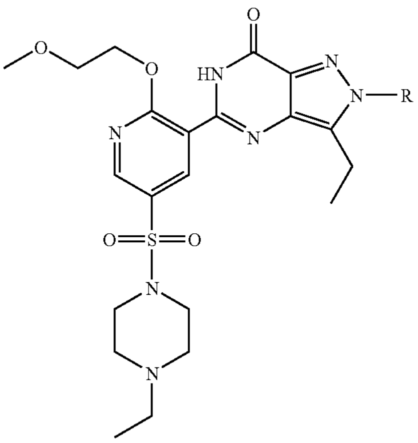

were prepared from the corresponding pyrazole carboxamide and 2-methoxyethanol, following a similar method to that described in example 87.

| Ex no. | R | Yield (%) | Data |
|---|---|---|---|
| 88[1] | 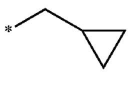 | 15 | $^1$Hnmr($CDCl_3$, 400MHz)δ: 0.43(2H, m), 0.60 (2H, m), 0.80(1H, m), 1.00(3H, t), 1.40(3H, t), 2.40(2H, q), 2.54(4H, m), 3.00(2H, q), 3.07(4H, m), 3.50(3H, s), 3.80(2H, m), 4.20 (2H, d), 4.78(2H, m), 8.60(1H, s), 8.97(1H, s), 10.57(1H, br s). Anal. Found: C, 52.68; H, 6.27; N, 17.19. $C_{25}H_{35}N_7O_5S.H_2O$ requires C,53.27; H, 6.26; N, 17.39%. |
| 89[2] | 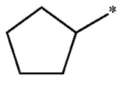 | 39 | $^1$Hnmr($CDCl_3$, 400MHz)δ: 1.02(3H, t), 1.38 (3H, t), 1.72(2H, m), 2.00–2.19(4H, m), 2.28 (2H, m), 2.40(2H, q), 2.56(4H, m), 3.04(2H, q), 3.16(4H, m), 3.57(3H, s), 3.86(2H, t), 4.78(2H, t), 4.82(1H, m), 8.61(1H, d), 8.98 (1H, d), 10.73(1H, s). LRMS: m/z 560.4($MH^+$) Anal. Found: C, 55.30; H, 6.79;N, 17.49. $C_{26}H_{37}N_7O_5S$ requires C, 55.80; H, 6.66; N, 17.52%. |
| 90[2] | 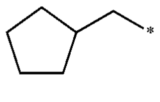 | 40 | $^1$Hnmr($CDCl_3$, 400MHz)δ: 1.02(3H, t), 1.32 (2H, m), 1.40(3H, t), 1.58(2H, m), 1.70(4H, m), 2.40(2H, q), 2.56(4H, m), 2.62(1H, m), 3.01(2H, q), 3.16(4H, m), 3.57(3H, s), 3.86 (2H, t), 4.21(2H, d), 4.79(2H, t), 8.61(1H, s), 8.98(1H, s), 10.74(1H, s). LRMS: m/z 574.8($MH^+$) Anal. Found: C, 54.88; H, 6.89;N, 16.63. $C_{27}H_{39}N_7O_5S$; $H_2O$ requires C, 54.80; H, 6.98; N, 16.57%. |
| 91 | 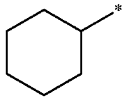 | 46 | $^1$Hnmr($CDCl_3$, 400MHz)δ: 1.02(3H, t), 1.38 (6H, m), 1.77(1H, m), 1.98(4H, m), 2.22(2H, m), 2.41(2H, q), 2.57(4H, m), 3.02(2H, q), 3.14(4H, m), 3.56(3H, s), 3.84(2H, t), 4.22 (1H, m), 4.78(2H, t), 8.61(1H, d), 8.98(1H, d), 10.71(1H, s). |

-continued

| Ex no. | R | Yield (%) | Data |
|---|---|---|---|
| 92 | 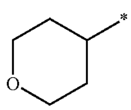 | 21 | [1]Hnmr($CDCl_3$, 300MHz)δ: 1.00(3H, t), 1.40 (3H, t), 1.83(2H, m), 2.40(2H, q), 2.55(6H, m), 3.06(2H, q), 3.10(4H, m), 3.55(3H, s), 3.60(2H, t), 3.80(2H, t), 4.20(2H, m), 4.48 (1H, m), 4.80(2H, t), 8.60(1H, s), 9.00(1H, s), 10.80(1H, s). LRMS: m/z 576.6($MH^+$) |

[1]additionally purified by ether trituration
[2]purified by ether trituration

EXAMPLE 93

5-[2-n-Butoxy-5-(4-methylpiperazin-1-ylsulphonyl)pyridin-3-yl]-3-ethyl-2-(2-methoxyethyl)-2,6-dihydro-7H-pyrazolo[4,3-d]pyrimidinone

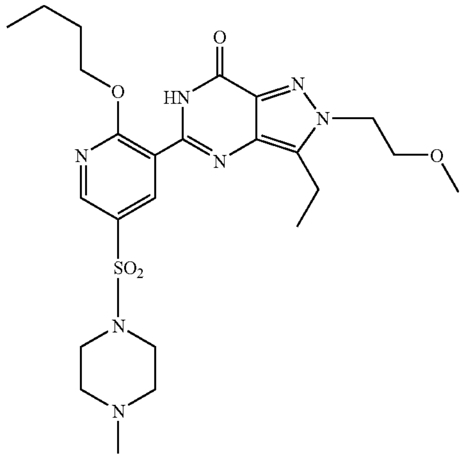

Potassium bis(trimethylsilyl)amide (123 mg, 0.62 mmol) was added to a solution of the compound from preparation 27 (162 mg, 0.31 mmol) in n-butanol, and the reaction mixture heated at 120° C. for 18 hours. The cooled mixture was concentrated under reduced pressure and the residual yellow oil purified by column chromatography on silica gel using an elution gradient of dichloromethane:methanol:0.88 ammonia (98:2:0.2 to 95:5:0.5). The product was triturated with ether to give the title compound as a white solid, 78 mg.

[1]Hnmr ($CDCl_3$, 300 MHz) δ: 1.03 (3H, t), 1.41 (3H, t), 1.54 (2H, m), 1.94 (2H, m), 2.28 (3H, s), 2.51 (4H, m), 3.07 (2H, m), 3.14 (4H, m), 3.30 (3H, s), 3.95 (2H, t), 4.46 (2H, t), 4.67 (2H, t), 8.63 (1H, m), 9.04 (1H, m), 10.60 (1H, m).

Anal. Found: C, 53.64; H, 6.64; N, 18.15. $C_{24}H_{35}N_7O_5S$ requires C, 54.02; H, 6.61; N, 18.37%.

EXAMPLE 94

3-Ethyl-5-[2-(2-methoxyethoxy)-5-(4-methylpiperazin-1-ylsulphonyl)pyridin-3-yl]-2-[(1S)-1-methylpropyl]-2,6-dihydro-7H-pyrazolo[4,3-d]pyrimidinone

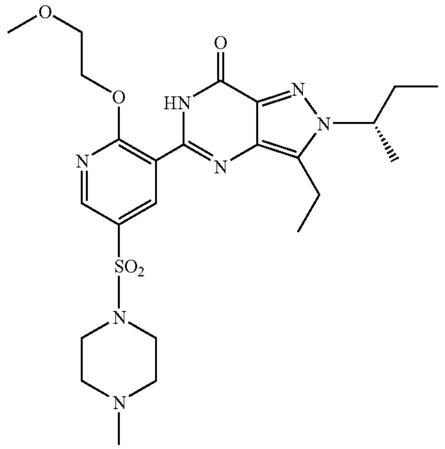

Potassium bis(trimethylsilyl)amide (960 mg, 4.8 mmol) was added to a solution of the compound from preparation 93 (500 mg, 0.96 mmol) in 2-methoxyethanol (15 ml), and the reaction heated at 130° C. for 5 hours. The cooled reaction mixture was partitioned between ethyl acetate and water, and the mixture neutralised using solid carbon dioxide. The layers were separated, the organic phase washed with water, dried ($MgSO_4$) and evaporated under reduced pressure. The crude product was purified by column chromatography on silica gel using an elution gradient of dichloromethane:methanol (99:1 to 96:4) to give an oil. This was triturated with ether, to afford the title compound as a white powder, 170 mg.

[1]Hnmr ($CDCl_3$, 400 MHz) δ: 0.80 (3H, t), 1.40 (3H, t), 1.60 (3H, d), 1.90 (1H, m), 2.20 (1H, m), 2.22 (3H, s), 2.50 (4H, m), 3.00 (2H, m), 3.10 (4H, m), 3.58 (3H, s), 3.80 (2H, m), 4.40 (1H, m), 4.80 (2H, m), 8.60 (1H, s), 9.00 (1H, s), 10.70 (1H, s).

LRMS: m/z 534.6 ($MH^+$)

Anal. Found: C, 54.20; H, 6.68; N, 18.39. $C_{24}H_{35}N_7O_5S$ requires C, 54.08; H, 6.71; N, 18.40%.

$[\alpha]_D$+26.0° (c=0.1, methanol).

EXAMPLE 95

3-Ethyl-5-[2-(2-methoxyethoxy)-5-(4-methylpiperazin-1-ylsulphonyl)pyridin-3-yl]-2-[(1R)-1-methylpropyl]-2,6-dihydro-7H-pyrazolo[4,3-d]pyrimidinone

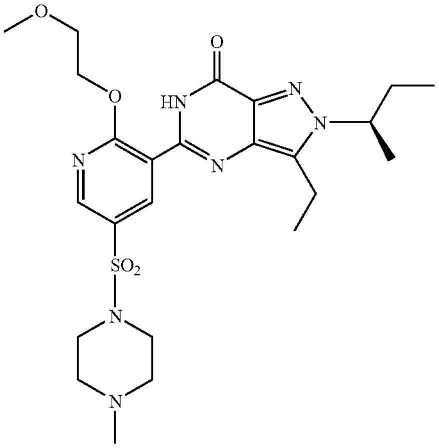

The title compound was obtained as a white powder in 23% yield from the compound from preparation 94 and 2-methoxyethanol, following the procedure described in example 94.

[1]Hnmr ($CDCl_3$, 400 MHz) δ: 0.80 (3H, t), 1.40 (3H, t), 1.60 (3H, d), 1.90 (1H, m), 2.20 (1H, m), 2.22 (3H, s), 2.50 (4H, m), 3.00 (2H, m), 3.10 (4H, m), 3.58 (3H, s), 3.80 (2H, m), 4.40 (1H, m), 4.80 (2H, m), 8.60 (1H, s), 9.00 (1H, s), 10.70 (1H, s).

LRMS: m/z 534.6 ($MH^+$)

EXAMPLE 96

2-n-Butyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidinone

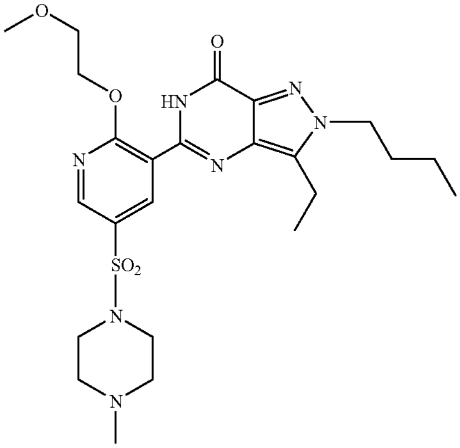

The title compound was obtained as a solid in 54% yield from the compound from preparation 91 and 2-methoxyethanol, following a similar procedure to that described in example 95.

[1]Hnmr ($CDCl_3$, 400 MHz) δ: 0.95 (3H, t), 1.40 (5H, m), 1.97 (2H, m), 2.35 (3H, s), 2.58 (4H, m), 3.01 (2H, q), 3.18 (4H, m), 3.56 (3H, s), 3.85 (2H, t), 4.28 (2H, t), 4.78 (2H, t), 8.62 (1H, d), 8.98 (1H, d), 10.75 (1H, s).

LRMS: m/z 535 ($MH^+$)

EXAMPLE 97

2-Cyclopropylmethyl-3-ethyl-5-[2-(2-methoxyethoxy)-5-(4-methylpiperazin-1-ylsulphonyl)pyridin-3-yl]-2,6-dihydro-7H-pyrazolo[4,3-d]pyrimidinone

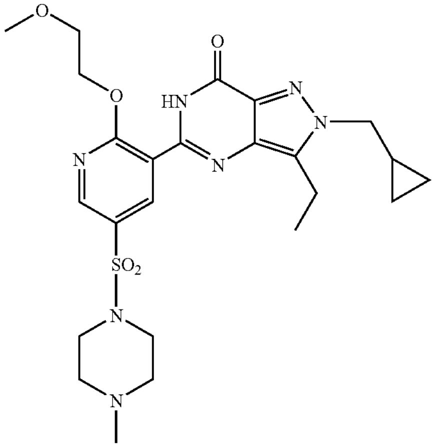

The title compound was obtained as a solid in 41% yield from the compound from preparation 92 and 2-methoxyethanol, following a similar procedure to that described in example 95.

[1]Hnmr ($CDCl_3$, 400 MHz) δ: 0.46 (2H, m), 0.62 (2H, m), 1.40 (4H, m), 2.27 (3H, s), 2.50 (4H, m), 3.05 (2H, q), 3.16 (4H, m), 3.57 (3H, s), 3.84 (2H, t), 4.20 (2H, d), 4.58 (2H, t), 8.61 (1H, d), 8.98 (1H, d), 10.77 (1H, s).

LRMS: m/z 532.2 ($MH^+$)

EXAMPLE 98

2-Cyclobutylmethyl-3-ethyl-5-[5-(4-ethylpiperazin-1-ylsulphonyl)-2-(tetrahydro-2-furanylmethoxy)pyridin-3-yl]-2,6-dihydro-7H-pyrazolo[4,3-d]pyrimidinone

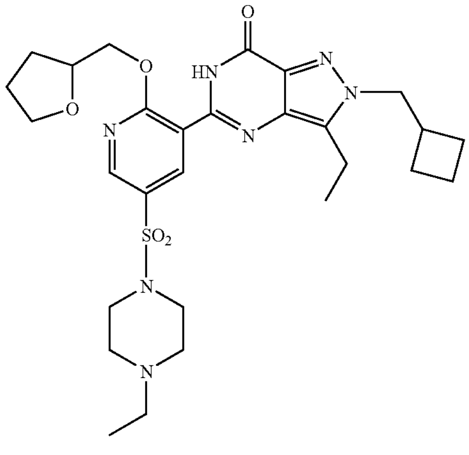

A mixture of the compound from example 7 (200 mg, 0.38 mmol) and potassium bis(trimethylsilyl)amide (371 mg, 1.86 mmol) in tetrahydrofurfuryl alcohol (2.5 ml) was heated under reflux for 18 hours. The cooled mixture was concentrated under reduced pressure, and the residue purified by column chromatography on silica gel using an elution gradient of dichloromethane:methanol (100:0 to 90:10). The product was recrystallised from ether to afford the title compound, 20 mg.

$^1$Hnmr ($CDCl_3$, 300 MHz) δ: 1.01 (3H, t), 1.40 (3H, t), 1.75–2.18 (10H, m), 2.40 (2H, q), 2.55 (4H, m), 3.00 (3H, m), 3.15 (4H, m), 3.88 (1H, m), 4.16 (1H, m), 4.30 (2H, d), 4.38 (1H, m), 4.59 (1H, m), 4.75 (1H, m), 8.60 (1H, d), 8.98 (1H, d), 10.73 (1H, s).

LRMS: m/z 587 ($MH^+$)

EXAMPLE 99

3-Ethyl-5-[5-(4-ethylpiperazin-1-ylsulphonyl)-2-(2-methoxyethoxy)pyridin-3-yl]-2-(2-methoxyethoxy)-2,6-dihydro-7H-pyrazolo[4,3-d]pyrimidinone

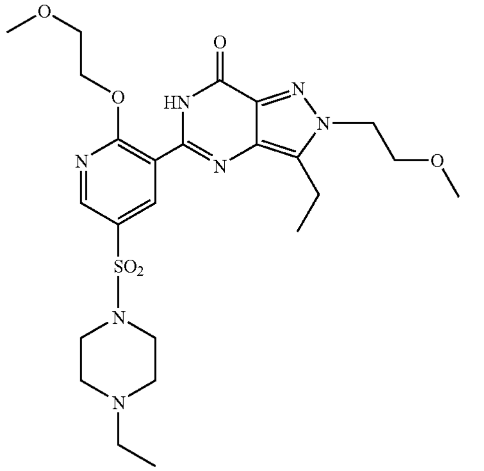

The title compound was obtained as a solid, from the compound from example 8 and 2-methoxyethanol, following a similar procedure to that described in example 98.

$^1$Hnmr ($CDCl_3$, 300 MHz) δ: 1.02 (6H, m), 1.84 (2H, m), 2.42 (2H, q), 2.56 (4H, m), 3.01 (2H, t), 3.15 (4H, m), 3.29 (3H, s), 3.57 (3H, s), 3.88 (2H, m), 4.44 (2H, t), 4.78 (2H, t), 8.61 (1H, s), 8.98 (1H, s), 10.76 (1H, s).

LRMS: m/z 564 ($MH^+$)

EXAMPLE 100

5-[2-Ethoxy-5-(4-iso-propylpiperazin-1-ylsulphonyl)pyridin-3-yl]-3-ethyl-2-(2-methoxyethyl)-2,6-dihydro-7H-pyrazolo[4,3-d]pyrimidinone

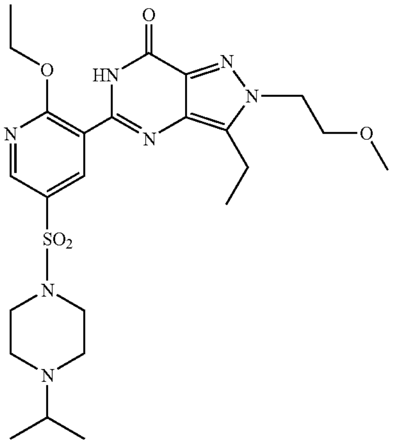

Sodium nitrite (116 mg, 1.68 mmol) was added to a cooled (−20° C.) solution of the amine from preparation 82 (400 mg, 1.12 mmol) in acetic acid (5 ml) and concentrated hydrochloric acid (5 ml), and the solution allowed to warm to room temperature over 4 hours. The solution was then re-cooled to −15° C., liquid sulphur dioxide (3 ml) added followed by a solution of copper (II) chloride (450 mg, 3.34 mmol) in water (2 ml), and the solution stirred for 2 hours, then allowed to warm to room temperature. The reaction was diluted with water and extracted with dichloromethane (100 ml). The combined organic extracts were dried ($Na_2SO_4$), concentrated under reduced pressure and the residue azeotroped with toluene. The product was dissolved in ethanol (5 ml), N-isopropylpiperazine (500 μl, 3.56 mmol) added and the reaction stirred at room temperature for 18 hours. The reaction mixture was evaporated under reduced pressure and the crude product purified by column chromatography on silica gel using dichloromethane:methanol:0.88 ammonia (96:4:0.5) as eluant. The resulting pale yellow solid was recrystallised from isopropyl ether:dichloromethane to give the title compound, 211 mg.

$^1$Hnmr ($CDCl_3$, 300 MHz) δ: 1.00 (6H, 2×s), 1.40 (3H, t), 1.56 (3H, t), 2.60 (4H, m), 2.66 (1H, m), 3.08 (6H, m), 3.27 (3H, s), 3.92 (2H, t), 4.45 (2H, t), 4.75 (2H, q), 8.61 (1H, d), 9.02 (1H, d), 10.61 (1H, s).

LRMS: m/z 534.5 ($MH^+$)

Anal. Found: C, 54.00; H, 6.69; N, 18.24. $C_{24}H_{35}N_7O_5S$ requires C, 54.02; H, 6.61; N, 18.37%.

EXAMPLE 101

5-[2-Ethoxy-5-(4-n-propylpiperazin-1-ylsulphonyl)pyridin-3-yl)-3-ethyl-2-(2-methoxyethyl)-2,6-dihydro-7H-pyrazolo[4,3-d]pyrimidinone

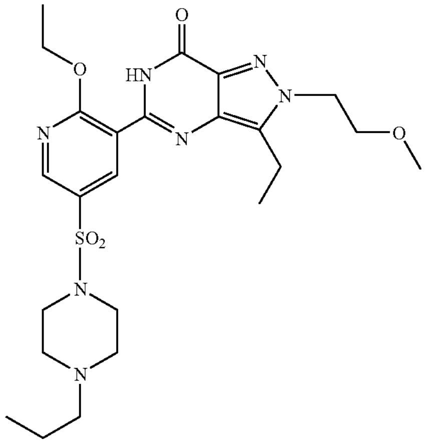

The title compound was obtained in 21% yield from the amine of preparation 82 and n-propyl piperazine (prepared from the hydrobromide salt, in the presence of excess triethylamine), following the procedure described in Example 100.

$^1$Hnmr ($CDCl_3$, 300 MHz) δ: 0.84 (3H, t), 1.40 (3H, t), 1.55 (5H, m), 2.30 (2H, m), 2.55 (4H, m), 3.08 (6H, m), 3.28 (3H, s), 3.94 (2H, t), 4.44 (2H, t), 4.75 (2H, q), 8.62 (1H, d), 9.03 (1H, d), 10.61 (1H, s).

LRMS: m/z 534.4 ($MH^+$)

EXAMPLE 102

1-(6-Ethoxy-5-[3-ethyl]-6,7-dihydro-2-(2-methoxy-ethyl)-7-oxo-2H-pyrazole[4,3-d]pyrimidin-5-yl-3-pyridylsulfonyl)-4-ethylpiperazine.ethyl acetate solvate

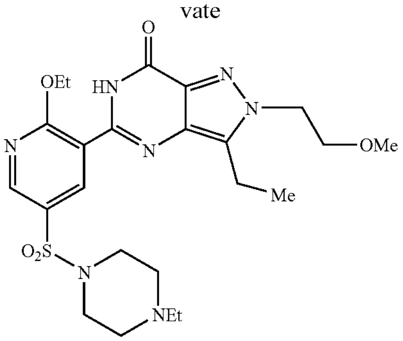

To prepare the compound of Example 8 a mixture of N-[3-carbamoyl-5-ethyl-1-(2-methoxyethyl)-1H-pyrazol-4-yl}-2-ethoxy-5-(4-ethyl-1-piperazinyl sulfonyl) nicotinamide (1.18 kg, 2.2 Mol), potassium tert-butoxide (500 g, 4.4 moles) and ethyl acetate (193 g) in ethanol (11.8 L) was heated at 120° C. for 20 hours. The reaction mixture was then concentrated under reduced pressure, in total approx. 10 L of solvent were distilled. To the residue water (2.9 L) was added and the mixture stirred at room temperature while aqueous HCl was added until pH 7.5 was obtained. Ethyl acetate (7.5 L) was added and the two phase mixture was warmed to 55° C. The organic phase was separated and the aqueous phase was extracted with further ethyl acetate (3.0 L). The combined organic phases were distilled at atmospheric pressure to a final volume of 4 L. The precipitated solids were granulated at 5° C. for 1 h, filtered and washed with ethyl acetate (1.2 L) and dried under vacuum. This afforded 1-(6-Ethoxy-5-[3-ethyl]-6,7-dihydro-2-(2-methoxyethyl)-7-oxo-2H-pyrazole[4,3-d]pyrimidin-5-yl]-3-pyridylsulfonyl)-4-ethylpiperazine as a light yellow crystalline solid, 877 g, 78%. m.p.=157° C. Found: C, 52.65; H, 6.46; N, 17.76. $C_{23}H_{33}N_7O_5S.0.2C_2H_5CO_2CH_3$ requires C, 53.21; H, 6.49; N, 18.25%.

δ ($CDCl_3$): 1.07 (3H, t), 1.42 (3H, t), 1.61 (3H, t), 2.44 (2H, q), 2.57 (4H, m), 3.08 (2H, q), 3.15 (4H, m), 3.32 (3H, s), 3.92 (2H, q), 4.48 (2H, q), 4.77 (2H, q), 8.65 (1H, d), 9.06 (1H, d). The spectrum also has signals that correspond to a solvate with ethyl acetate.

LRMS: m/z=520 $(M+1)^+$

EXAMPLE 103

1-{6-ethoxy-5-[3-ethyl-6,7-dihydro-2-(2-methoxy-ethyl)-7-oxo-2H-pyrazolo[4,3-d]pyrimidin-5-yl]-3-pyridylsulfonyl}-4-ethylpiperazine

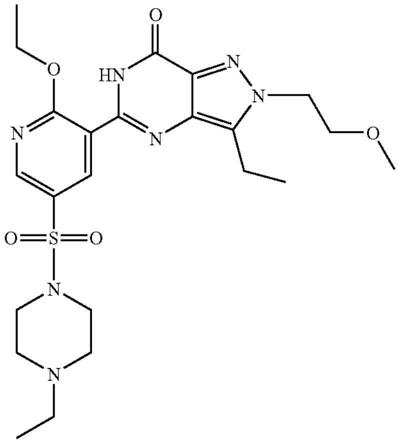

10 g (0.019 mol) of the compound of Example 8 and Example 102, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine ethyl acetate solvate, was charged followed by 12 ml/g (120 mls) of 16% water in ethyl alcohol. The slurry was heated to reflux to yield a solution and 6 ml/g (60 mls) distilled off at atmospheric pressure. The solution was then cooled to room temperature with crystallisation occurring at 40° C. The slurry was then cooled to 5–10° C. and granulated for 30 minutes following which it was filtered and washed with 2 ml/g ethyl alcohol (20 mls). The damp solid was dried in vacuo overnight at 55–60° C. to yield a white crystalline solid. (Yield 7.6 g, 76%). Melting Point 162–165° C.

δ ($CDCl_3$): 1.05 (3H, t), 1.42 (3H, t), 1.58 (3H, t), 2.43 (2H, q), 2.57 (4H, t), 3.09 (2H, t), 3.15 (4H, t), 3.30 (3H, s), 3.93 (2H, t), 4.48 (2H, t), 4.90 (2H, q), 8.65 (1H, d), 9.05 (1H, d), 10.65 (1H, s).

In the process of Example 103, water and pharmaceutically acceptable alcohols such as methanol, ethanol, propanol, butanol and mixtures thereof can be used to prepare the compound of Examples 8 and 102.

EXAMPLE 104

1-{6-ethoxy-5-[3-ethyl-6,7-dihydro-2-(2-methoxy-ethyl)-7-oxo-2H-pyrazolo[4,3-d]pyrimidin-5-yl]-3-pyridylsulfonyl}-4-ethylpiperazine benzene-sulfonate salt

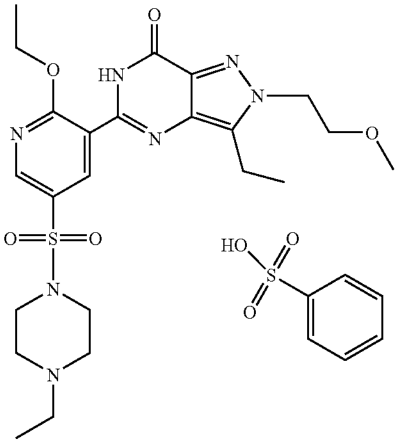

170 g (0.33 mol) of the compound of Example 103, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, was charged followed by a water/ 2-butanone (4% v/v) at 10 ml/g (1.7 litres) and warmed to reflux. 53 g (0.33 mol) of benzene sulfonic acid dissolved in water (23 mls, resulting in 70% w/w solution) was added to the refluxing solution over 30 minutes.5.3 ml/g (0.9 litres) of 2-butanone were striped and replaced and the slurry cooled. The slurry was cooled to 5–10° C. and granulated for 2 hours after which it was filtered and washed with 2 ml/g (0.3 litres) of 2-butanone. The salt was dried overnight in vacuo at 55–60° C. to yield a white crystalline solid. Yield 215 g, 96.4%. Mpt 242–244° C.

δ (DMSO): 1.17 (3H, t), 1.28 (3H, t), 1.35 (3H, t), 2.73 (2H, q), 2.97 (2H, q), 3.2 (3H, s), 3.58 (2H, t), 3.78 (3H, t), 3.81 (2H, t), 4.49 (2H, t) 4.51 (2H, q), 7.29–7.33 (3H, m), 7.57–7.60 (2H, m), 8.28 (1H, d), 8.73 (1H, d), 9.13 (1H, s), 11.90(1H, s).

The powder X-ray diffraction (PXRD) pattern for this salt, having Mpt 242–244° C., was determined using a Siemens D5000 powder X-ray diffractometer fitted with a theta-theta goniometer, automatic beam divergence slits, a secondary monochromator and a scintillation counter. The specimen was rotated whilst being irradiated with copper K-alpha1 X-rays (Wavelength=1.5046 Angstroms) filtered with a graphite monochromator (λ=0.15405 nm) with the X-ray tube operated at 40 kWmA.

The main peaks (in degrees θ) of the PXRD pattern are illustrated in Table I.

TABLE I

| Angle 2-Theta ° | Intensity % % | Angle 2-Theta ° | Intensity % % | Angle 2-Theta ° | Intensity % % |
|---|---|---|---|---|---|
| 4.208 | 8.6 | 22.294 | 91.9 | 34.952 | 5.5 |
| 7.292 | 52.5 | 22.708 | 13.4 | 35.497 | 5.6 |
| 8.153 | 12.6 | 23.414 | 12.6 | 35.830 | 5.4 |
| 8.422 | 4.1 | 23.682 | 4.7 | 36.507 | 4.5 |
| 9.426 | 10.2 | 24.132 | 4.6 | 36.816 | 8.4 |
| 10.957 | 100.0 | 24.361 | 13.3 | 37.047 | 16.0 |
| 12.645 | 11.4 | 24.554 | 12.9 | 37.641 | 5.5 |
| 14.150 | 18.6 | 24.844 | 6.9 | 38.362 | 8.7 |
| 14.639 | 3.1 | 24.902 | 7.6 | 38.582 | 17.7 |
| 14.928 | 2.7 | 25.444 | 15.2 | 39.203 | 8.8 |
| 15.080 | 4.9 | 25.854 | 43.0 | 40.549 | 7.8 |
| 15.363 | 1.8 | 26.054 | 16.4 | 41.277 | 6.7 |
| 16.070 | 4.5 | 26.369 | 12.5 | 41.487 | 11.9 |
| 16.245 | 5.4 | 27.016 | 9.5 | 42.376 | 8.4 |
| 16.351 | 11.4 | 27.706 | 4.8 | 42.759 | 7.1 |
| 16.892 | 33.9 | 28.302 | 7.2 | 43.450 | 8.0 |
| 17.554 | 35.1 | 28.504 | 10.9 | 44.400 | 4.5 |
| 18.178 | 11.8 | 28.998 | 4.0 | 45.043 | 8.3 |
| 18.562 | 3.2 | 29.615 | 16.1 | 45.888 | 6.2 |
| 18.903 | 3.0 | 30.197 | 5.2 | 46.393 | 6.2 |
| 19.174 | 3.1 | 31.039 | 12.5 | 46.897 | 7.3 |
| 19.591 | 31.6 | 31.445 | 7.7 | 48.197 | 7.8 |
| 20.392 | 43.3 | 32.094 | 6.5 | 48.373 | 7.9 |
| 20.598 | 6.8 | 32.611 | 6.4 | 49.163 | 5.3 |
| 20.965 | 12.8 | 32.734 | 9.3 | 50.501 | 6.0 |
| 21.136 | 7.8 | 33.014 | 6.5 | 50.619 | 5.9 |
| 21.485 | 32.9 | 33.110 | 7.2 | 52.248 | 14.6 |
| 22.000 | 24.0 | 33.740 | 3.5 | 52.746 | 5.7 |
| | | 34.255 | 3.4 | 54.668 | 5.1 |

The same besylate salt, as defined by the XRD pattern described in Table 1, when made via alternative routes can have a melting point in the range of from 235–246° C. (measured using a Perkin Elmer DSC7 at a heating rate of 20° C./minute).

EXAMPLE 104

1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine p-toluene sulfonate salt

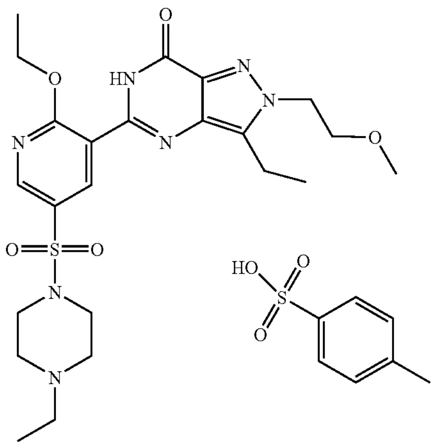

5 g (0.0096 mol) of the compound of Example 103, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, was charged followed by 10 ml/g (50 mls) of ethyl alcohol and warmed to reflux. 1.86 g (0.0097 mol) of p-toluene sulfonic acid dissolved in 10 mls ethyl alcohol was added to the refluxing solution over 15 seconds. The solution was allowed cool and allowed granulate for 1 hour at <R.T. The slurry was filtered and washed with 3 mlg (15 mls) of ethyl alcohol. The salt was dried overnight in vacuo at 55–60° C. to yield a white crystalline solid. Yield 6.12 g, 92.3%. Mpt 208° C.

δ (DMSO): 1.18 (3H, t), 1.28 (3H, t), 1.36 (3H, t), 2.28 (3H, s), 2.78 (2H, q), 2.99 (2H, q), 3.23 (4H, t) 3.25 (3H, s), 3.55 (2H, t), 3.80 (2H, t), 3.82 (2H, t), 4.51 (2H, t), 4.53 (2H, q), 7.11 (2H, d), 7.47-(2H, d), 8.30 (1H, d), 8.73 (1H, d), 9.2 (1H, s), 11.90 (1H, s).

EXAMPLE 105

1-{6-ethoxy-5-[3-ethyl-6,7-dihydro-2-[(2-methoxyethyl)-7-oxo-2H-pyrazolo[4,3-d]pyrimidin-5-yl]-3-pyridylsulfonyl}-4-ethylpiperazine (+) camphorsulfonate salt

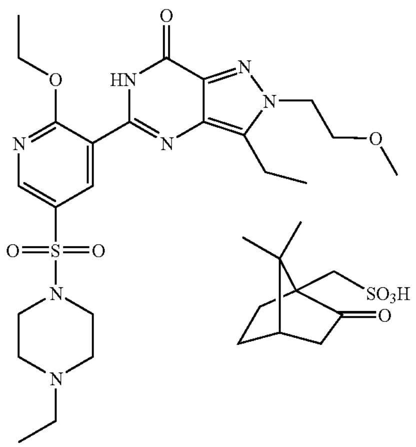

3 g (0.006 mol) of the compound of Example 103, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, was charged followed by a 2-butanone/water (4% v/v) at 10 ml/g (30 mls) and warmed to reflux. 1.48 g (0.006 mol) of (+)-camphor sulphonic acid dissolved in 5 mls 2-butanone and 1 ml water was added to the refluxing solution in <1 minute. 3.3 ml/g (10 mls) were azeotroped out and the solution cooled with crystallisation occurring at 45° C. approximately. The slurry was cooled to 5–10° C. and granulated for 0.5 hours after which it was filtered and washed with 5 ml/g (15 mls) of 2-butanone. The salt was dried overnight in vacuo at 55–60° C. to yield a white crystalline solid. (Yield 3.4 g, 77%). Mpt 222–225° C.

δ (DMSO): 0.75 (3H, s), 1.03 (3H, s), 1.18 (3H, t), 1.28 (3H, t), 1.36 (3H, t), 1.20–1.40 (2H, m), 1.79–198 (3H, m), 2.2–2.3 (1H, m), 2.5–2.62 (2H, m), 2.78 (2H, q), 2.99 (2H, q), 3.02 (1H, d), 3.23 (4H, t) 3.25 (3H, s), 3.55 (2H, t), 3.79 (2H, t), 3.82 (2H, t), 4.51 (2H, t), 4.50 (2H, q), 8.29 (1H, d), 8.73 (1H, d), 9.33 (1H, s), 11.85 (1H, s).

EXAMPLE 106

1-{6-ethoxy-5-[3-ethyl-6,7-dihydro-2-(2-methoxyethyl]-7-oxo-2H-pyrazolo[4,3-d]pyrimidin-5-yl]-3-pyridylsulfonyl}-4-ethylpiperazine (+/−)-camphor sulfonate salt

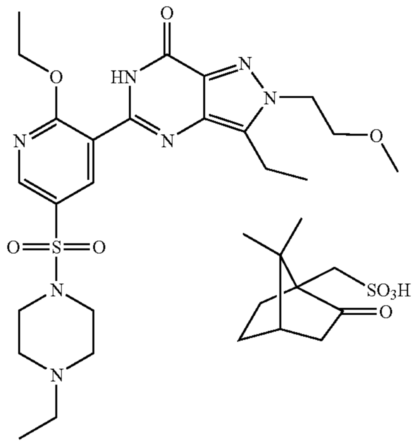

17 g (0.033 mol) of the compound of Example 103, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, was charged followed by ethyl alcohol at 10 ml/g (170 mls) and warmed to reflux. 7.75 g (0.035 mol) of racemic camphor sulphonic acid dissolved in 30 mls ethyl alcohol was added to the refluxing solution instantaneously. The solution was allowed cool and crystallisation occurred at 65–66° C. The slurry was cooled to 5–10° C. and granulated for 1 hours after which it was filtered and washed with 3 ml/g (51 mls) of ethyl alcohol. The salt was dried overnight in vacuo at 55–60° C. to yield a white crystalline solid. (Yield 22.1 g, 89.8%).

δ (DMSO): 0.75 (3H, s), 1.03 (3H, s), 1.18 (3H, t), 1.28 (3H, t), 1.36 (3H, t), 1.20–1.40 (2H, m), 1.79–198 (3H, m), 2.2–2.3 (1H, m), 2.5–2.62 (2H, m), 2.78 (2H, q), 2.99 (2H, q), 3.02 (1H, d), 3.23 (4H, t), 3.25 (3H, s), 3.55 (2H, t), 3.79 (2H, t), 3.82 (2H, t), 4.51 (2H, t), 4.50 (2H, q), 8.29 (1H, d), 8.73 (1H, d), 9.33 (1H, s), 11.85 (1H, s).

EXAMPLE 107

1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine ethane-sulfonate salt

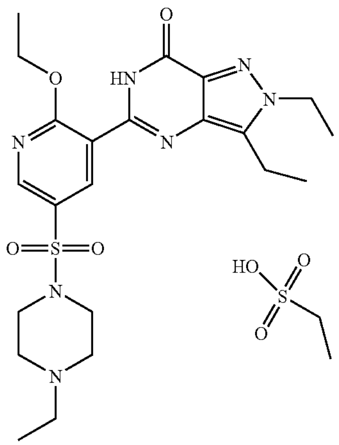

5 g (9.6 mmol) of the title compound of Example 102, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine, was charged followed by a 10 ml/g (0.05 litres) Ethanol and warmed to reflux. 1.1 g (10.5 mmol) of ethane sulfonic acid diluted in 2 ml ethanol was added to the refluxing solution. The slurry was cooled with crystallisation occurring at 26–30° C. The slurry was granulated filtered and washed with 2 ml/g (0.01 litres) of ethanol. The salt was dried overnight in vacuo at 55–60° C. to yield a white crystalline solid. Yield 5.2 g, 86.1%. Mpt 205–210° C. δ ($CDCl_3$): 1.16 (3H, t), 1.39 (3H, t), 1.41 (3H, t), 1.52 (3H, t), 2.73 (2H, q), 3.03 (2H, t), 3.09 (2H, q, 3.16 (2H, t), 3.30 (3H, s), 3.35(2H, t), 3.65 (2H, t), 3.89 (2H, t), 3.90 (2H, q), 4.46 (2H, t), 4.71 (2H, q), 8.63 (1H, d), 8.71 (1H, d), 10.76 (1H, s), 11.29 (1H, s).

Biological Activity

The following Table illustrates both the in vitro activities for a range of the compounds of the invention as inhibitors of cGMP $PDE_5$ as well as their selectivity for cGMP $PDE_5$ versus cGMP $PDE_6$.

The $IC_{50}$ measurements for cGMP $PDE_5$ were based upon data generated on human corpus cavernosum tissue and the $IC_{50}$ measurements for rod cGMP PDE6 were based upon data generated on bovine retina tissue and wherein the selectivity ratio for cGMP $PDE_5$ to cGMP $PDE_6$ quoted is based upon $IC_{50}$ PDE5/$IC_{50}$ $PDE_6$.

TABLE

| EXAMPLE | $IC_{50}$ (nM) | Selectivity (PDE 5/6) |
|---|---|---|
| 5 | 1.0 | — |
| 8 | 1.68 | 223.8 |
| 17 | 0.90 | 254.1 |
| 22 | 6.4 | 325.3 |

TABLE-continued

| EXAMPLE | $IC_{50}$ (nM) | Selectivity (PDE 5/6) |
|---|---|---|
| 24 | 1.52 | 134.9 |
| 27 | 0.85 | 161 |
| 53 | 1.09 | — |
| 60 | 0.45 | 343.7 |

PREPARATION 1

3-Ethyl-1-(2-methoxyethyl)-4-nitropyrazole-5-carboxamide and

PREPARATION 2

3-Ethyl-2-(2-methoxyethyl)-4-nitropyrazole-5-carboxamide

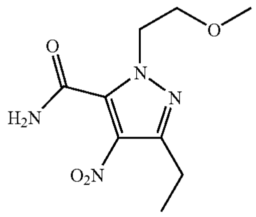

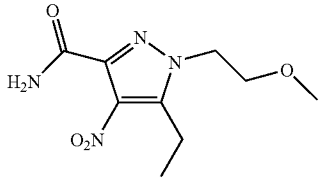

A mixture of 3-ethyl-4-nitro-1H-pyrazole-5-carboxamide (WO, 9849166), (1.7 g, 8.8 mmol), 2-bromoethyl methyl ether (0.85 ml, 8.85 mmol) and cesium carbonate (2.9 g, 9.0 mmol) in N,N-dimethylformamide (20 ml) was stirred at room temperature for 20 hours. The reaction mixture was concentrated under reduced pressure and the residue was partitioned between ethyl acetate (125 ml) and brine (100 ml). The phases were separated, and the organic layer was dried ($Na_2SO_4$), and evaporated under reduced pressure. The crude product was purified by column chromatography on silica gel, using ethyl acetate:methanol (97:3) as eluant to afford the title compound of preparation 1, 831 mg, δ ($DMSOd_6$): 1.19 (3H, t), 2.82 (2H, q), 3.20 (3H, s), 3.68 (2H, t), 4.22 (2H, t), 8.18 (1H, s), 8.38 (1H, s).

LRMS: m/z 260 $(M+18)^+$ and the title compound of preparation 2, 793 mg.

δ ($CDCl_3$): 1.18 (3H, t), 2.98 (2H, q), 3.22 (3H, s), 3.70 (2H, t), 4.28 (2H, t), 7.65 (1H, s), 7.94 (1H, s).

LRMS: m/z 243 $(M+1)^+$

PREPARATION 3

1-(2-Methoxyethyl)-4-nitro-3-n-propylpyrazole-5-carboxamide and

PREPARATION 4

2-(2-Methoxyethyl)-4-nitro-3-n-propylpyrazole-5-carboxamide

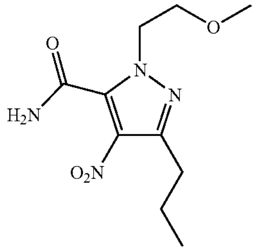

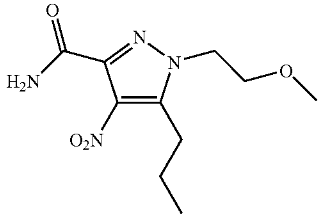

A mixture of 4-nitro-3-n-propyl-1H-pyrazole-5-carboxamide (WO, 9849166), (7.3 g, 37.0 mmol), 2-bromoethyl methyl ether (3.85 ml, 41.0 mmol) and cesium carbonate (24.0 g, 74.0 mmol) in N,N-dimethylformamide (300 ml) was heated at 70° C. for 4 hours. The cooled mixture was concentrated under reduced pressure and the residue partitioned between ethyl acetate (100 ml) and brine (100 ml) and the phases separated. The aqueous layer was extracted with ethyl acetate (2×100 ml), the combined organic solutions dried ($Na_2SO_4$) and evaporated under reduced pressure. The residue was triturated with ether and the resulting precipitate filtered and dried, to give some of the N2 isomer. The filtrate was evaporated under reduced pressure and the residue was purified by column chromatography on silica gel, using an elution gradient of ethyl acetate:methanol (100:0 to 99:1). The product of preparation 3 was suspended in ether, the mixture filtered and the filtrate evaporated under reduced pressure to afford the title compound of preparation 3, 1.07 g, δ ($CDCl_3$): 1.00 (3H, t), 1.74 (2H, m), 2.88 (2H, t), 3.35 (3H, s), 3.78 (2H, t), 4.47 (2H, t), 6.06 (1H, s), 7.24 (1H, s).

LRMS: m/z 257 $(M+1)^+$

More of the N2 isomer (preparation 4) was also obtained to give a total of 3.85 g.

δ ($DMSOd_6$): 1.04 (3H, t), 1.68 (2H, m), 2.98 (2H, t), 3.30 (3H, s), 3.79 (2H, t), 4.29 (2H, t), 5.85 (1H, s), 7.35 (1H, s).

LRMS: m/z 257 $(M+1)^+$

PREPARATION 5

2-(2-{[tert-Butyl(dimethyl)silyl]oxy}ethyl)-3-ethyl-4-nitropyrazole-5-carboxamide

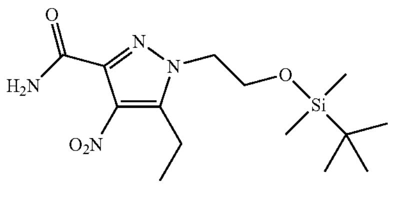

A mixture of 3-ethyl-4-nitro-1H-pyrazole-5-carboxamide (WO, 9849166), (4.9 g, 26.6 mmol), cesium carbonate (21.0 g, 64.5 mmol) and (2-bromoethoxy)-tert-butyldimethylsilane (7.0 g, 29.0 mmol) in acetonitrile (400 ml) was stirred at 80° C. for 20 hours. The cooled mixture was concentrated under reduced pressure and the residue was partitioned between ethyl acetate (200 ml) and water (100 ml). The layers were separated, the organic phase washed with water (3×50 ml), dried ($Na_2SO_4$) and evaporated under reduced pressure. The crude product was purified by column chromatography on silica gel, using ethyl acetate as eluant, and repeated using an elution gradient of pentane:ethyl acetate (50:50 to 0:100), to give some of the desired compound.

The crude product containing both the N1 and N2 isomers was triturated with pentane, the resulting precipitate filtered and dried to afford the title compound as a solid (1.7 g, in total)

δ ($CDCl_3$): −0.05 (6H, s), 0.81 (9H, s), 1.28 (3H, t), 3.08 (2H, q), 4.03 (2H, t), 4.24 (2H, t), 5.80 (1H, s), 7.34 (1H, s).

LRMS: m/z 343 $(M+1)^+$

PREPARATION 6 tert-Butyl 3-iodo-1-azetidinecarboxylate

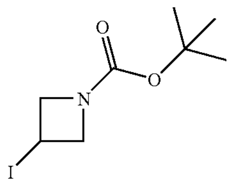

A mixture of tert-butyl 3-[(methylsulphonyl)oxy]-1-azetidinecarboxylate (Synlett; 1998; 379), (5.0 g, 19.9 mmol), and potassium iodide (16.5 g, 99.4 mmol) in N,N-dimethylformamide (25 ml), was heated at 100° C. for 42 hours. The cooled mixture was partitioned between water and ethyl acetate, and the layers separated. The organic phase was dried ($MgSO_4$), concentrated under reduced pressure and the residue azeotroped with xylene. The crude product was purified by column chromatography on silica gel using dichloromethane as eluant, to give the title compound, 3.26 g.

δ ($CDCl_3$): 1.43 (9H, s), 4.28 (2H, m), 4.46 (1H, m), 4.62 (2H, m),

LRMS: m/z 284 $(M+1)^+$

PREPARATION 7 tert-Butyl 3-[3-(aminocarbonyl)-5-ethyl-4-nitropyrazol-1-yl-1-azetidinecarboxylate

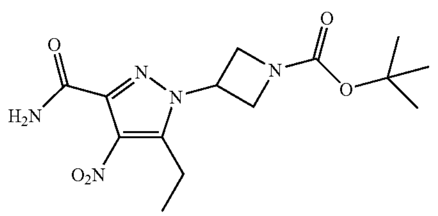

A mixture of 3-ethyl-4-nitro-1H-pyrazole-5-carboxamide (WO, 9849166), (6.59 g, 35.8 mmol), cesium carbonate (12.25 g, 37.6 mmol), and the title compound of preparation 6 (10.3 g, 37.6 mmol) in N,N-dimethylformamide (60 ml) was heated at 60° C. for 3 days. The cooled reaction was poured into 2% aqueous sodium bicarbonate solution (250 ml), and extracted with ethyl acetate (1×230 ml, 1×100 ml). The combined organic extracts were dried ($MgSO_4$) and evaporated under reduced pressure. The residual oil was purified by column chromatography on silica gel, using an elution gradient of ethyl acetate:pentane (50:50 to 100:0) to give the N1-isomer (5.0 g) and the title compound of preparation 7, 4.1 g.

δ ($CDCl_3$): 1.25 (3H, t), 1.46 (9H, s), 2.96 (2H, q), 4.37 (2H, m), 4.44 (2H, m), 5.06 (1H, m), 5.82 (1H, s), 6.63 (1H, s).

PREPARATION 8

Benzyl 2-[3-(aminocarbonyl)-5-ethyl-4-nitropyrazol-1-yl]ethyl(methyl)carbamate

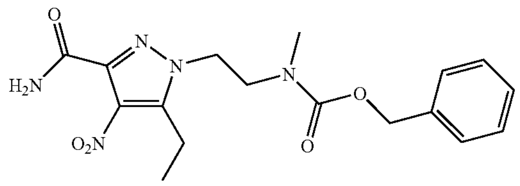

Obtained (25%) from 3-ethyl-4-nitro-1H-pyrazole-5-carboxamide (WO, 9849166), and 2-[(benzyloxy)carbonyl](methyl)amino]ethyl methanesulphonate (J.Med.Chem. 37; 23; 1994; 3977) following a similar procedure to that described in preparation 7.

δ ($CDCl_3$): (rotamers in 0.42:0.58 ratio) 1.03 and 1.20 (3H, t), 2.69 and 2.87 (2H, q), 2.80 and 2.92 (3H, s), 3.72 (2H, m), 4.20 and 4.33 (2H, t), 5.02 and 5.14 (2H, s), 5.86 (1H, m), 7.35 (6H, m).

PREPARATION 9

4-Amino-3-ethyl-2-(2-methoxyethyl)pyrazole-5-carboxamide

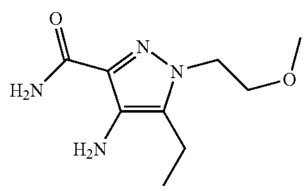

A mixture of the title compound from preparation 2 (500 mg, 2.07 mmol) and 10% palladium on charcoal (50 mg) in ethanol (20 ml) was hydrogenated at 50 psi and room temperature for 18 hours. The reaction mixture was filtered through Arbocel®, and the filtrate evaporated under reduced pressure to afford the title compound as a white solid.

δ ($DMSOd_6$): 1.03 (3H, t), 2.57 (2H, q), 3.20 (3H, s), 3.63 (2H, t), 4.09 (2H, t), 4.39 (2H, s), 6.90 (1H, s), 7.01 (1H, s).

LRMS: m/z 213 (M+1)+

PREPARATIONS 10 TO 12

The compounds of the general structure:

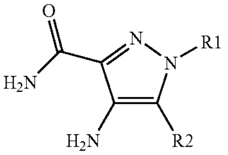

were prepared from the corresponding nitropyrazole, following a similar procedure to that described in preparation 9.

sodium bicarbonate solution (400 ml). The pH of the solution was adjusted to 8 using solid sodium carbonate, and this solution was then extracted with ethyl acetate (2×350 ml). The combined organic extracts were dried ($MgSO_4$) and evaporated under reduced pressure to afford the title compound, 1.5 g.

δ ($CDCl_3$): (rotamers in a 0.46:0.54 ratio), 1.00 and 1.14 (3H, t), 2.38 and 2.50 (2H, q), 2.68 and 2.80 (3H, s), 3.63 (2H, m), 3.95 (2H, s), 4.04 and 4.17 (2H, t), 5.10 and 5.14 (2H, s), 5.14 (1H, s), 6.53 (1H, s), 7.36 (5H, m).

PREPARATION 14

4-Amino-3-ethyl-1-(2-methoxyethyl)pyrazole-5-carboxamide

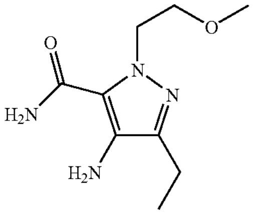

Obtained from the title compound of preparation 1 (95%), using a similar procedure to that described in preparation 9, and after purification by column chromatography using dichloromethane:methanol (90:10) as eluant.

| Prep No. | $R_1$ | $R_2$ | Yield (%) | m/z | $^1$Hnmr |
|---|---|---|---|---|---|
| 10 | 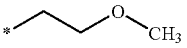 | $(CH_2)_2CH_3$ | 95 | 227 $(M + 1)^+$ | δ($CDCl_3$): 0.98(3H, t), 1.60 (2H, m), 2.47(2H, t), 3.30(3H, s), 3.74(2H, t), 3.94(2H, s), 4.15(2H, t), 5.20(1H, s), 6.58 (1H, s). |
| 11 | 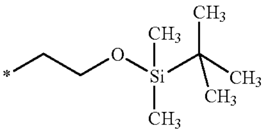 | $CH_2CH_3$ | | 335 $(M + 23)^+$ | δ($CDCl_3$): −0.03(6H, s), 0.85 (9H, s), 1.18(3H, t), 2.63(2H, q), 3.94(4H, m), 4.08(2H, t), 5.15(1H, s), 6.57(1H, s). |
| 12 | 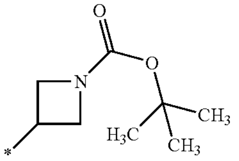 | $CH_2CH_3$ | 73 | | δ($CDCl_3$): 1.14(3H, t), 1.46 (9H, s), 2.55(2H, q), 3.98(2H, s), 4.29(2H, m), 4.40(2H, m), 4.94(1H, m), 5.23(1H, s), 6.64 (1H, s). |

PREPARATION 13

Benzyl 2-[4-amino-3-(aminocarbonyl)-5-ethylpyrazol-1-yl]ethyl(methyl)carbamate

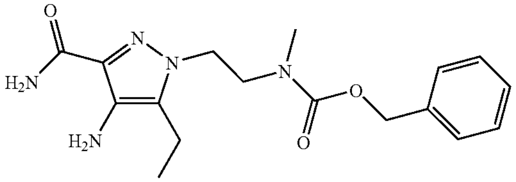

A mixture of the title compound of preparation 8 (1.92 g, 5.28 mmol), iron powder (3.04 g) and water (2.5 ml) in acetic acid (50 ml) was stirred at room temperature for 25 minutes. The reaction mixture was filtered through Arbocel®, and the filtrate poured slowly into saturated δ ($CDCl_3$): 1.26 (3H, t), 2.58 (2H, q), 3.37 (3H, s), 3.60 (2H, s), 3.82 (2H, t), 4.50 (2H, t).

LRMS: m/z 213 $(M+1)^+$

PREPARATION 15

4-Amino-1-(2-methoxyethyl)-3-n-propylpyrazole-5-carboxamide

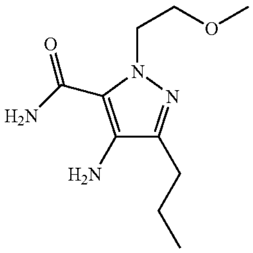

Obtained as a solid (99%) from the title compound of preparation 3, using the procedure described in preparation 9.

δ ($CDCl_3$): 0.95 (3H, t), 1.63 (2H, m), 2.48 (2H, t), 3.30 (3H, s), 3.78 (2H, t), 4.46 (2H, t).

LRMS: m/z 227 $(M+1)^+$

PREPARATION 16

Pyridine-2-amino-5-sulphonic acid

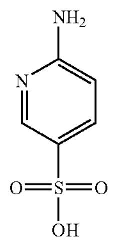

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound as a solid, 111.3 g.

LRMS: m/z 175 $(M+1)^+$

PREPARATION 17

Pyridine-2-amino-3-bromo-5-sulphonic acid

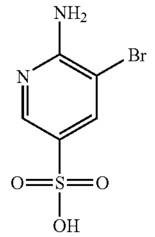

Bromine (99 g, 0.62 mol) was added dropwise over an hour, to a hot solution of the title compound of preparation 16 (108 g, 0.62 mol) in water (600 ml) so as to maintain a steady reflux. Once the addition was complete the reaction was cooled and the resulting mixture filtered. The solid was washed with water and dried under suction to afford the title compound, 53.4 g.

δ ($DMSOd_6$, 300 MHz): 8.08 (1H, s), 8.14 (1H, s).

LRMS: m/z 253 $(M)^+$

PREPARATION 18

Pyridine-3-bromo-2-chloro-5-sulphonyl chloride

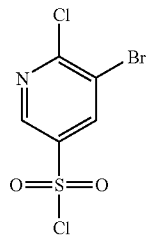

A solution of sodium nitrite (7.6 g, 110.0 mmol) in water (30 ml) was added dropwise to an ice-cooled solution of the title compound of preparation 17 (25.3 g, 100.0 mmol) in aqueous hydrochloric acid (115 ml, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144.0 mmol) and phosphorus oxychloride (1 ml, 10.8 mmol) was heated at 125° C. for 3 hours, and then cooled. The reaction mixture was poured onto ice (100 g) and the resulting solid filtered, and washed with water. The product was dissolved in dichloromethane, dried ($MgSO_4$), and evaporated under reduced pressure to afford the title compound as a yellow solid, 26.589.

δ ($CDCl_3$, 300 MHz): 8.46 (1H, s), 8.92 (1H, s).

PREPARATION 19

3-Bromo-2-chloro-5-(4-ethylpiperazin-1-ylsulphonyl)pyridine

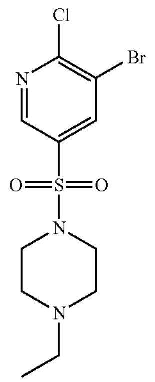

A solution of 1-ethylpiperazine (11.3 ml, 89.0 mmol) and triethylamine (12.5 ml, 89.0 mmol) in dichloromethane (150 ml) was added dropwise to an ice-cooled solution of the title compound of preparation 18 (23.09, 79.0 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid, 14.5 g.

δ ($CDCl_3$, 300 MHz): 1.05 (3H, t), 2.42 (2H, q), 2.55 (4H, m), 3.12 (4H, m), 8.24 (1H, s), 8.67 (1H, s).

PREPARATION 20

3-Bromo-2-chloro-5-(4-methylpiperazin-1-ylsulphonyl)pyridine

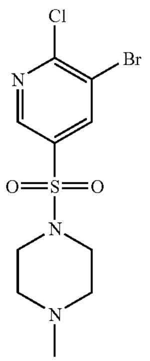

N-Methylpiperazine (7.65 ml, 69.0 mmol) was added dropwise to a solution of the title compound of preparation 18 (10.0 g, 34.5 mmol) in ethanol (200 ml), and the reaction stirred at room temperature for 3 hours. The mixture was concentrated under reduced pressure and the residue partitioned between dichloromethane (200 ml) and water (100 ml) and the layers separated. The organic phase was dried ($Na_2SO_4$), and evaporated under reduced pressure to afford the title compound, 10.53 g, as a yellow solid.

δ ($CDCl_3$): 2.28 (3H, s), 2.51 (4H, m), 3.14 (4H, m), 8.24 (1H, s), 8.67 (1H, s).

PREPARATION 21

3-Bromo-2-ethoxy-5-(4-ethylpiperazin-1-ylsulphonyl)pyridine

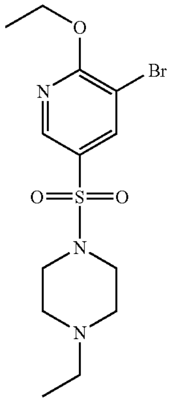

A mixture of the title compound of preparation 19 (6.60 g, 17.9 mmol) and sodium ethoxide (6.099, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried ($MgSO_4$) and evaporated under reduced pressure to afford the title compound as a brown solid, 6.41 g.

Found: C, 41.27; H, 5.33; N, 11.11. $C_{13}H_{20}BrN_3O_3S$ requires C, 41.35; H, 5.28; N, 10.99%.

δ ($CDCl_3$, 300 MHz): 1.06 (3H, t), 1.48 (3H, t), 2.42 (2H, q), 2.56 (4H, m), 3.09 (4H, m), 4.54 (2H, q), 8.10 (1H, s), 8.46 (1H, s).

LRMS: m/z 378, 380 $(M+1)^+$

PREPARATION 22

3-Bromo-2-ethoxy-5-(4-methylpiperazin-1-ylsulphonyl)pyridine

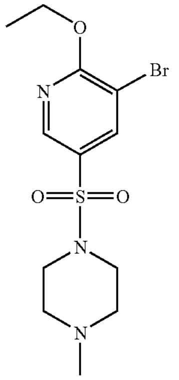

A mixture of the title compound of preparation 20 (10.09, 39.1 mmol), potassium bis(trimethylsilyl)amide (5.92 g, 29.7 mmol) and ethanol (3.5 ml) in tetrahydrofuran (150 ml) was stirred at room temperature for 24 hours. The reaction mixture was concentrated under reduced pressure and the residue partitioned between ethyl acetate (150 ml) and brine (50 ml). The layers were separated, and the organic phase dried ($Na_2SO_4$), filtered and evaporated under reduced pressure, to afford the title compound, 9.1 g.

δ ($CDCl_3$): 1.44 (3H, t), 2.29 (3H, s), 2.51 (4H, m), 3.08 (4H, m), 4.54 (2H, q), 8.10 (1H, s), 8.44 (1H, s).

LRMS: m/z 365 $(M+1)^+$

PREPARATION 23

Pyridine 2-ethoxy-5-(4-ethylpiperazin-1-ylsulphonyl)-3-carboxylic acid ethyl ester

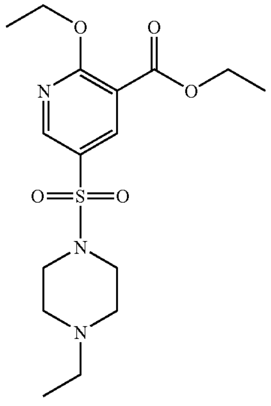

A mixture of the title compound of preparation 21 (6.40 g, 16.92 mmol), triethylamine (12 ml, 86.1 mmol), andpalladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound as an orange oil, 6.29.

δ ($CDCl_3$, 300 MHz): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s).

LRMS: m/z 372 $(M+1)^+$

PREPARATION 24

Pyridine 2-ethoxy-5-(4-methylpiperazin-1-ylsulphonyl)-3-carboxylic acid ethyl ester

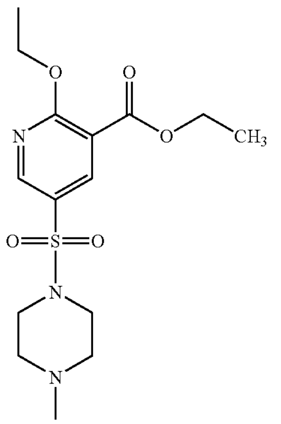

Obtained (85%) as an orange solid, from the title compound of preparation 22 using a similar procedure to that described in preparation 23.

δ ($CDCl_3$): 1.40 (3H, t), 1.46 (3H, t), 2.28 (3H, s), 2.50 (4H, m), 3.09 (4H, m), 4.40 (2H, q), 4.57 (2H, q), 8.40 (1H, s), 8.63 (1H, s).

LRMS: m/z 358 $(M+1)^+$

PREPARATION 25

Pyridine 2-ethoxy-5-(4-ethylpiperazin-1-ylsulphonyl)-3-carboxylic acid

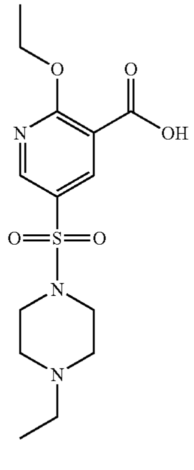

A mixture of the title compound of preparation 23 (4.96 g, 13.35 mmol) and aqueous sodium hydroxide solution (25 ml, 2N, 50.0 mmol) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried ($MgSO_4$) and evaporated under reduced pressure to afford the title compound as a tan coloured solid, 4.02 g.

δ ($DMSOd_6$, 300 MHz): 1.18 (3H, t), 1.37 (3H, t), 3.08 (2H, q), 3.17–3.35 (8H, m), 4.52 (2H, q), 8.30 (1H, s), 8.70 (1H, s).

PREPARATION 26

Pyridine 2-ethoxy-5-(4-methylpiperazin-1-ylsulphonyl)-3-carboxylic acid hydrochloride

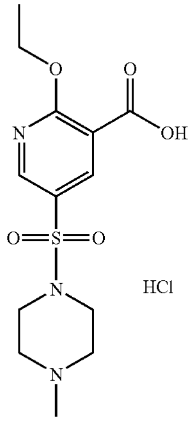

Sodium hydroxide solution (21 ml, 2M, 42.0 mmol) was added to a solution of the title compound of preparation 24 (7.57 g, 21.0 mmol) in dioxan (150 ml) and the reaction stirred at room temperature for 18 hours. The mixture was neutralised using hydrochloric acid, the dioxan removed under reduced pressure and the remaining aqueous solution acidified to pH 2, using hydrochloric acid. The solution was evaporated under reduced pressure, the residue re-suspended in hot ethanol, filtered, and the filtrate re-evaporated to afford the title compound, 5.46 g.

δ ($DMSOd_6$): 1.37 (3H, t), 2.50 (4H, m), 2.72 (3H, s), 3.13–3.39 (4H, m), 4.53 (2H, q), 8.30 (1H, s), 8.75 (1H, s).

LRMS: m/z 330 $(M+1)^+$

PREPARATION 27

4-[2-Ethoxy-5-(4-methylpiperazin-1-ylsulphonyl)pyridin-3-ylcarboxamido]-3-ethyl-2-(2-methoxyethyl)pyrazole-5-carboxamide

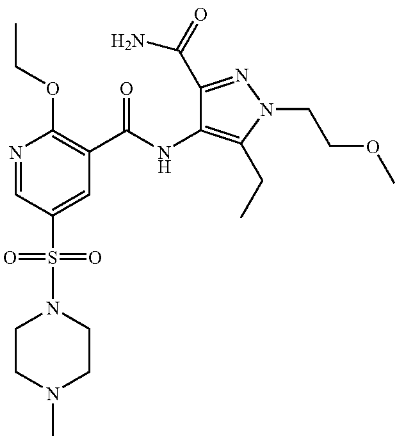

Oxalyl chloride (500 ml, 5.73 mmol) was added dropwise to an ice-cooled solution of the title compound of preparation 26 (522 mg, 1.43 mmol) and N,N-dimethylformamide (1 drop) in dichloromethane (20 ml), and the reaction stirred for 2 hours. The mixture was concentrated under reduced pressure and azeotroped several times with dichloromethane to give the intermediate acid chloride. A solution of this product in dichloromethane (20 ml) was added to a solution of the title compound of preparation 9 (250 mg, 1.18 mmol) and triethylamine (500 ml, 3.18 mmol) in dichloromethane (20 ml), and the reaction stirred at room temperature for 18 hours. The mixture was washed with water, dried ($Na_2SO_4$) and evaporated under reduced pressure. The residue was purified by column chromatography on silica gel, using an elution gradient of dichloromethane:methanol (100:0 to 95:5) to afford the title compound, 428 mg.

δ ($CDCl_3$): 1.20 (3H, t), 1.59 (3H, t), 2.28 (3H, s), 2.50 (4H, m), 2.95 (2H, m), 3.10 (4H, m), 3.36 (3H, s), 3.80 (2H, t), 4.25 (2H, t), 4.78 (2H, q), 5.26 (1H, s), 6.65 (1H, s), 8.65 (1H, s), 8.85 (1H, s), 10.51 (1H, s).

LRMS: m/z 524 $(M+1)^+$

PREPARATION 28

4-[2-Ethoxy-5-(4-methylpiperazin-1-ylsulphonyl) pyridin-3-ylcarboxamido]-2-(2-methoxyethyl)-3-n-propylpyrazole-5-carboxamide

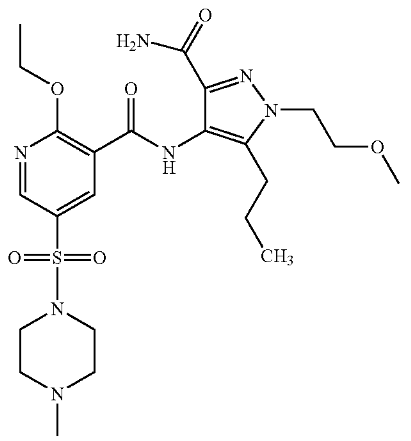

The title compound was obtained as a white solid (79%), from the title compounds from preparation 10 and 26, following the procedure described in preparation 27.

δ ($CDCl_3$): 0.92 (3H, t), 1.58 (5H, m), 2.24 (3H, s), 2.47 (4H, m), 2.90 (2H, t), 3.10 (4H, m), 3.35 (3H, s), 3.78 (2H, t), 4.23 (2H, t), 4.78 (2H, q), 5.42 (1H, br s), 6.68 (1H, brs), 8.62 (1H, d), 8.82 (1H, d), 10.48 (1H, s).

LRMS: m/z 538 $(M+1)^+$

PREPARATION 29

4-[2-Ethoxy-5-(4-ethylpiperazin-1-ylsulphonyl)pyridin-3-ylcarboxamido]-3-ethyl-2-(2-methoxyethyl) Pyrazole-5-carboxamide

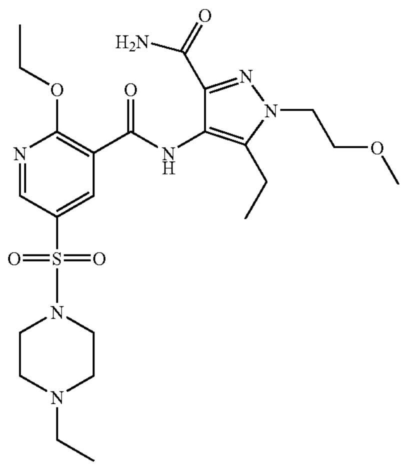

1-(3-Dimethylaminopropyl)-3-ethylcarbodiimide hydrochloride (5.26 g, 27.4 mmol) was added to a solution of the title compounds from preparation 25 (7.25 g, 21.1 mmol), and preparation 9 (4.45 g, 20.9 mmol), 1-hydroxybenzotriazole hydrate (3.71 g, 27.4 mmol), and N-diisopropylethylamine (10.96 ml, 63.3 mmol) in dichloromethane (70 ml), and the reaction stirred for 18 hours. The reaction mixture was diluted with dichloromethane (100 ml), washed with water (100 ml), saturated aqueous sodium bicarbonate solution (100 ml), and brine (100 ml), dried ($MgSO_4$), and evaporated under reduced pressure. The crude product was purified by column chromatography on silica gel using an elution gradient of dichloromethane:methanol (100:0 to 95:5) to give the title compound as a foam, 10.05 g.

δ ($CDCl_3$): 1.03 (3H, t), 1.20 (3H, t), 1.58 (3H, t), 2.40 (2H, q), 2.54 (4H, m), 2.95 (2H, q), 3.10 (4H, m), 3.37 (3H, s), 3.80 (2H, t), 4.26 (2H, t), 4.78 (2H, q), 5.27 (1H, s), 6.66 (1H, s), 8.65 (1H, s), 8.85 (1H, s), 10.51 (1H, s).

LRMS: m/z 538 $(M+1)^+$

PREPARATION 30

4-[2-Ethoxy-5-(4-ethylpiperazin-1-ylsulphonyl)pyridin-3-ylcarboxamido]-2-(2-methoxyethyl)-3-n-propylpyrazole-5-carboxamide

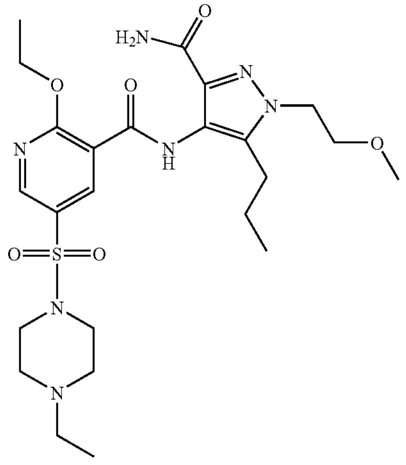

N-Diisopropylethylamine. (0.92 ml, 5.3 mmol) was added to a solution of the title compounds from preparation 25 (1.0 g, 2.65 mmol), and preparation 10 (600 mg, 2.65 mmol),1-hydroxybenzotriazole hydrate (465 mg, 3.45 mmol), and 1-(3-dimethylaminopropyl)-3-ethylcarbodiimide hydrochloride (660 mg, 3.45 mmol) in dichloromethane (20 ml), and the reaction stirred for 18 hours. The reaction mixture was washed with brine, dried ($MgSO_4$), and evaporated under reduced pressure. The crude product was purified by column chromatography on silica gel using an elution gradient of dichloromethane:methanol (100:0 to 95:5) to afford the title compound, 740 mg.

δ ($CDCl_3$): 0.94 (3H, t), 1.03 (3H, t), 1.59 (5H, m), 2.40 (2H, q), 2.54 (4H, m), 2.92 (2H, t), 3.11 (4H, m), 3.37 (3H, s), 3.80 (2H, t), 4.25 (2H, t), 4.78 (2H, q), 5.26 (1H, s), 6.66 (1H, s), 8.65 (1H, s), 8.83 (1H, s), 10.48 (1H, s).

LRMS: m/z 552 $(M+1)^+$

PREPARATION 31

2-(2-{[tert-Butyl(dimethyl)silyl]oxy}ethyl)-4-[2-ethoxy-5-(4-ethylpiperazin-1-ylsulphonyl)pyridin-3-ylcarboxamido]-3-ethylpyrazole-5-carboxamide

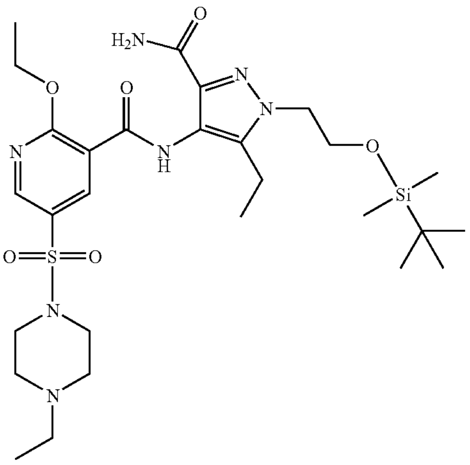

Obtained as a white solid (67%) from the title compounds of preparations 25 and 0.11 following a similar procedure to that described in preparation 27.

δ ($CDCl_3$): 0.00 (6H, s), 0.85 (9H, s), 1.04 (3H, t), 1.22 (3H, t), 1.57 (3H, t), 2.40 (2H, q), 2.53 (4H, m), 2.94 (2H, q), 3.10 (4H, m), 4.02 (2H, t), 4.19 (2H, t), 4.78 (2H, q), 5.39 (1H, s), 6.66 (1H, s), 8.64 (1H, s), 8.83 (1H, s), 10.49 (1H, s).

LRMS: m/z 638 $(M+1)^+$

PREPARATION 32

Benzyl 2-{3-(aminocarbonyl)-4-[({2-ethoxy-5-[(4-ethyl-1-piperazinyl)sulphonyl]-3-pyridinyl}carbonyl)amino]-5-ethylpyrazol-1-yl}ethyl(methyl)carbamate

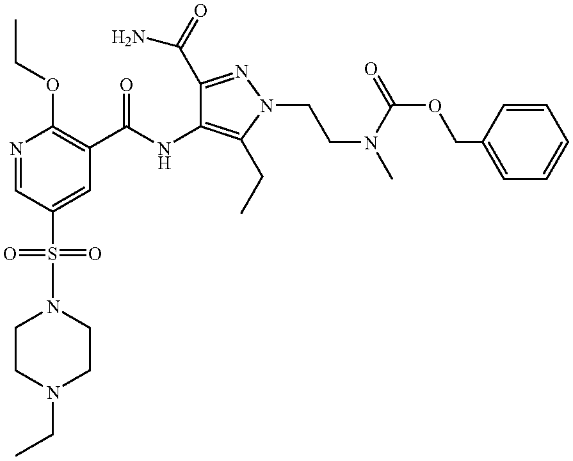

Triethylamine (1.0 ml, 7.2 mmol) was added to a solution of the title compounds from preparation 25 (1.5 g, 4.5 mmol), and preparation 13 (1.7 g, 4.95 mmol), 1-hydroxybenzotriazole hydrate (833 mg, 5.44 mmol), and 1-(3-dimethylaminopropyl)-3-ethylcarbodiimide hydrochloride (1.28 g, 6.68 mmol) in dichloromethane (50 ml), and the reaction stirred for 3 days at room temperature. The reaction mixture was concentrated under reduced pressure and the residue partitioned between saturated aqueous sodium bicarbonate solution and ethyl acetate, and the layers separated. The aqueous phase was extracted with ethyl acetate (2×50 ml), and the combined organic solutions, dried ($MgSO_4$), and evaporated under reduced pressure. The crude product was purified by column chromatography on silica gel using dichloromethane:methanol (95:5) as eluant to afford the title compound, 3.0 g.

δ ($CDCl_3$): 1.00–1.20 (6H, m), 1.58 (3H, t), 2.40 (2H, q), 2.54 (4H, m), 2.70–2.91 (5H, m), 3.10 (4H, m), 3.70 (2H, m), 4.16–4.32 (2H, m), 4.79 (2H, q), 5.12 (2H, m), 5.24 (1H, s), 6.62 (1H, s), 7.37 (5H, m), 8.64 (1H, s), 8.82 (1H, s), 10.50 (1H, s).

PREPARATION 33

2-(1-tert-Butyloxycarbonylazetidin-3-yl)-4-[2-ethoxy-5-(4-ethylpiperazin-1-ylsulphonyl pyridin-3-ylcarboxamido]-3-ethylyrazole-5-carboxamide

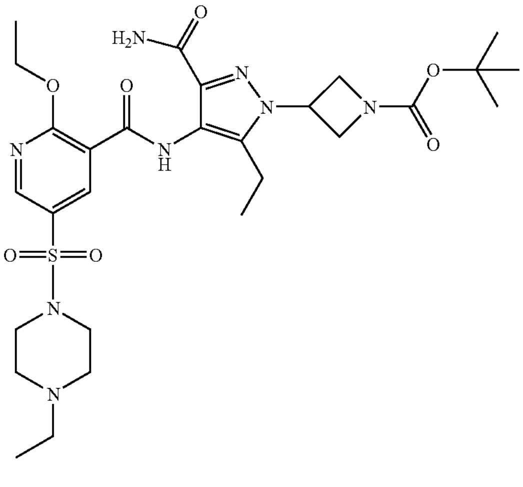

The title compound was obtained (72%) from the title compounds from preparation 25 and preparation 12, following a similar procedure to that described in preparation 32.

δ ($CDCl_3$): 1.01 (3H, t), 1.19 (3H, t), 1.47 (9H, s), 1.58 (3H, t), 2.40 (2H, q), 2.54 (4H, m), 2.86 (2H, q), 3.10 (4H, m), 4.38 (2H, m), 4.41 (2H, m), 4.79 (2H, q), 5.10 (1H, m), 5.30 (1H, br s), 6.77 (1H, br s), 8.63 (1H, d), 8.82 (1H, d), 10.57 (1H, s).

PREPARATION 34

4-[2-Ethoxy-5-(4-ethylpiperazin-1-ylsulphonyl)pyridin-3-ylcarboxamido]-1H-3-ethylpyrazole-5-carboxamide

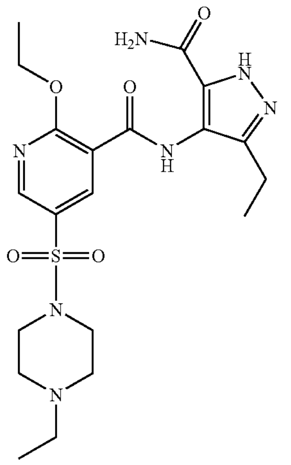

A solution of 3-ethyl-1H-pyrazole-5-carboxamide (WO, 9849166) (9.2 g, 59.8 mmol) in N,N-dimethylformamide (60 ml) was added to a solution of the title compound from preparation 25 (21.7 g, 62.9 mmol), 1-hydroxybenzotriazole hydrate (10.1 g, 66.0 mmol) and triethylamine (13.15 ml, 94.3 mmol) in dichloromethane (240 ml). 1-(3-Dimethylaminopropyl)-3-ethylcarbodiimide hydrochloride (13.26 g, 69.2 mmol) was added and the reaction stirred at room temperature for 6 hours. The dichloromethane was removed under reduced pressure, the remaining solution poured into ethyl acetate (400 ml), and this mixture washed with aqueous sodium bicarbonate solution (400 ml). The resulting crystalline precipitate was filtered, washed with ethyl acetate and dried under vacuum, to afford the title compound, as a white powder, 22 g.

δ ($CDCl_3$+1 drop $DMSOd_6$) 0.96 (3H, t), 1.18 (3H, t), 1.50 (3H, t), 2.25–2.56 (6H, m), 2.84 (2H, q), 3.00 (4H, m), 4.70 (2H, q), 5.60 (1H, br s), 6.78 (1H, br s), 8.56 (1H, d), 8.76 (1H, d), 10.59 (1H, s), 12.10–12.30 (1H, s).

LRMS: m/z 480 $(M+1)^+$

PREPARATION 35

4-[2-Ethoxy-5-(4-methylpiperazin-1-ylsulphonyl)pyridin-3-ylcarboxamido]-1H-3-ethylpyrazole-5-carboxamide

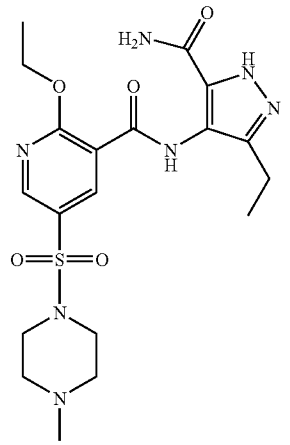

Oxalyl chloride (9.5 ml, 108 mmol) was added dropwise to an ice-cold solution of the title compound from preparation 26 (10.0 g, 27.0 mmol) and N,N-dimethylformamide (160 μl) in dichloromethane (150 ml), and once addition was complete, the reaction was stirred at room temperature for 5½ hours. The mixture was evaporated under reduced pressure and the residue azeotroped with toluene, to give a yellow solid.

Triethylamine (11.2 ml, 81.0 mmol) was added to a solution of the intermediate acid chloride (10.5 g, 27.3 mmol) and 4-amino-3-ethyl-1H-pyrazole-5-carboxamide (WO, 9849166), (4.2 g, 27.3 mmol) in dichloromethane (150 ml), and the reaction stirred at room temperature for 18 hours. The mixture was diluted with water, and the layers separated. The aqueous phase was extracted with dichloromethane (2×), and the combined organic solutions dried ($Na_2SO_4$) and evaporated under reduced pressure. The crude product was triturated with ether, and the resulting solid filtered to give the title compound, 10.1 g.

δ ($CDCl_3$) 1.21 (3H, t), 1.59 (3H, t), 2.26 (3H, s), 2.50 (4H, m), 2.94 (2H, q), 3.10 (4H, m), 4.79 (2H, q), 5.50 (1H, br s), 6.80 (1H, br s), 8.64 (1H, d), 8.84 (1H, d), 10.65 (1H, s).

PREPARATION 36

2-iso-Butyl-4-[2-Ethoxy-5-(4-ethylpiperazin-1-ylsulphonyl)pyridin-3-ylcarboxamido]-3-ethylpyrazole-5-carboxamide

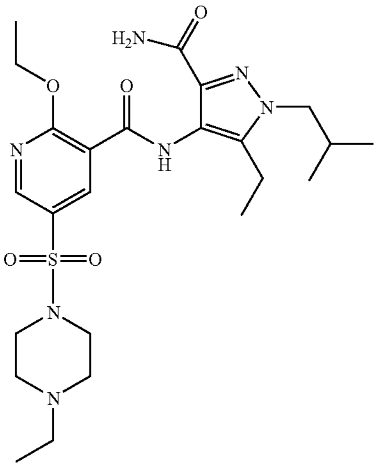

1-Bromo-2-methylpropane (187 μl, 1.72 mmol) was added to a solution of the title compound from preparation 34 (750 mg, 1.56 mmol) and cesium carbonate (1.12 g, 3.44 mmol) in N,N-dimethylformamide (15 ml) and the reaction stirred at 60° C. for 18 hours. The cooled mixture was partitioned between water and ethyl acetate, and the layers separated. The organic layer was dried ($MgSO_4$), concentrated under reduced pressure and azeotroped with toluene to give a solid. This product was recrystallised from ether, to afford the title compound as a white solid, 152 mg.

δ ($CDCl_3$): 0.96 (6H, d), 1.02 (3H, t), 1.19 (3H, t), 1.58 (3H, t), 2.26 (1H, m), 2.40 (2H, q), 2.52 (4H, m), 2.94 (2H, q), 3.10 (4H, m), 3.88 (2H, d), 4.78 (2H, q), 5.25 (1H, s), 6.65 (1H, s), 8.64 (1H, d), 8.83 (1H, d), 10.54 (1H, s).

LRMS: m/z 536 $(M+1)^+$

PREPARATIONS 37 TO 41

The following tabulated compounds of the general formula:

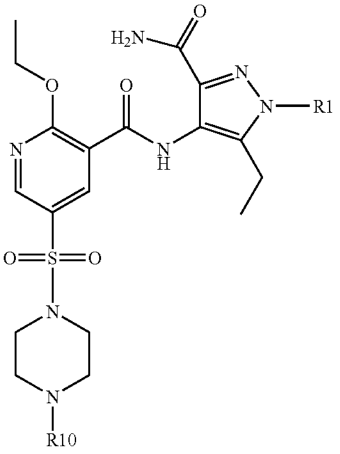

were prepared from the title compound from preparation 34 and the appropriate bromide, following a similar procedure to that described in preparation 36.

| Prep no | R1 | R10 | Yield (%) | m/z $(M + 1)^+$ | $^1$Hnmr |
|---|---|---|---|---|---|
| 37 | 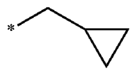 | Et | 48 | 534 | δ($CDCl_3$): 0.42(2H, m), 0.63(2H, m), 1.02(3H, t), 1.20(3H, t), 1.58 (3H, t), 2.40(2H, q), 2.54(4H, m), 2.95(2H, q), 3.10(4H, m), 3.47(1H, m), 3.98(2H, d), 4.78(2H, q), 5.22 (1H, br s), 6.65(1H, br s), 8.63(1H, s), 8.83(1H, s), 10.57(1H, s). |
| 38 | 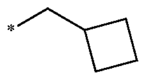 | Et | 51 | 548 | δ($CDCl_3$): 1.01(3H, t), 1.18(3H, m), 1.58(3H, t), 1.80–1.97(4H, m), 2.08(2H, m), 2.40(2H, q), 2.54(4H, m), 2.80–2.97(3H, m), 3.10(4H, m), 4.10(2H, d), 4.78(2H, q), 5.11(1H, br s), 6.63(1H, br s), 8.63(1H, s), 8.83(1H, s), 10.53(1H, s). |
| 39 | 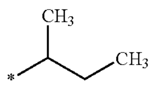 | Et | 51 | 536 | δ($CDCl_3$): 0.83(3H, t), 1.03(3H, t), 1.21(3H, t), 1.48(3H, d), 1.60(3H, t), 1.80(1H, m), 2.00(1H, m), 2.40 (2H, q), 2.55(4H, m), 2.90(2H, m), 3.12(4H, m), 4.24(1H, m), 4.78 (2H, q), 5.22(1H, br s), 6.70(1H, br s), 8.64(1H, s), 8.83(1H, s), 10.50 (1H, s). |
| 40 | 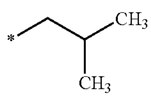 | Me | 44 | 522 | δ($CDCl_3$): 0.96(6H, d), 1.17(3H, t), 1.59(3H, t), 2.27(4H, m), 2.48(4H, m), 2.91(2H, q), 3.09(4H, m), 3.88 (2H, d), 4.78(2H, q), 5.24(1H, br s), 6.67(1H, br s), 8.65(1H, m), 8.84 (1H, m), 10.54(1H, s). |

-continued

| Prep no | R1 | R10 | Yield (%) | m/z (M + 1)+ | 1Hnmr |
|---|---|---|---|---|---|
| 41 | 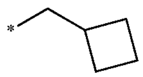 | Me | 33 | 546 | δ($CDCl_3$): 1.19(3H, t), 1.58(3H, m), 1.87(4H, m), 2.10(2H, m), 2.26 (3H, s), 2.48(4H, m), 2.92(3H, m), 3.10(4H, m), 4.10(2H, d), 4.79(2H, q), 5.24(1H, br s), 6.65(1H, br s), 8.64(1H, d), 8.84(1H, d), 10.55 (1H, s). |

PREPARATION 42

4-[2-Ethoxy-5-(4-ethylpiperazin-1-ylsulphonyl)pyridin-3-ylcarboxamido]-3-ethyl-2-(tetrahydrofuran-2-yl)methylpyrazole-5-carboxamide

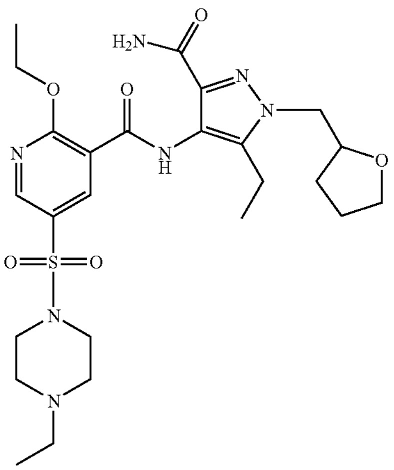

Cesium carbonate (1.63 g, 5.0 mmol) was added to an ice-cold solution of the title compound from preparation 34 (2.0 g, 4.18 mmol) in N,N-dimethylformamide (40 ml), and the solution stirred for 30 minutes. Tetrahydrofuryl bromide (0.6 ml, 5.28 mmol) was added, and the reaction heated at 60° C. for 72 hours. The cooled mixture was evaporated under reduced pressure, and the residue partitioned between water and dichloromethane. The phases were separated, and the organic layer was dried ($MgSO_4$), and evaporated under reduced pressure. The crude product was purified by column chromatography on silica gel using an elution gradient of dichloromethane:methanol (100:0 to 95:5) to afford the title compound, 1.20 g.

δ ($CDCl_3$): 1.01 (3H, t), 1.18 (3H, t), 1.58 (3H, t), 1.70–2.12 (4H, m), 2.40 (2H, q), 2.54 (4H, m), 2.97 (2H, m), 3.10 (4H, m), 3.74–3.94 (2H, m), 4.16 (2H, m), 4.32 (1H, m), 4.78 (2H, q), 5.32 (1H, br s), 6.64 (1H, br s), 8.63 (1H, s), 8.82 (1H, s), 10.50 (1H, s).

LRMS: m/z 564 $(M+1)^+$

PREPARATION 43

2-Methoxy-1-methylethyl methanesulphonate

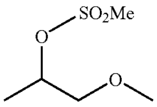

Methanesulphonyl chloride (2.86 ml, 36.9 mmol) was added dropwise to an ice-cooled solution of 1-methoxy-2-propanol (3 ml, 30.7 mmol) and triethylamine (10.27 ml, 73.7 mmol) in dichloromethane (150 ml), and the reaction stirred at room temperature for 18 hours. The mixture was washed with water, then 2M hydrochloric acid, dried ($MgSO_4$) and evaporated under reduced pressure to give the title compound as a yellow oil, 5.24 g.

δ ($CDCl_3$): 1.39 (3H, d), 3.03 (3H, s), 3.39 (3H, s), 3.46 (2H, m), 4.88 (1H, m).

LRMS: m/z 186 $(M+18)^+$

PREPARATION 44

2-[(tert-Butoxycarbonyl)(methyl)amino]ethyl methanesulphonate

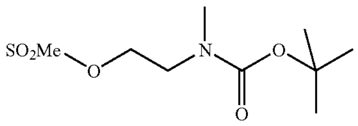

Methanesulphonyl chloride (2.98 ml, 38.6 mmol) was added to an ice-cold solution of tert-butyl 2-hydroxyethyl (methyl)carbamate (Synth. Commun. 1993; 23(17); 2443) (4.5 g, 25.7 mmol) in pyridine (40 ml), and the reaction stirred for 2 hours. The solution was poured into water (150 ml), and extracted with ethyl acetate (2×50 ml). The combined organic extracts were washed with 10% aqueous citric acid solution, dried ($MgSO_4$) and evaporated under reduced pressure. The crude product was purified by column chromatography on silica gel using an elution gradient of ethyl acetate:pentane (34:66 to 40:60) to give the title compound, 1.0 g.

δ ($CDCl_3$): 1.46 (9H, s), 2.96 (3H, s), 3.02 (3H, s), 3.56 (2H, m), 4.34 (2H, m).

PREPARATION 45

4-[2-Ethoxy-5-(4-ethylpiperazin-1-ylsulphonyl)pyridin-3-ylcarboxamido]-3-ethyl-2-(1-methyl-2-methoxyethyl)pyrazole-5-carboxamide

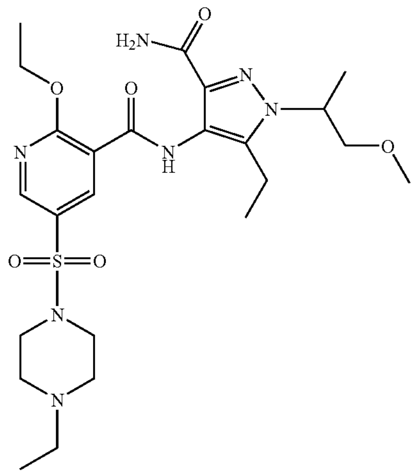

Sodium hydride (64 mg, 60% dispersion in mineral oil, 1.6 mmol) was added to a solution of the title compound from preparation 34 (700 mg, 1.46 mmol) in tetrahydrofuran (10 ml), and the solution stirred for 10 minutes. The title compound from preparation 43 (270 mg, 1.60 mmol) was added and the reaction stirred at 60° C. for 3 days. The cooled mixture was partitioned between ethyl acetate and aqueous sodium bicarbonate solution, and the phases separated. The aqueous layer was extracted with ethyl acetate, the combined organic solutions dried ($MgSO_4$) and evaporated under reduced pressure. The residue was purified by column chromatography on silica gel using dichloromethane:methanol (98:2) as eluant to afford the title compound as a white foam, 310 mg.

δ ($CDCl_3$): 1.02 (3H, t), 1.22 (3H, m), 1.50 (3H, d), 1.59 (3H, t), 2.40 (2H, q), 2.55 (4H, m), 2.92 (2H, m), 3.10 (4H, m), 3.30 (3H, s), 3.60 (1H, m), 3.78 (1H, m), 4.57 (1H, m), 4.78 (2H, q), 5.25 (1H, br s), 6.68 (1H, br s), 8.64 (1H, s), 8.83 (1H, s), 10.48 (1H, s).

LRMS: m/z 552 $(M+1)^+$

PREPARATION 46

2-(1-tert-Butoxycarbonylpiperidin-4-yl)-4-[2-ethoxy-5-(4-ethylpiperazin-1-ylsulphonyl) pyridin-3-ylcarboxamido]-3-ethylpyrazole-5-carboxamide

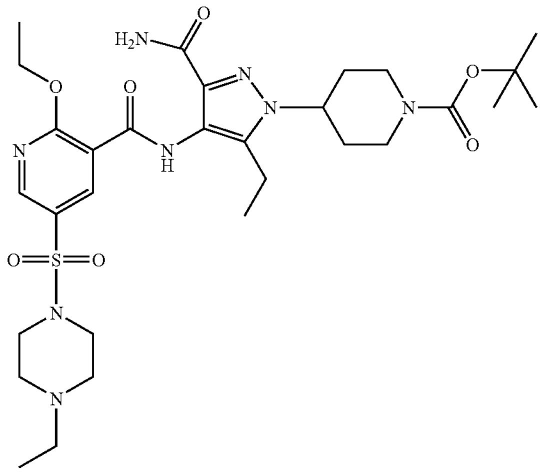

The title compound was obtained (43%), from the title compound from preparation 34 and tert-butyl 4-[(methylsulphonyl)oxy]-1-piperidinecarboxylate (WO, 9319059), following the procedure described in preparation 45.

δ ($CDCl_3$): 1.02 (3H, t), 1.23 (3H, t), 1.49 (9H, s), 1.57 (3H, m), 1.93 (2H, m), 2.16 (2H, m), 2.40 (2H, q), 2.54 (4H, m), 2.82–2.97 (4H, m), 3.10 (4H, m), 4.30 (3H, m), 4.79 (2H, q), 5.23 (1H, s), 6.65 (1H, s), 8.63 (1H, d), 8.82 (1H, d), 10.57 (1H, s).

PREPARATION 47

2-{2-[(tert-Butoxycarbonyl)(methyl)amino]ethyl}-4-[2-ethoxy-5-(4-ethylpiperazin-1-ylsulphonyl)pyridin-3-ylcarboxamido]-3-ethylpyrazole-5-carboxamide

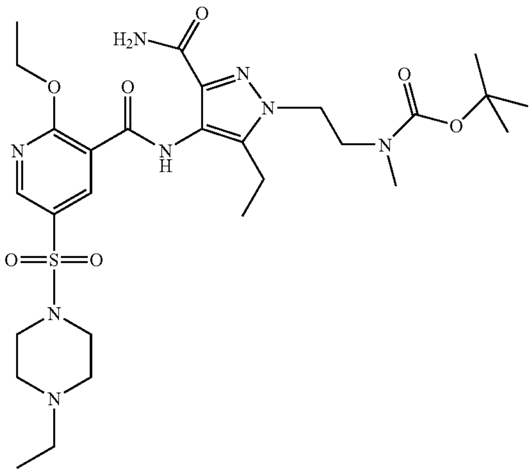

The title compound was prepared from the title compounds from preparation 34 and 44 following a similar procedure to that described in preparation 45. The crude product was purified by column chromatography on silica gel using ethyl acetate:diethylamine (95:5) as eluant to give the title compound, 30%.

δ ($CDCl_3$): 1.02 (3H, t), 1.20 (3H, t), 1.46 (9H, s), 1.57 (3H, t), 2.40 (2H, q), 2.53 (4H, m), 2.88 (3H, s), 3.10 (4H, m), 3.58 (1H, m), 3.64 (2H, m), 4.22 (2H, m), 4.30 (1H, m), 4.79 (2H, q), 5.24 (1H, s), 6.65 (1H, s), 8.62 (1H, d), 8.82 (1H, d), 10.53 (1H, s).

PREPARATION 48

4-[2-Ethoxy-5-(4-ethylpiperazin-1-ylsulphonyl)pyridin-3-ylcarboxamido]-3-ethyl-2-[2-(pyrazole-1-yl)ethyl]pyrazole-5-carboxamide

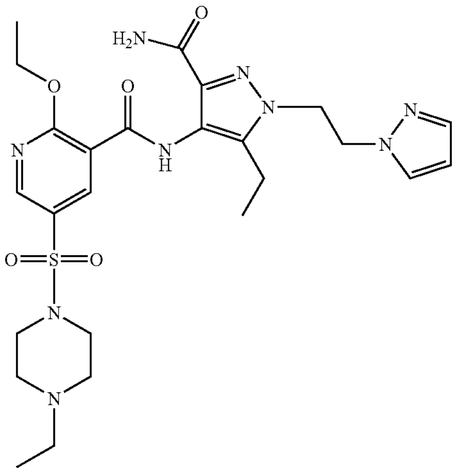

Sodium hydride (88 mg, 60% dispersion in mineral oil, 2.19 mmol) was added to an ice-cold solution of the title compound from preparation 34 (1.0 g, 2.09 mmol) in tetrahydrofuran (25 ml), and the solution stirred for an hour. 1-(2-Chloroethyl)pyrazole (WO 9849166) (410 mg, 3.14 mmol) was added and the reaction heated under reflux for 18 hours. The cooled mixture was concentrated under reduced pressure and the residue partitioned between water and ethyl acetate and the layers separated. The aqueous phase was extracted with ethyl acetate, the combined organic solutions dried ($MgSO_4$) and evaporated under reduced pressure. The crude product was purified by column chromatography on silica gel using an elution gradient of dichloromethane: methanol (100:0 to 90:10) to give the title compound, 300 mg.

δ ($CDCl_3$): 1.02 (6H, m), 1.58 (3H, t), 2.40 (2H, q), 2.56 (6H, m), 3.10 (4H, m), 4.50 (2H, t), 4.63 (2H, t), 4.78 (2H, q), 6.20 (1H, m), 7.06 (1H, m), 7.58 (1H, m), 8.63 (1H, d), 8.80 (1H, d), 10.46 (1H, s).

PREPARATION 49

4-[2-Ethoxy-5-(4-ethylpiperazin-1-ylsulphonyl)pyridin-3-ylcarboxamido]-3-ethyl-2-(4-nitrophenyl)pyrazole-5-carboxamide

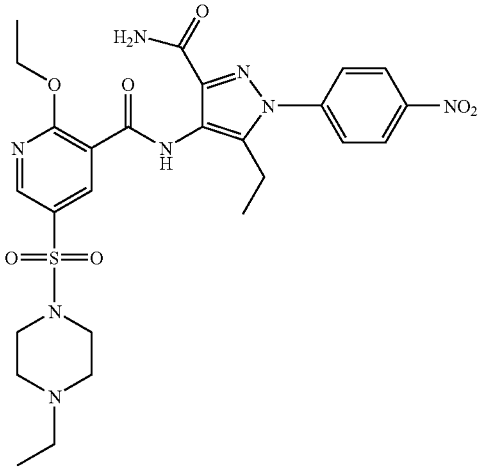

Sodium hydride (80 mg, 80% dispersion in mineral oil, 2.67 mmol) was added to a cooled (−78° C.) solution of the title compound from preparation 34 (1.0 g, 2.08 mmol) in tetrahydrofuran (10 ml), and the mixture allowed to warm slowly to room temperature. 4-Fluoronitrobenzene (0.5 ml, 4.7 mmol) was added, and the reaction heated at 65° C. for 72 hours. The cooled mixture was partitioned between aqueous ammonium chloride solution and ethyl acetate, and the layers separated. The aqueous phase was extracted with ethyl acetate, the combined organic solutions washed with water, then brine, dried ($MgSO_4$) and evaporated under reduced pressure. The crude product was purified by column chromatography on silica gel using an elution gradient of dichloromethane:methanol (100:0 to 95:5) to afford the title compound, 630 mg.

δ ($CDCl_3$): 0.93 (6H, m), 1.52 (3H, t), 2.32 (2H, m), 2.44 (4H, m), 2.98 (6H, m), 4.72 (2H, q), 5.96 (1H, s), 6.76 (1H, s), 7.62 (2H, d), 8.32 (2H, d), 8.58 (1H, d), 8.75 (1H, d), 10.63 (1H, s).

LRMS: m/z 601 $(M+1)^+$

PREPARATION 50

2-[3-Dimethylamino-n-propyl]-4-[2-ethoxy-5-(4-ethylpiperazin-1-ylsulphonyl)pyridin-3-ylcarboxamido]-3-ethylpyrazole-5-carboxamide

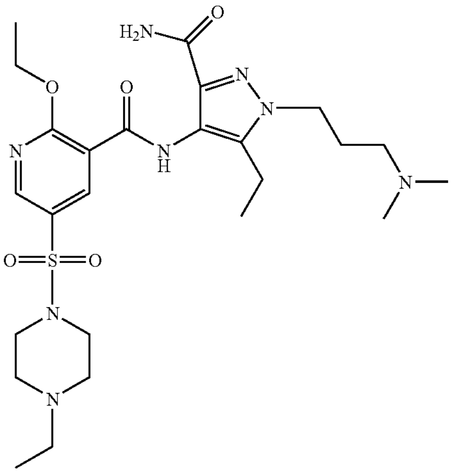

Methanesulphonyl chloride (4.95 ml, 64.0 mmol) was added to an ice-cold solution of 3-dimethylamino-1-propanol (6 g, 58.2 mmol) and triethylamine (9.7 ml, 69.8 mmol) in dichloromethane (200 ml), and the reaction stirred at room temperature for 16 hours. The mixture was partitioned between ethyl acetate and aqueous sodium bicarbonate solution, and the phases separated. The aqueous layer was extracted with ethyl acetate, and the combined organic solutions dried ($Na_2SO_4$) and evaporated under reduced pressure. The residue was immediately purified by column chromatography on silica gel using dichloromethane:methanol (90:10) as eluant to give an oily solid, 1.5 g. This was immediately re-dissolved in dichloromethane (3 ml), filtered, and the filtrate diluted with tetrahydrofuran (10 ml).

Sodium hydride (70 mg, 60% dispersion in mineral oil, 1.75 mmol) was added portionwise to an ice-cooled solution of the title compound from preparation 34 (760 mg, 1.59 mmol) in tetrahydrofuran (15 ml), and once addition was complete, the solution was stirred at room temperature for an hour.

The previously prepared solution of mesylate was then added, and the reaction stirred at 70° C. for 16 hours. The cooled mixture was poured into saturated sodium bicarbonate solution (120 ml), and extracted with ethyl acetate (2×100 ml). The combined organic extracts were dried ($Na_2SO_4$) and evaporated under reduced pressure. The crude product was purified by column chromatography on silica gel using dichloromethane:methanol:0.88 ammonia (89:10:1) as eluant to afford the title compound, 140 mg.

δ ($CDCl_3$): 1.02 (3H, t), 1.21 (3H, t), 1.58 (3H, t), 2.32 (6H, s), 2.40 (2H, q), 2.54 (4H, m), 2.78 (2H, t), 2.92 (2H, q), 3.08 (4H, m), 4.18 (2H, t), 4.78 (2H, q), 5.25 (1H, s), 6.66 (1H, s), 8.64 (1H, s), 8.83 (1H, s), 10.54 (1H, s).

PREPARATION 51

4-[2-Ethoxy-5-(4-ethylpiperazin-1-ylsulphonyl)pyridin-3-ylcarboxamido]-3-ethyl-2-(piperidin-4-yl) pyrazole-5-carboxamide ditrifluoroacetate

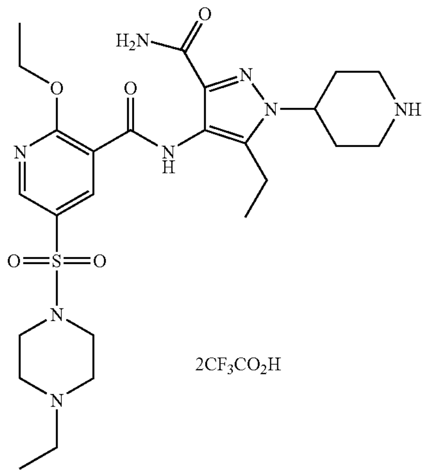

$2CF_3CO_2H$

Trifluoroacetic acid (3 ml) was added to a solution of the title compound from preparation 46 (309 mg, 0.47 mmol) in dichloromethane (4 ml), and the solution stirred for 2½ hours. The reaction was evaporated under reduced pressure and the residue triturated well with ether. The resulting solid was sonicated in ether for 1 minute, the resulting precipitate filtered and dried to afford the title compound as a white solid, 278 mg.

δ ($DMSOd_6$): 1.15 (6H, m), 1.46 (3H, t), 2.04 (2H, m), 2.20 (2H, m), 2.40–2.84 (6H, m), 3.00–3.22 (6H, m), 3.25–3.60 (4H, m), 3.76 (1H, m), 4.62 (4H, m), 7.27 (1H, s), 7.40 (1H, s), 8.41 (2H, m), 8.70 (2H, m), 10.24 (1H, s).

PREPARATION 52

4-[2-Ethoxy-5-(4-ethylpiperazin-1-ylsulphonyl)pyridin-3-ylcarboxamido]-3-ethyl-2-(1-methylpiperidin-4-yl)pyrazole-5-carboxamide

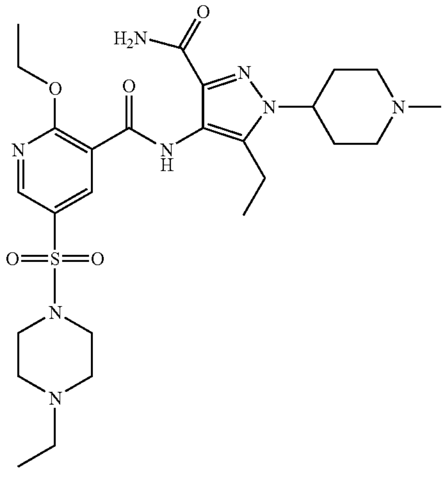

Trifluoroacetic acid (1.5 ml) was added to a solution of the title compound from preparation 46 (320 mg, 0.48 mmol) in dichloromethane (2 ml) and the solution stirred at room temperature for 2½ hours. The reaction mixture was evaporated under reduced pressure and the residue triturated well with ether and dried under vacuum, to provide a white solid.

Formaldehyde (217 µl, 37% aqueous, 2.90 mmol) was added to a solution of the intermediate amine in dichloromethane (8 ml), and the solution stirred vigorously for 30 minutes. Acetic acid (88 µl, 1.69 mmol) was added, the solution stirred for a further 30 minutes, then sodium triacetoxyborohydride (169 mg, 0.80 mmol) was added and the reaction stirred at room temperature for 16 hours. The reaction mixture was poured into aqueous sodium bicarbonate solution, and extracted with ethyl acetate. The combined organic extracts were dried ($MgSO_4$) and evaporated under reduced pressure. The residue was purified by column chromatography on silica gel using dichloromethane:methanol:0.88 ammonia (91.75:7.5:0.75) as eluant to afford the title compound, 70 mg.

δ ($CDCl_3$): 1.02 (3H, t), 1.22 (3H, t), 1.58 (3H, t), 1.92 (2H, m), 2.14 (2H, m), 2.25–2.45 (7H, m), 2.54 (4H, m), 2.91 (2H, q), 2.99–3.16 (6H, m), 4.08 (1H, m), 4.78 (2H, q), 5.11 (1H, br s), 6.65 (1H, br s), 8.63 (1H, d), 8.83 (1H, d), 10.53 (1H, s).

PREPARATION 53

4-[2-Ethoxy-5-(4-ethylpiperazin-1-ylsulphonyl)pyridin-3-ylcarboxamido]-3-ethyl-2-(1-methylazetidin-3-yl)pyrazole-5-carboxamide

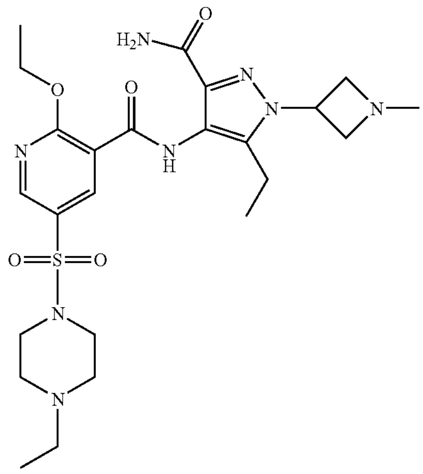

Trifluoroacetic acid (2.5 ml) was added to a solution of the title compound from preparation 33 (700 mg, 1.1 mmol) in dichloromethane (3.5 ml) and the solution stirred at room temperature for 2½ hours. The reaction mixture was evaporated under reduced pressure and the residue triturated well with ether and dried under vacuum. The solid was suspended in saturated aqueous sodium bicarbonate solution, extracted with ethyl acetate, and the combined organic extracts evaporated under reduced pressure.

Formaldehyde (280 µl, 37% aqueous, 4.4 mmol) was added to a solution of the intermediate amine in dichloromethane (8 ml), and the solution stirred vigorously for 30 minutes. Acetic acid (53 µl, 1.1 mmol) was added, the solution stirred for a further 30 minutes, then sodium triacetoxyborohydride (238 mg, 1.12 mmol) was added and the reaction stirred at room temperature for 16 hours. The reaction mixture was poured into aqueous sodium bicarbonate solution (30 ml), and extracted with ethyl acetate (2×30 ml). The combined organic extracts were dried ($MgSO_4$) and evaporated under reduced pressure. The residue was purified by column chromatography on silica gel using dichloromethane:methanol:0.88 ammonia (91.75:7.5:0.75) to afford the title compound, 470 mg.

δ ($CDCl_3$): 1.01 (3H, t), 1.18 (3H, t), 1.58 (3H, t), 2.40 (2H, q), 2.48 (3H, s), 2.54 (4H, m), 2.85 (2H, q), 3.10 (4H, m), 3.59 (2H, t), 3.82 (2H, t), 4.79 (2H, q), 4.96 (1H, m), 5.32 (1H, br s), 6.79 (1H, br s), 8.64 (1H, d), 8.82 (1H, d), 10.52 (1H, s).

PREPARATION 54

4-[2-Ethoxy-5-(4-ethylpiperazin-1-ylsulphonyl)pyridin-3-ylcarboxamido]-3-ethyl-2-[2-(methylamino)ethyl]pyrazole-5-carboxamide

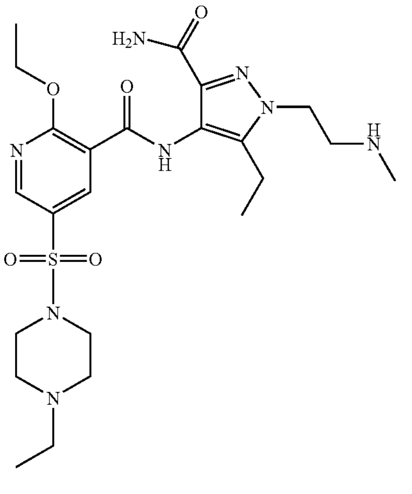

A mixture of the title compound of preparation 32 (250 mg, 0.37 mmol) and 10% palladium on charcoal (35 mg) in methanol (3 ml) was hydrogenated at 60 psi and room temperature for 16 hours. The reaction mixture was filtered through Arbocel®, the filter pad washed with methanol and the combined filtrates evaporated under reduced pressure. The residue was purified by column chromatography on silica gel, using an elution gradient of dichloromethane:methanol:0.88 ammonia (90:10:0 to 89:10:1) to afford the title compound (135 mg, 68%) as a white foam.

δ ($CDCl_3$): 1.02 (3H, t), 1.20 (3H, t), 1.60 (3H, t), 2.40 (2H, q), 2.48 (3H, s), 2.52 (4H, m), 2.94 (2H, q), 3.10 (6H, m), 4.22 (2H, t), 4.79 (2H, q), 5.28 (1H, s), 6.67 (1H, s), 8.64 (1H, s), 8.83 (1H, s), 10.54 (1H, s).

PREPARATION 55

2-[2-(Dimethylamino)ethyl]-4-[2-ethoxy-5-(4-ethylpiperazin-1-ylsulphonyl)pyridin-3-ylcarboxamido]-3-ethylpyrazole-5-carboxamide

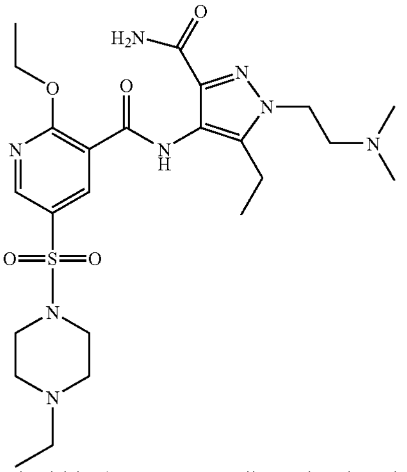

Sodium hydride (88 mg, 60% dispersion in mineral oil, 2.2 mmol) was added portionwise to an ice-cold solution of the title compound from preparation 34 (1.0 g, 2.1 mmol) in tetrahydrofuran (25 ml), and the solution stirred for 30 minutes.

2-Dimethylaminoethylchloride hydrochloride (451 mg, 3.15 mmol) was treated with saturated aqueous sodium bicarbonate solution, and this mixture extracted with dichloromethane (2×15 ml). The combined extracts were concentrated under reduced pressure at room temperature to a volume of about 2 ml, and this solution diluted with tetrahydrofuran (10 ml). This was then added to the previously prepared solution, and the reaction heated under reflux for 20 hours. The cooled mixture was poured into aqueous saturated sodium bicarbonate solution, and extracted with ethyl acetate (100 ml). The organic extract was evaporated under reduced pressure, and the residual foam was purified by column chromatography on silica gel using ethyl acetate:diethylamine (95:5) as eluant to afford the title compound, 300 mg.

δ ($CDCl_3$): 1.02 (3H, t), 1.22 (3H, t), 1.59 (9H, m), 2.40 (2H, q), 2.54 (4H, m), 2.78 (2H, t), 2.94 (2H, q), 3.09 (4H, m), 4.19 (2H, t), 4.78 (2H, q), 5.25 (1H, s), 6.65 (1H, s), 8.62 (1H, s), 8.83 (1H, s), 10.54 (1H, s).

PREPARATION 56

4-[2-Ethoxy-5-(4-ethylpiperazin-1-ylsulphonyl)pyridin-3-ylcarboxamido]-3-ethyl-1-(2-methoxyethyl)pyrazole-5-carboxamide

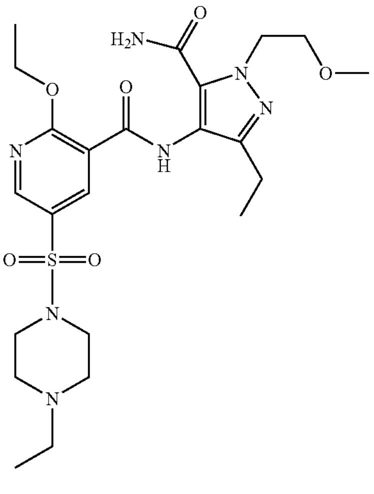

The title compound was obtained (70%) from the title compounds of preparations 25 and 14, following a similar procedure to that described in preparation 27.

δ ($CDCl_3$) 1.04 (3H, t), 1.27 (3H, t), 1.59 (3H, t), 2.42 (2H, q), 2.57 (4H, m), 2.72 (2H, q), 3.12 (4H, m), 3.38 (3H, s), 3.85 (2H, t), 4.55 (2H, t), 4.77 (2H, q), 5.57 (1H, s), 7.92 (1H, s), 8.68 (1H, s), 8.86 (1H, s), 9.82 (1H, s).

LRMS: m/z 538 $(M+1)^+$

PREPARATION 57

4-[2-Ethoxy-5-(4-methylpiperazin-1-ylsulphonyl) pyridin-3-ylcarboxamido]-1-(2-methoxyethyl)-3-n-propylpyrazole-5-carboxamide

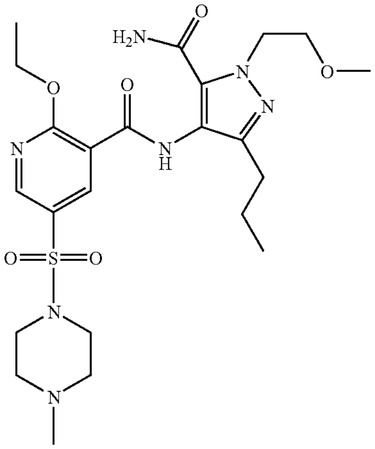

A mixture of the title compounds of preparations 26 (585 mg, 1.77 mmol) and 15 (300 mg, 1.32 mmol), 1-hydroxybenzotriazole hydrate (189 mg, 1.40 mmol), 1-(3-dimethylaminopropyl)-3-ethylcarbodiimide hydrochloride (267 mg, 1.40 mmol) and N-ethyldiisopropylamine (0.39 ml, 2.25 mmol) in dichloromethane (20 ml) was stirred at room temperature for 18 hours. The mixture was washed with brine (10 ml), then water (10 ml) and then extracted with hydrochloric acid (1M, 3×20 ml). The combined acidic extracts were neutralised using sodium bicarbonate solution, and this aqueous solution extracted with dichloromethane (3×30 ml). The combined organic extracts were dried ($Na_2SO_4$), and evaporated under reduced pressure to afford the title compound as a white solid, 446 mg.

δ ($CDCl_3$): 0.97 (3H, t), 1.67 (5H, m), 2.28 (3H, s), 2.50 (4H, m), 2.65 (2H, t), 3.10 (4H, m), 3.37 (3H, s), 3.82 (2H, t), 4.52 (2H, t), 4.76 (2H, q), 5.57 (1H, s), 7.87 (1H, s), 8.67 (1H, s), 8.85 (1H, s), 9.77 (1H, s).

LRMS: m/z 538 $(M+1)^+$

PREPARATION 58

5-[2-Ethoxy-5-(4-ethylpiperazin-1-ylsulphonyl)pyridin-3-yl]-3-ethyl-2,6-dihydro-7H-pyrazolo[4,3-d]pyrimidin-7-one

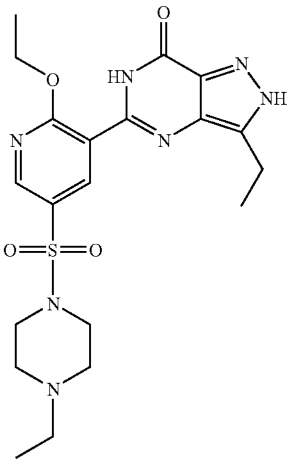

Potassium bis(trimethylsilyl)amide (8.28 g, 41.6 mmol) was added to a solution of the title compound from preparation 34 (10.0 g, 20.8 mmol) and ethyl acetate (2 ml, 20 mmol) in ethanol (160 ml), and the reaction mixture heated at 120° C. for 12 hours in a sealed vessel. The cooled mixture was evaporated under reduced pressure and the residue was purified by column chromatography on silica gel using dichloromethane:methanol:0.88 ammonia (95:5:0.5) as eluant, to give the title compound, 3.75 g.

δ ($CDCl_3$): 1.03 (3H, t), 1.42 (3H, t), 1.60 (3H, t), 2.42 (2H, q), 2.58 (4H, m), 3.02 (2H, q), 3.16 (4H, m), 4.78 (2H, q), 8.66 (1H, d), 9.08 (1H, d), 11.00 (1H, s) 11.05–11.20 (1H, br s).

LRMS: m/z 462 $(M+1)^+$

PREPARATION 59

5-[2-n-Butoxy-5-(4-ethylpiperazin-1-ylsulphonyl) pyridin-3-yl]-3-ethyl-2,6-dihydro-7H-pyrazolo[4,3-d]pyrimidin-7-one

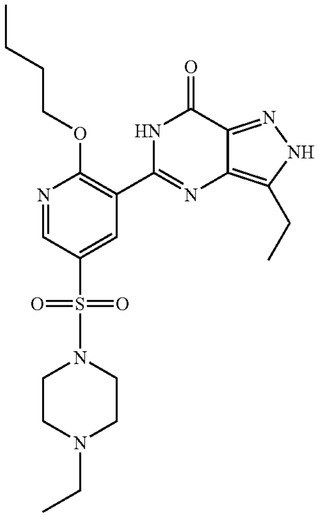

A mixture of the title compound from preparation 34 (500 mg, 1.04 mmol), and potassium bis(trimethylsilyl)amide (436 mg, 2.19 mmol) in n-butanol (12 ml) was heated at 130° C. for 16 hours in a sealed vessel. The cooled mixture was poured into saturated aqueous sodium bicarbonate solution, and extracted with ethyl acetate, and the combined organic extracts dried ($MgSO_4$) and evaporated under reduced pressure. The crude product was purified by column chromatography on silica gel using dichloromethane:methanol (96:4) as eluant to afford the title compound, 128 mg.

δ ($CDCl_3$): 1.04 (6H, m), 1.42 (3H, t), 1.59 (2H, m), 1.96 (2H, m), 2.46 (2H, m), 2.60 (4H, m), 3.01 (2H, q), 3.19 (4H, m), 4.70 (2H, t), 8.64 (1H, d), 9.03 (1H, d), 11.09 (1H, s).

LRMS: m/z 490 $(M+1)^+$

PREPARATION 60

2-(2-{[tert-Butyl(dimethyl)silyl]oxy}ethyl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

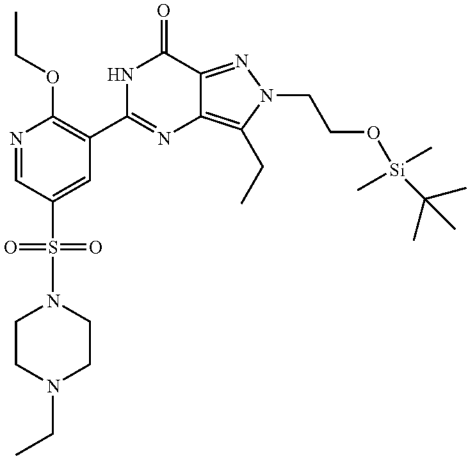

A mixture of the title compound of preparation 31 (2.02 g, 3.17 mmol), and potassium bis(trimethylsilyl)amide (950 mg, 4.76 mmol) in 3-methyl-3-pentanol (50 ml) was stirred under reflux for 8 hours. The cooled mixture was concentrated under reduced pressure, the residue suspended in ethyl acetate (100 ml), washed with water (50 ml) and brine (50 ml), dried ($MgSO_4$) and evaporated under reduced pressure. The crude product was purified by column chromatography on silica gel, using an elution gradient of dichloromethane:methanol (100:0 to 90:10) to afford the title compound, 124 mg.

δ ($CDCl_3$): −0.08 (6H, s), 0.81 (9H, s), 1.02 (3H, t), 1.40 (3H, t), 1.57 (3H, t) 2.41 (2H, q), 2.56 (4H, m), 3.14 (6H, m), 4.15 (2H, t), 4.40 (2H, t), 4.74 (2H, q), 8.62 (1H, s), 9.03 (1H, s), 10.68 (1H, s).

LRMS: m/z 620 $(M+1)^+$

PREPARATION 61

2-[2-[(tert-Butoxycarbonyl)(methyl)amino]ethyl]-5-[5-(4-ethylpiperazin-1-ylsulphonyl)-2-n-propoxypyridin-3-yl]-3-ethyl-2,6-dihydro-7H-pyrazolo[4,3-d]pyrimidin-7-one

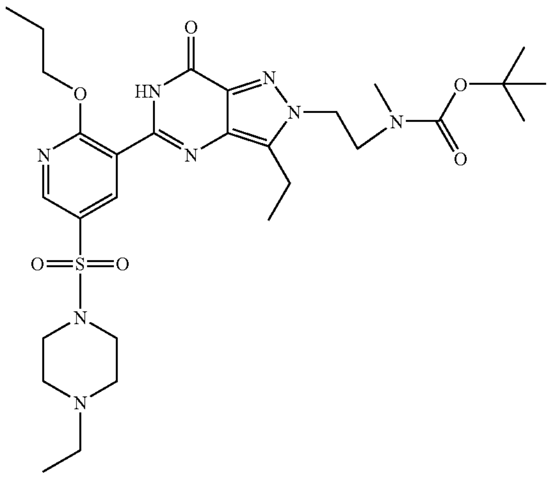

A mixture of the title compound from example 14 (100 mg, 0.16 mmol) and potassium bis(trimethylsilyl)amide (161 mg, 0.81 mmol) in n-propanol (3 ml) was heated at 100° C. for 16 hours. The cooled reaction mixture was poured into saturated sodium bicarbonate solution (20 ml), extracted with ethyl acetate (2×30 ml), and the combined organic extracts evaporated under reduced pressure. The crude product was purified by column chromatography on silica gel using dichloromethane:methanol (97:3) as eluant to afford the title compound, 71 mg.

δ ($CDCl_3$): 1.03 (3H, t), 1.14 (3H, t), 1.41 (3H, t), 1.45 (9H, s), 2.00 (2H, m), 2.42 (2H, q), 2.58 (7H, m), 3.01 (2H, q), 3.16 (4H, m), 3.78 (2H, t), 4.46 (2H, m), 4.63 (2H, t), 8.63 (1H, d), 9.04 (1H, d), 10.66 (1H, br s).

PREPARATION 62

5-[2-n-Butoxy-5-(4-ethylpiperazin-1-ylsulphonyl)pyridin-3-yl]-2-{2-[(tert-butoxycarbonyl)(methyl)amino]ethyl}-3-ethyl-2,6-dihydro-7H-pyrazolo[4,3-d]pyrimidin-7-one

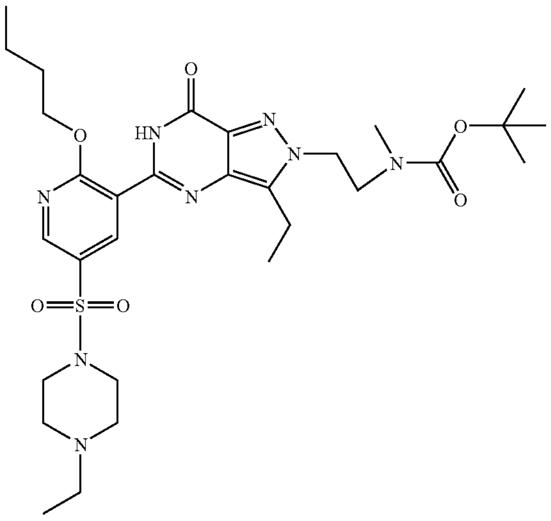

A mixture of the title compound from example 14 (123 mg, 0.20 mmol), potassium bis(trimethylsilyl)amide (198 mg, 1.0 mmol) and ethyl acetate (18 mg, 0.20 mmol) in n-butanol (12 ml) was heated at 110° C. for 8 hours in a sealed vessel. The cooled mixture was poured into aqueous saturated sodium bicarbonate solution (60 ml), and extracted with ethyl acetate (2×60 ml). The combined organic extracts were dried ($MgSO_4$), and evaporated under reduced pressure. The crude product was purified by column chromatography on silica gel using dichloromethane:methanol (97:3) as eluant to give the title compound as a beige foam, 36 mg.

δ ($CDCl_3$): 1.02 (6H, t), 1.40 (3H, t), 1.45 (9H, s), 1.55 (2H, m), 1.95 (2H, m), 2.41 (2H, q), 2.58 (7H, m), 3.01 (2H, q), 3.16 (4H, m), 3.78 (2H, t), 4.45 (2H, m), 4.67 (2H, t), 8.63 (1H, d), 9.03 (1H, d), 10.64 (1H, s).

PREPARATION 63

2-(1-Butoxycarbonylazetidin-3-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

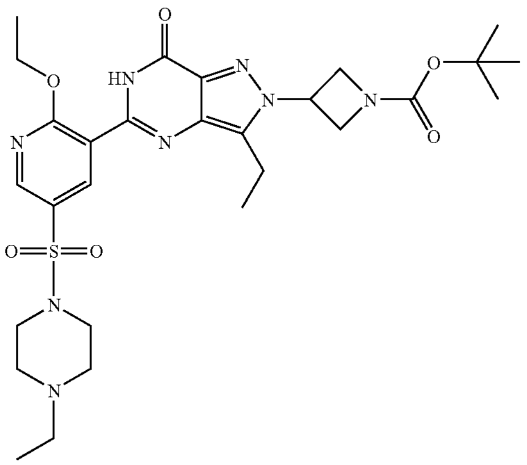

A mixture of the title compound of preparation 33 (1.3 g, 2.05 mmol) and potassium bis(trimethylsilyl)amide (490 mg, 2.46 mmol) in ethanol (35 ml) was heated at 130° C. in a sealed vessel for 16 hours. The cooled reaction mixture was concentrated under reduced pressure, the residue dissolved in water (15 ml), the solution neutralised using hydrochloric acid (2N), and then saturated sodium bicarbonate added. This aqueous solution was extracted with dichloromethane (5×30 ml), the combined organic extracts dried ($MgSO_4$) and evaporated under reduced pressure. The residual gum was purified by column chromatography on silica gel, using ethyl acetate:diethylamine (96:4) as eluant to afford the title compound, 350 mg.

δ ($CDCl_3$): 1.02 (3H, t), 1.38 (3H, t), 1.48 (9H, s), 1.58 (3H, t), 2.40 (2H, q), 2.57 (4H, m), 3.02 (2H, q), 3.14 (4H, m), 4.37 (2H, t), 4.42 (2H, m), 4.77 (2H, q), 5.25 (1H, m), 8.64 (1H, s), 8.81 (1H, s), 10.57 (1H, s).

PREPARATION 64

2-(1-Butoxycarbonylpiperidin-4-yl)-5-[2-ethoxy-5-(4-ethylpiperazin-1-ylsulphonyl)pyridin-3-yl]-3-ethyl-2,6-dihydro-7H-pyrazolo[4,3-d]pyrimidin-7-one

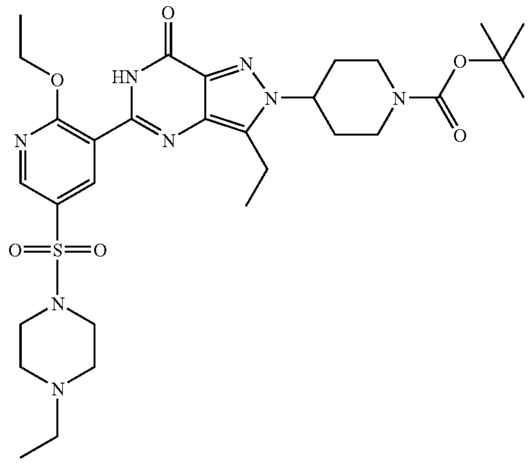

The title compound was prepared from the title compound from preparation 46, following a similar procedure to that described in preparation 63. The crude product was purified by column chromatography on silica gel using dichloromethane:methanol (95:5) as eluant to give the title compound (62%).

δ ($CDCl_3$): 1.03 (3H, t), 1.38–1.60 (15H, m), 1.94 (2H, m), 2.41 (4H, m), 2.57 (4H, m), 2.90 (2H, m), 3.10 (6H, m), 4.26–4.48 (3H, m), 4.77 (2H, q), 8.62 (1H, d), 9.02 (1H, d), 10.60 (1H, s).

PREPARATION 65

5-[2-n-Butoxy-5-(4-ethylpiperazin-1-ylsulphonyl)pyridin-3-yl]-2-(1-tert-butoxycarbonylazetidin-3-yl)-3-ethyl-2,6-dihydro-7H-pyrazolo[4,3-d]pyrimidin-7-one

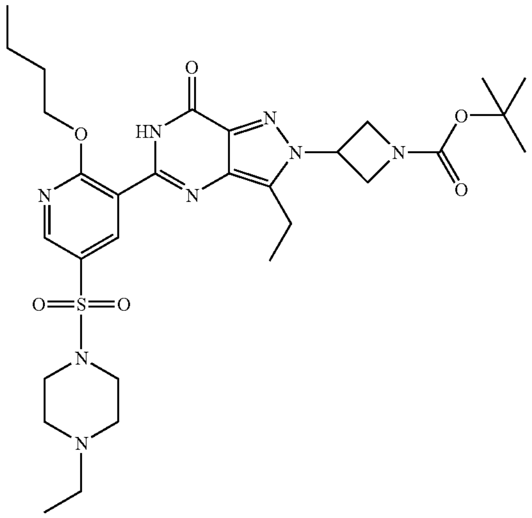

The title compound was obtained (67%) from the title compound from preparation 63 and n-butanol, following a similar procedure to that described in preparation 61.

δ ($CDCl_3$): 1.02 (6H, t), 1.38 (3H, t), 1.48 (9H, s), 1.57 (2H, m), 1.96 (2H, m), 2.41 (2H, q), 2.57 (4H, m), 3.02 (2H, q), 3.15 (4H, m), 4.39 (2H, m), 4.68 (4H, m), 5.26 (1H, m), 8.62 (1H, m), 9.02 (1H, m), 10.67 (1H, s).

PREPARATION 66

2-(1-tert-Butoxycarbonylazetidin-3-yl)-5-[5-(4-ethylpiperazin-1-ylsulphonyl)-1-methylbutoxypyridin-3-yl]-3-ethyl-2,6-dihydro-7H-pyrazolo[4,3-d]pyrimidin-7-one

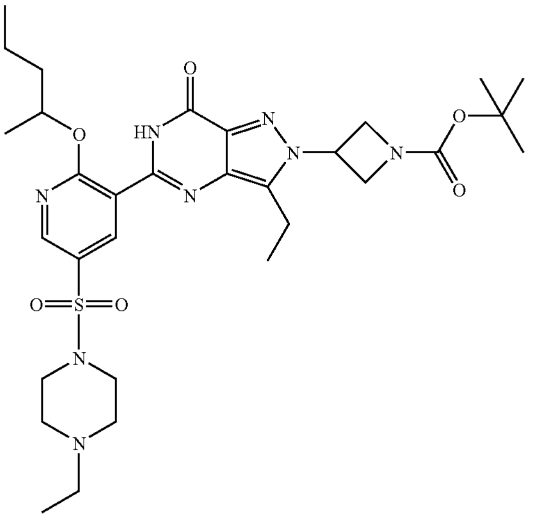

A mixture of the title compound from preparation 63 (100 mg, 0.16 mmol) and potassium bis(trimethylsilyl)amide (0.157 mg, 0.79 mmol) in (R)-pentan-2-ol (1 ml), and the mixture heated at 120° C. for 4 days. The cooled mixture was suspended in aqueous saturated sodium bicarbonate solution (35 ml) and extracted with ethyl acetate (2×35 ml). The combined organic extracts were dried ($MgSO_4$) and evaporated under reduced pressure. The crude product was purified by column chromatography on silica gel using dichloromethane:methanol:0.88 ammonia (95:4.7:0.3) as eluant to give the title compound, 14 mg.

δ ($CDCl_3$): 1.02 (6H, m), 1.38 (3H, t), 1.48 (12H, m), 1.80 (1H, m), 1.98 (1H, m), 2.42 (2H, q), 2.58 (4H, m), 3.02 (2H, q), 3.16 (4H, m), 4.40 (2H, t), 4.67 (2H, m), 5.25 (1H, m), 5.62 (1H, m), 8.62 (1H, s), 9.02 (1H, s), 10.70 (1H, s).

PREPARATION 67

5-[2-n-Butoxy-5-(4-ethylpiperazin-1-ylsulphonyl)pyridin-3-yl]-2-(1-tert-butoxycarbonylpiperidin-4-yl)-3-ethyl-2,6-dihydro-7H-pyrazolo[4,3-d]pyrimidin-7-one

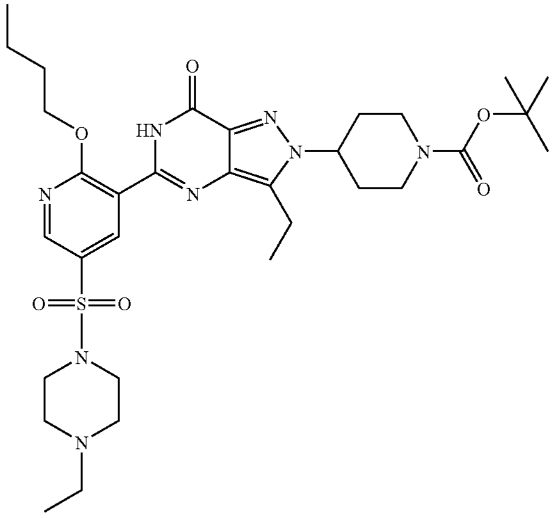

The title compound was obtained (69%) from the title compound from preparation 46 and n-butanol, following a similar procedure to that described in preparation 62.

δ ($CDCl_3$): 1.01 (6H, t), 1.34–1.60 (14H, m), 1.93 (4H, m), 2.41 (4H, m), 2.57 (4H, m), 2.90 (2H, m), 3.00–3.20 (6H, m), 4.38 (3H, m), 4.66 (2H, t), 8.61 (1H, d), 9.00 (1H, s), 10.58 (1H, s).

PREPARATION 68

5-[2-Ethoxy-5-(4-ethylpiperazin-1-ylsulphonyl)pyridin-3-yl]-3-ethyl-2-(piperidin-4-yl)-2,6-dihydro-7H-pyrazolo[4,3-d]pyrimidin-7-one ditrifluoroacetate

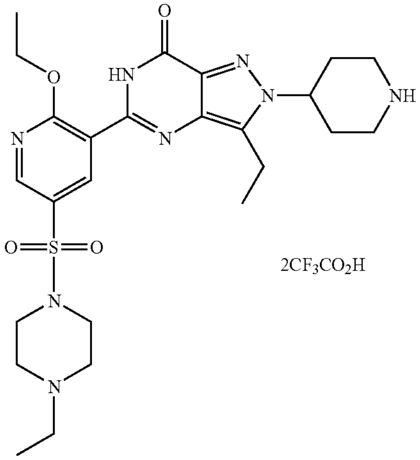

$2CF_3CO_2H$

A solution of the title compound from preparation 64 (48 mg, 0.075 mmol) in trifluoroacetic acid (0.5 ml) and dichloromethane (0.5 ml) was stirred at room temperature for 2½ hours. The mixture was concentrated under reduced pressure and the residue triturated well with ether. The solid was then sonicated in ether for a minute, and the resulting precipitate filtered and dried to give the title compound, 54 mg.

δ ($DMSOd_6$): 1.16 (3H, t), 1.22–1.38 (6H, m), 2.10 (2H, m), 2.38 (2H, m), 3.00 (2H, q), 3.07–3.54 (14H, m), 4.50 (2H, q), 5.85 (1H, m), 8.24 (1H, s), 8.44 (1H, br s), 8.74 (2H, m), 11.90 (1H, s).

PREPARATION 69

5-[5-(4-Ethylpiperazin-1-ylsulphonyl)-2-(2-methoxyethoxy)pyridin-3-yl]-3-ethyl-2.6-dihydro-7H-pyrazolo[4,3-d]pyrimidin-7-one

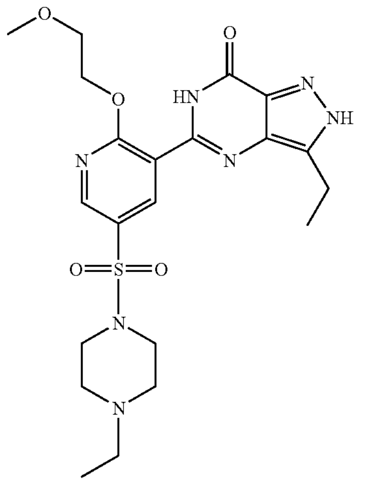

A mixture of the title compound from preparation 58 (1.0 g, 2.2 mmol), and potassium bis(trimethylsilyl)amide (2.16 g, 10.8 mmol) in 2-methoxyethanol (20 ml) was heated under reflux for 18 hours. The cooled mixture was evaporated under reduced pressure and the residue purified by column chromatography on silica gel using an elution gradient of dichloromethane:methanol (100:0 to 90:10) to give the title compound, 860 mg.

δ ($CDCl_3$): 1.03 (3H, t), 1.42 (3H, t), 2.43 (2H, q), 2.59 (4H, m), 3.02 (2H, q), 3.18 (4H, m), 3.59 (3H, s), 4.80 (2H, t), 8.63 (1H, d), 9.00 (1H, d), 11.25 (1H, brs).

LRMS: m/z 492 $(M+1)^+$

PREPARATION 70

4-[2-Ethoxy-5-(4-ethylpiperazin-1-ylsulphonyl)pyridin-3-ylcarboxamido]-2-(2-ethoxyethyl)-3-ethylpyrazole-5-carboxamide

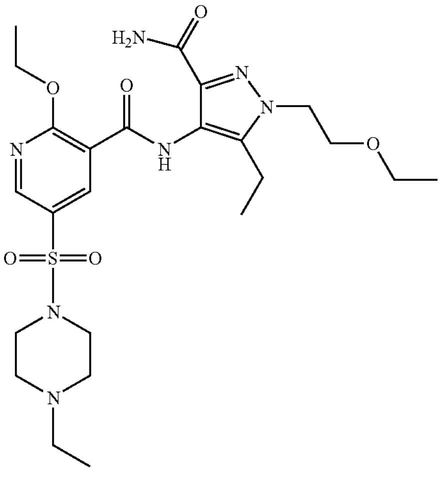

2-Bromoethyl ethyl ether (0.28 ml, 2.50 mmol) was added to a mixture of the title compound from preparation 34 (1.0 g, 2.09 mmol) and cesium carbonate (816 mg, 2.50 mmol) in N,N-dimethylformamide (20 ml), and the reaction stirred at 60° C. for 12 hours. The mixture was diluted with water (100 ml), and extracted with ethyl acetate (2×100 ml). The combined organic extracts were dried ($MgSO_4$), evaporated under reduced pressure and the residue azeotroped with toluene. The crude product was triturated with ether, the resulting solid filtered and dried to afford the title compound as a crystalline solid, 550 mg.

d ($DMSOd_6$): 0.92 (3H, t), 1.10 (6H, m), 1.44 (3H, t), 2.30 (2H, q), 2.42 (4H, m), 2.80 (2H, q), 2.96 (4H, m), 3.40 (2H, q), 3.78 (2H, t), 4.24 (2H, t), 4.63 (2H, q), 7.29 (1H, s), 7.40 (1H, s), 8.40 (1H, d), 8.66 (1H, d), 10.40 (1H, s).

LRMS: m/z 552 $(M+1)^+$

PREPARATION 71

Cyclopentylmethyl 4-methylbenzenesulphonate

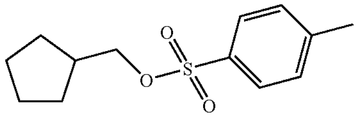

p-Toluenesulphonyl chloride (2.12 g, 11.1 mmol) was added to a solution of cyclopentanemethanol (1 ml, 9.25 mmol) in ether (25 ml), and the solution cooled in an ice/salt bath. Freshly powdered potassium hydroxide (4.7 g, 83.3 mmol) was added and the reaction mixture allowed to warm to room temperature, over 2 hours. The reaction was diluted with water, the phases separated, and the aqueous layer extracted with ether. The combined organic solutions were dried ($MgSO_4$), and evaporated under reduced pressure, to give the title compound as a clear oil, 2.18 g.

$^1$Hnmr ($CDCl_3$, 400 MHz) δ: 1.20 (2H, m), 1.55 (4H, m), 1.74 (2H, m), 2.20 (1H, m), 2.43 (3H, s), 3.92 (2H, d), 7.36 (2H, d), 7.80 (2H, d).

LRMS: m/z 277 $(MNa^+)$

PREPARATION 72

Tetrahydro-2H-pyran-4-yl methanesulphonate

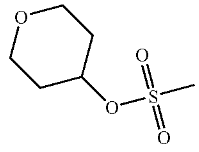

Methanesulphonyl chloride (1.82 ml, 23.5 mmol) was added dropwise over 10 minutes to an ice-cold solution of tetrahydro-2H-pyran-4-ol (2.0 g, 19.6 mmol) and triethylamine (3.56 ml, 25.5 mmol) in dichloromethane (20 ml), and the reaction then stirred at room temperature for 72 hours. The reaction was washed with saturated aqueous sodium bicarbonate solution (10 ml), dried ($MgSO_4$) and evaporated under reduced pressure to give an orange oil, that solidified on standing, 3.1 g.

$^1$Hnmr ($CDCl_3$, 400 MHz) δ: 1.88 (2H, m), 2.03 (2H, m), 3.01 (3H, s), 3.55 (2H, m), 3.95 (2H, m), 4.90 (1H, m).

LRMS: m/z 198 $(MNH_4)^+$

Anal. Found: C, 39.90; H, 6.74. $C_6H_{12}O_4S$ requires C, 39.99; H, 6.71%.

PREPARATION 73

Methanesulphonic Acid Cyclohexylester

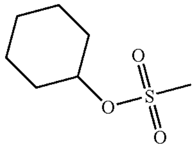

The title compound was prepared according to the method described in Tetrahedron 41; 17; 1985; 3447.

PREPARATION 74

(1R)-1-Methylpropyl methanesulphonate

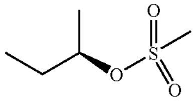

A solution of methanesulphonic anhydride (8.33 g, 47.8 mmol) in dichloromethane (30 ml) was added dropwise over 30 minutes to an ice-cooled solution of (R)-2-butanol (4.0 ml, 43.5 mmol) and triethylamine (6.65 ml, 47.8 mmol) in dichloromethane (70 ml). The reaction was then allowed to warm to room temperature and stirred for 18 hours. The mixture was then washed with water, 2N hydrochloric acid, then dried ($Na_2SO_4$) and evaporated under reduced pressure to give the title compound as a pale yellow oil, 7.0 g.

$^1$Hnmr ($CDCl_3$, 300 MHz) δ: 0.98 (3H, t), 1.40 (3H, d), 1.62–1.80 (2H, m), 3.00 (3H, s), 4.76 (1H, m).

PREPARATION 75

(1S)-1-Methylpropyl methanesulphonate

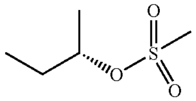

The title compound was obtained as an oil, in 54% yield from (S)-2-butanol and methanesulphonic anhydride, following the procedure described in preparation 74.

$^1$Hnmr ($CDCl_3$, 300 MHz) δ: 0.96 (3H, t), 1.38 (3H, d), 1.60–1.76 (2H, m), 2.96 (3H, s), 4.70 (1H, m).

PREPARATION 76

(2R)-1-Methoxypropan-2-ol

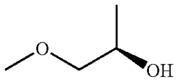

Sodium methoxide (54 g, 1.0 mol) was added portionwise to ice-cooled methanol (1000 ml), and the resulting solution stirred for 20 minutes in an ice-bath. (R)-Propylene oxide (58 g, 1 mol) was added dropwise over 30 minutes, and once addition was complete, the reaction was stirred at room temperature for 18 hours. The mixture was concentrated under reduced pressure, and acidified, with ice-cooling, using (1M) ethereal hydrochloric acid, and the resulting mixture stirred for an hour, then filtered. The filtrate was dried ($K_2CO_3$), filtered and evaporated under reduced pressure. The residue was heated to 70° C. over dried calcium oxide for 30 minutes, then distilled at atmospheric pressure to afford the title compound as an oil, 25.4 g.

b.p. 118–120° C.

$^1$Hnmr ($CDCl_3$, 300 MHz) δ: 1.16 (3H, d), 2.28 (1H, d), 3.20 (1H, m), 3.36 (1H, m), 3.40 (3H, s), 3.97 (1H, m).

$[\alpha]_D$–20.83° (c=1.02, dichloromethane)

PREPARATION 77

(1R)-2-Methoxy-1-methylethyl methanesulphonate

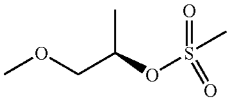

Triethylamine (8.5 ml, 61 mmol) was added to a solution of the alcohol from preparation 76 (5.0 g, 55 mmol) in dichloromethane (100 ml), and the solution cooled in an ice/acetone bath. A solution of methanesulphonic anhydride (10.64 g, 61 mmol) in dichloromethane (50 ml) was added dropwise over 30 minutes, then the reaction stirred at room temperature for 18 hours. The reaction mixture was washed with water, and 2M hydrochloric acid, then dried ($Na_2SO_4$), and evaporated under reduced pressure to give the title compound, 2.77 g.

$^1$Hnmr ($CDCl_3$, 300 MHz) δ: 1.39 (3H, d), 3.03 (3H, s), 3.38 (3H, s), 3.44 (2H, m), 4.87 (1H, m).

PREPARATION 78

(1S)-2-Methoxy-1-methylethyl methanesulphonate

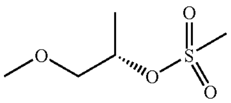

S(−)-propylene oxide (17.58 g, 0.30 mol) was added dropwise over 45 minutes, to a freshly prepared solution of sodium (7.0 g, 0.30 mol) in methanol (100 ml), and the mixture stirred at room temperature for 18 hours. The reaction was diluted with pentane (150 ml), then acetic acid (17 ml, 0.30 mol) added slowly. The resulting mixture was filtered through Celite®, and the filtrate concentrated under reduced pressure. The residual oil was distilled at 30 Torr, and fractions boiling at 30° C. were collected, to give 3.3 g of an oil, containing about 30% methanol.

Triethylamine (5.56 ml, 0.04 mol) was added to a solution of this oil in dichloromethane (60 ml), then the solution cooled in ice. A solution of methanesulphonic anhydride (7.03 g, 0.04 mol) in dichloromethane (30 ml) was added dropwise over 30 minutes, then the reaction stirred at room temperature for 18 hours. The mixture was washed with water, and 2M hydrochloric acid, then dried ($MgSO_4$), and evaporated under reduced pressure to give the title compound, 3.3 g, which was used without further purification.

$^1$Hnmr ($CDCl_3$, 300 MHz) δ: 1.39 (3H, d), 3.03 (3H, s), 3.38 (3H, s), 3.44 (2H, m), 4.87 (1H, m).

PREPARATION 79

2-Ethoxy-5-nitro-3-pyridinecarboxylic acid

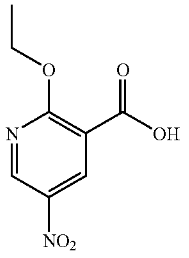

A suspension of 2-ethoxy-3-pyridinecarboxylic acid (16.4 g, 98 mmol), and cesium carbonate (32 g, 98 mmol) in N,N-dimethylformamide (240 ml) was stirred at room temperature for 2 hours. Ethyl iodide (7.85 ml, 98 mmol) was added and the reaction stirred for a further 24 hours. The reaction mixture was concentrated under reduced pressure and the residue partitioned between aqueous sodium carbonate solution (100 ml) and ethyl acetate (100 ml). The phases were separated and the aqueous layer extracted with ethyl acetate (2×100 ml). The combined organic solutions were washed with brine, dried ($Na_2SO_4$) and evaporated under reduced pressure to afford the ethyl ester, 18.0 g, as a pale yellow oil.

Ammonium nitrate (5.36 g, 66 mmol) was added portionwise to an ice-cooled solution of the oil (4.66 g, 22.3 mmol) in trifluoroacetic anhydride (50 ml) and the reaction stirred for 18 hours at room temperature. The reaction mixture was carefully poured into ice water (200 ml) and the resulting suspension stirred for an hour. The precipitate was filtered off, washed with water and dried under suction to afford the nitro ester as a solid, 3.29 g.

Aqueous sodium hydroxide solution (4 ml, 5N, 20 mmol) was added dropwise to a solution of the solid (5.1 g, 20 mmol) in ethanol (100 ml) and the reaction stirred at room temperature for 18 hours. The reaction mixture was concentrated under reduced pressure, the residue suspended in water (50 ml) and acidified to pH 3 with hydrochloric acid. This aqueous solution was extracted with ethyl acetate (3×100 ml), the combined organic layers washed with brine (100 ml), dried ($Na_2SO_4$) and evaporated under reduced pressure to give a beige solid. The crude product was recrystallised from ethyl acetate/hexane to afford the title compound, 3.32 g, as beige crystals.

$^1$Hnmr ($CDCl_3$, 300 MHz) δ: 1.55 (3H, t), 4.78 (2H, q), 9.17 (1H, s), 9.23 (1H, s).

PREPARATION 80

4-(2-Ethoxy-5-nitropyridin-3-ylcarboxamido)-3-ethyl-2-(2-methoxyethyl)pyrazole-5-carboxamide

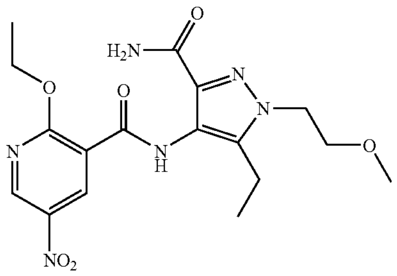

A mixture of the acid from preparation 79 (4.46 g, 21.0 mmol), the pyrazole from preparation 9 (4.15 g, 19.6 mmol), 1-hydroxybenzotriazole hydrate (3.51 g, 26.0 mmol), 1-(3-dimethylaminopropyl)-3-ethylcarbodiimide hydrochloride (4.98 g, 26.0 mmol) and N-ethyldiisopropylamine (10.38 ml, 60.0 mmol) in dichloromethane (110 ml) was stirred at room temperature for 18 hours. The reaction was diluted with dichloromethane (100 ml), then washed consecutively with water (70 ml), 10% aqueous sodium bicarbonate solution (70 ml), and brine (70 ml), then dried ($Na_2SO_4$) and concentrated under reduced pressure. The residual yellow solid was purified by column chromatography on silica gel using dichloromethane:methanol (95:5) as eluant. The product was recrystallised from ethyl acetate to afford the title compound as a pale yellow crystalline solid, 3.96 g.

$^1$Hnmr ($CDCl_3$, 400 MHz) δ: 1.21 (3H, t), 1.59 (3H, t), 2.94 (2H, q), 3.35 (3H, s), 3.80 (2H, t), 4.27 (2H, t), 4.83 (2H, q), 5.29 (1H, br s), 6.62 (1H, br s), 9.15 (1H, d), 9.32 (1H, d), 10.51 (1H, brs).

LRMS: m/z 407.5 ($MH^+$)

Anal. Found: C, 50.21; H, 5.39; N, 20.66. $C_{17}H_{22}N_6O_6$ requires C, 50.24; H, 5.46; N, 20.68%.

PREPARATION 81

4-(5-Amino-2-ethoxypyridin-3-ylcarboxamido)-3-ethyl-2-(2-methoxyethyl)pyrazole-5-carboxamide

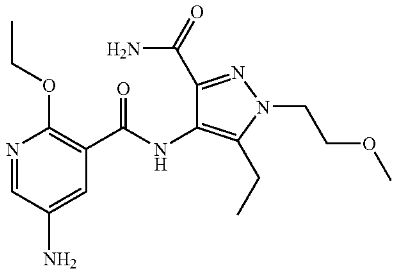

A mixture of the nitro compound from preparation 80 (3.86 g, 9.50 mmol), and 10% palladium on charcoal (200 mg) in dichloromethane (75 ml) and ethanol (25 ml) was hydrogenated at 50 psi and room temperature for 2 hours. The mixture was diluted with dichloromethane, then filtered through Solkafloc®, and the filtrate evaporated under reduced pressure to give the title compound, 3.63 g.

$^1$Hnmr (DMSOd$_6$, 400 MHz) δ: 1.06 (3H, t), 1.37 (3H, t), 2.75 (2H, q), 3.23 (3H, s), 3.72 (2H, t), 4.24 (2H, t), 4.39 (2H, q), 5.02 (2H, br s), 7.25 (1H, br s), 7.37 (1H, br s), 7.70 (2H, m), 10.33 (1H, s).

LRMS: m/z 377.2 (MH$^+$)

PREPARATION 82

5-(5-Amino-2-ethoxypyridin-3-yl)-3-ethyl-2-(2-methoxyethyl)pyrazole-2.6-dihydro-7H-pyrazolo[4,3-d]pyrimidinone

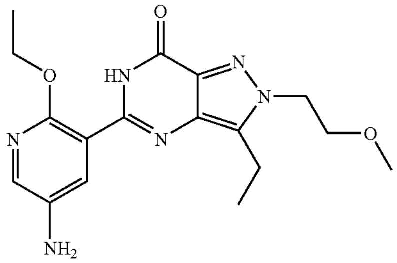

A mixture of the amine from preparation 81 (2.53 g, 6.72 mmol), and potassium bis(trimethylsilyl)amide (5.56 g, 27.9 mmol) in ethanol (50 ml) was heated at 120° C. in a sealed vessel for 8 hours. The cooled reaction was evaporated under reduced pressure and the residue purified by column chromatography on silica gel using an elution gradient of ethyl acetate:ethanol (100:0 to 96:4) to afford the title compound, 1.96 g.

$^1$Hnmr (CDCl$_3$, 400 MHz) δ: 1.40 (3H, t), 1.51 (3H, t), 3.06 (2H, q), 3.30 (3H, s), 3.57 (2H, br s), 3.90 (2H, t), 4.45 (2H, t), 4.55 (2H, q), 7.77 (1H, d), 8.18 (1H, d), 11.03 (1H, br s).

LRMS: m/z 359.1 (MH$^+$)

PREPARATION 83

2-Cyclobutyl-4-[2-ethoxy-5-(4-ethylpiperazin-1-ylsulphonyl)pyridin-3-ylcarboxamido]-3-ethylypyrazole-5-carboxamide

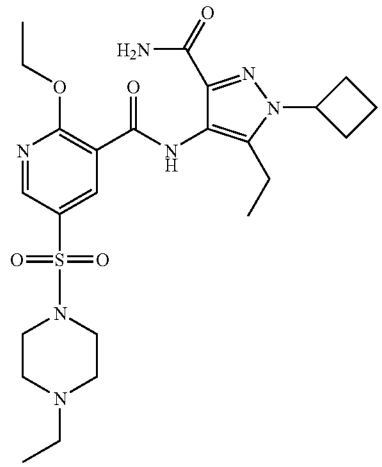

Cesium carbonate (2.7 g, 8.31 mmol) was added to a solution of the compound from preparation 34 (1.8 g, 3.76 mmol) in N,N-dimethylformamide (40 ml), followed by cyclobutyl bromide (388 μl, 4.13 mmol), and the reaction mixture stirred at 60° C. for 3 days. The cooled solution was partitioned between ethyl acetate and sodium bicarbonate solution, and the layers separated. The aqueous phase was extracted with ethyl acetate (3×), the combined organic solutions dried (MgSO$_4$), and evaporated under reduced pressure. The residual yellow solid was triturated with ether to afford the title compound as a pale yellow powder, 762 mg.

$^1$Hnmr (CDCl$_3$, 400 MHz) δ: 1.00 (3H, t), 1.20 (3H, t), 1.57 (3H, t), 1.88 (2H, m), 2.40 (4H, m), 2.52 (4H, m), 2.70 (2H, m), 2.82 (2H, q), 3.08 (4H, m), 4.78 (3H, m), 5.24 (1H, br s), 6.75 (1H, br s), 8.62 (1H, s), 8.81 (1H, s), 10.50 (1H, s).

PREPARATIONS 84 TO 88

The compounds of the following general structure:

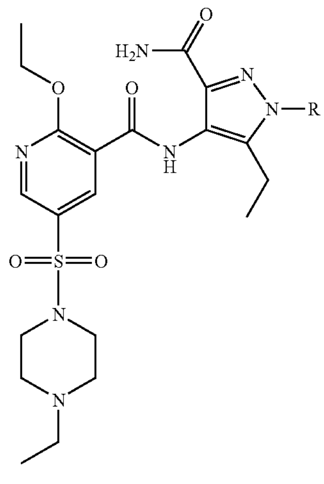

| Prep. No. | R | Alkylating agent | Yield (%) | Data |
|---|---|---|---|---|
| 84 | 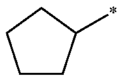 | bromide | 54 | $^1$Hnmr($CDCl_3$, 400MHz)δ: 1.02(3H, t), 1.22(3H, t), 1.58(3H, t), 1.71(2H, m), 1.97(2H, m), 2.08(4H, m), 2.40(2H, q), 2.52(4H, m), 2.92(2H, q), 3.10(4H, m), 4.65(1H, m), 4.78(2H, q), 5.21(1H, br s), 6.66(1H, br s), 8.64(1H, d), 8.82 (1H, d), 10.50(1H, s). LRMS: m/z 548 ($MH^+$) |
| 85 | 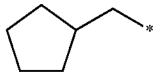 | tosylate | 52 | $^1$Hnmr($CDCl_3$, 400MHz)δ: 1.02(3H, t), 1.15–1.38(6H, m), 1.58–1.72(6H, m), 2.37–2.57(7H, m), 2.94(2H, m), 3.16 (4H, m), 4.00(2H, d), 4.78(2H, q), 5.20 (1H, br s), 6.64(1H, br s), 8.64(1H, s), 8.83(1H, s), 10.54(1H, s). LRMS: m/z 561.8($M^+$) |
| 86[1] | 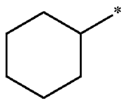 | mesylate | 25 | $^1$Hnmr($CDCl_3$, 300MHz)δ: 1.01(3H, t), 1.21(3H, t), 1.42(2H, m), 1.58(3H, t), 1.94(6H, m), 2.40(4H, m), 2.52(4H, m), 2.88(2H, q), 3.08(4H, m), 4.76(3H, m), 5.20(1H, br s), 6.66(1H, br s), 8.62 (1H, d), 8.82(1H, d), 10.60(1H, s). LRMS: m/z 562.3($MH^+$) |
| 87 | 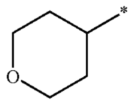 | mesylate | 21 | $^1$Hnmr($CDCl_3$, 300MHz)δ: 1.00(3H, t), 1.30(3H, t), 1.55(3H, t), 1.80(2H, m), 2.35(2H, m), 2.40(2H, q), 2.55(4H, m), 2.90(2H, q), 3.10(4H, m), 3.50(2H, t), 4.14(2H, m), 4.30(1H, m), 4.80(2H, q), 5.22(1H, br s), 6.66(1H, br s), 8.60 (1H, s), 8.80(1H, s), 10.50(1H, s). LRMS: m/z 565($MH^+$) |
| 88 | 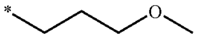 | bromide | 52 | $^1$Hnmr($CDCl_3$, 300MHz)δ: 1.00(3H, t), 1.20(3H, t), 1.60(3H, t), 2.18(2H, m), 2.40(2H, q), 2.50(4H, m), 2.90(2H, q), 3.08(4H, m), 3.32(3H, s), 3.40(2H, t), 4.20(2H, t), 4.80(2H, q), 5.22(1H, br s), 6.64(1H, br s), 8.60(1H, s), 8.80 (1H, s), 10.50(1H, br s). LRMS: m/z 553($MH^+$) |

[1]product purified by column chromatography eluting with dichloromethane:methanol(97:3).

PREPARATION 89

4-[2-Ethoxy-5-(4-ethylpiperazin-1-ylsulphonyl)pyridin-3-ylcarboxamido]-3-ethyl-2-[(1R)-1-methyl-2-methoxyethyl]pyrazole-5-carboxamide

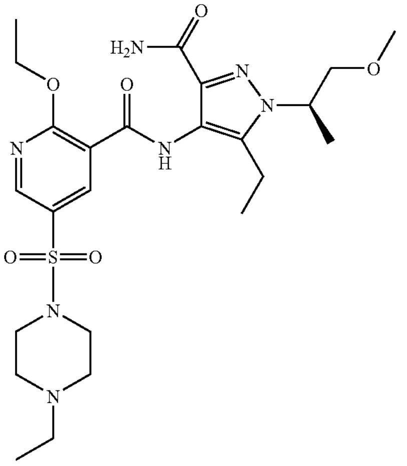

Cesium carbonate (3.00 g, 9.20 mmol) was added to a solution of the compound from preparation 34 (2.0 g, 4.17 mmol) in N,N-dimethylformamide (30 ml), and the mixture stirred for 30 minutes. The mesylate from preparation 78 (0.77 g, 4.58 mmol) was added and the reaction stirred at 60° C. for 8 hours. The cooled mixture was partitioned between ethyl acetate and water, and the pH adjusted to 8, using solid carbon dioxide. The layers were separated, and the aqueous phase extracted with ethyl acetate (2×). The combined organic extracts were dried ($Na_2SO_4$), and evaporated under reduced pressure. The crude product was purified by column chromatography on silica gel using an elution gradient of methanol:dichloromethane (1:99 to 8:92) to afford the title compound, 300 mg.

$^1$Hnmr ($CDCl_3$, 300 MHz) δ: 1.02 (3H, t), 1.23 (3H, t), 1.48 (3H, d), 1.58 (3H, t), 2.40 (2H, q), 2.52 (4H, m), 2.90 (2H, m), 3.08 (4H, m), 3.30 (3H, s), 3.60 (1H, m), 3.78 (1H, m), 4.56 (1H, m), 4.78 (2H, q), 5.30 (1H, br s), 6.66 (1H, br s), 8.63 (1H, d), 8.82 (1H, d), 10.48 (1H, s).

LRMS: m/z 552.3 ($MH^+$)

PREPARATION 90

4-[2-Ethoxy-5-(4-ethylpiperazin-1-ylsulphonyl)pyridin-3-ylcarboxamido]-3-ethyl-2-[(1S)-1-methyl-2-methoxyethyl)pyrazole-5-carboxamide

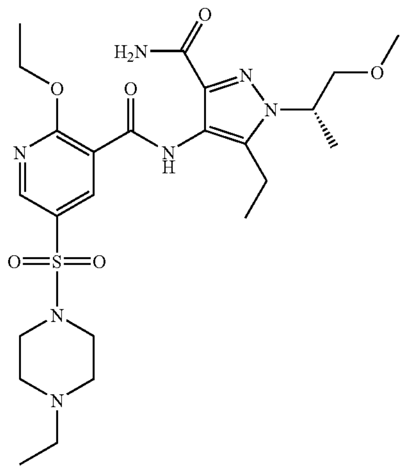

The title compound was obtained as an oil in 52% yield, from the compound from preparation 34 and the mesylate from preparation 77, following the procedure described in preparation 89.

$^1$Hnmr ($CDCl_3$, 300 MHz) δ: 1.01 (3H, t), 1.22 (3H, t), 1.48 (3H, d), 1.58 (3H, t), 2.40 (2H, q), 2.54 (4H, m), 2.90 (2H, m), 3.08 (4H, m), 3.30 (3H, s), 3.61 (1H, m), 3.78 (1H, m), 4.56 (1H, m), 4.78 (2H, q), 5.25 (1H, br s), 6.66 (1H, br s), 8.63 (1H, d), 8.82 (1H, d), 10.48 (1H, s).

LRMS: m/z 552.4 ($MH^+$)

PREPARATIONS 91 TO 94

The compounds of the following general structure:

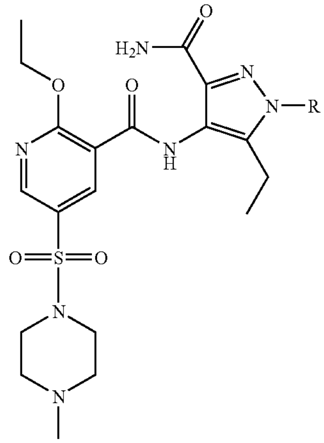

were prepared from the compound from preparation 35 and the appropriate alkylating agent, following a similar method to that described in preparation 83.

| Prep. No. | R | Alkylating agent | Yield (%) | Data |
|---|---|---|---|---|
| 91[1] | 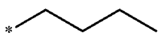 | bromide | 34 | $^1$Hnmr($CDCl_3$, 400MHz)δ: 0.95 (3H, t), 1.20(3H, t), 1.40(2H, m), 1.60(3H, t), 1.86(2H, m), 2.25(3H, s), 2.46(4H, m), 2.88(2H, q), 3.09 (4H, m), 4.05(2H, t), 4.75(2H, t), 5.25(1H, br s), 6.65(1H, br s), 8.65 (1H, s), 8.85(1H, s), 10.55(1H, s). |
| 92 | 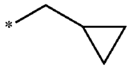 | bromide | 47 | $^1$Hnmr($CDCl_3$, 400MHz)δ: 0.41 (2H, m), 0.62(2H, m), 1.22(4H, m), 1.59(3H, t), 2.26(3H, s), 2.48(4H, m), 2.98(2H, q), 3.10(4H, m), 3.98 (2H, d), 4.78(2H, q), 5.27(1H, br s), 6.68(1H, br s), 8.65(1H, d), 8.85 (1H, d), 10.57(1H, s). |
| 93 | 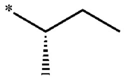 | mesylate | 45 | $^1$Hnmr($CDCl_3$, 400MHz)δ: 0.82 (3H, t), 1.22(3H, t), 1.60(6H, m), 1.80(1H, m), 2.00(1H, m), 2.23(3H, s), 2.50(4H, m), 2.85(2H, m), 3.10 (4H, m), 4.22(1H, m), 4.80(2H, q), 5.20(1H, br s), 6.70(1H, br s), 8.60 (1H, s), 8.82(1H, s), 10.50(1H, s). LRMS: m/z 522.0($MH^+$) |
| 94 | 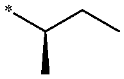 | mesylate | 42 | $^1$Hnmr($CDCl_3$, 400MHz)δ: 0.82 (3H, t), 1.22(3H, t), 1.60(6H, m), 1.80(1H, m), 2.00(1H, m), 2.23(3H, s), 2.50(4H, m), 2.85(2H, m), 3.10 (4H, m), 4.22(1H, m), 4.80(2H, q), 5.20(1H, br s), 6.70(1H, br s), 8.60 (1H, s), 8.82(1H, s), 10.50(1H, s). LRMS: m/z 522.0($MH^+$) |

[1]purified by column chromatography on silica gel, using dichloromethane:methanol(100:0 to 98:2).

PREPARATION 95

2-Ethoxy-5-(4-ethyl-1-piperazinylsulfonyl)nicotinic acid (a) 2-Hydroxy-5-sulfonicotinic acid 2-Hydroxynicotinic acid (27 Kg, 194.2 mol) was added portionwise to 30% oleum (58.1 Kg) at 50° C. over 1 hr. This caused an exotherm to 82° C. The reaction mixture was heated further to 140° C. After maintaining this temperature for 12 hrs the reactor contents were cooled to 15C and filtered. The filter cake was then re-slurried with acetone (33 Kg) at room temperature, filtered and dried to afford the title compound (35.3 Kg, 83%) as a white solid. Decomposition pt 273° C. δ ($DMSO_{d6}$): 7.93 (1H, d), 8.42 (1H, d). m/z (Found:220 $[M+H]^+$, 100%. $C_6H_6NO_6S$ requires 220.17).

(b) Ethyl 2-hydroxy-5-sulfonicotinoate

2-Hydroxy-5-sulfonicotinic acid (500 g, 2.28 mol) was dissolved in ethanol (2.5 L) with stirring and heated to 80° C. After 30 mins 0.5 L of solvent was distilled off, then replaced with fresh ethanol (0.5 L) and taken back to 80° C. After a further 60 mins 1.0 L of solvent was distilled off, then replaced with fresh ethanol (1.0 L) and taken back to 80° C. After a further 60 mins 1.0 L of solvent was distilled off, the reaction cooled to 22° C. and stirred for 16 hr. The precipitated product was filtered, washed with ethanol (0.5 L) and dried at 50° C. under vacuum to afford the title compound (416 g, 74%) as a white solid. Decomposition pt 237° C. δ ($DMSOd_6$): 1.25 (3H, t), 4.19 (2H, q), 7.66 (1H, d), 8.13 (1H, d). m/z (Found:248 $[M+H]^+$, 100%. $C_8H_{10}NO_6S$ requires 248.22).

(c) Ethyl 2-chloro-5-chlorosulfonicotinoate

Ethyl 2-hydroxy-5-sulfonicotioate (24.7 g, 0.1 mol) was slurried in thionyl chloride (238 g, 2.0 mol) and dimethylformamide (1.0 mL) with stirring. The reaction mixture was then heated to reflux for 2.5 hr. The bulk of the thionyl chloride was removed under vacuum with residual thionyl chloride removed with a toluene azeotrope to afford the crude title compound (30.7 g, 108%) as a yellow oil. d ($CDCl_3$): 1.46 (3H, t), 4.50 (2H, q), 8.72 (1H, d), 9.09 (1H, d). This was taken directly onto the next step.

(d) Ethyl 2-chloro-5-(4-ethyl-1-piperazinylsulfonyl)nicotinoate

Crude ethyl 2-chloro-5-chlorosulfonicotinoate (30.7 g, 0.1 mol assumed) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (50 mL), carefully over 30 mins, keeping the internal temperature below 10° C. Once the addition was complete the reaction was allowed to warm to 22° C. and stir for 1 hr. The solid was filtered off and the remaining filtrate was concentrated under vacuum to afford the crude title compound (37.1 g, 103%) as a crude yellow gum. δ ($CDCl_3$): 1.10 (3H, t), 1.42 (3H, m), 2.50 (2H, m), 2.60 (4H, m), 3.19 (4H, m), 4.43 (2H, q), 8.40 (1H, d), 8.80 (1H, d). m/z (Found:362 $[M+H]^+$, 100%. $C_{14}H_{21}ClN_3O_4S$ requires 362.85).

(e)Ethyl 2-ethoxy-5-(4-ethyl-1-piperazinylsulfonyl)nicotinoate

A solution of Ethyl 2-chloro-5-(4-ethyl-1-piperazinylsulfonyl)nicotinoate (36.1 g, 0.1 mol) in ethanol (180 mL) was cooled to 10° C. with stirring. Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the title compound (12.6 g, 34%) as a light brown solid. M.p. 66–68° C. δ ($CDCl_3$): 1.04 (3H, t), 1.39 (3H, t), 1.45 (3H, t), 2.41 (2H, q), 2.52 (4H, m), 3.08 (4H, m), 4.38 (2H, q), 2.57 (2H, q), 8.38 (1H, d), 8.61 (1H, d). m/z (Found:372 $[M+H]^+$, 100%. $C_{16}H_{26}N_3O_5S$ requires 372.46).

(f) 2-Ethoxy-5-(4-ethyl-1-piperazinylsulfonyl)nicotinic acid

Ethyl 2-ethoxy-5-(4-ethyl-1-piperazinylsulfonyl)nicotinoate (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH=5.6 by addition of c. hydrochloric acid. The precipitated product was slurried with ice cooling for 15 minutes, filtered, water washed and dried under vacuo at 50° C. to afford the title compound as an off-white solid. Mpt 206–207° C. δ ($CDCl_3$): 1.25 (3H, t), 1.39 (3H, t), 2.82 (2H, q), 3.03 (4H, m), 3.25 (4H, m), 4.50 (2H, q), 8.25 (1H, d), 8.56 (1H, d). m/z (Found:344 $[M+H]^+$, 100%. $C_{14}H_{22}N_3O_5S$ requires 344.38).

This step 95(f) is already set out in preparation 23 of PCT/IB99/00519 (herein incorporated by reference) and the yield obtained is 88%.

PREPARATION 96

N-[3-Carbamoyl-5-ethyl-1-(2-methoxyethyl)-1H-pyrazol-4-yl]-2-ethoxy-5-(4-ethyl-1-piperazinylsulfonyl)nicotinamide (a) Ethyl 3-ethyl-1H-pyrazole-5-carboxylate

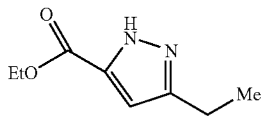

To a stirred solution of 2,2-dimethoxybutane (10 g, 84.7 mMol) in $CH_2Cl_2$ (50 mL) under a nitrogen atmosphere at 0° C. was added pyridine (13.7 mL, 169.5 mMol). The reaction mixture was maintained at 0° C. and a solution of trichloroacetyl chloride (18.9 mL, 169.5 mMol) in $CH_2CL_2$ (35 mL) was added over 1 hour with constant stirring. The yellow-orange solution begins to precipitate a white solid as the reaction progresses. The reaction mixture is allowed to warm to room temperature over 20 h. The reaction mixture was diluted with ethanol (150 mL) and re-cooled to 0° C. before treatment with hydrazine hydrate (8.2 mL, 169.5 mMol) as a solution in ethanol (35 mL) over 30 min. The reaction was heated to 50° C. and solvent was distilled at atmospheric pressure. The temperature was increased until the head temperature reached 78° C. Reflux was maintained for a further 2 h, before cooling to room temperature. The reaction mixture was diluted with water (250 mL) and ethanol was removed by evaporation at reduced pressure. The resultant mixture was extracted with $CH_2Cl_2$ (3×200 mL). The combined organics were dried ($MgSO_4$), filtered and evaporated at reduced pressure to afford the title compound as a brown oil, 12.05 g, 85%.

$^1H$ NMR (300 MHz, $CDCl_3$): δ=1.20 (3H, t), 1.28 (3H, t), 2.67 (2H, q), 4.29 (2H, q), 6.55 (1H, s), 12.56 (1H, s).

LRMS m/z=167.1 $[M-H]^+$, $C_8H_{12}N_2O_2$ requires 168.2.

(b) Ethyl 3-ethyl-1H-pyrazole-5-carboxylic acid

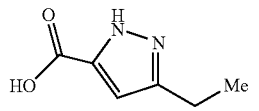

Aqueous sodium hydroxide solution (10M; 100 ml, 1.0 mol) was added dropwise to a stirred suspension of the title compound of Preparation 96(a) (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g). δ ($DMSO_{d6}$): 1.13 (3H, t), 2.56 (2H, q), 6.42 (1H, s).

(c) 4-Nitro-3-n-propyl-1H-pyrazole-5-carboxylic acid

Fuming sulphuric acid (17.8 ml) was added dropwise to stirred, ice-cooled fuming nitric acid (16.0 ml), the resulting solution heated to 50° C., then 3-n-propyl-1H-pyrazole-5-carboxylic acid (Chem. Pharm. Bull., 1984, 32, 1568; 16.4 g, 0.106 mol) added portionwise over 30 minutes whilst maintaining the reaction temperature below 60° C. The resulting solution was heated for 18 hours at 60° C., allowed to cool, then poured onto ice. The white precipitate was collected, washed with water and dried by suction to yield the title compound (15.4 g), m.p. 170–172° C. Found: C, 42.35; H, 4.56; N, 21.07. $C_7H_9N_3O_4$ requires C, 42.21; H, 4.55; N, 21.10%. δ ($DMSOd_6$): 0.90 (3H, t), 1.64 (2H, m), 2.83 (2H, m), 14.00 (1H, s).

(d) 3-Ethyl-4-nitro-1H-pyrazole-5-carboxylic acid

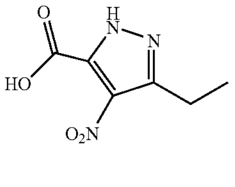

Obtained from the title compound of Preparation 96(b), by analogy with the process of Preparation 96(c), as a brown solid (64%). δ ($DMSO_{d6}$): 1.18 (3H, t), 2.84 (2H, m), 13.72 (1H, s).

(e) 4-Nitro-3-n-propyl-1H-pyrazole-5-carboxamide

A solution of the title compound of Preparation 96(c) (15.4 g, 0.077 mol) in thionyl chloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound (14.3 g), m.p. 197–199° C. Found: C, 42.35; H, 5.07; N, 28.38. $C_7H_{10}N_4O_3$ requires C, 42.42; H, 5.09; N, 28.27%. δ ($DMSOd_6$): 0.90 (3H, t), 1.68 (2H, m), 2.86 (2H, t), 7.68 (1H, s), 8.00 (1H, s).

(f) 3-Ethyl-4-nitro-1H-pyrazole-5-carboxamide

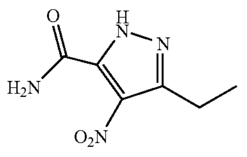

Obtained from the title compound of Preparation 96(d), by analogy with Preparation 96(e), as a white solid (90%). 6 ($DMSOd_6$): 1.1.7 (3H, t), 2.87 (2H, m), 7.40 (1H, s), 7.60 (1H, s), 7.90 (1H, s). LRMS: m/z 185 $(M+1)^+$.

(g)(i) 5-Ethyl-1-(2-methoxyethyl)-4-nitro-1H-pyrazole-3-carboxamide.

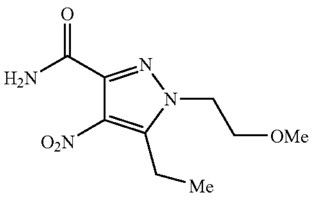

A mixture of 3-ethyl-4-nitro-1H-pyrazole-5-carboxamide (2.5 kg, 13.6 Mol), sodium carbonate (1.8 Kg, 17.0 Mol) and 2-bromoethyl methyl ether (1.98 kg, 14.2 Mol) in THF (22.5 L) and water (2.5 L) was heated under reflux and stirred for 20 hours. The mixture was cooled to ambient temperature and $CH_2Cl_2$ (67.5 L) and water (22.5 L) were added. The resultant organic and aqueous layers were separated. The aqueous phase was extracted with $CH_2Cl_2$ (22.5 L) and the combined organic solution was distilled under atmospheric pressure and replaced with ethyl acetate (33 L) to a final volume of 17 L. The cooled mixture was granulated at ambient temperature for 2 hours, filtered and washed with ethyl acetate (2.5 L). This afforded 5-ethyl-1-(2-methoxyethyl)-4-nitro-1H-pyrazole-3-carboxamide as a white crystalline solid, 2.10 kg, 57%. m.p.=140° C. Found: C, 44.46; H, 5.79; N, 23.01. $C_9H_{14}N_4O_4$ requires C, 44.63; H, 5.79; N, 23.14%.

δ ($CDCl_3$): 1.18 (3H, t), 2.98 (2H, q), 3.22 (3H, s), 3.77 (2H, t), 4.28 (2H, q), 6.03 (1H, s), 7.36 (1H, s).

LRMS: m/z=243 $(M+1)^+$ (g)(ii) 5-Ethyl-1-(2-methoxyethyl)-4-nitro-1H-pyrazole-3-carboxamide.

A mixture of 3-ethyl-4-nitro-1H-pyrazole-5-carboxamide (25 g, 0.136 Mol), sodium carbonate (18 g, 0.17 Mol) and sodium iodide (20.4 g, 0.136 Mol) were suspended in ethyl methyl ketone (125 mL) at room temperature. 2-bromoethyl methyl ether (12.8 mL, 0.142 Mol) was added and the mixture was heated to reflux and stirred for 70 hours. The mixture was cooled to ambient temperature and water (250 mL) was added. The resultant slurry was warmed to reflux and held at that temperature for 30 min before cooling to room temperature. The resultant precipitate was granulated at room temperature for 3 h, filtered and vacuum dried to afford 5-ethyl-1-(2-methoxyethyl)-4-nitro-1H-pyrazole-3-carboxamide as a yellow crystalline solid 24.3 g, 74%. Data as reported for Example (b)(i).

(h) 4-Amino-5-ethyl-1-(2-methoxyethyl)-1H-pyrazole-3-carboxamide.

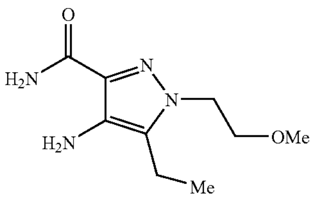

A mixture of 5-ethyl-1-(2-methoxyethyl)-4-nitro-1H-pyrazole-3-carboxamide (20 g, 82.6 mMol) and 5% Pd/C (1 g) in methanol (200 mL) was pressurised at 50 psi/25° C. in a sealed vessel and stirred for 15 hours. At the end of the reaction the mixture was filtered through arbocel and the filter cake was washed with methanol. The methanolic solution was distilled at atmospheric pressure and replaced with ethyl acetate to a final volume of 100 mL. The cooled mixture was granulated at ambient temperature for 2 h filtered and washed with ethyl acetate (20 mL) to afford 4-amino-5-ethyl-1-(2-methoxyethyl)-1H-pyrazole-3-carboxamide as a white crystalline solid, 15 g, 88%. m.p.=131° C. Found: C, 50.75; H, 7.62; N, 26.38. $C_9H_{16}N_4O_2$ requires C, 50.94; H, 7.55; N, 26.42%.

δ ($CDCl_3$): 1.20 (3H, t), 2.63 (2H, q), 3.32 (3H, s), 3.74 (2H, t), 3.95 (2H, s), 4.15 (2H, t), 5.27 (1H, s), 6.59 (1H, s).

LRMS: m/z=213 $(M+1)^+$ (i) N-[3-Carbamoyl-5-ethyl-1-(2-methoxyethyl)-1H-pyrazol-4-yl]-2-ethoxy-5-(4-ethyl-1-piperazinylsulfonyl) nicotinamide.

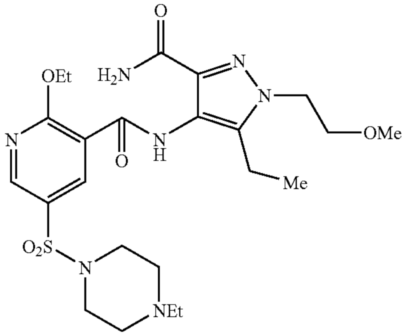

2-ethoxy-5-(4-ethyl-1-piperazinylsulfonyl)nicotinic acid (2.31 kg, 6.73 Mol) was suspended in ethyl acetate (16.2 L) and 1,1-carbonyldimidazole (1.09 kg, 6.73 Mol) was added at room temperature. The reaction mixture was heated at 45° C. for 40 minutes and then the reaction was stirred for a further 40 minutes at reflux. After cooling to ambient temperature 4-amino-5-ethyl-1-(2-methoxyethyl)-1H-pyrazole-3-carboxamide (1.5 kg, 7.06 Mol) was added to the cooled mixture, and the reaction stirred for a further 15 hours under reflux. The mixture was cooled filtered and the filter cake was washed with 90% water/10% ethyl acetate, (2 mL/g) to afford N-[3-carbamoyl-5-ethyl-1-(2-methoxyethyl)-1H-pyrazol-4-yl}-2-ethoxy-5-(4-ethyl-1-piperazinylsulfonyl)nicotinamide as an off white crystalline solid, 3.16 kg, 88%. m.p.=156° C. Found: C, 51.33; H, 6.56; N, 18.36. $C_{23}H_{35}N_7O_6S$ requires C, 51.40; H, 6.53; N, 18.25%.

δ ($CDCl_3$): 1.04 (3H, t), 1.22 (3H, t), 1.60 (3H, t), 2.44 (2H, q), 2.54 (4H, m), 2.96 (2H, q), 3.12 (4H, m), 3.36 (3H, s), 3.81 (2H, t), 4.27 (2H, t), 4.80 (2H, q), 5.35 (1H, s), 6.68 (1H, s), 8.66 (1H, d), 8.86 (1H, d), 10.51 (1H, s).

LRMS: m/z=539 $(M+1)^+$

Additionally, in accordance with the invention, the intermediate compounds (XIV) and (XB) (as illustrated in Schemes 2 and 3) can be prepared from commercially available starting materials (2-hydroxy nicotinic acid) in better yield than the corresponding reaction sequence in PCT/IB99/00519. For example, compound (XIV) (wherein Q and W are OEt) is formed in a yield of 14.5% in preparation 18 of PCT/IB99/00519 (i.e. from a reaction sequence of prepation 1,3,5,7 and 18) whereas the same compound is prepared in a yield of 23% in accordance with the present invention (see Preparation 95). More preferably the whole or part of the reaction sequence for the formation of compounds (XIV) and (XB) can be telescoped together in accordance with the invention to provide an even better yield. Thus compound (XB) (wherein X is OEt) is prepared in a yield of 35% (see Preparation 95 herein). Furthermore, the reaction scheme of the present invention is safer and cheaper to operate, and in the case of the telescoped process also involves less steps (and processing time).

It will be appreciated that formation of compounds of formula (XB) and (XIV) from (XV) respectively is an independent invention and is preferably prepared from 2-hydroxynicotinic acid as outlined herein. Likewise each and every step (and telescoped step) in Schemes 2 and 3 are independent inventions, although in a preferred aspect compounds of formula (I), (IA) and (IB) are prepared from nicotinic acid in accordance with Schemes 2 and 3.

Thus in a further aspect of the invention a compound of formula (XVII) is formed by reacting 2-hydroxynicotinic acid or a salt thereof in the presence of $SO_3$ in a solvent.

The invention claimed is:

1. A process for the preparation of a compound of formula (I):

(I)

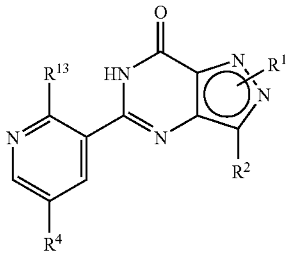

wherein $R^1$ is $C_1$ to $C_6$ alkyl or $C_3$ to $C_6$ alkenyl, $C_3$ to $C_6$ cycloalkyl or $C_4$ to $C_6$ cycloalkenyl wherein said alkyl group may be branched or straight chain and wherein when $R^1$ is $C_1$ to $C_3$ alkyl said alkyl group is substituted by;

and wherein when $R^1$ is $C_4$ to $C_6$ alkyl, $C_3$ to $C_6$ alkenyl or $C_3$ to $C_6$ cycloalkyl said alkyl, alkenyl or cycloalkyl group is optionally substituted by;

one or more substituents selected from:

hydroxy;

$C_1$ to $C_4$ alkoxy;

$C_3$ to $C_6$ cycloalkyl;

phenyl substituted with one or more substitutents selected from $C_1$ to $C_3$ alkyl, $C_1$ to $C_4$ alkoxy, $C_1$ to $C_4$ haloalkyl, $C_1$ to $C_4$ haloalkoxy, halo, CN, $NO_2$, $NHR^{11}$, $NHCOR^{12}$, $NHSO_2R^{12}$, $SO_2R^{12}$, $SO_2NHR^{11}$, $COR^{11}$ or $CO_2R^{11}$ wherein said haloalkyl and haloalkoxy groups contain one or more halo atoms;

$NR^7R^8$, $CONR^7R^8$ or $NR^7COR^{11}$ wherein $R^7$ and $R^8$ are each independently selected from H, $C_1$ to $C_4$ alkyl, $C_3$ to $C_4$ alkenyl, $CO_2R^9$ or $SO_2R^9$ and wherein said alkyl or alkenyl groups are optionally substituted by $C_1$ to $C_4$ haloalkyl or $C_1$ to $C_4$ haloalkoxy;

$Het^1$;

$Het^2$ or $Het^3$;

or $R^1$ is $Het^4$ or phenyl wherein said phenyl group is optionally substituted by one or more substituents selected from $C_1$ to $C_4$ alkyl, $C_3$ to $C_4$ alkenyl, $C_1$ to $C_4$ alkoxy, halo, CN, $CF_3$, $OCF_3$, $NO_2$, $NHR^{11}$, $NHCOR^{12}$, $NHSO_2R^{12}$, $SO_2R^{12}$, $SO_2NHR^{11}$, $COR^{11}$ or $CO_2R^{11}$;

$R^2$ is $C_1$ to $C_6$ alkyl, $C_3$ to $C_6$ alkenyl or $(CH_2)_n(C_3$ to $C_6$ cycloalkyl) wherein n is 0, 1 or 2;

$R^{13}$ is $OR^3$ or $NR^5R^6$;

$R^3$ is $C_1$ to $C_6$ alkyl optionally substituted with one or two substituents selected from $C_3$ to $C_5$ cycloalkyl, hydroxy, $C_1$ to $C_4$ alkoxy, benzyloxy, $NR^5R^6$, phenyl, $Het^1$, $He^2$, $Het^3$ or $Het^4$ wherein the $C_1$ to $C_6$ alkyl and $C_1$ to $C_4$ alkoxy groups may optionally be terminated by $CF_3$ and wherein the $C_3$–$C_5$ cycloalkyl group may optionally be substituted by $C_1$–$C_4$ alkyl, hydroxy or halo;

$C_3$ to $C_6$ cycloalkyl; $Het^1$, $Het^2$, $Het^3$ or $Het^4$;

$R^4$ is a piperazin-1-ylsulphonyl group having a substituent $R^{10}$ at the 4-position of the piperazinyl group wherein said piperazinyl group is optionally substituted with one or two $C_1$ to $C_4$ alkyl groups and is optionally in the form of its 4-N-oxide;

$R^5$ and $R^6$ are each independently selected from H and $C_1$ to $C_4$ alkyl optionally substituted with $C_3$ to $C_5$ cycloalkyl or $C_1$ to $C_4$ alkoxy, or, together with the nitrogen atom to which they are attached, form an azetidinyl, pyrrolidinyl, piperidinyl or morpholinyl group;

$R^7$ and $R^8$ are each independently selected from H, $C_1$ to $C_4$ alkyl, $C_3$ to $C_4$ alkenyl, $CO_2R^9$ or $SO_2R^9$;

$R^9$ is $C_1$ to $C_4$ alkyl optionally substituted with $C_1$ to $C_4$ haloalkyl, $C_1$ to $C_4$ haloalkoxy or phenyl wherein said phenyl group is optionally substituted by one or more substituents selected from $C_1$ to $C_4$ alkyl optionally substituted by $C_1$ to $C_4$ haloalkyl or $C_1$ to $C_4$ haloalkoxy, $C_1$ to $C_4$ alkoxy, halo, CN, $NO_2$, $NHR^{11}$, $NHCOR^{12}$, $NHSO_2R^{12}$, $SO_2R^{12}$, $SO_2NHR^{11}$, $COR^{11}$ or $CO_2R^{11}$;

$R^{10}$ is H; $C_1$ to $C_4$ alkyl optionally substituted with one or two substituents selected from hydroxy, $NR^5R^6$, $CONR^5R^6$, phenyl optionally substituted with $C_1$ to $C_4$ alkyl or $C_1$ to $C_4$ alkoxy; $C_3$ to $C_6$ alkenyl or $Het^4$;

$R^{11}$ is H, $C_1$ to $C_4$ alkyl, $C_3$ to $C_4$ alkenyl, CO($C_1$ to $C_4$ alkyl) or $C_1$ to $C_4$ haloalkyl;

$R^{12}$ is $C_1$ to $C_4$ alkyl, $C_3$ to $C_4$ alkenyl, $C_1$ to $C_4$ haloalkyl or $C_1$ to $C_4$ haloalkoxy;

$Het^1$ is an N-linked 4-, 5- or 6-membered nitrogen-containing heterocyclic group optionally containing one or more further heteroatoms selected from S, N or O;

Het[2] is a C-linked 5-membered heterocyclic group containing an O, S or N heteroatom optionally containing one or more heteroatoms selected from N, O or S;

Het[3] is a C-linked 6-membered heterocyclic group containing an O or S heteroatom optionally containing one or more heteroatoms selected from O, S or N or Het[3] is a C-linked 6-membered heterocyclic group containing three N heteroatoms;

Het[4] is a C-linked 4-, 5- or 6-membered heterocyclic group containing one, two or three heteroatoms selected from S, O or N; and wherein any of said heterocyclic groups $Het^1$, $Het^2$, $Het^3$ or $Het^4$ may be saturated, partially unsaturated or aromatic and wherein any of said heterocyclic groups may be optionally substituted with one or more substituents selected from $C_1$ to $C_4$ alkyl, $C_3$ to $C_4$ alkenyl, $C_1$ to $C_4$ alkoxy, halo, $CF_3$, $CO_2R^{11}$, $COR^{11}$, $SO_2R^{12}$, $NHR^{11}$ or $NHCOR^{12}$ and/or wherein any of said heterocyclic groups is benzo-fused;

with the provisos that (a) when $R^1$ is $C_1$ to $C_3$ alkyl then $Het^1$ is not morpholinyl or piperidinyl and (b) when $R^1$ is $C_1$ to $C_3$ alkyl substituted by phenyl then said phenyl group is not substituted by $C_1$ to $C_4$ alkoxy, CN, halo, $CF_3$, $OCF_3$ or $C_1$ to $C_4$ alkyl which precess comprises cyclisation of a compound of formula (IX):

(IX)

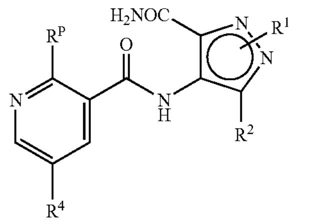

wherein $R^P$ is $R^{13}$ or $R^P$ is X which is a leaving group and $R^1$, $R^2$, $R^4$ and $R^{13}$ are as defined above wherein said cyclisation reaction is optionally followed by formation of a pharmaceutically or veterinarily acceptable salt of the required product or a pharmaceutically or veterinarily acceptable solvate or pro-drug of the required product.

2. A process according to claim 1 wherein the cyclisation reaction is base-mediated, using an alkali metal salt of a sterically hindered alcohol or amine.

3. A process for the preparation of compounds of the formula (IX) as defined in claim 1 via a coupling reaction, using conventional amide bond-forming techniques, between compounds of the formula (VII):

(VII)

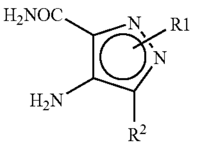

wherein $R^1$ and $R^2$ are defined im claim 1 and compounds of the formula (X):

(X)

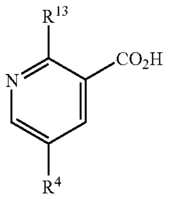

wherein $R^{13}$ and $R^4$ are as previously defined for formula (I) in claim 1.

4. A process for the preparation of a compound of formula (I):

(I)

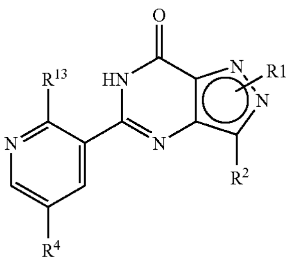

wherein $R^1$, $R^2$, and $R^4$ are as defined in claim 1 and $R^{13}$ is $OR^3$ as defined in claim 1, which process comprises conversion of a compound of formula (XXX):

(XXX)

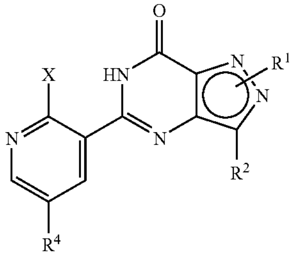

wherein X is a leaving group and $R^1$, $R^2$ and $R^4$ are as defined in claim 1 and wherein said conversion reaction is optionally followed by formation of a pharmaceutically or veterinarily acceptable salt of the required product or a pharmaceutically or veterinarily acceptable solvate or pro-drug of the required product.

5. A process for the preparation of a compound of the formula (I) from a compound of formula (IXB) via:

i) cyclisation (IXB to XXX) followed by displacement (XXX to I);

ii) cyclisation (IXCa to XXX) followed by displacement (XXX to I);

iii) displacement (IXB to IXC) followed by cyclisation (IXC to I);

iv) displacement (IXCa to IXC) followed by cyclisation (IXC to I) wherein in compounds (XXX) and (IXCa) have the formulae:

(XXX)

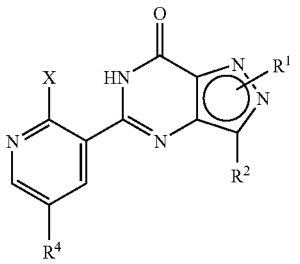

(IXCa)

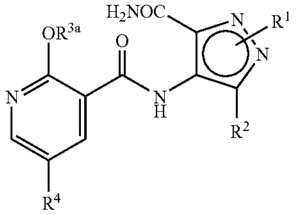

wherein $R^1$, $R^2$, $R^4$ and X are as defined in claim 1 and $OR^{3a}$ is an alkoxy group which is different from and displaceable by the desired $OR^3$ group on the final compounds of formula (I) and wherein $R^{3a}$ selected from $C_1$ to $C_6$ alkyl optionally substituted; or v) direct cyclisation of (IXB) to (I).

* * * * *